(12) United States Patent
Hils et al.

(10) Patent No.: US 11,472,838 B2
(45) Date of Patent: Oct. 18, 2022

(54) INHIBITORS OF BLOOD COAGULATION FACTOR XIII

(71) Applicant: Zedira GmbH, Darmstadt (DE)

(72) Inventors: Martin Hils, Darmstadt (DE); Ralf Pasternack, Griesheim (DE); Christian Büchold, Karben (DE)

(73) Assignee: Zedira GmbH, Darmstadt (DE)

( * ) Notice: Subject to any disclaimer, the term of this patent is extended or adjusted under 35 U.S.C. 154(b) by 0 days.

(21) Appl. No.: 17/047,704

(22) PCT Filed: Apr. 17, 2019

(86) PCT No.: PCT/EP2019/060030
§ 371 (c)(1),
(2) Date: Oct. 15, 2020

(87) PCT Pub. No.: WO2019/202052
PCT Pub. Date: Oct. 24, 2019

(65) Prior Publication Data
US 2021/0147478 A1    May 20, 2021

(30) Foreign Application Priority Data
Apr. 17, 2018  (WO) ................ PCT/EP2018/059798

(51) Int. Cl.
| | |
|---|---|
| *A61K 38/08* | (2019.01) |
| *C07K 5/097* | (2006.01) |
| *A61P 7/02* | (2006.01) |
| *C07K 1/10* | (2006.01) |
| *C07K 5/117* | (2006.01) |
| *C07K 7/06* | (2006.01) |
| *C07K 7/08* | (2006.01) |
| *A61K 38/00* | (2006.01) |

(52) U.S. Cl.
CPC .............. *C07K 5/0821* (2013.01); *A61P 7/02* (2018.01); *C07K 1/10* (2013.01); *C07K 5/1024* (2013.01); *C07K 7/06* (2013.01); *C07K 7/08* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,386,011 | A | * | 1/1995 | Wiedeman ............. A61P 37/08 530/328 |
| 2011/0229568 | A1 | | 9/2011 | Oertel |
| 2015/0203535 | A1 | | 7/2015 | Buchold et al. |
| 2016/0137990 | A1 | | 5/2016 | Hils et al. |

FOREIGN PATENT DOCUMENTS

WO    2008/055488    5/2008

OTHER PUBLICATIONS

International Search Report and Written Opinion for International Patent Application No. PCT/EP2019/060030 dated Jul. 16, 2019, 12 pages.

* cited by examiner

*Primary Examiner* — Fred H Reynolds
(74) *Attorney, Agent, or Firm* — Amin, Turocy & Watson, LLP

(57) ABSTRACT

The invention relates to a compound of general formula (I) as novel inhibitor of blood coagulation factor XIII, methods for synthesis thereof and to use thereof for the prophylaxis or treatment of diseases associated with blood coagulation factor XIII.

13 Claims, 7 Drawing Sheets

A

B

A.

D.

E.

INHIBITORS OF BLOOD COAGULATION FACTOR XIII

The invention relates to novel inhibitors of blood coagulation factor XIII, methods for their synthesis and to their use for the prophylaxis or treatment of diseases associated with blood coagulation factor XIII.

BACKGROUND OF THE INVENTION

Substantial effort has been dedicated to the development of drugs targeting coagulation factors or platelet activation in order to prevent and treat venous thromboembolism, acute coronary syndrome or for reducing the risk of stroke in patients with atrial fibrillation. Coagulation factor XIII (FXIII, F13) is a promising but yet widely untapped and challenging target for drug development (LORAND L., JACOBSEN A., Nature 1962; 195: 911-2; Stieler M, et al., Angew Chemie Int Ed 2013; 52:11930-4; Bohm M, et al., J Med Chem 2014; 57: 10355-65.) Whereas all the other enzymes within the coagulation cascade are serine proteases, the FXIII-A subunit belongs to the transglutaminase family (EC 2.3.2.13: protein-glutamine γ-glutamyltransferase) consisting of eight human isoenzymes (FXIII-A and TG1-TG7). The most characteristic catalytic function for transglutaminases is the formation of isopeptide bonds between the side chains of susceptible protein bound glutamine and lysine residues in a tightly controlled manner.

FXIII plays a key role in clot formation, maturation and composition (Muszbek L, et al., Physiol Rev 2011; 91:931-72; Byrnes J R, et al. Blood 2015, 126, 1940-8). FXIII recognizes fibrin as substrate and covalently cross-links fibrin γ-chains and, in an ordered sequence, fibrin α-chains providing mechanical stability to the fibrin fibers. In parallel, enzymatic incorporation of anti-fibrinolytic proteins such as $\alpha_2$-antipiasmin renders the clot biochemically stable. In blood, the non-covalent FXIII-$A_2B_2$ heterotetramer (pFXIII) is bound to fibrinogen. During activation thrombin cleaves the N-terminal activation peptide from the FXIII-A subunits. Subsequent binding of calcium ions promotes dissociation of the carrier B-subunits yielding active FXIIIa.

The clot-modulating function and the positioning downstream of thrombin make FXIII a promising target for drug development (Lorand L, Arterioscler Thromb. Vasc. Biol., 2000; 20: 2-9.). Specific inhibitors targeting FXIII would not interfere with thrombin generation, fibrin formation or with platelet activation. Blocking thrombin—directly or via upstream FXa—by the currently available anticoagulants is characterized by an enhanced bleeding risk, thus excluding many patients from beneficial treatment (Griffin J H, Nature, 1995; 378: 337-8.). Considering this well-known medical need, novel therapeutic approaches with minimal or no bleeding risk are desperately needed (Weitz J I, Fredenburgh J C., Front Med 2017; 4.). Even if the development of FXIII inhibitors might provide one such option, noticeably few FXIII-blockers have been identified or synthesized so far.

Finney et al. reported that the 66 amino acid polypeptide "tridegin" from the salivary gland of the giant Amazon leech Haementeria ghilianii is a potent FXIII inhibitor (Finney S, et al., Biochem J, 1997; 324 (Pt 3:797-805.). Further, in the late 1980s, a series of small molecules irreversibly inhibiting FXIIIa were explored in animal models of thrombosis in the presence of t-PA facilitating increased clot lysis in vivo (Leidy E M, et al., Thromb Res, 1990; 59: 15-26; Shebuski R J, et al., Blood 1990; 75: 1455-9.). Due to the lack of selectivity and potency along with short plasma half-lives of only a few minutes, these inhibitors were solely considered as pharmacological tools but not as prospective drug candidates. The pharmacokinetic profile of an irreversibly acting inhibitor carrying a thiadiazole warhead was studied in rabbits in order to support and facilitate the design and selection of drug candidates (Novakovic J, et al., J Pharm Biomed Anal 2005; 38: 293-7.). Further, medicinal chemists reported cyclopropenone derivatives from fungi and synthetic analogues as potent FXIIIa inhibitors (Kogen H, et al., J. Am. Chem. Soc. 2000, 122, 1842-1843.). In both cases, from a drug discovery perspective, the low potency of the compounds disqualifies them for further development. In accordance with this assumption no (pre)clinical studies have been reported.

Potent, drug-like FXIII-inhibitors are a prerequisite that is still lacking for further exploring the therapeutic concept.

The objective of the present invention is to provide novel, most probably irreversible inhibitors of blood coagulation factor XIII and methods for the synthesis thereof as well as their use for the prophylaxis and treatment of diseases associated with blood coagulation factor XIII.

Said objective is solved by the technical teachings of the independent claims. Further advantageous embodiments, aspects and details of the invention are evident from the dependent claims, the description and the examples.

Surprisingly, it was found that certain peptidomimetic inhibitors carrying a Michael-acceptor warhead are potent and selective inhibitors of FXIIIa. The patent application discloses preferred structures characterized by the position 2 towards the C-terminus of the warhead. It was found that exactly at that position constrained peptide-mimetic amino acids are preferred to obtain potent and/or selective FXIIIa-blockers. The peptide-mimetic backbone positions the soft electrophilic warhead in perfect orientation to the active site cysteine. The mechanism-based inhibitors efficiently inactivate FXIIIa even if the intrinsic reactivity of the Michael-acceptor warhead is low—a prerequisite to avoid side effects and toxicity.

Thus, the present invention relates to a compound of the general formula (I):

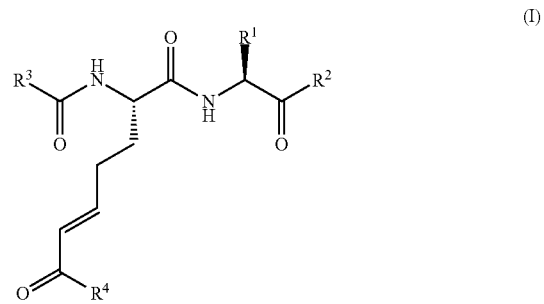

wherein
$R^1$ represents —H, —$CH_3$, —$C(CH_3)_3$, -cyclo-$C_3H_5$, -cyclo-$C_4H_7$, -cyclo-$C_5H_9$, -cyclo-$C_6H_{11}$, —$CH_2$—$CH(CH_3)_2$, —$CH_2CH_3$, —$CH_2CH_2CH_3$, —$CH_2CH_2CH_2CH_3$, —$CH_2CH_2CH_2CH_2CH_3$, —$CH_2CH_2CH_2CH_2CH_2CH_3$, —$CH(CH_3)_2$, —$CH_2$—$C(CH_3)_3$, —$CH_2CH_2SCH_3$, —$CH_2$-cyclo-$C_3H_5$, —$CH_2$-cyclo-$C_4H_7$, —$CH_2$-cyclo-$C_5H_9$ or —$CH_2$-cyclo-$C_6H_{11}$;

$R^2$ represents -$A^1$-$A^2$-$A^3$-E, -$A^1$-$A^2$-$A^3$-$A^4$-E or -$A^1$-$A^2$-$A^3$-$A^4$-$A^5$-E;

R³ represents
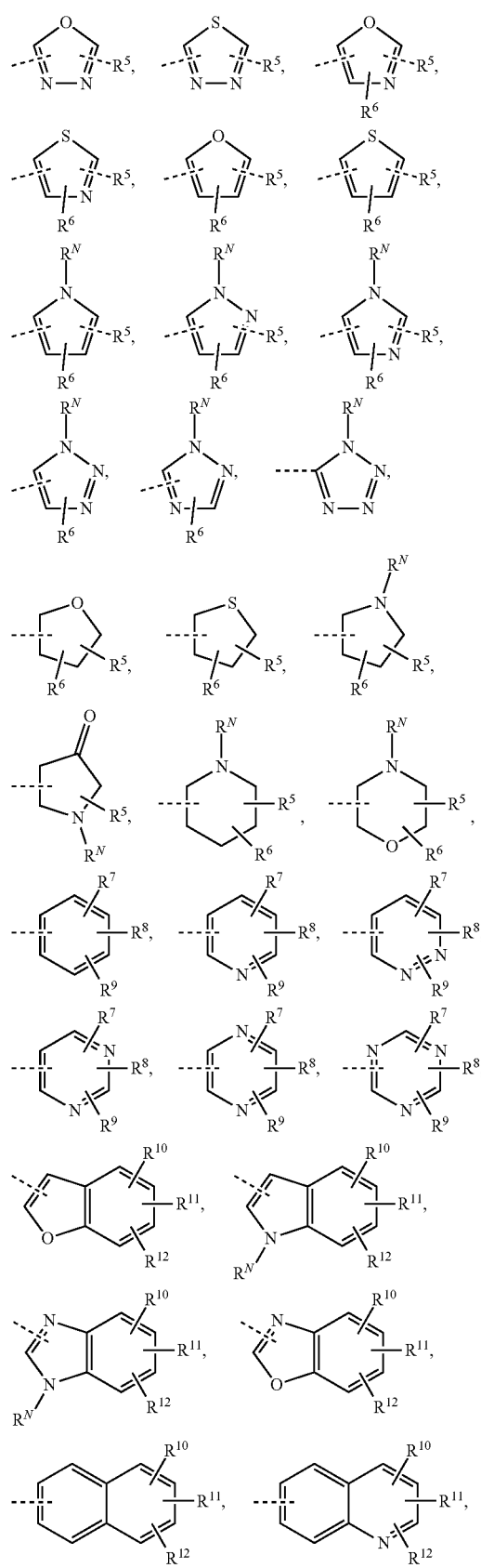
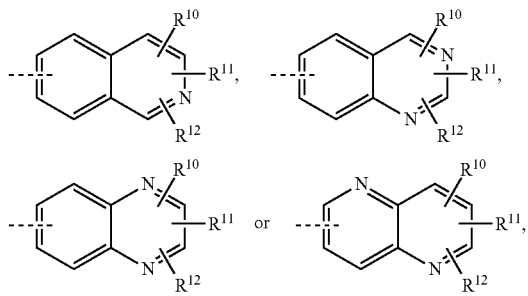
R⁴ represents —OR*, —NH₂, —NHR^# or —NR*R^#;
R* and R^# represent independently of each other —CH₃, —CH₂CH₃, —CH(CH₃)₂, —CH₂CH₂CH₃, —CH₂CH(CH₃)₂, —C(CH₃)₃, -cyclo-C₃H₅, -cyclo-C₄H₇, -cyclo-C₅H₉, -cyclo-C₆H₁₁, —CH₂-cyclo-C₃H₅, —CH₂-cyclo-C₄H₇, —CH₂-cyclo-C₅H₉, —CH₂-cyclo-C₆H₁₁, —CH-Ph, —CH₂OCH₃, —CH₂OCH₂CH₃, —CH₂CH₂OCH₃, or —CH₂CH₂SCH₃;
A¹ represents
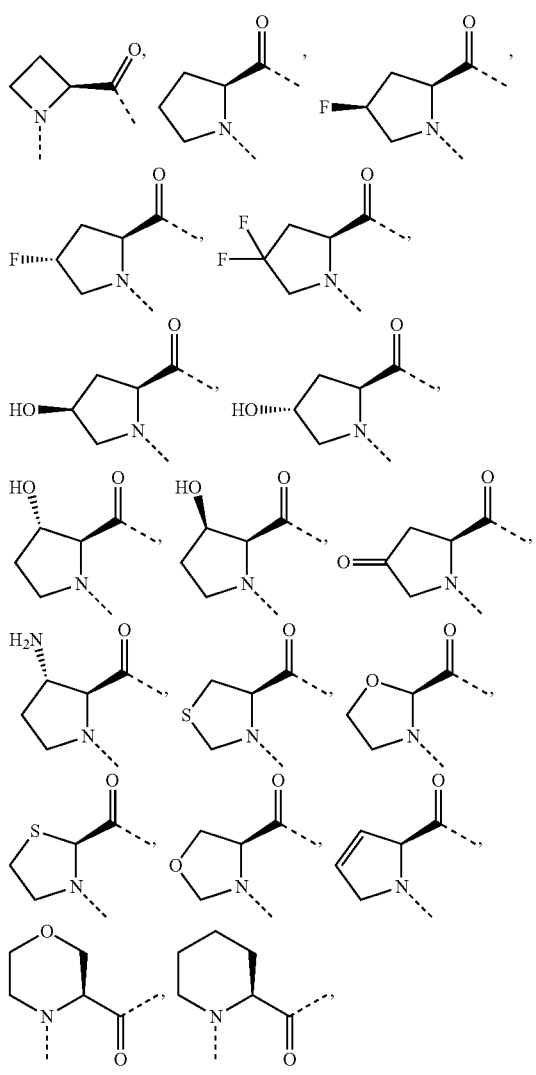

5
-continued
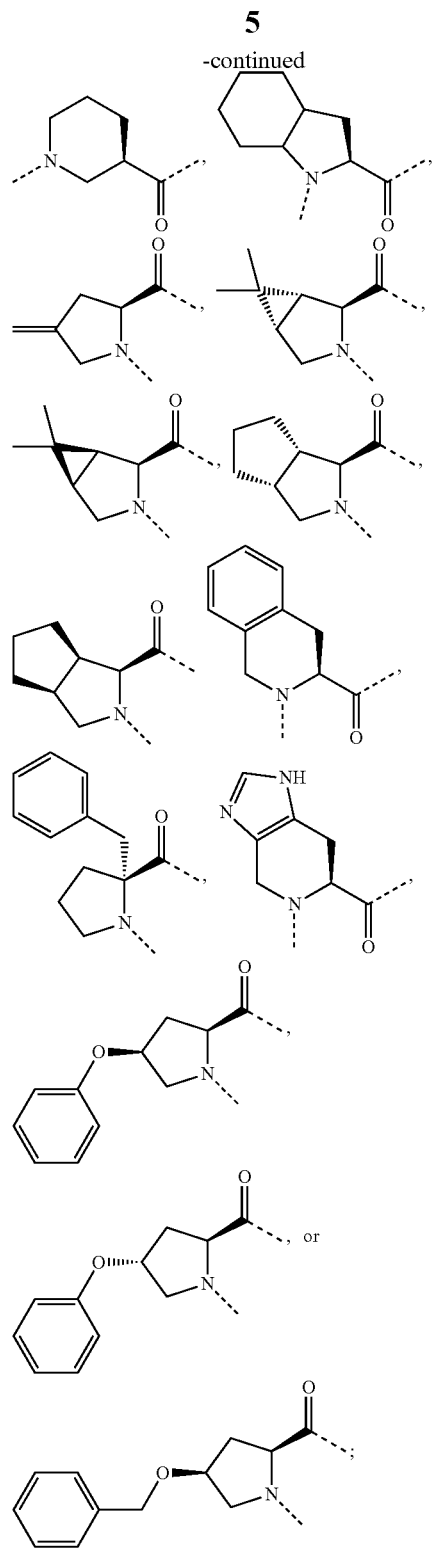
$A^2-A^5$ represent independently of each other
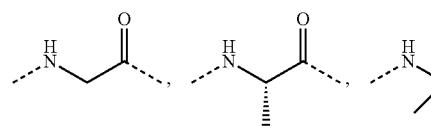
6
-continued
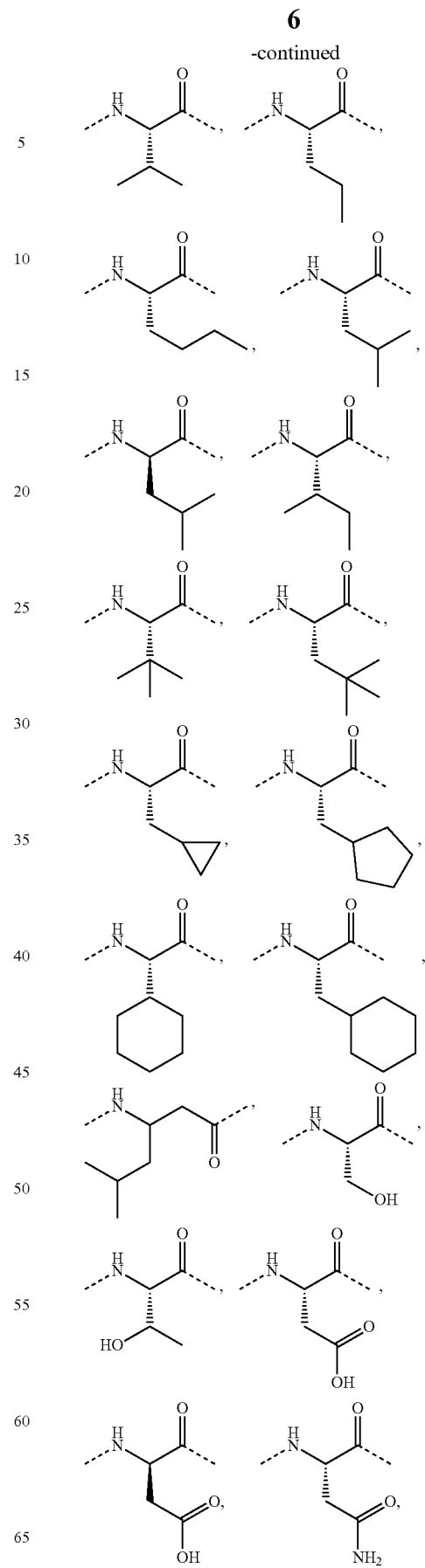

-continued
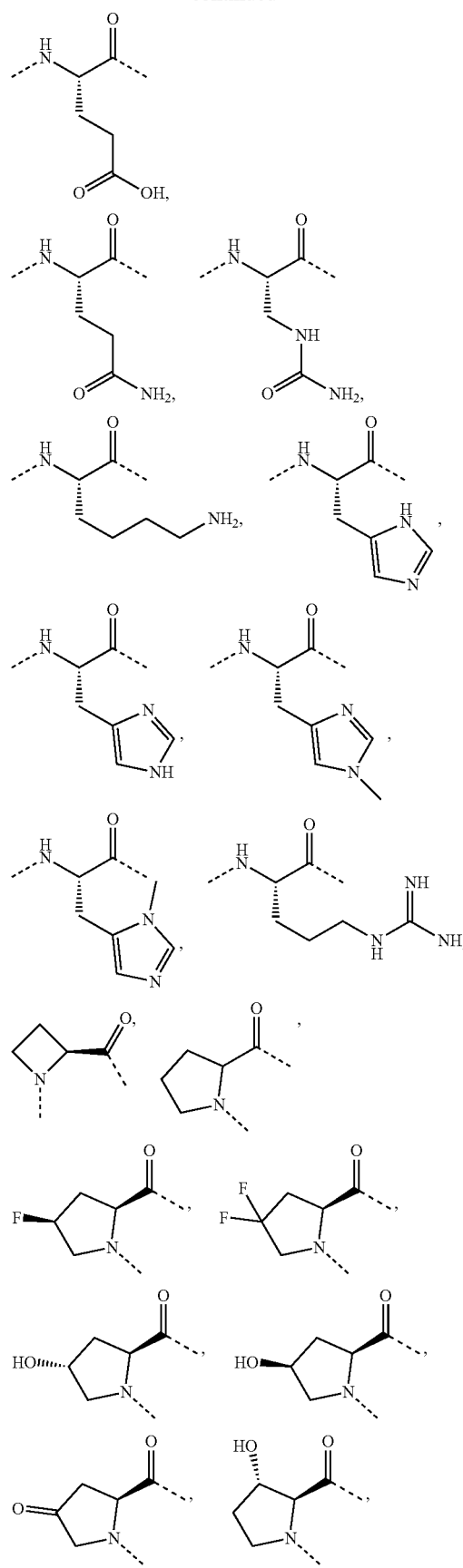
-continued
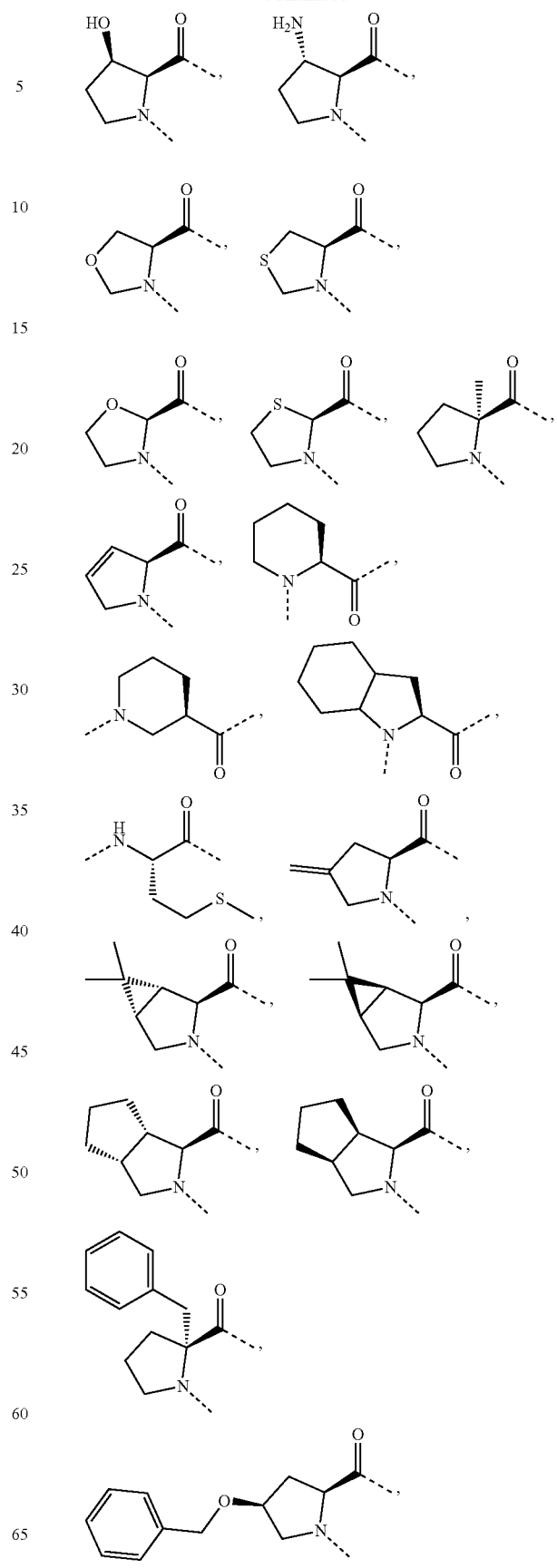

-continued
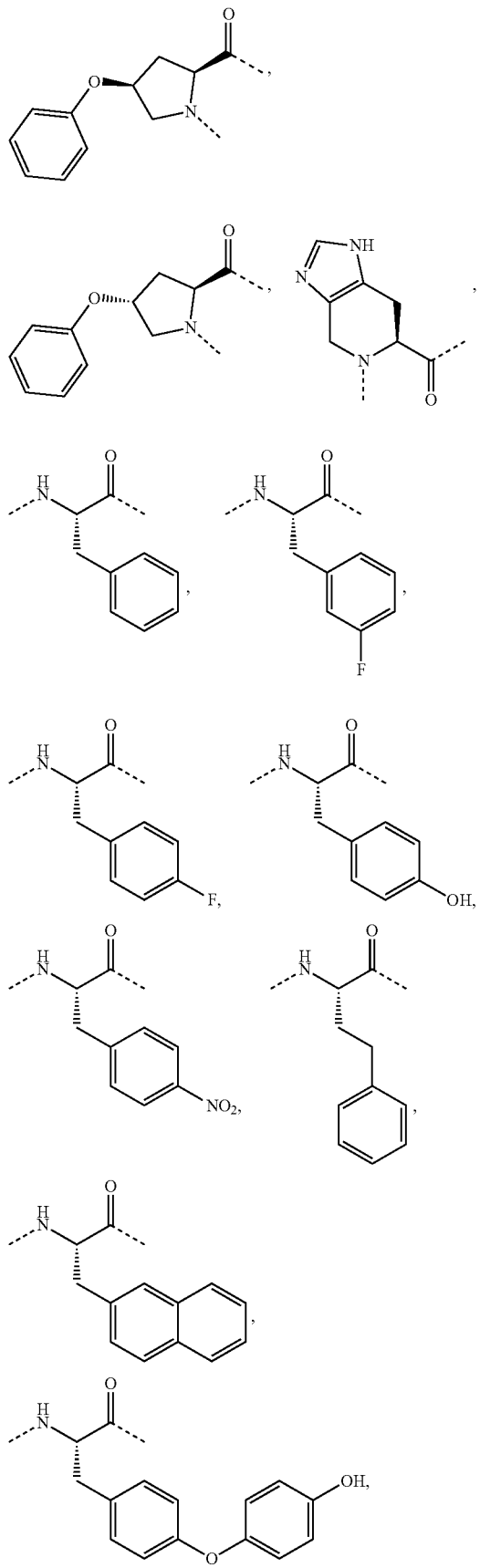
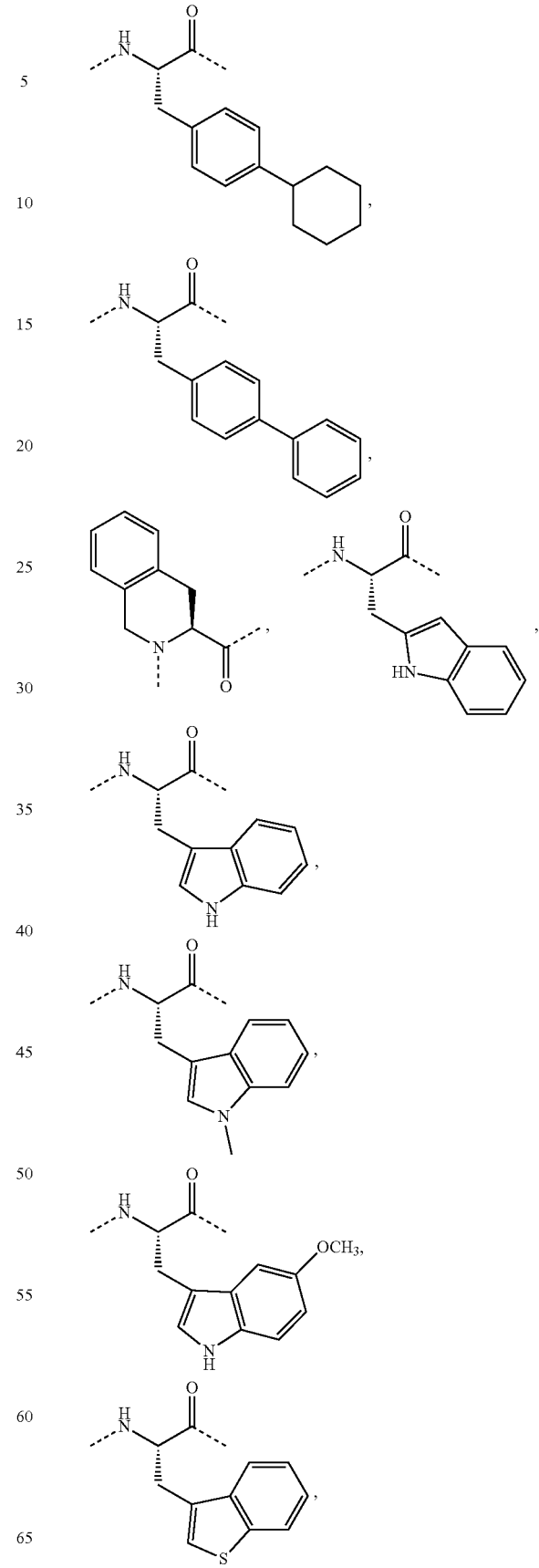

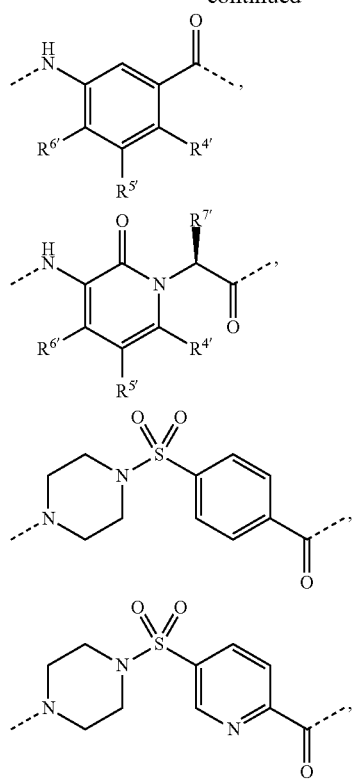
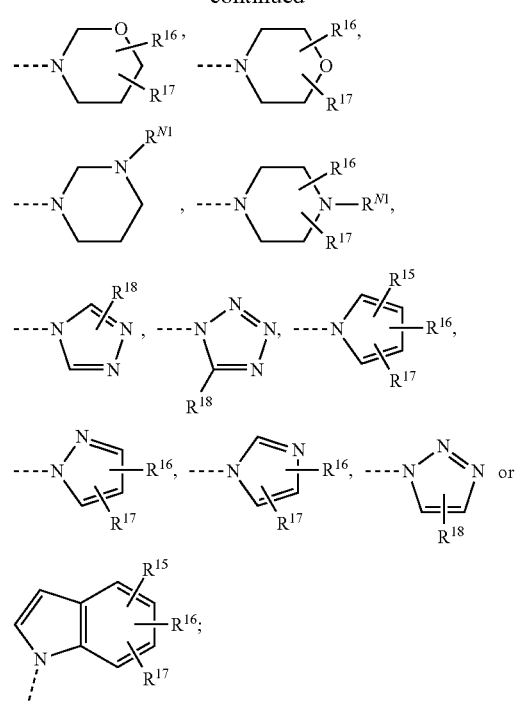
E represents: —OR$^{13}$, —NR$^{13}$R$^{14}$, —NHSO$_2$R$^{13}$, —O-L$_1$-R$^{13}$, —NH-L$_1$-O—R$^{13}$, —NH-L$_1$-NR$^{13}$R$^{14}$, —NHSO$_2$-L$_1$-R$^{13}$,
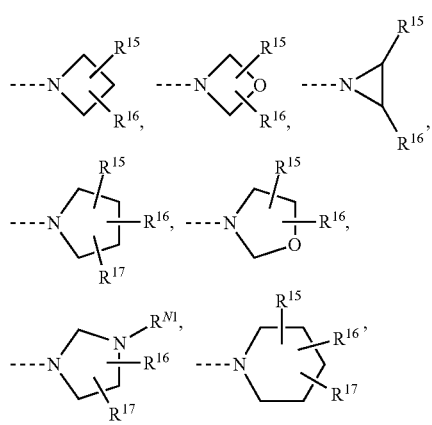
R$^{13}$ and R$^{14}$ represent independently of each other: —H, —CH$_3$, —CH$_2$CH$_3$, —C(CH$_3$)$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$,
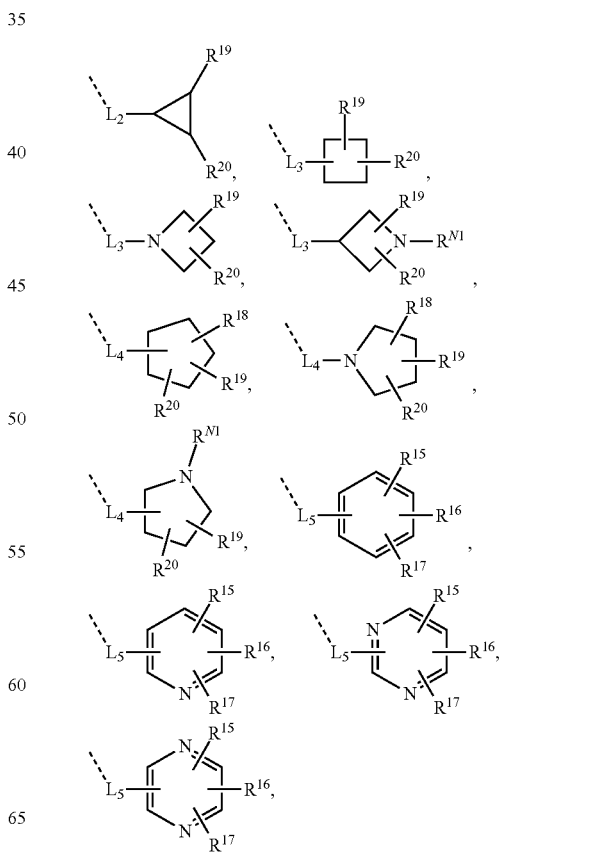

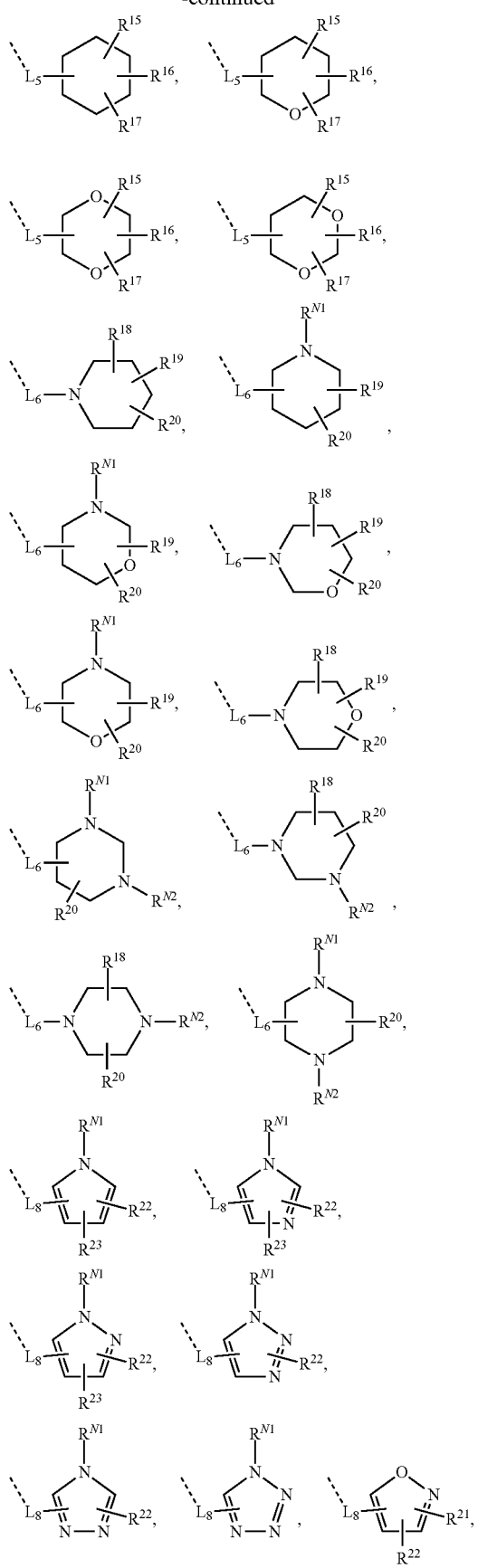

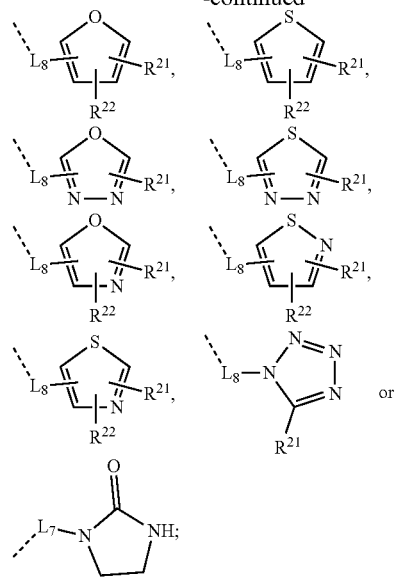

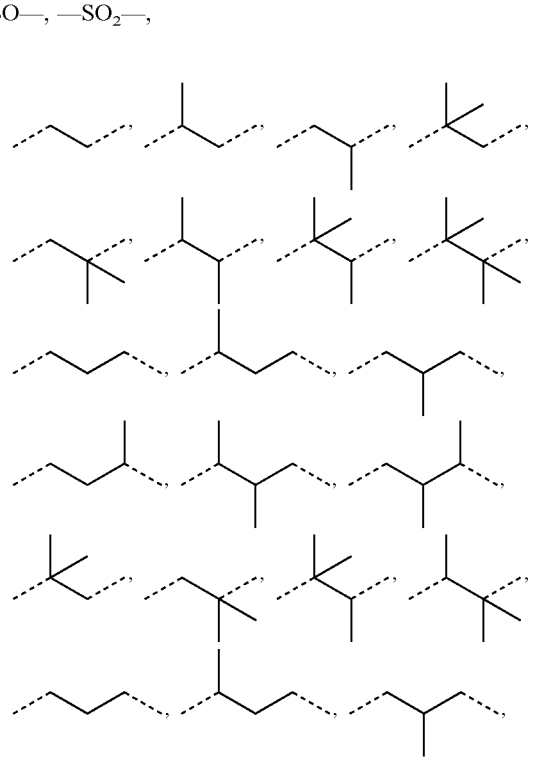

$R^N$, $R^{N1}$ and $R^{N2}$ represents independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, or —COOC(CH$_3$)$_3$;

$L^1$-$L^8$ represents independently of each other a covalent bond, —CH$_3$—, —CH(CH$_3$)—, —CH(CH$_3$)$_2$—, —CO—, —SO—, —SO$_2$—,

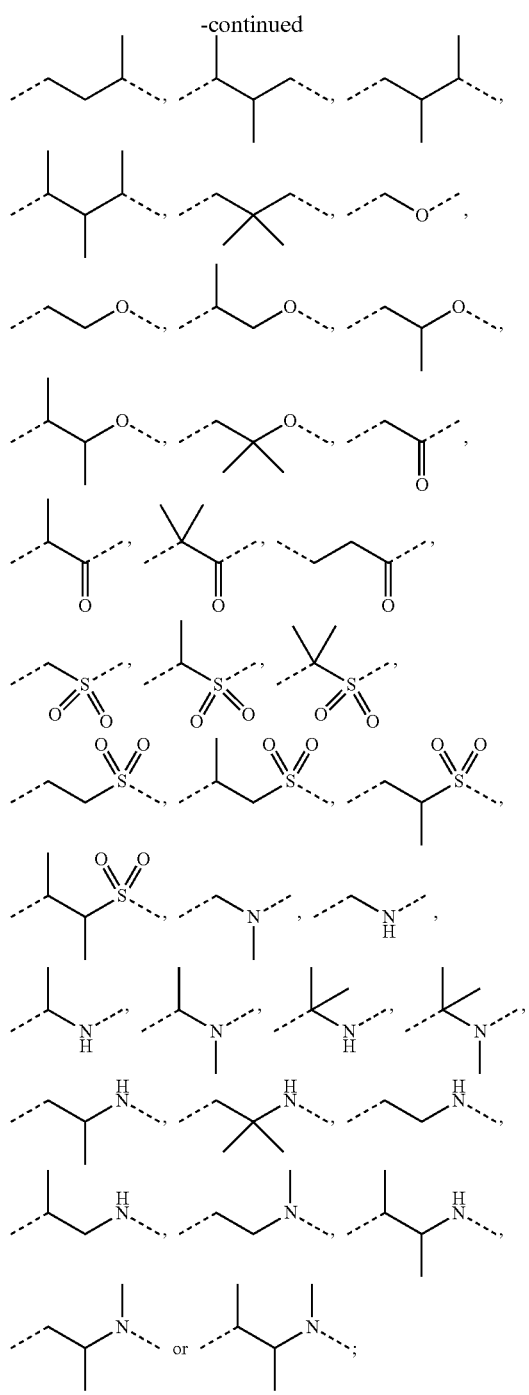

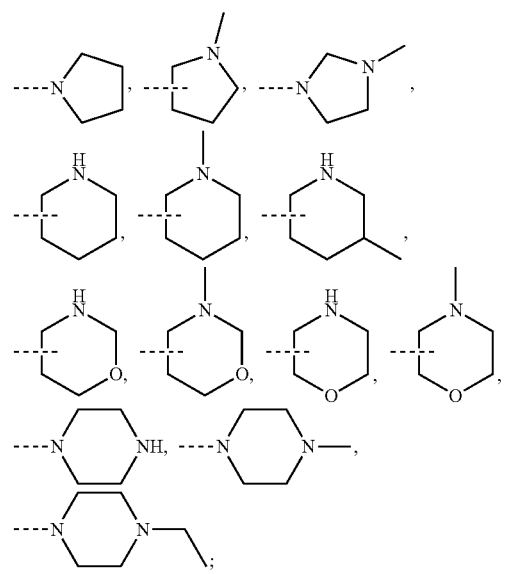

$R^5$—$R^{12}$, $R^{4'}$—$R^{7'}$, and $R^{15}$—$R^{23}$ represents independently of each other —H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C(CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH=CH$_2$, —CH$_2$—CH=CH$_2$, —C(CH$_3$)=CH$_2$, —CH=CH—CH$_3$, —C≡CH, —C≡C—CH$_3$, —CH$_2$—C≡CH, -Ph, —O-Ph, or —O—CH$_2$-Ph, or $R^7$ and $R^8$ or $R^8$ and $R^9$ form together one of the following ring moieties;

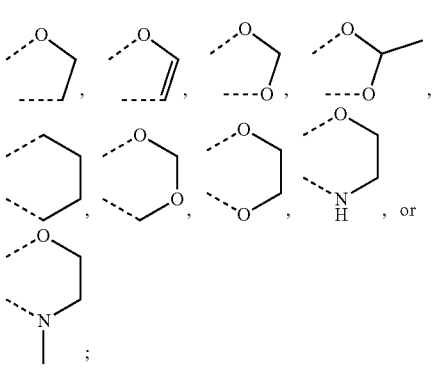

or E/Z-isomer, regiomer, diastereomer, enantiomer, a mixture of E/Z-isomers, a mixture of regiomers, a mixture of diastereomers, a mixture of enantiomers, prodrug, solvate, hydrate, or pharmaceutically acceptable salts thereof.

Surprisingly it was found that good factor XIII or FXIIIa inhibitors, both terms are used synonymously herein, have to be irreversible inhibitors with certain peptidic or peptidomimetic backbones. Reversible inhibitor have been proven to be less efficient in comparison to the irreversible inhibitors disclosed herein which in addition are very specific for FXIIIa and consequently show a minimum of side effects in case certain structural requirements are fulfilled. Further, irreversible acting inhibitors avoid the potential rebound of FXIII activity. One specific requirement is that the peptidic or peptidomimetic backbone has to have a certain length of at least 5 amino acids including amino acid derivatives and peptidomimetics as disclosed herein (cf. Ref. 6 and Ref. 7). Consequently, is $R^2=-A^1-A^2-A^3-E$ a pentapeptide results and with $R^2=-A^1-A^2-A^3-A^4-E$ a hexapeptide and with $R^2=-A^1-A^2-A^3-A^4-A^5-E$ a heptapeptide is obtained. Preferred are hexapeptides with $R^2=-A^1-A^2-A^3-A^4-E$ as well as heptapeptides with $-A^1-A^2-A^3-A^4-A^3-E$. The amino acid bearing the warhead is the first amino acid, second is the amino acid with substituent $R^1$, third amino acid is $A^1$ and so on. Longer peptides with more than 7 amino acids including amino acid derivatives and peptidomimetics are still good to moderate FXIIIa inhibitors in case only the inhibitory activity is considered, but of less therapeutical value because the inventors found that these longer peptides are degraded in blood within minutes and consequently due not have a sufficient half-life or stability in blood in order to become a therapeutically useful FXIIIa inhibitor (cf. Ref. 17 and Ref. 18). Consequently, the FXIIIa inhibitors disclosed herein are pentapeptides, hexapeptides and heptapeptides containing $A^1$ as being a conformational constraint amino acid, i.e. (S)-proline (L-proline) or a cyclic proline derivative as disclosed herein having the same configuration, i.e. L-proline derivative and $A^2$ as amino acid with an alkyl or cycloalkyl side chain. In addition to this required minimum length of the peptidic or peptidomimetic backbone the two amino acids attached c-terminal to the amino acid with the Michael system are very important. In general formula (I) the amino acid attached c-terminal to the Michael system bearing amino acid is drawn as

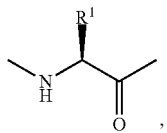

wherein the substituent $R^1$ is limited to a small group of alkyl and cycloalkyl residues and methionine. Ionic or polar groups (such as side chains of Glu or Gln) or aromatic groups or quite bulky groups with more than 7, preferably with more than 6 carbon atoms are found to decrease the inhibitor activity drastically (cf. Ref. 11, Ref. 20 and Ref. 21). Also the stereochemistry of the substituent $R^1$ is important as shown in general formula (I). Especially important is the amino acid connected to the amino acid with $R^1$ which is the second amino acid C-terminal to the amino acid with the Michael acceptor system (warhead). This amino acid or amino acid derivative is referred to herein as $A^1$. $A^1$ must be a cyclic amino acid, namely a proline or proline derivative as disclosed herein. The stereochemistry of $A^1$ is also very important and must be (S) or L in case of proline and in case of a proline derivative the same spatial orientation as (S)-proline is required which is most preferably the L configuration (cf. Ref. 4). Although the stereogenic center of the piperidine ring of $A^1$ in reference example 4 has (S) configuration, it has in comparison to the proline moiety the other spatial orientation and it was found to be inactive as factor XIII inhibitor. Moreover stereogenic center in the proline moiety $A^1$ must not have a further substituent, i.e. one hydrogen atom must be present at the stereogenic center of the proline moiety (cf. Ref. 5). In the reference example 5 a methyl group is present at the stereogenic center and that makes the compound completely inactive as factor XIII inhibitor. Moreover it has to be stressed that a pyridinone moiety is not a proline derivative and a pyridinone moiety as $A^1$ leads also to compounds inactive as factor XIII inhibitors (cf. Ref. 1-Ref. 3). Concerning $A^1$ the configuration, which is the L-configuration is very important and the fact that the chiral center must be a tertiary carbon atom (i.e. no fourth substituent). Moreover, to the N-terminus a cyclic group should be attached through a carbonyl function forming an amide bond. No further amino acid except an (oxo)-proline should be attached to the N-terminus. The N-terminal cyclic group is preferably six-membered cyclic group, more preferably an aromatic group, more preferably an aromatic six-membered carbocyclic or N-heterocyclic group such as phenyl and pyridyl. Therefore there is a tight structural relationship (SAR: Structure-Activity-Relationship) between the inhibitory activity in regard to FXIIIa and the structural features of the inhibitors disclosed herein. Such a SAR was not evident from the state of the art and is somehow surprising.

Preferably, the present invention relates to a compound of the general formula (I), wherein $R^1$ represents $-C(CH_3)_3$, -cyclo-$C_3H_5$, -cyclo-$C_4H_7$, -cyclo-$C_5H_9$, -cyclo-$C_6H_{11}$, $-CH_2-CH(CH_3)_2$, $-CH_2CH_2CH_2CH_3$, $-CH_2CH_2CH_2CH_2CH_3$, $-CH_2CH_2CH_2CH_2CH_2CH_3$, $-CH_2-C(CH_3)_3$, $-CH_2CH_2SCH_3$, $-CH_2$-cyclo-$C_3H_5$, $-CH_2$-cyclo-$C_4H_7$, $-CH_2$-cyclo-$C_5H_9$ or $-CH_2$-cyclo-$C_6H_{11}$;

$R^2$ represents -$A^1$-$A^2$-$A^3$-E, -$A^1$-$A^2$-$A^3$-$A^4$-E or -$A^1$-$A^2$-$A^3$-$A^4$-$A^5$-E;

$R^3$ represents

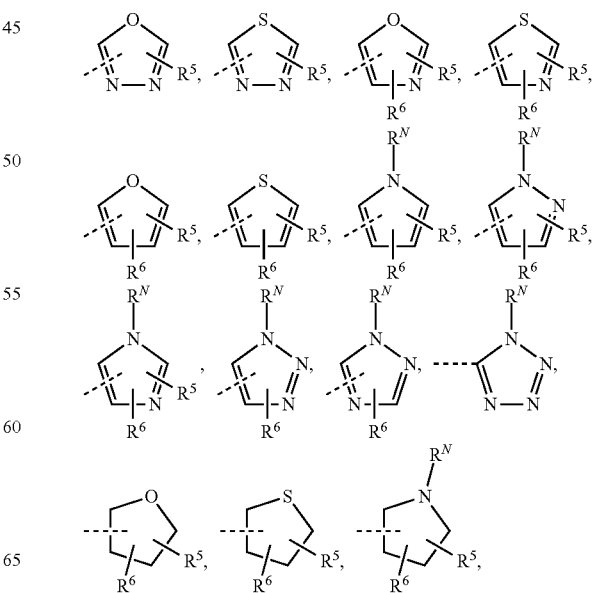

19
-continued
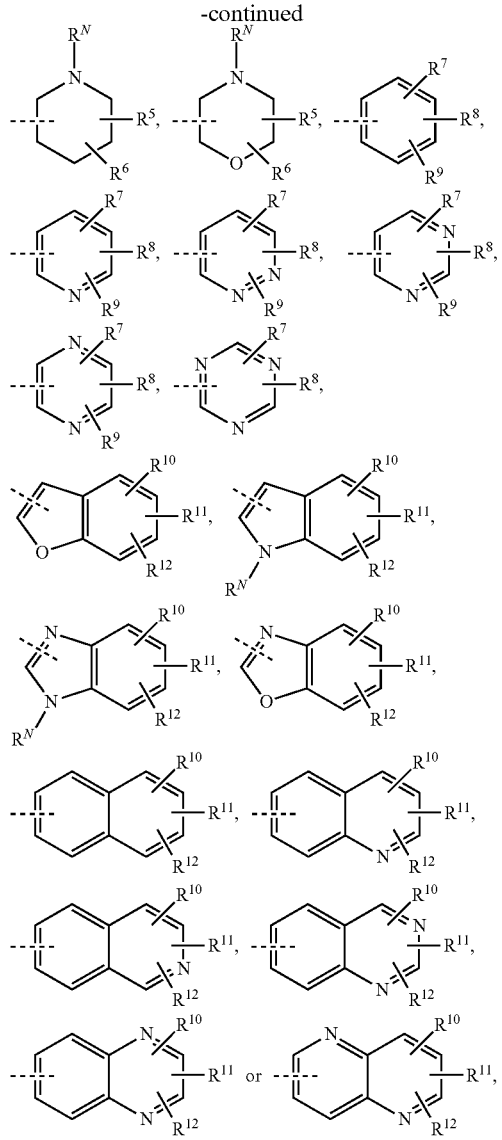
$R^4$ represents —OR*, —NH$_2$, —NHR# or —NR*R#;
R* and R# represent independently of each other —CH$_3$, —CH$_2$CH$_3$, —CH(CH$_3$)$_2$, —CH$_2$CH$_2$CH$_3$, —CH$_2$CH(CH$_3$)$_2$, —C(CH$_3$)$_3$, -cyclo-C$_3$H$_5$, -cyclo-C$_4$H$_7$, -cyclo-C$_5$H$_9$, -cyclo-C$_6$H$_{11}$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, —CH$_2$-Ph, —CH$_2$OCH$_3$, —CH$_2$OCH$_2$CH$_3$, —CH$_2$CH$_2$OCH$_3$;
A$^1$ represents
20
-continued
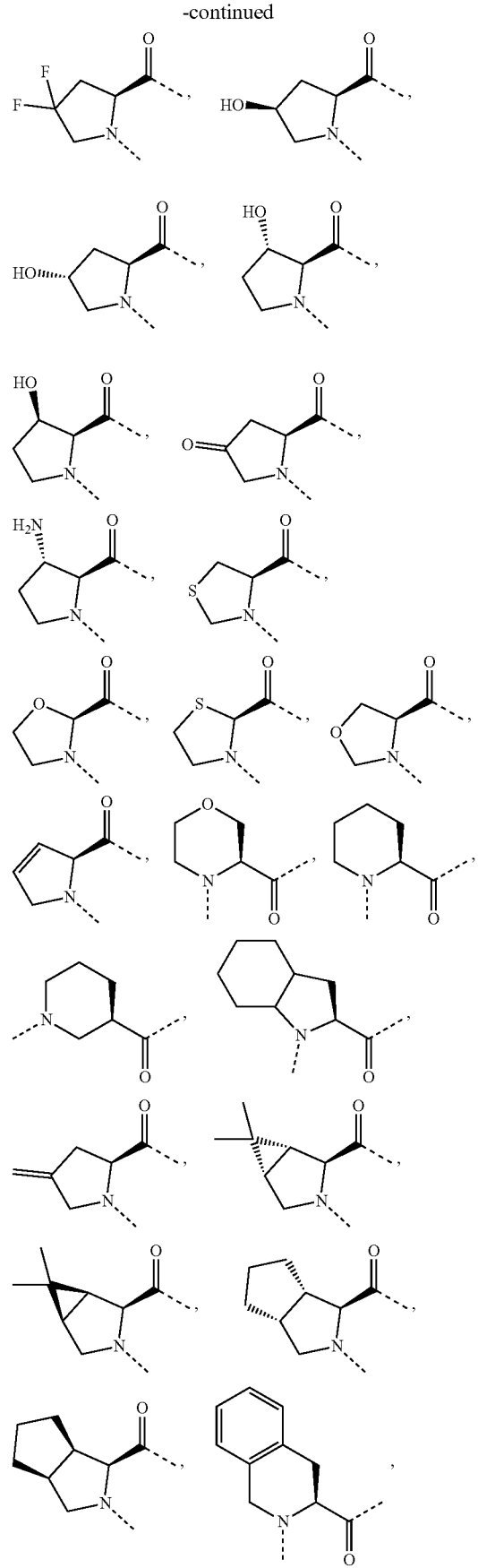

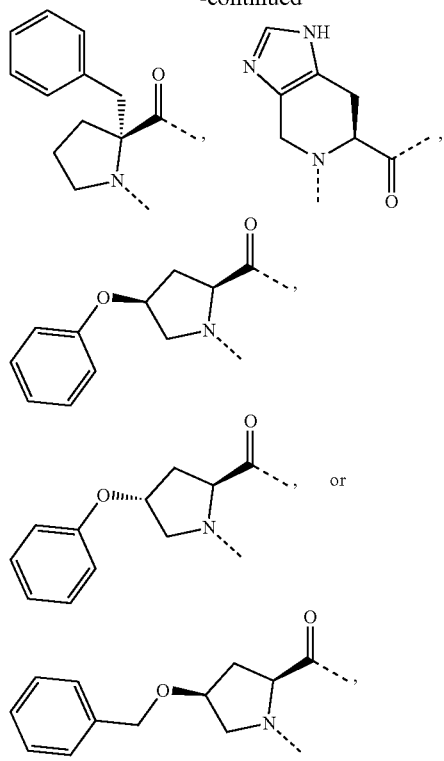
$A^2$-$A^9$ represent independently of each other
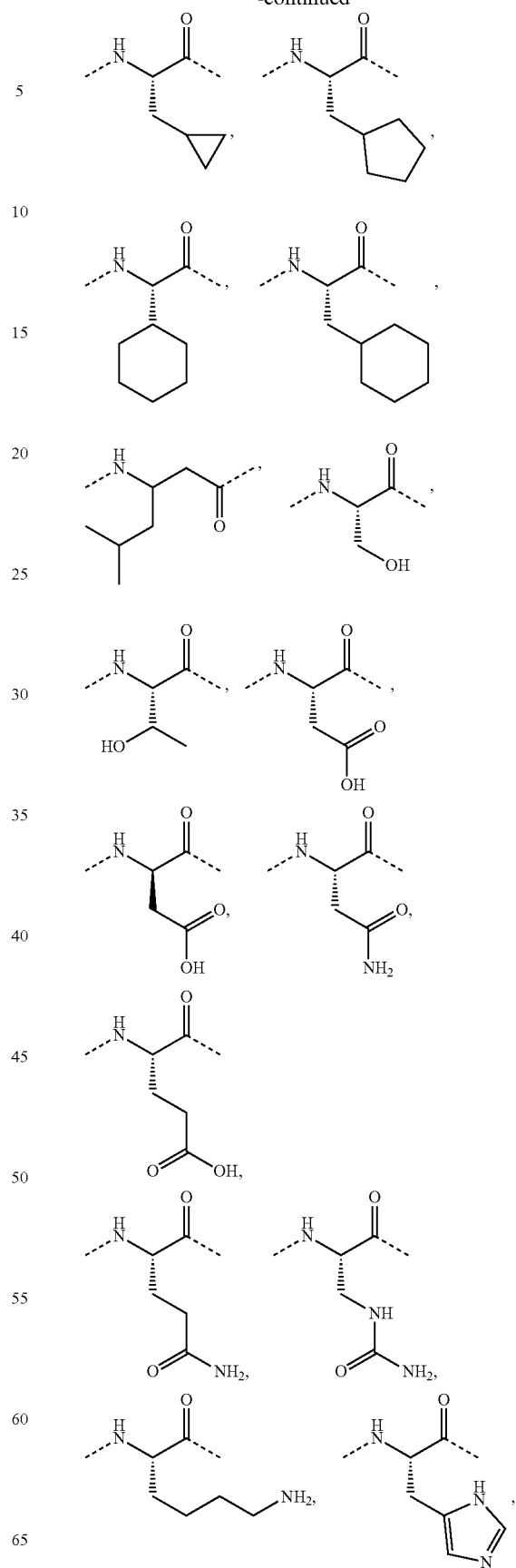

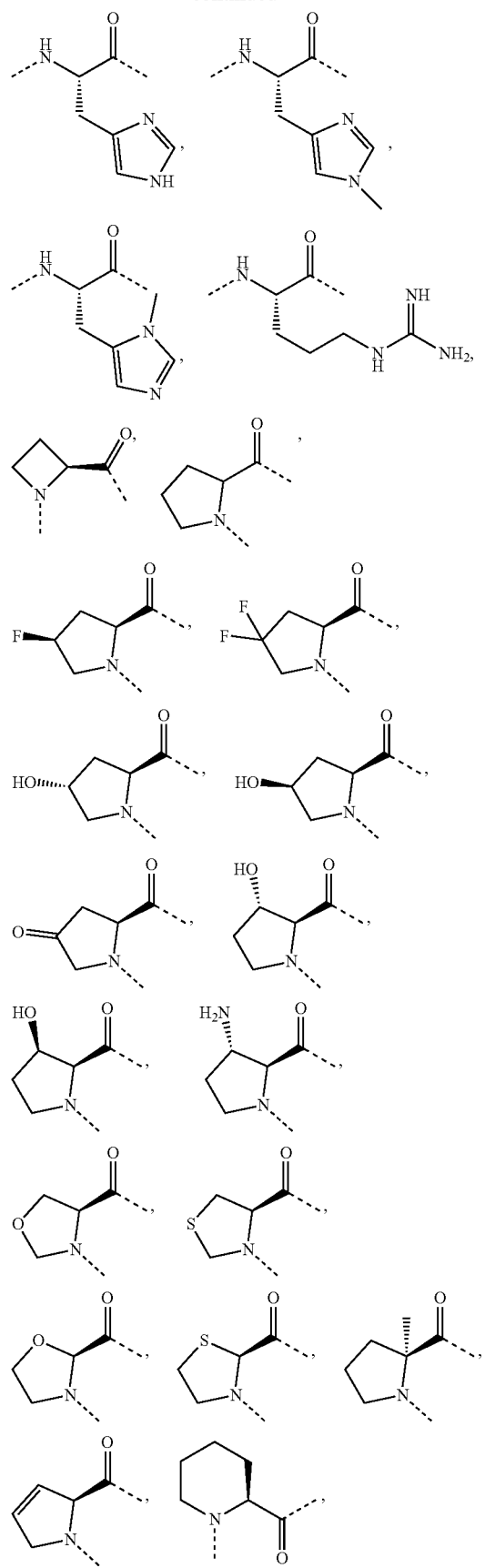
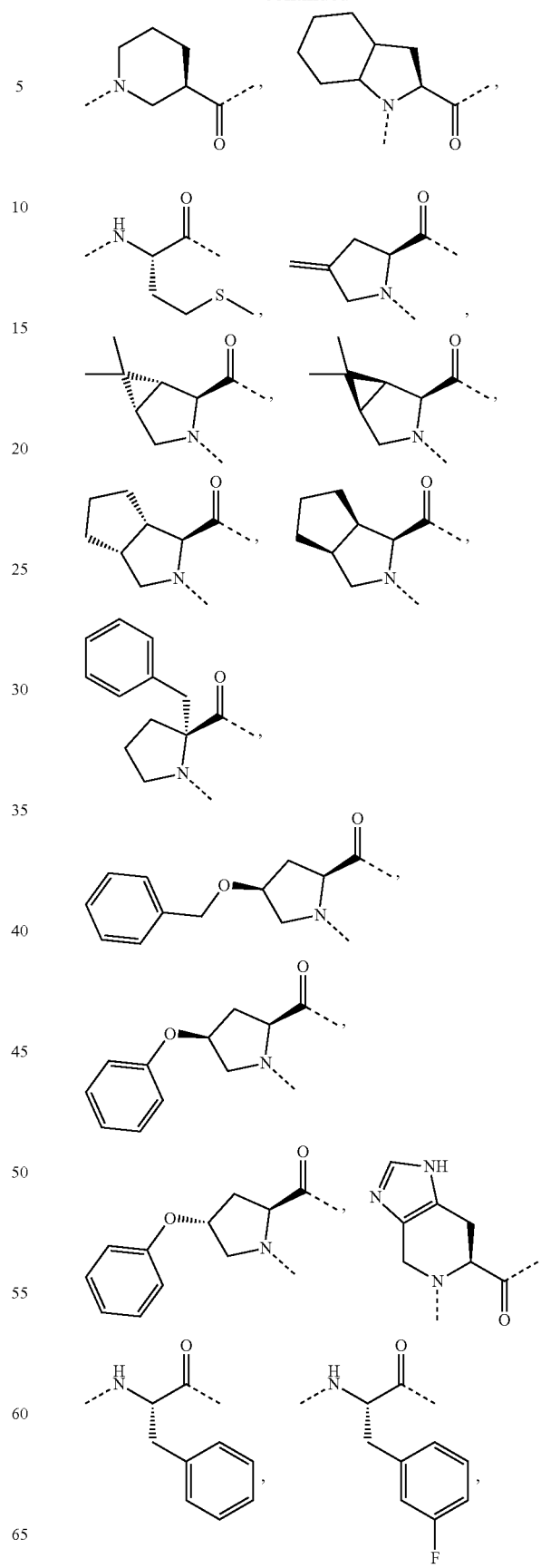

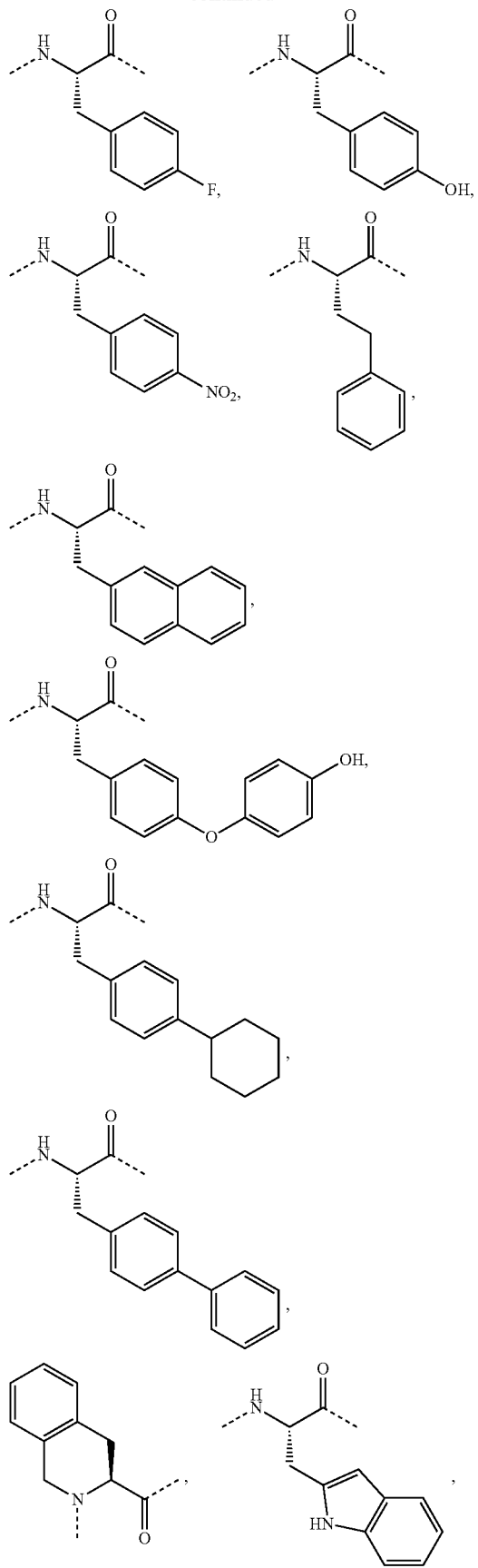
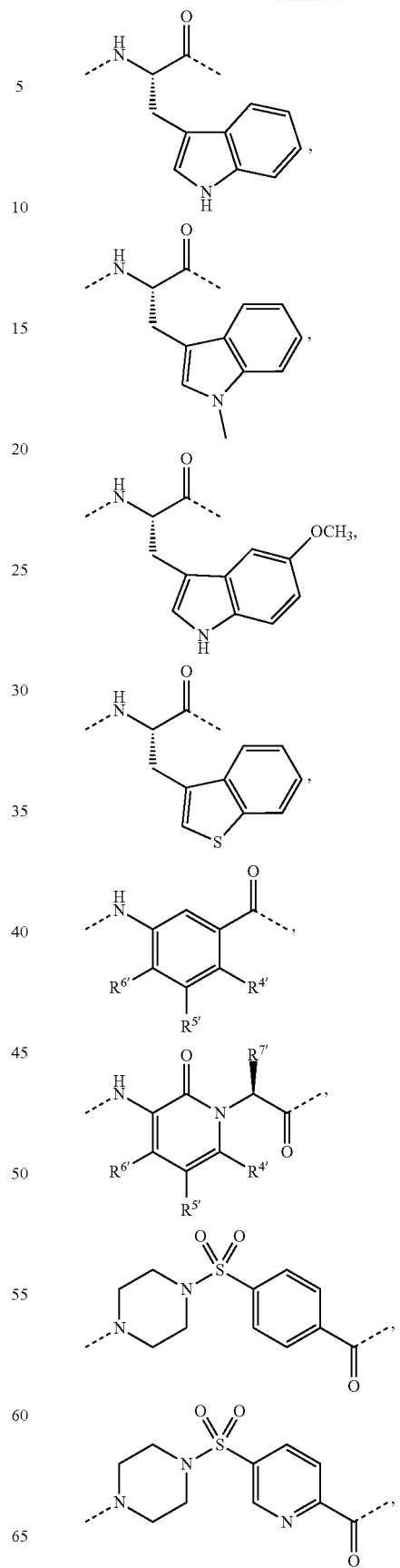

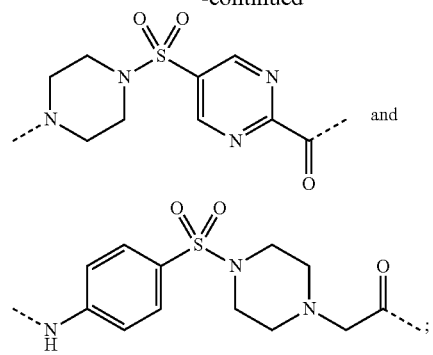
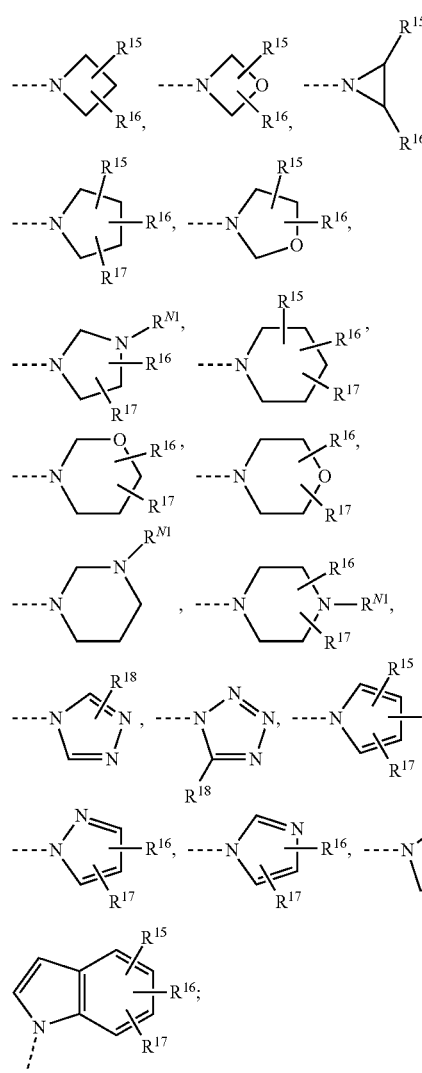
E represents: —OR$^{13}$, —NR$^{13}$R$^{14}$, —NHSO$_2$R$^{13}$, —O-L$_1$-R$^{13}$, —O-L$_1$-O—R$^{13}$, —NH-L$_1$-O—R$^{13}$, —NH-L$_1$-NR$^{13}$R$^{14}$, —NHSO$_2$-L$_1$-R$^{13}$,
R$^{13}$ and R$^{14}$ represent independently of each other: —H, —CH$_3$, —CH$_2$CH$_3$, —C(CH$_3$)$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$,
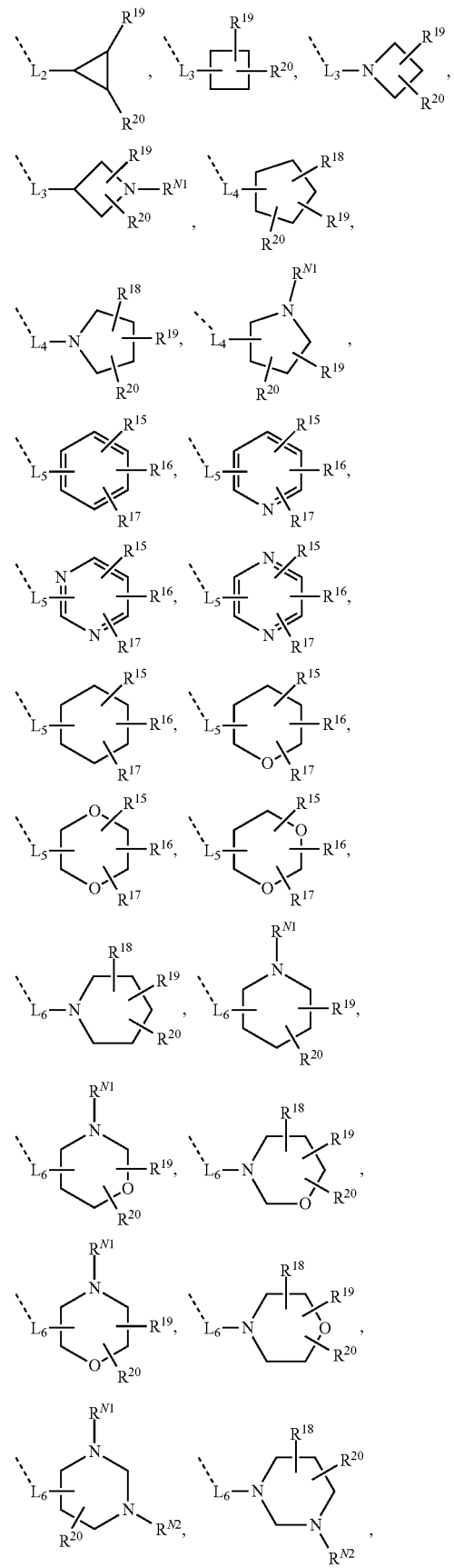

29

-continued

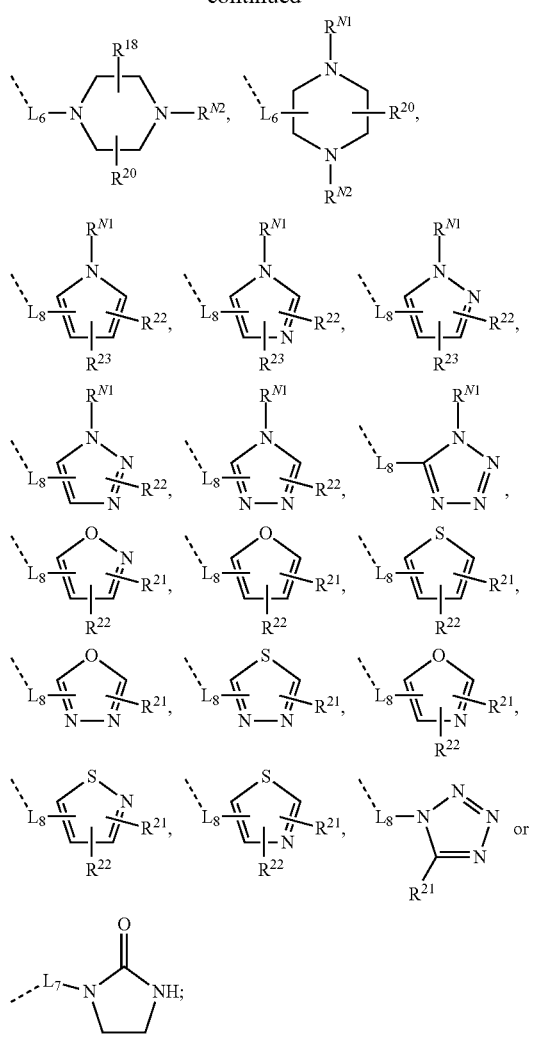

$R^N$, $R^{N1}$ and $R^{N2}$ represent —H;

$L^1$-$L^8$ represents independently of each other a covalent bond, —CH$_2$—, —CH(CH$_3$), —CH(CH$_3$)$_2$—,

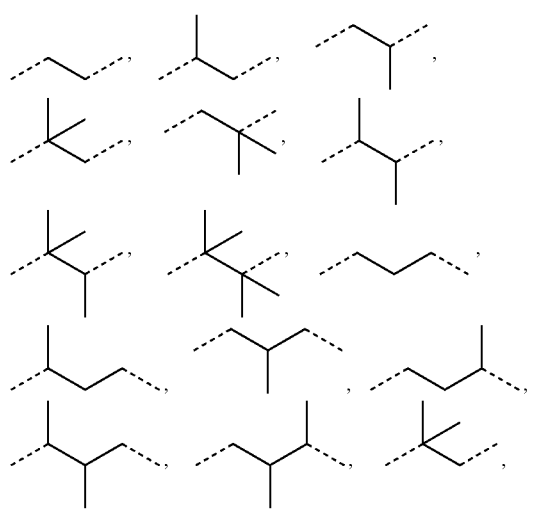

30

-continued

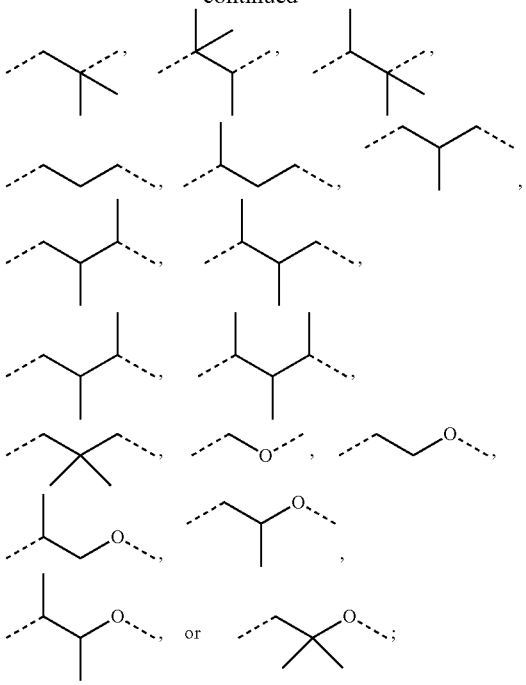

$R^{4'}$, $R^{5'}$, $R^{6'}$ and $R^{7'}$ represent —H;

$R^5$—$R^{12}$, and $R^{15}$—$R^{23}$ represents independently of each other —H, —F, —Cl, —Br, —OH, —NO$_2$, —CH$_3$, —C$_2$H$_5$, —C$_3$H$_7$, —CH(CH$_3$)$_2$, —C$_4$H$_9$, —CH$_2$—CH(CH$_3$)$_2$, —C(CH$_3$)$_3$, -cyclo-C$_3$H$_5$, —CH$_2$-cyclo-C$_3$H$_5$, —OCH$_3$, —OC$_2$H$_5$, —OC$_3$H$_7$, —OCH(CH$_3$)$_2$, —OC(CH$_3$)$_3$, —O-cyclo-C$_3$H$_5$, —OCH$_2$-cyclo-C$_3$H$_5$, —O—C$_2$H$_4$-cyclo-C$_3$H$_5$, —COOH, —COOCH$_3$, —COOC$_2$H$_5$, —COOC$_3$H$_7$, —COOCH(CH$_3$)$_2$, —COOC(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, or —N(C$_3$H$_7$)$_2$—CONH$_2$;

as well as E/Z-isomer, diastereomer, enantiomer, a mixture of E/Z-isomers, a mixture of diastereomers, a mixture of enantiomers, prodrugs, solvates, hydrates, or pharmaceutically acceptable salts thereof.

For all general formula disclosed herein unless otherwise defined, the amino acid residues $A^2$-$A^5$ preferably represent independently of each other

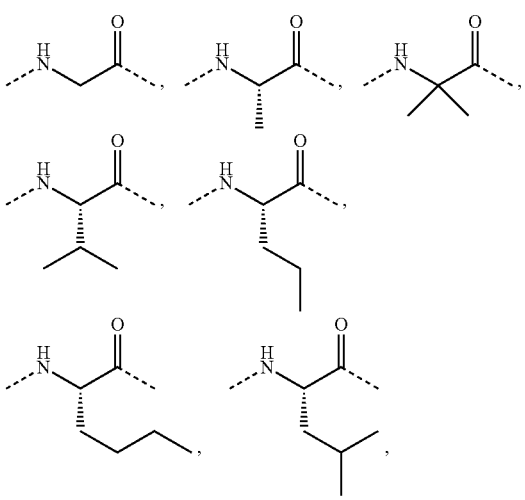

31
-continued
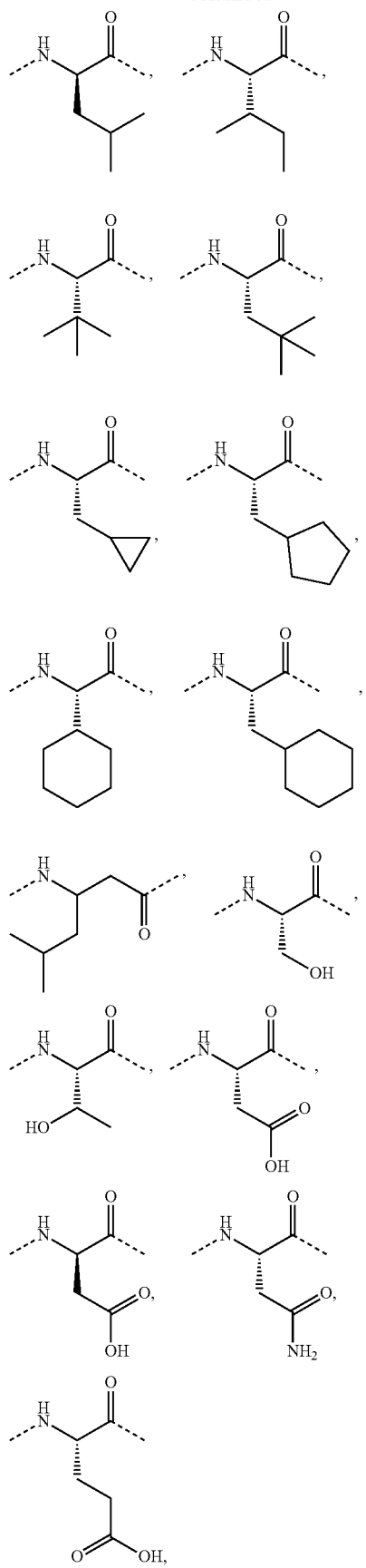
32
-continued
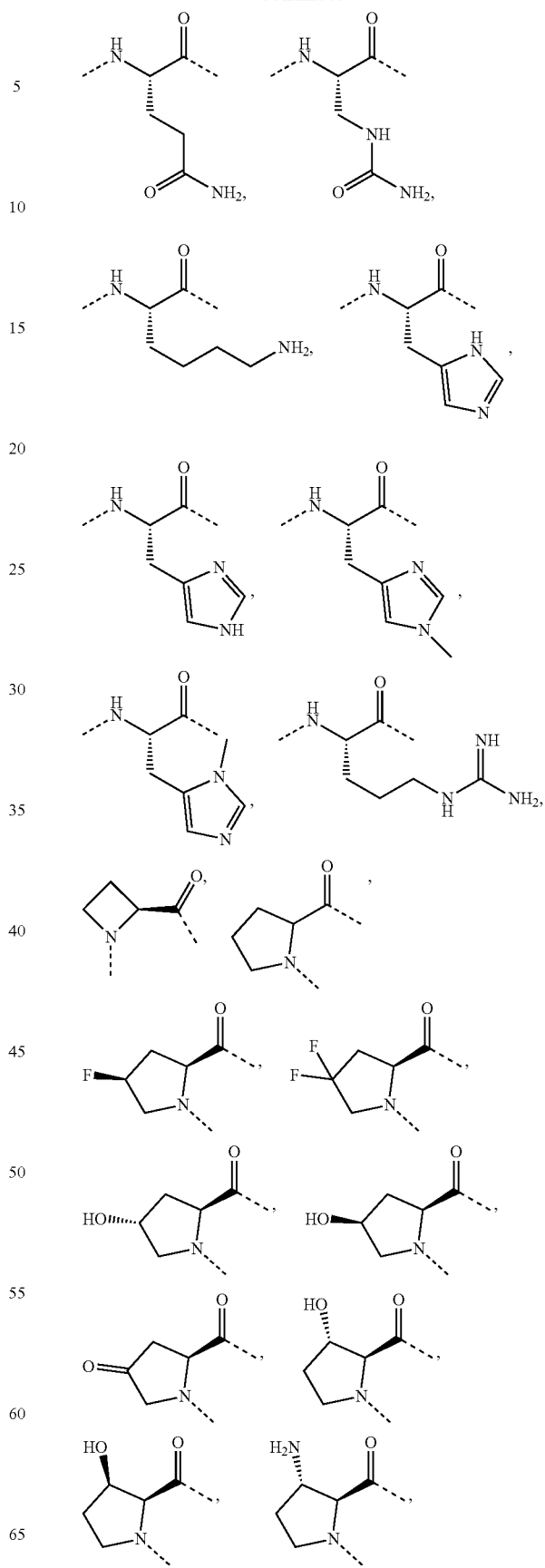

33
-continued
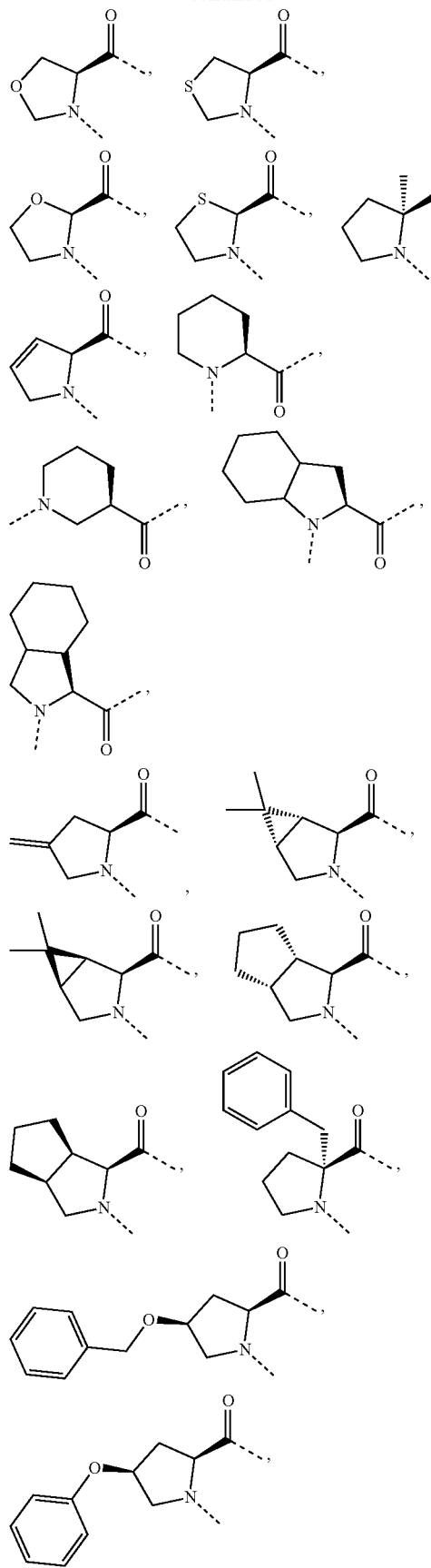
34
-continued
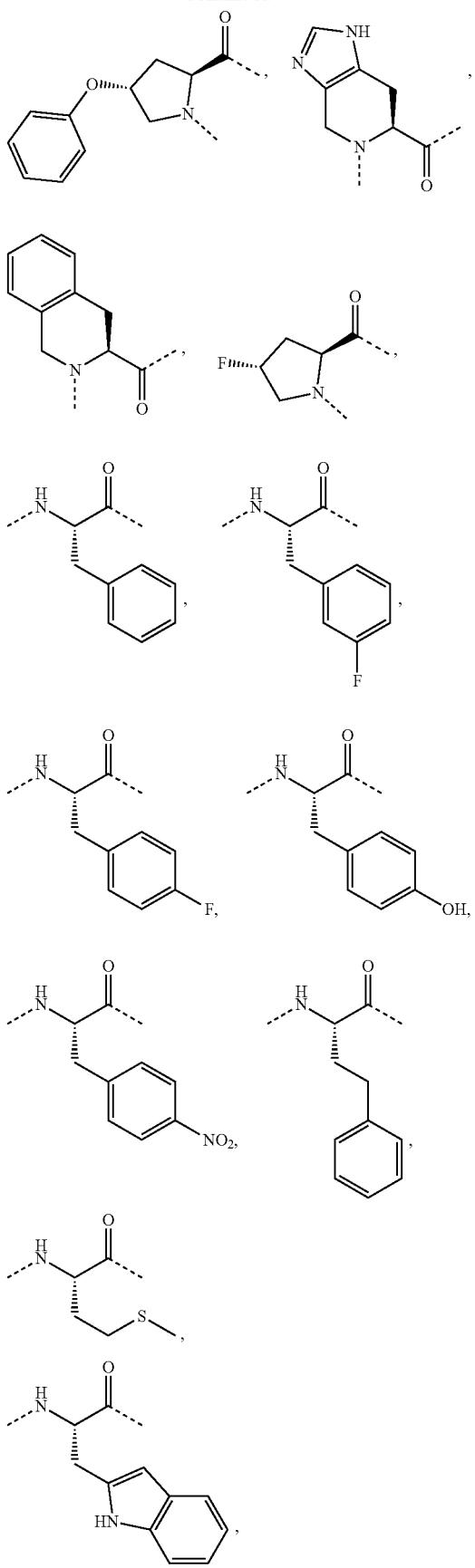

-continued

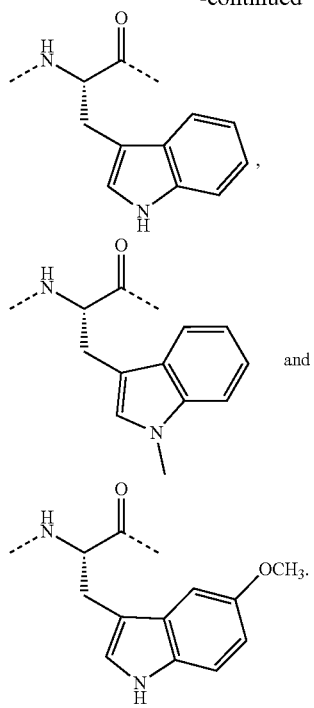

and

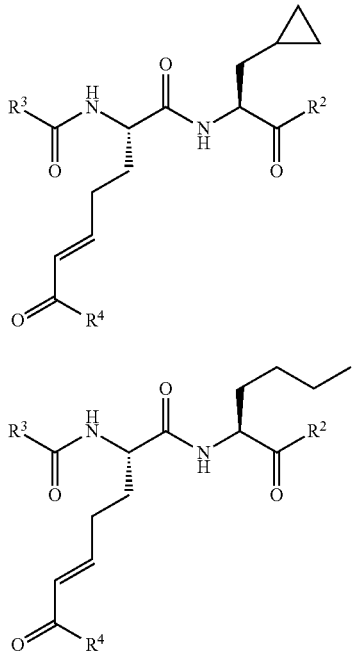

-continued wherein $R^2$, $R^3$, and $R^4$ have the same meanings as defined in formula (I).

Moreover, in any general formula disclosed herein and especially in any one of the formulae (I), and (II-1)-(II-3), $A^1$ is preferably selected from The oligopeptide residues -$A^1$-$A^*$-$A^3$-E, -$A^1$-$A^2$-$A^3$-$A^4$-E and -$A^1$-$A^2$-$A^3$-$A^4$-$A^5$-E represent a tri-, tetra- and pentapeptide, wherein the amino acids $A^1$, $A^2$, $A^3$, $A^4$, and $A^9$ are connected through an amide bond to each other and the N-terminus of the amino acid $A^1$ is attached to the C-terminus of the amino acid bearing the $R^1$ side chain which is next to the amino acid bearing the Michael system. Therefore, the direction the amino acids are attached to each other is well defined.

Preferably, in any general formula disclosed herein, $R^1$ represents —C(CH$_3$)$_3$, -cyclo-C$_3$H$_5$, -cyclo-C$_4$H$_7$, -cyclo-C$_5$H$_9$, -cyclo-C$_6$H$_{11}$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$—C(CH$_3$)$_3$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, or —CH$_2$CH$_2$SCH$_3$; more preferably, $R^1$ represents in any general formula disclosed herein —C(CH$_3$)$_3$, -cyclo-C$_3$H$_5$, —CH$_2$CH$_2$CH$_2$CH$_3$, —CH$_2$—C(CH$_3$)$_3$, —CH$_2$CH$_2$SCH$_3$, or —CH$_2$-cyclo-C$_3$H$_5$; and most preferably $R^1$ represents —C(CH$_3$)$_3$, —CH$_2$CH$_2$CH$_2$CH$_3$, —CH$_2$CH$_2$SCH$_3$, or —CH$_2$-cyclo-C$_3$H$_5$.

Therefore, preferred are compounds of any one of the formulae (II-1) to (II-3):

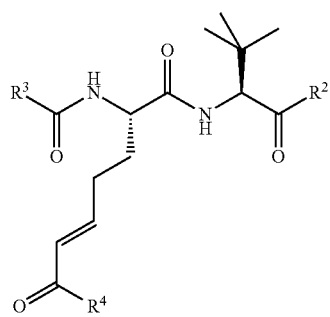

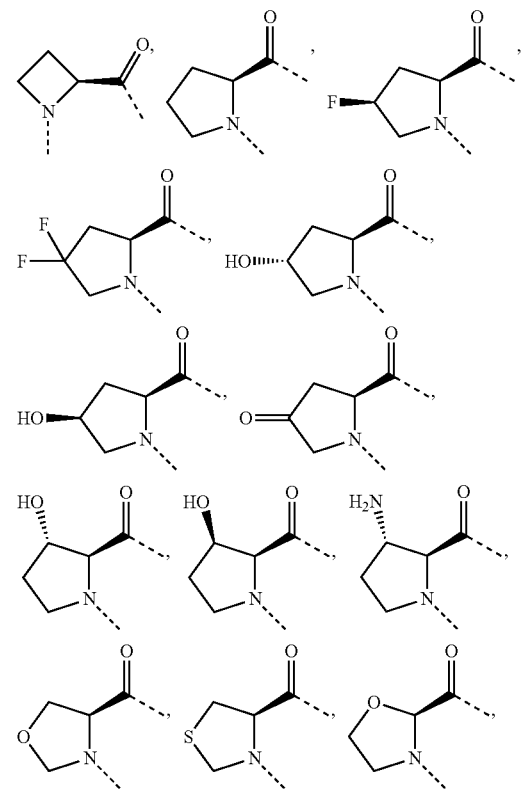

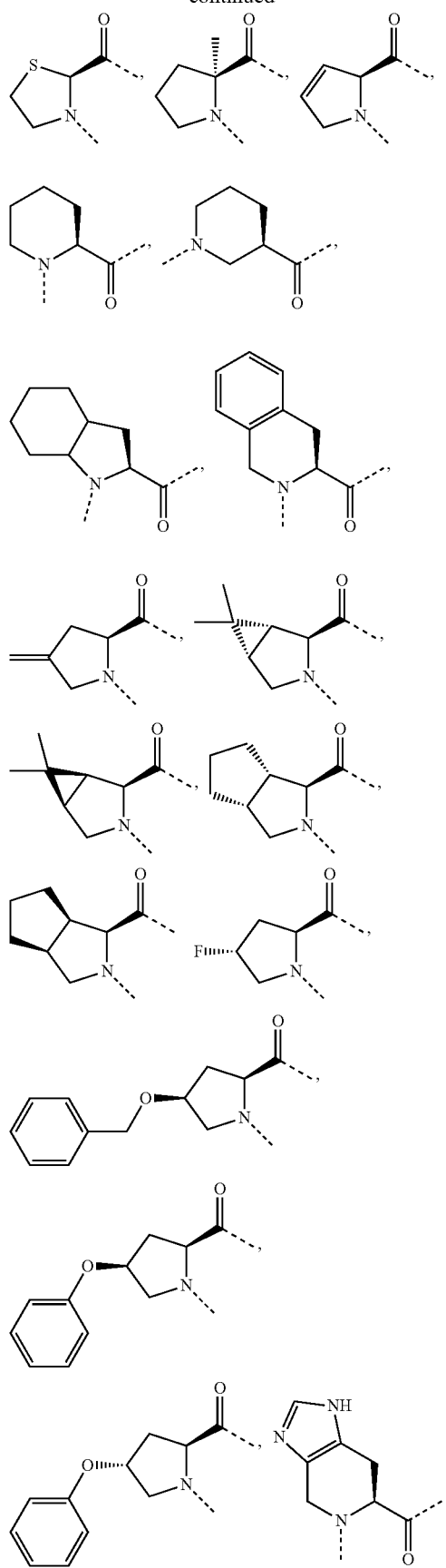
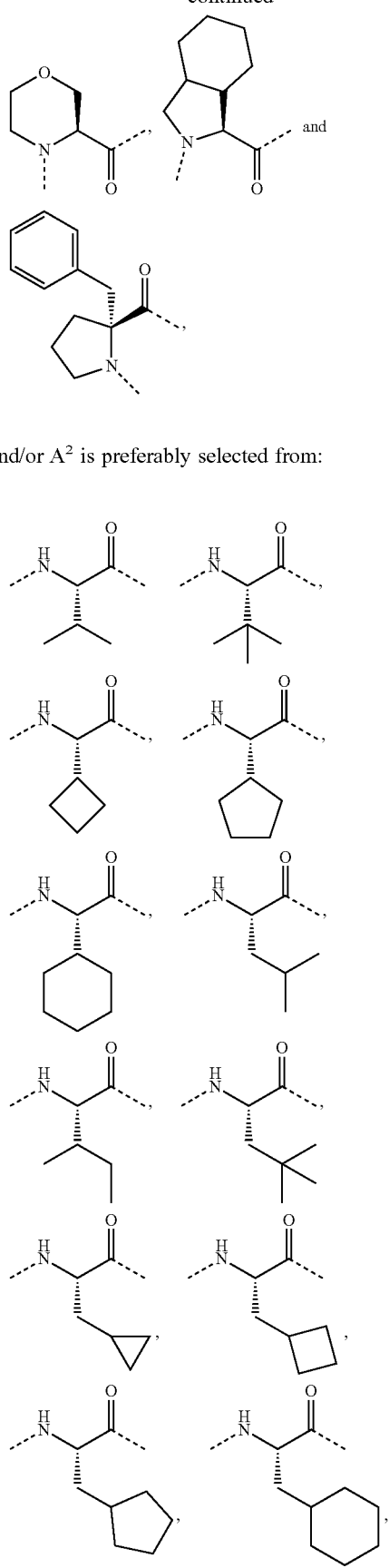
and/or $A^2$ is preferably selected from:

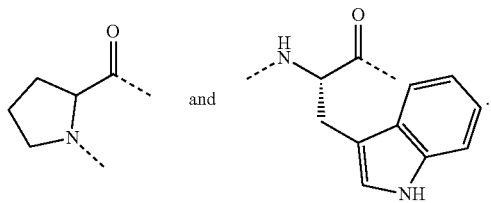
More preferably, in any general formula disclosed herein and especially in any one of the formulae (I), and (II-1)-(II-3), $A^1$ represents:
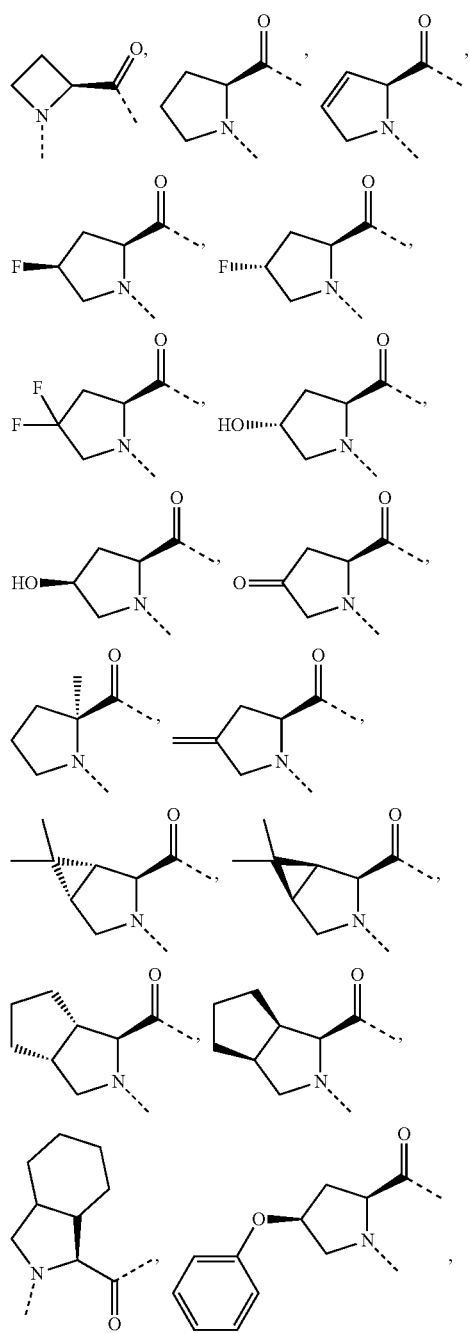
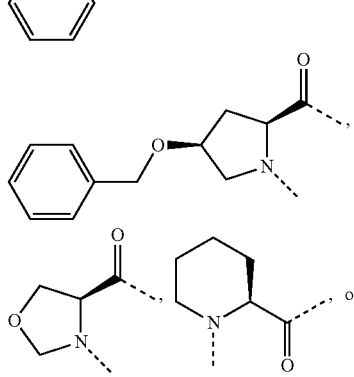
More preferably, in any general formula disclosed herein and especially in any one of the formulae (I), and (II-1)-(II-3), $A^2$ represents
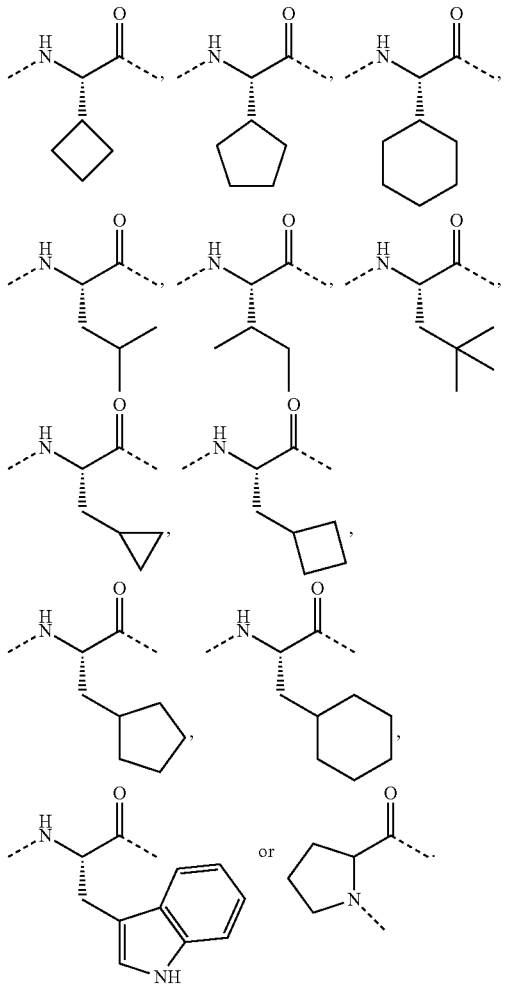

and most preferably A² represents
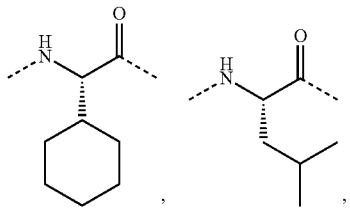,
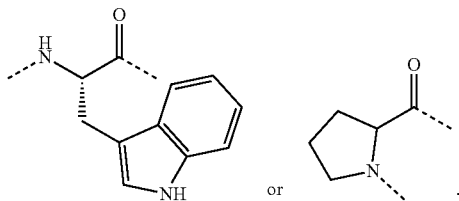 or .
Also preferred is that in any general formula disclosed herein and especially in the formulae (I), (II-1)-(II-3) the residue -A¹-A²- represents
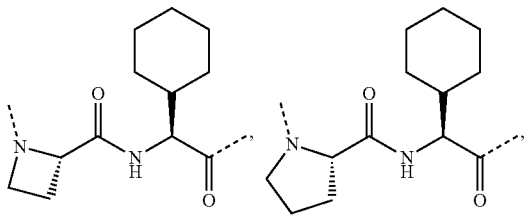
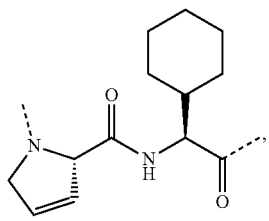
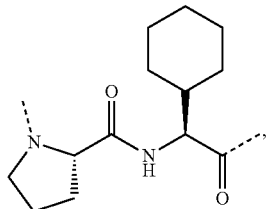
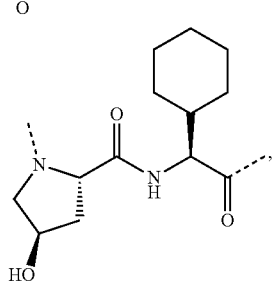
-continued
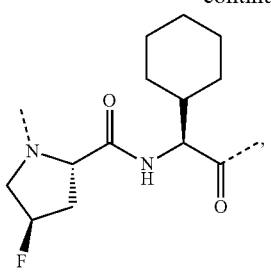
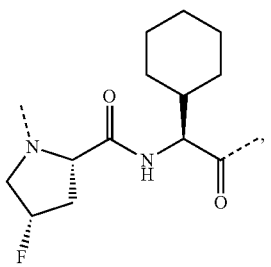
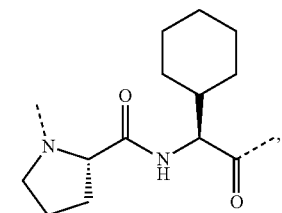
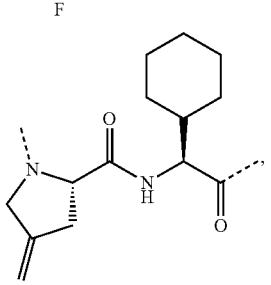
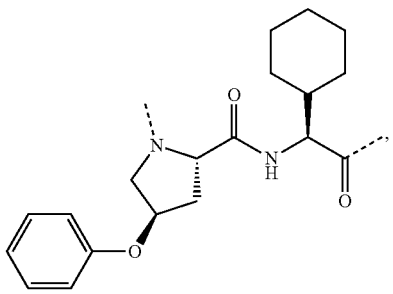
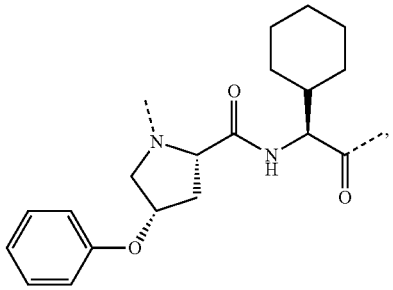

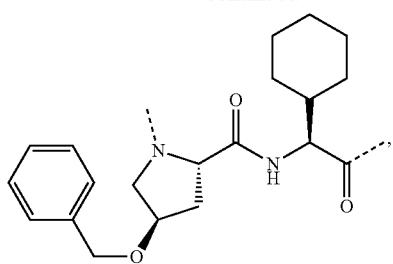
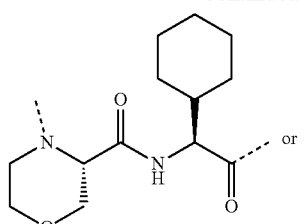
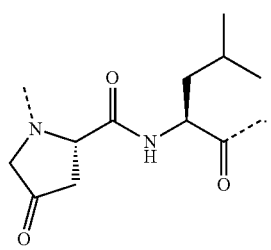
Preferably, in any general formula disclosed herein and especially in any one of the formulae (I), and (II-1)-(II-3), $A^3$ represents
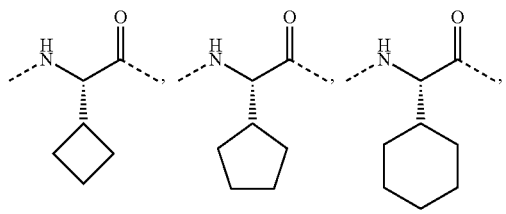
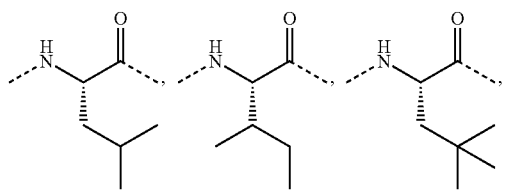
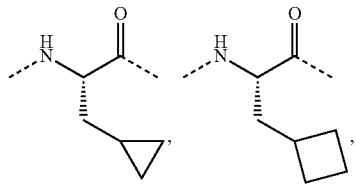
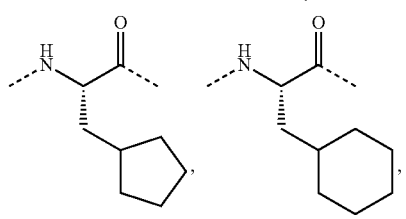
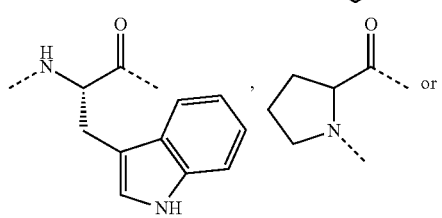

-continued
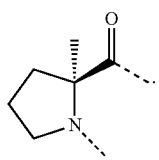
and more preferably -A*-A³- represents
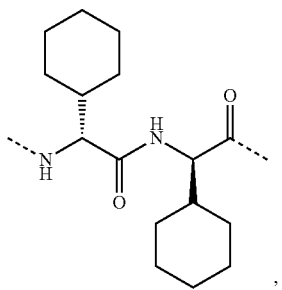
,
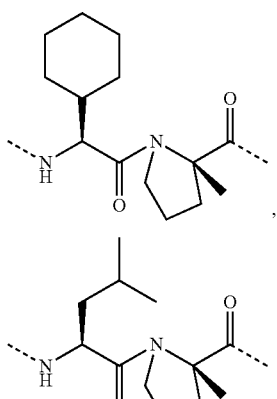
,
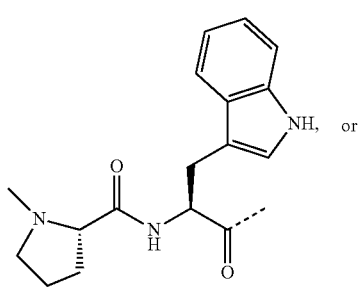
,
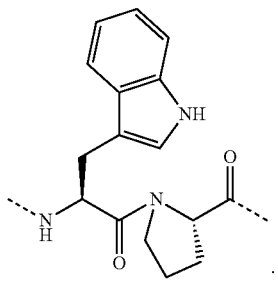
or
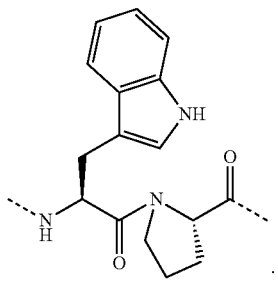
Preferably, in any general formula disclosed herein and especially in any one of the formulae (I), and (II-1)-(II-3), R³ represents
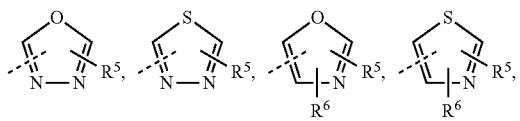
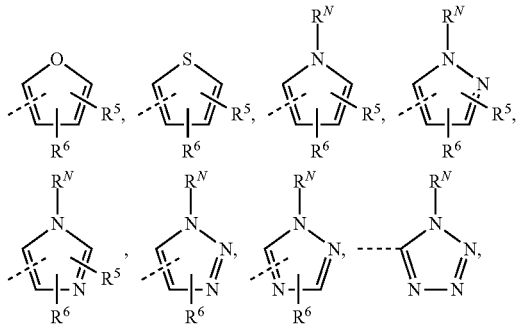
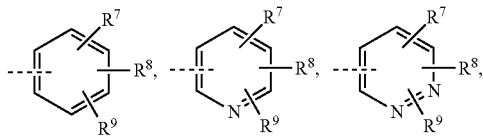
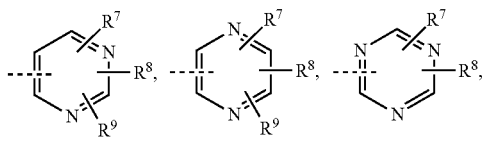
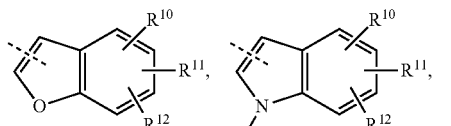
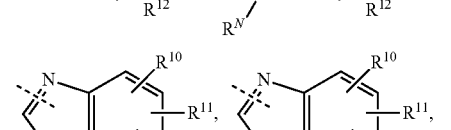
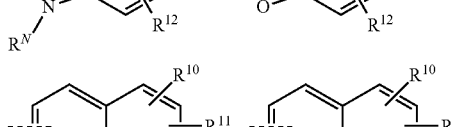
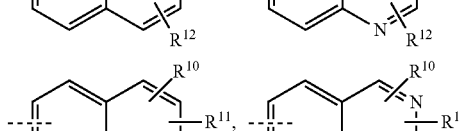
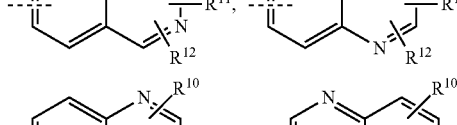
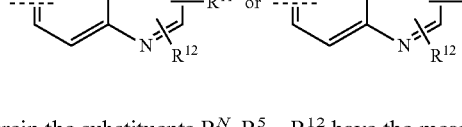
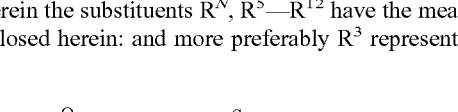
wherein the substituents $R^N$, $R^5$—$R^{12}$ have the meanings as disclosed herein: and more preferably $R^3$ represents
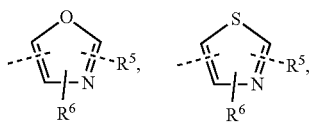

-continued
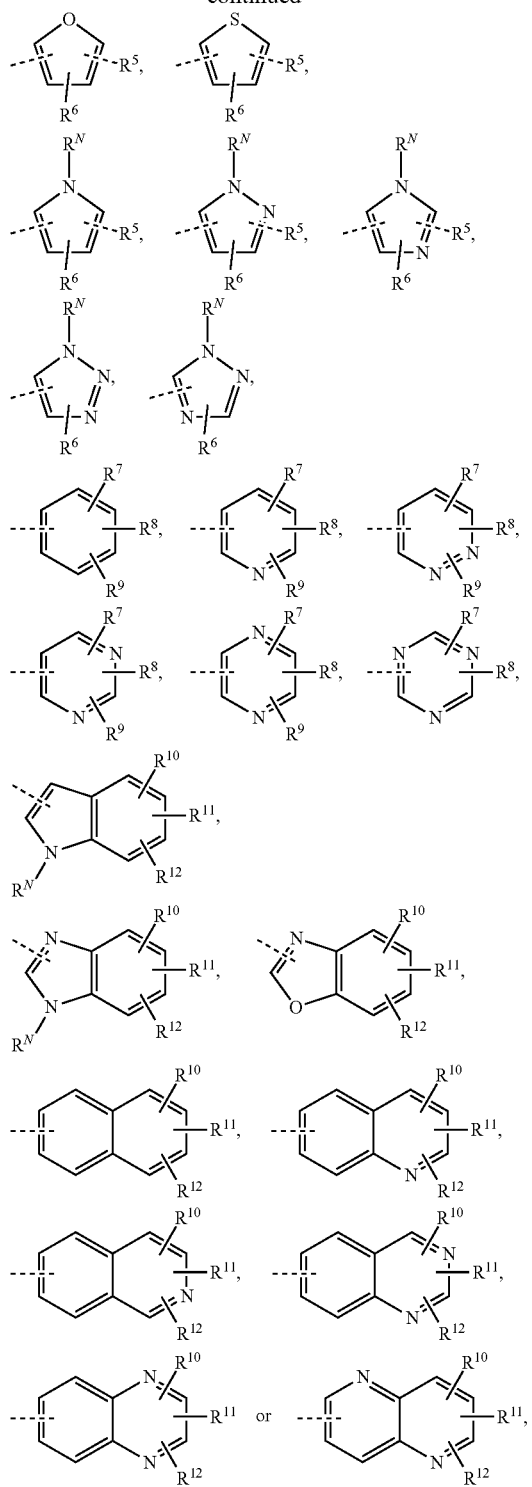
still more preferably R³ represents
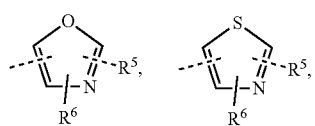
-continued
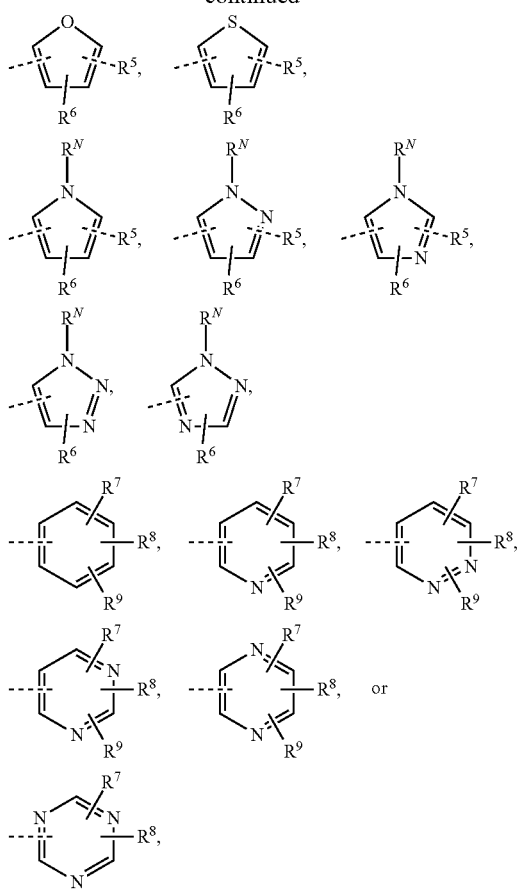
still more preferably R³ represents
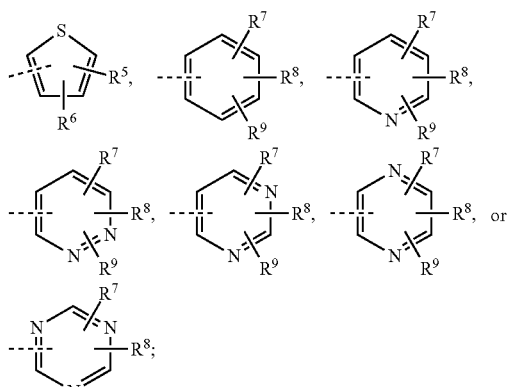
and $R^N$, $R^5$, $R^6$, $R^7$, $R^8$, and $R^9$ have the same meanings as defined herein or in formula (I), and still more preferably R³ represents
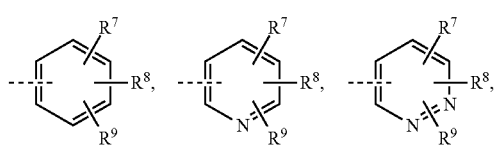

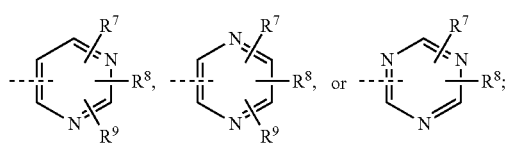

and most preferably, $R^3$ represents

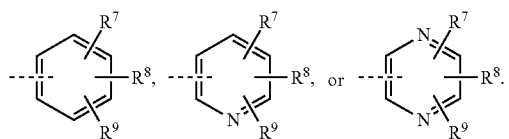

More preferably, the present invention is directed to a compound of formula (III):

(III)

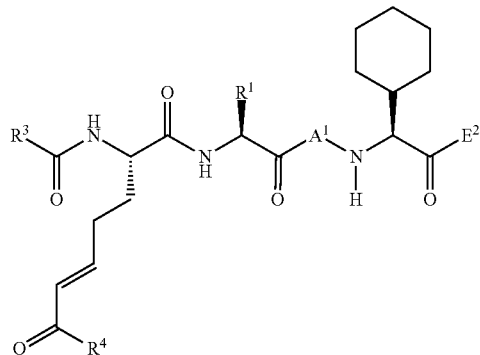

wherein
$E^2$ represents -E, -$A^3$-E, -$A^3$-$A^4$-E, or -$A^3$-$A^4$-$A^5$-E; and
$A^1$, $A^3$, $A^4$, $A^9$, $R^1$, $R^3$, $R^4$, and E have the meanings and preferred meanings as defined herein; or more specifically to a compound of formula (III-1) or (III-2):

(III-1)

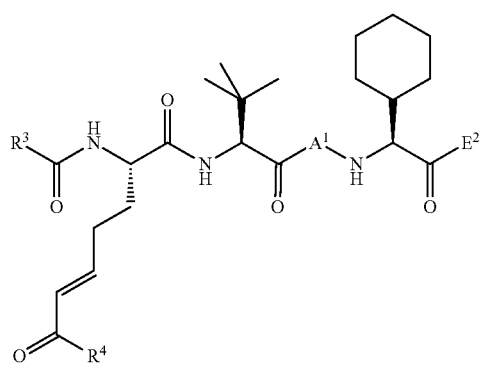

(III-2)

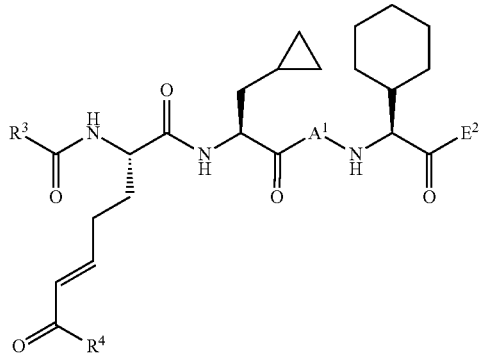

wherein
$E^2$ represents -E, -$A^3$-E, -$A^3$-$A^4$-E, or -$A^3$-$A^4$-$A^5$-E;
$R^3$, represents

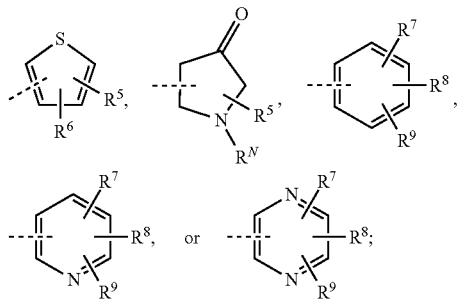

preferably

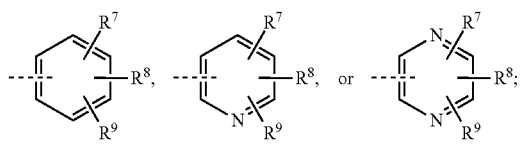

and
$A^1$, $A^3$, $A^4$, $A^5$, $R^N$, $R^4$, $R^5$, $R^9$, $R^7$, $R^8$, $R^9$ and E have the same meanings as defined herein.

Still more preferably, the present invention is directed to a compound of any one of the formulae (IV-1)-(IV-5):

(IV-1)

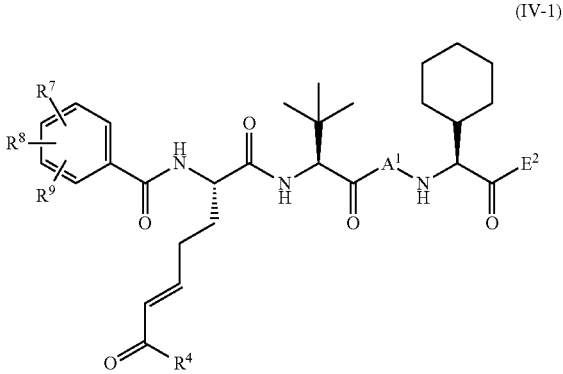

(IV-2)
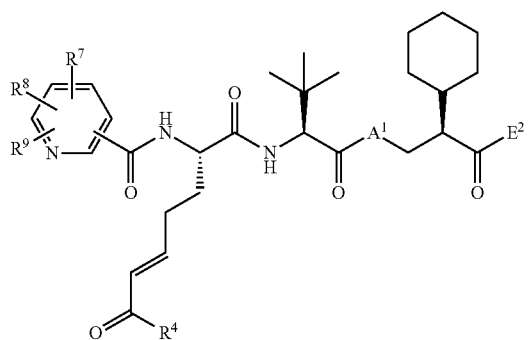

(IV-3)
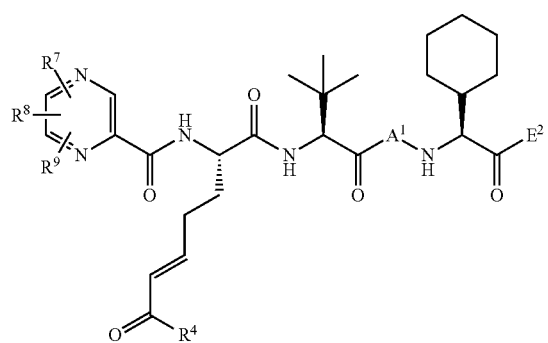

(IV-4)
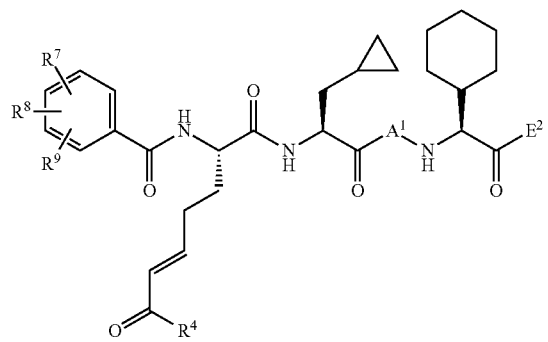

(IV-5)
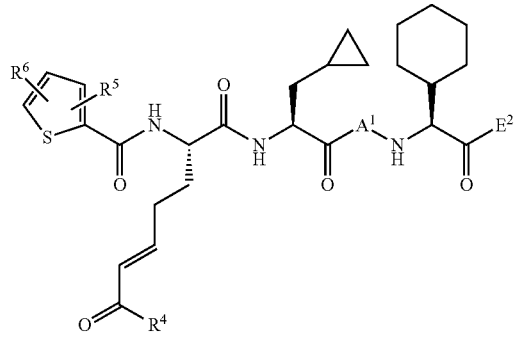

wherein
$E^2$ represents -E, -$A^3$-E, -$A^3$-$A^4$-E, or -$A^3$-$A^4$-$A^5$-E;
$R^4$ represents —$OCH_3$ or —$OC_2H_5$;
$R^5$, $R^6$, $R^7$, $R^8$, and $R^9$ represent independently of each other —H, —Cl, —OH, —$NO_2$ or —$CO_2H$; and $A^1$, $A^3$, $A^4$, $A^9$, and E have the same meanings as defined herein.

Still more preferred are compounds of any one of the formulae (V-1) and (V-2):

(V-1)
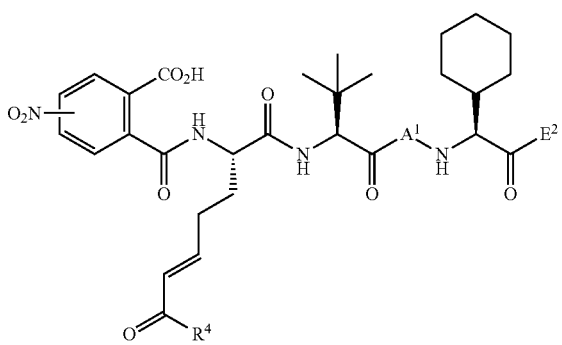

(V-2)
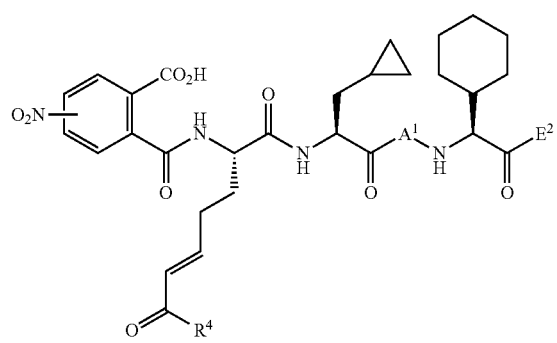

wherein
$E^2$ represents -E, -$A^3$-E, -$A^3$-$A^4$-E, or -$A^3$-$A^4$-$A^5$-E;
represents —$OCH_3$ or —$OC_2H_5$;
$A^1$ represents

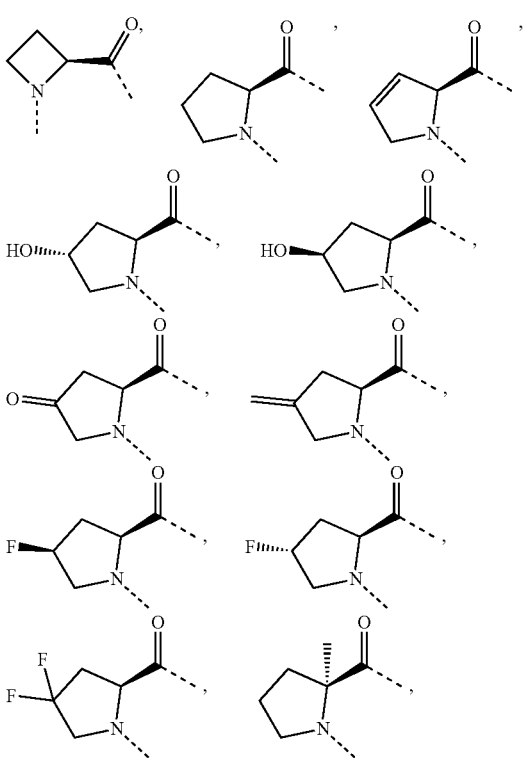

-continued

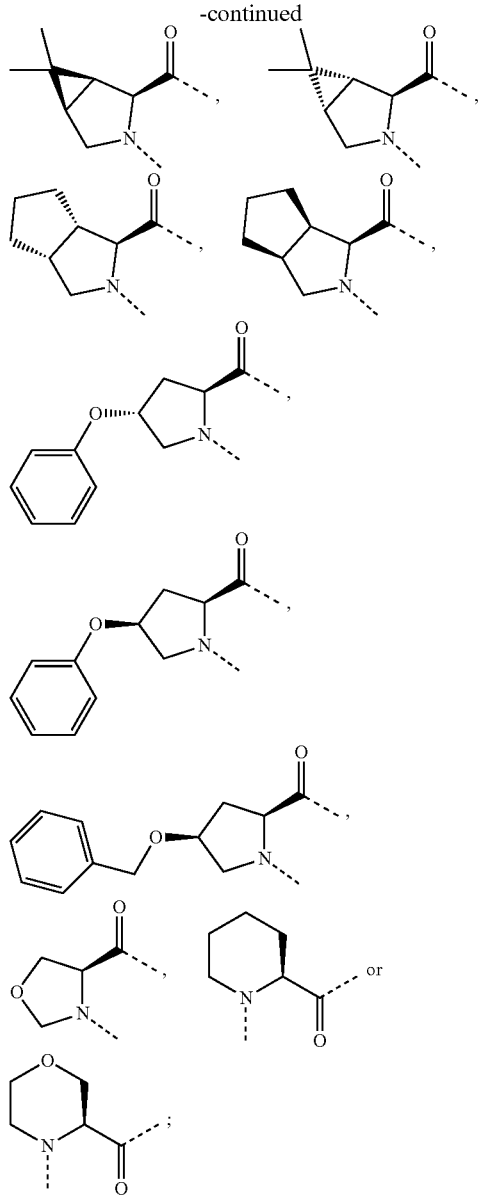

and $A^3$, $A^4$, $A^5$, and E have the same meanings as defined above.

Still more preferred is a compound of a formula (VI):

(VI)

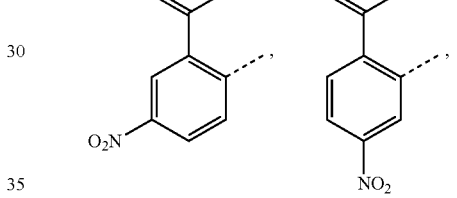

$E^1$ represents -E, -$A^4$-E, or -$A^4$-$A^5$-E;

$R^3$ represents

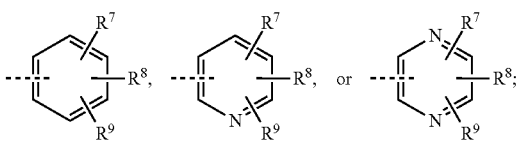

and $A^1$, $A^4$, $A^5$, $R^4$, $R^7$, $R^8$, $R^9$ and E have the same meanings as defined herein or more preferably as defined in formula (V-1).

Preferably, in any general formula disclosed herein, $R^3$ is selected from the group consisting of:

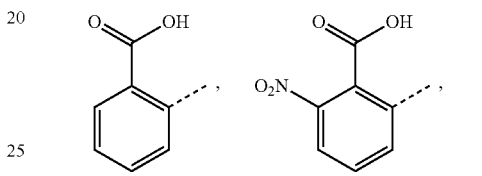

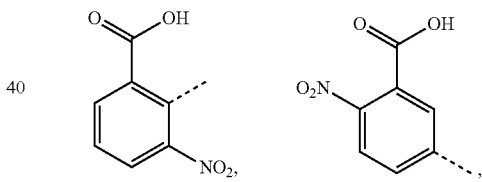

-continued

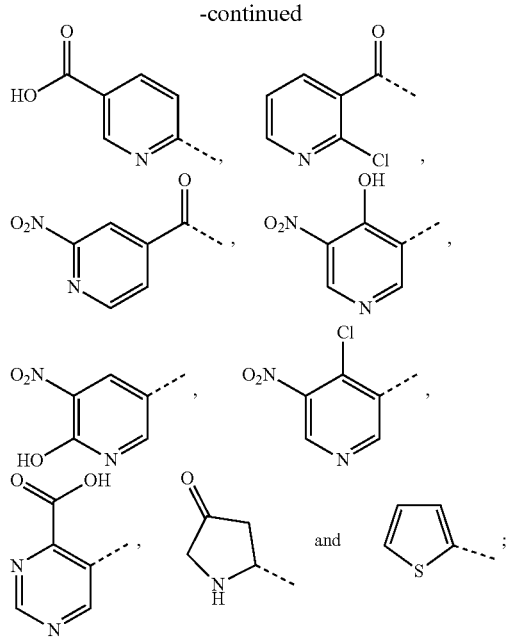

and more preferably R³ prepresents

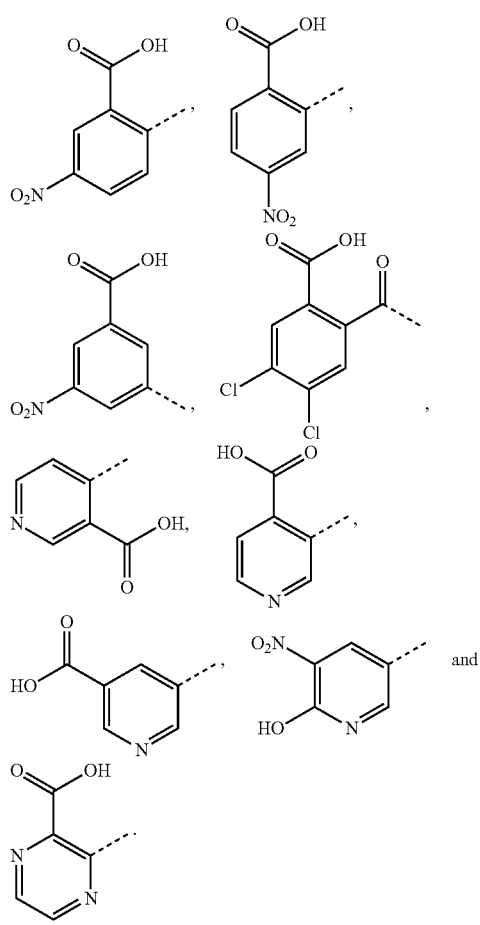

Preferably, in any general formula disclosed herein, R⁴', R⁵', R⁶', and R⁷' represent independently of each other: —H, —F, —Cl, —Br, —I, —CH₃, —CH₂CH₃, —CH(CH₃)₂, -cyclo-C₃H₅, —OCH₃, —CF₃, —OCF₃, —OH, —CN, —COCH₃, —CO₂H, —CO₂Me, —OCOCH₃, —NH₂, —NHCH₃, —N(CH₃)₂, —NHCOCH₃, —NHCOCF₃, —NHSO₂CH₃, —NHSO₂CF₃, —SCH₃, —SO₂CH₃, —SO₂CF₃, —SO₂NH₂, —SO₂NHCH₃, or —SO₂N(CH₃)₂; more preferably —H, —F, —Cl, —Br, —CH₃, —CH₂CH₃, —CH(CH₃)₂, -cyclo-C₃H₅, —OCH₃, —OH, —CO₂H, —CO₂Me, —NH₂, —NHCH₃, —N(CH₃)₂; and most preferably —H.

Preferably, in any general formula disclosed herein, E is selected from a C terminal group consisting of: —OH, —OCH₃, —NH₂, —NHCH₃, —N(CH₃)₂, —N(CH₂CH₃)₂,

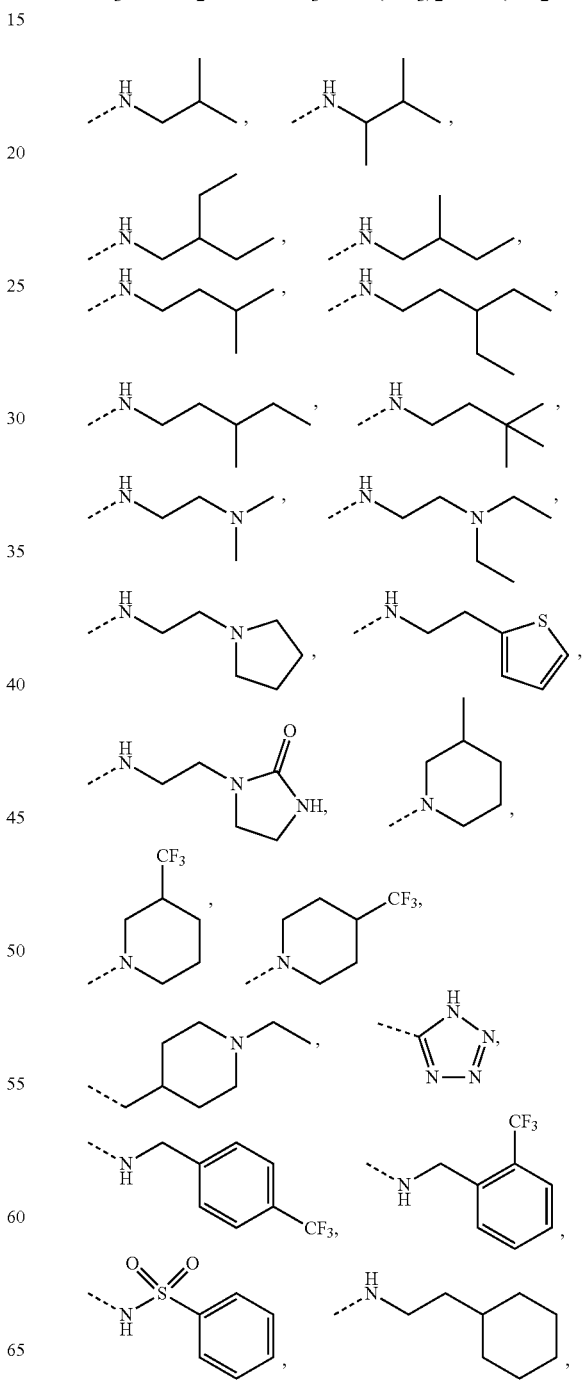

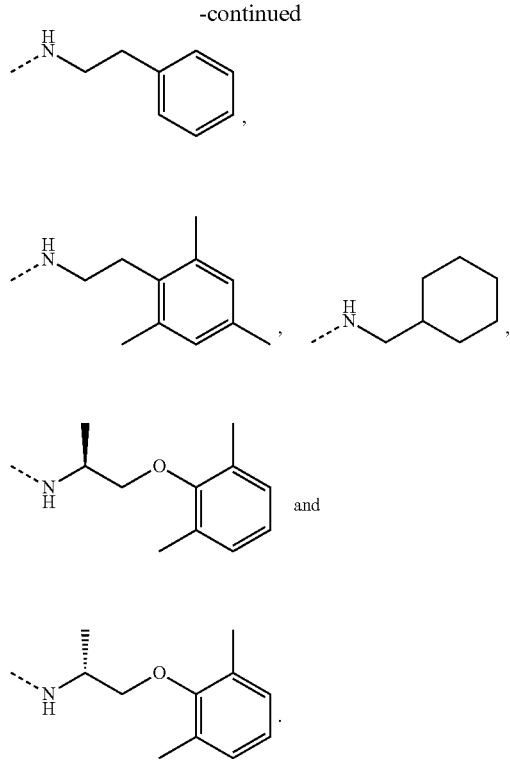
and more preferably E is selected from a C terminal group consisting of: —OH, —OCH₃, —NH₂, —NHCH₃, —N(CH₃)₂,
Also preferred are the following compounds selected from the group consisting of:
Compound 1a
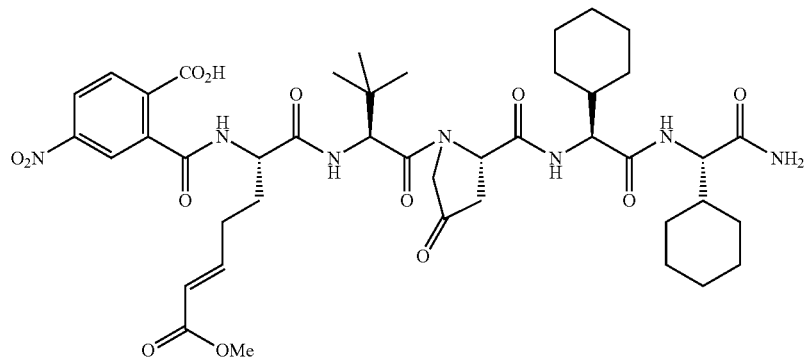
Compound 1b
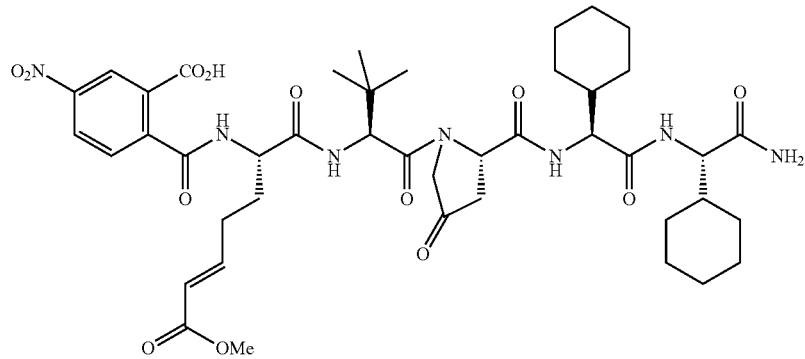

Compound 2a
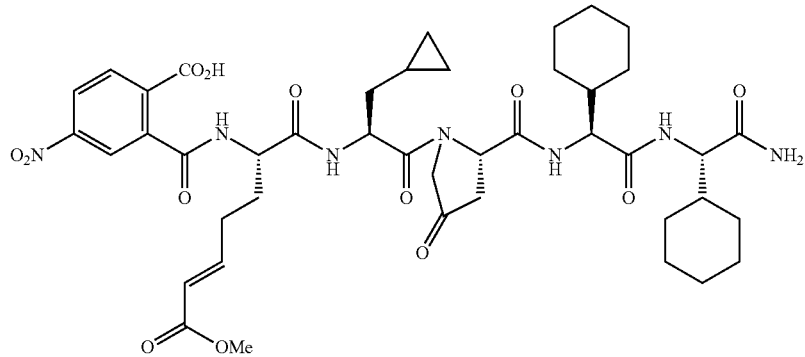
Compound 2b
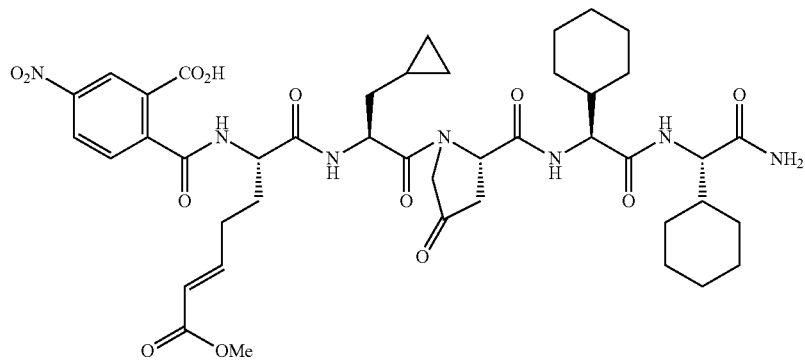
Compound 3
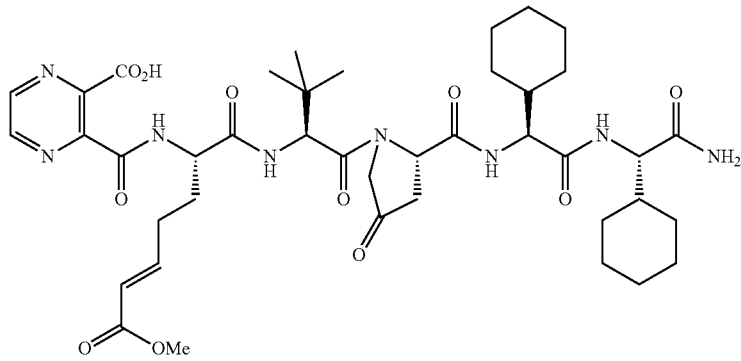
Compound 4
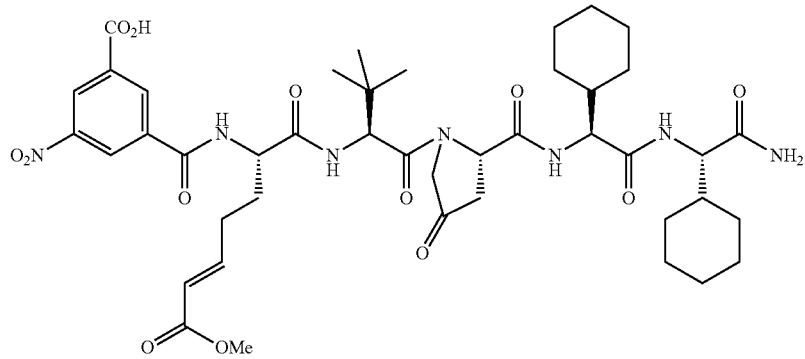

-continued
Compound 5a
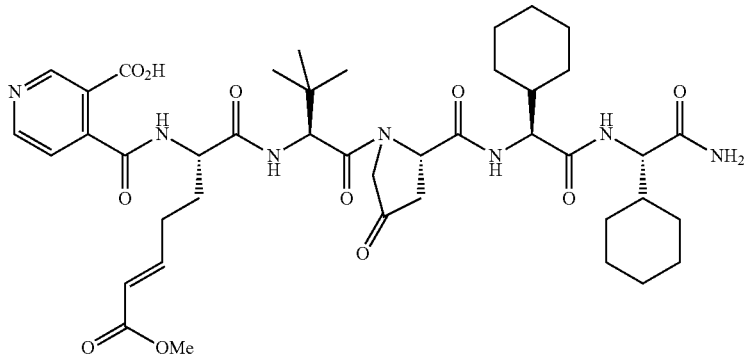
Compound 5b
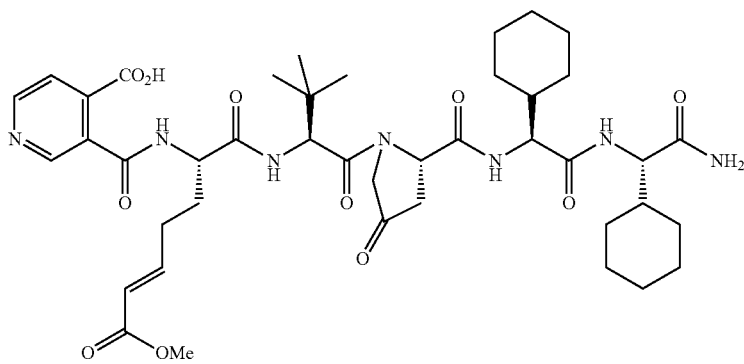
Compound 6
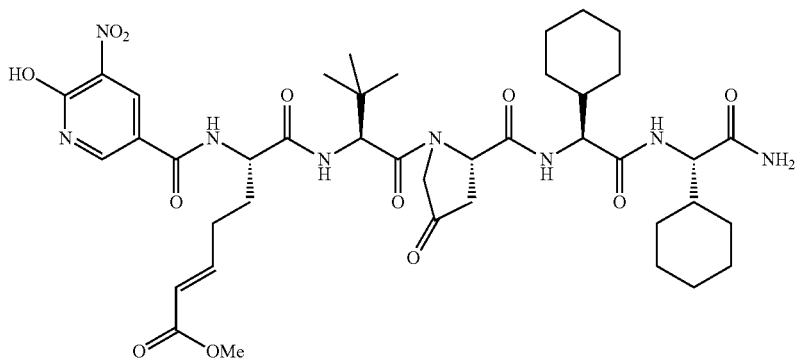
Compound 7a
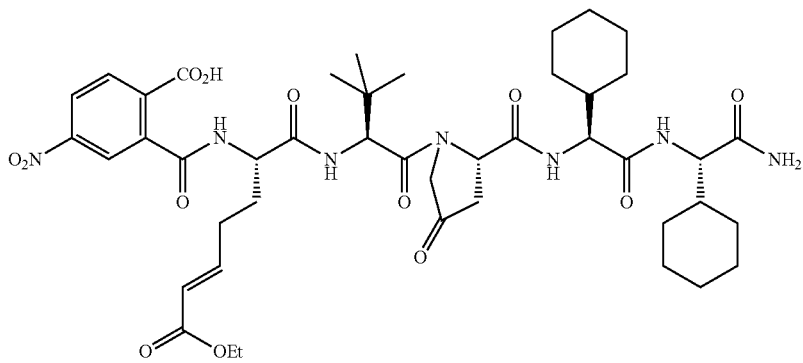

-continued
Compound 7b
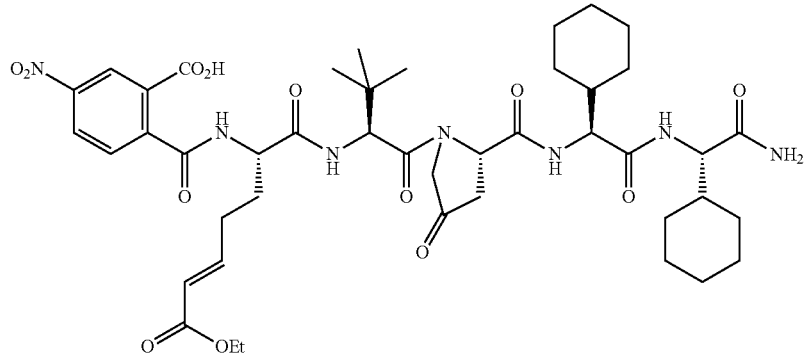
Compound 8a
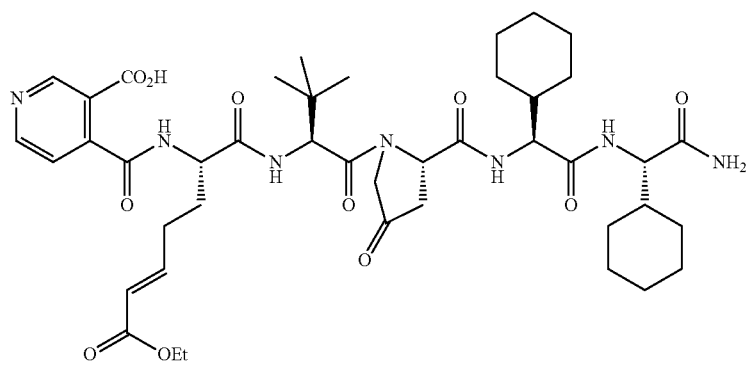
Compound 8b
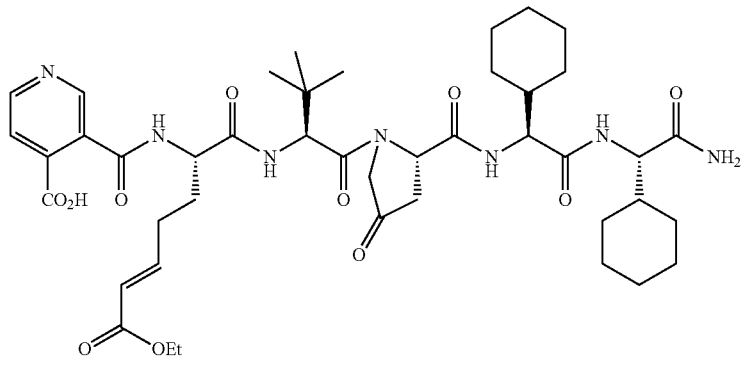
Compound 9a
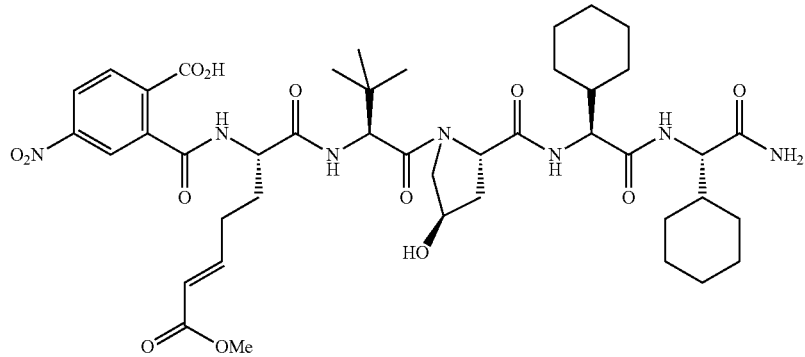

Compound 9b
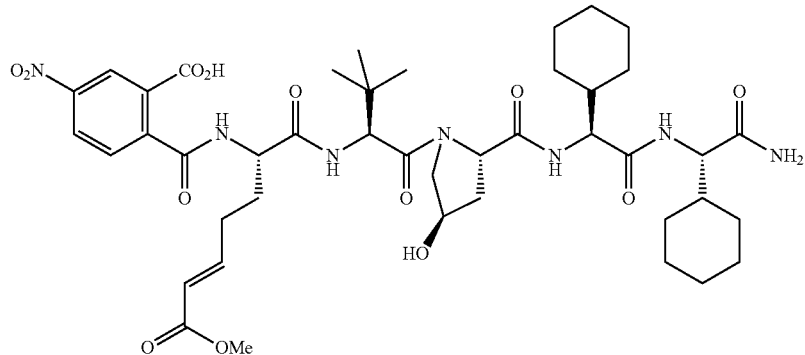
Compound 10a
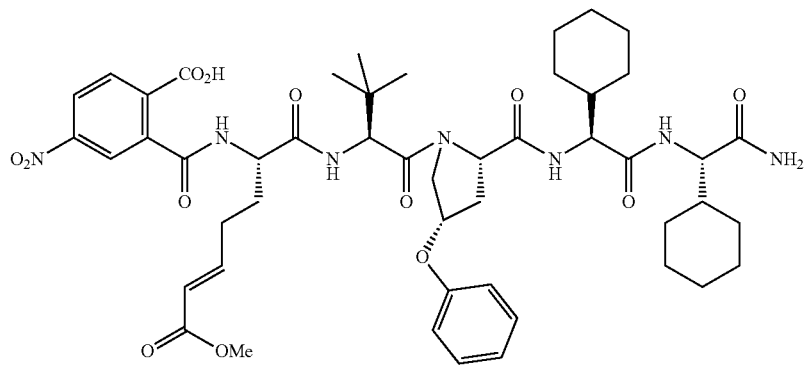
Compound 10b
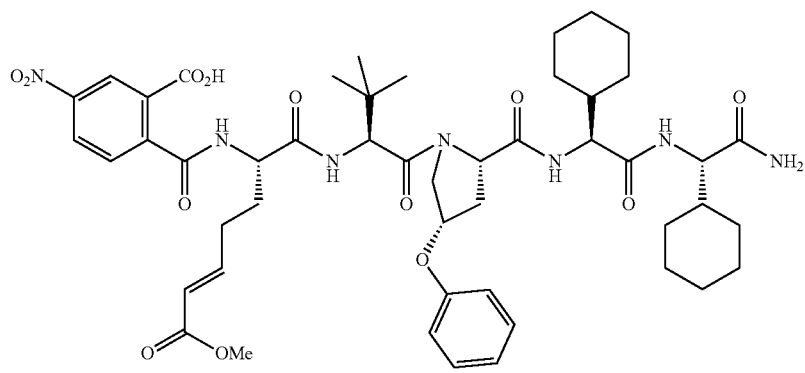
Compound 11a
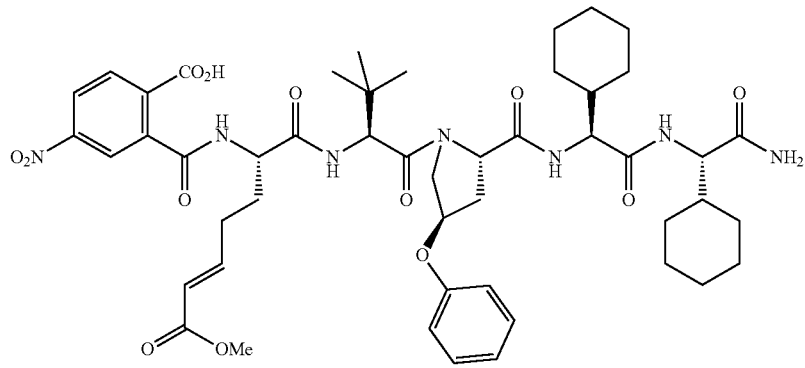

Compound 11b
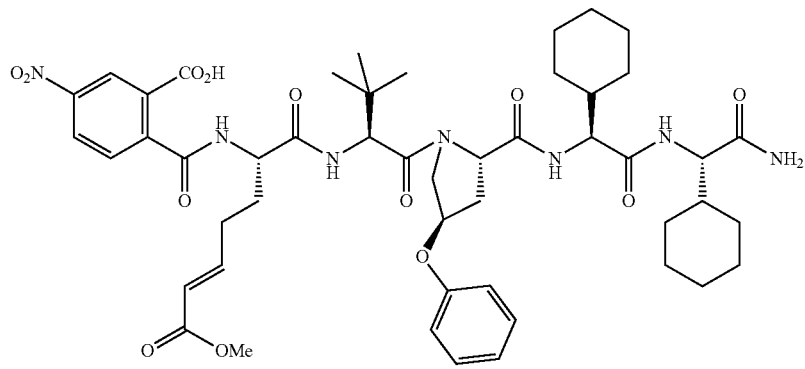
Compound 12a
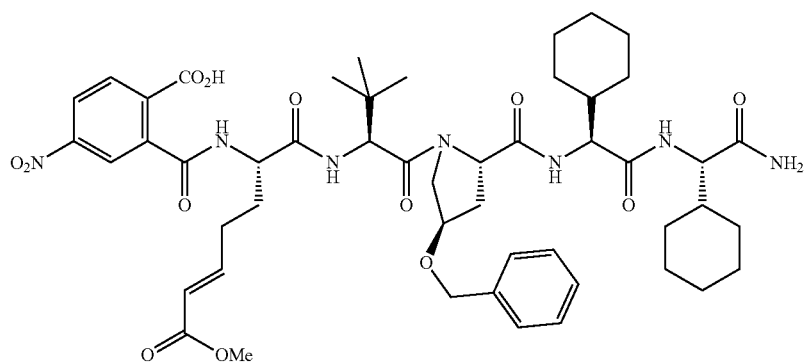
Compound 12b
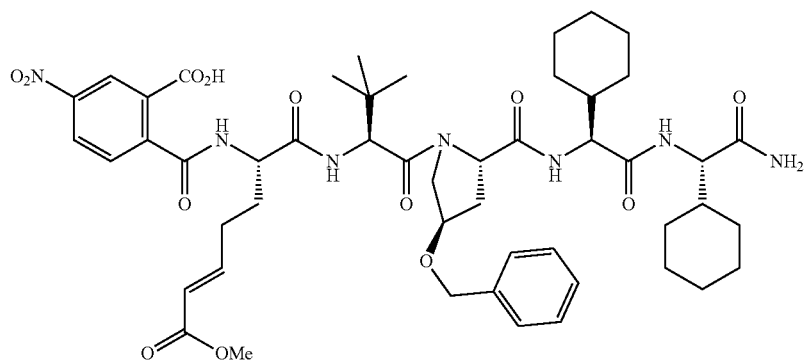
Compound 13a
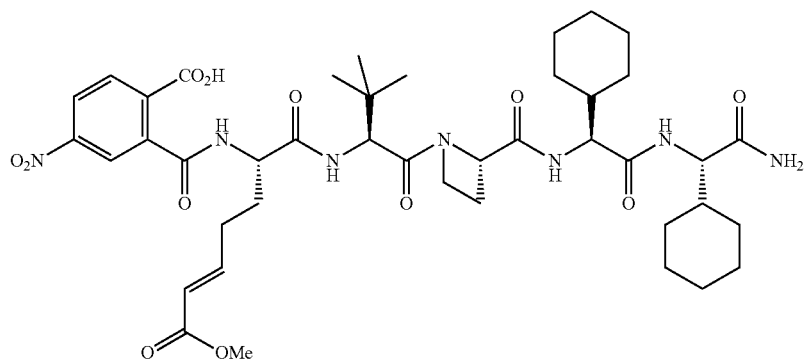

Compound 13b
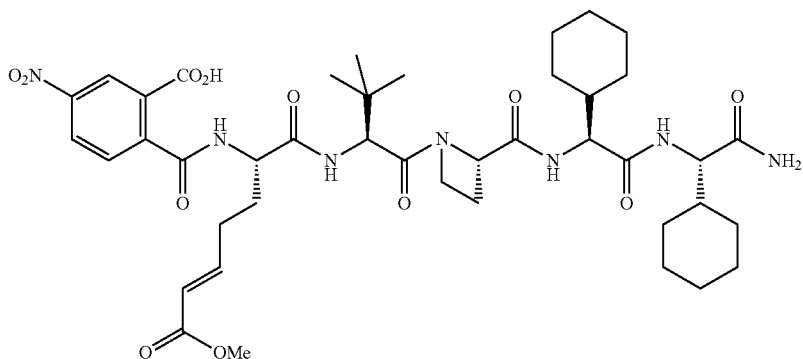
Compound 14a
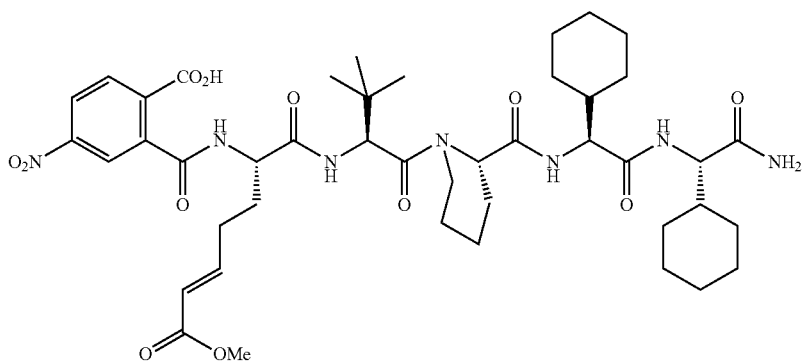
Compound 14b
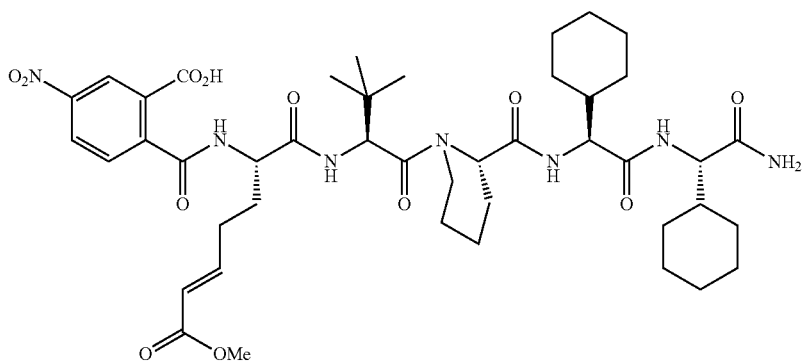
Compound 15a
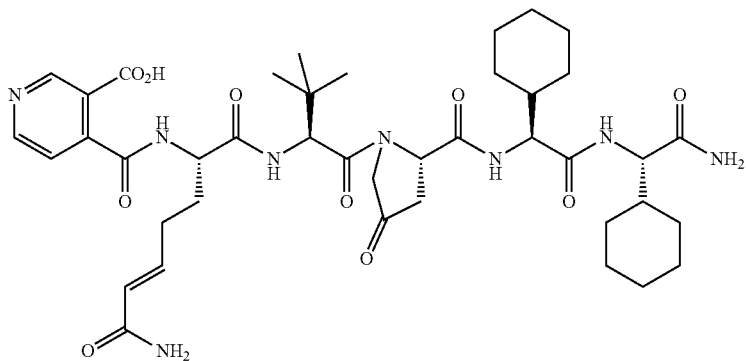

Compound 15b
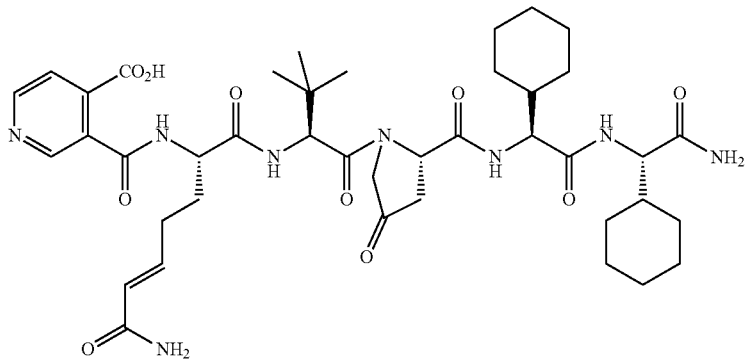
Compound 16a
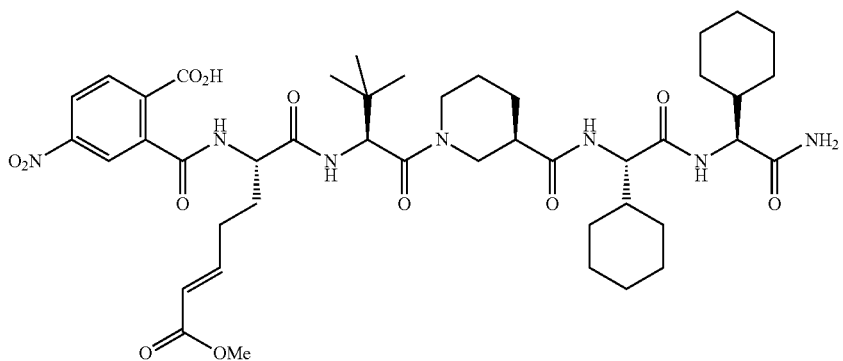
Compound 16b
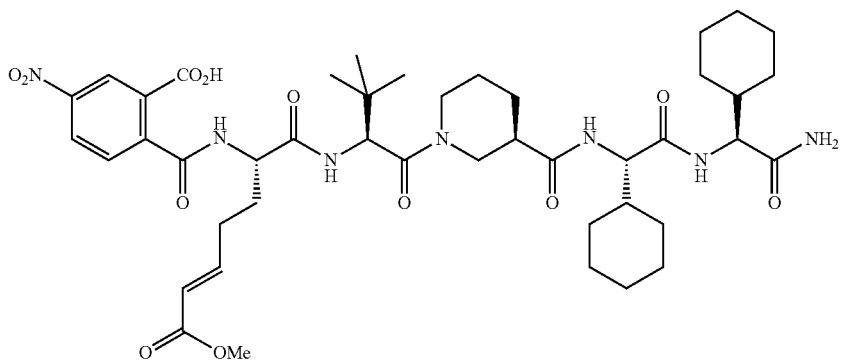
Compound 17a
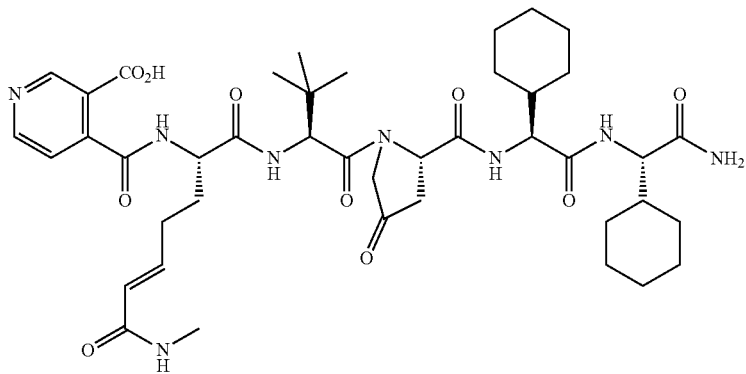

-continued
Compound 17b
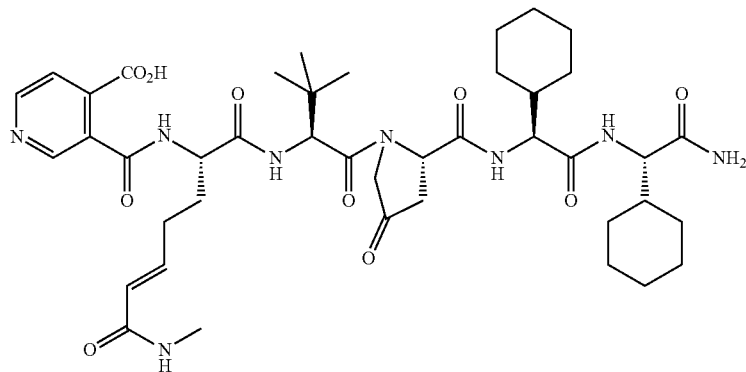
Compound 18a
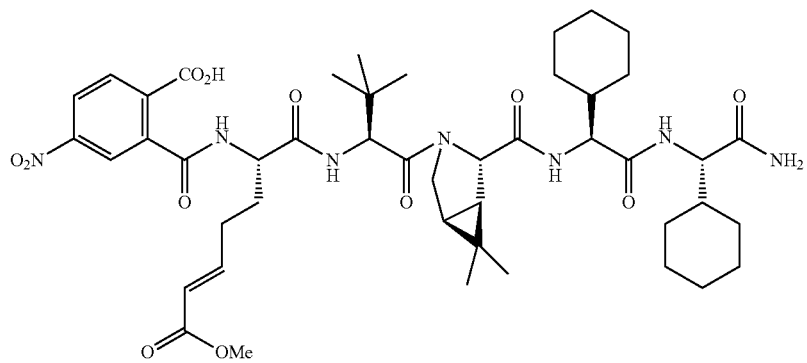
Compound 18b
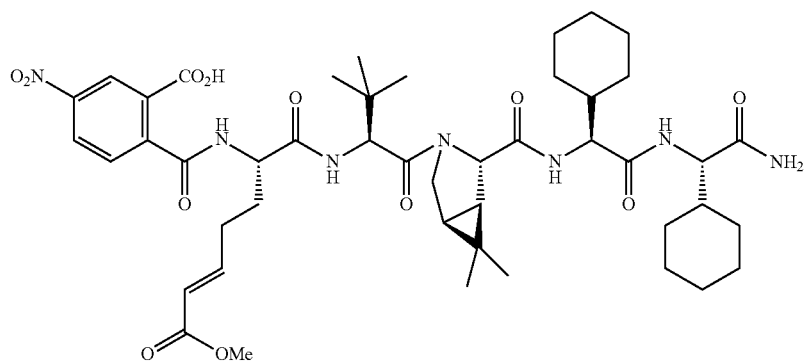
Compound 19a
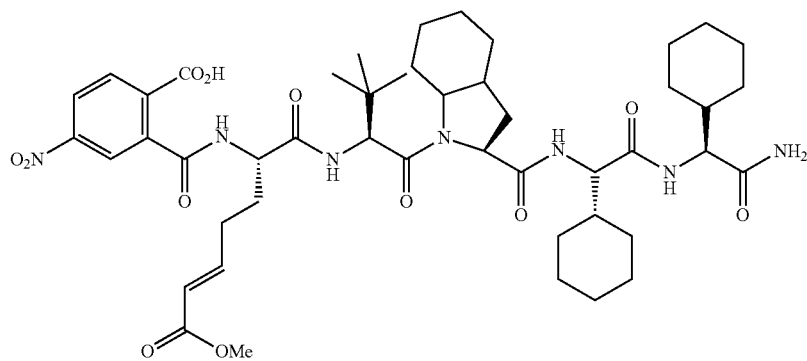

-continued
Compound 19b
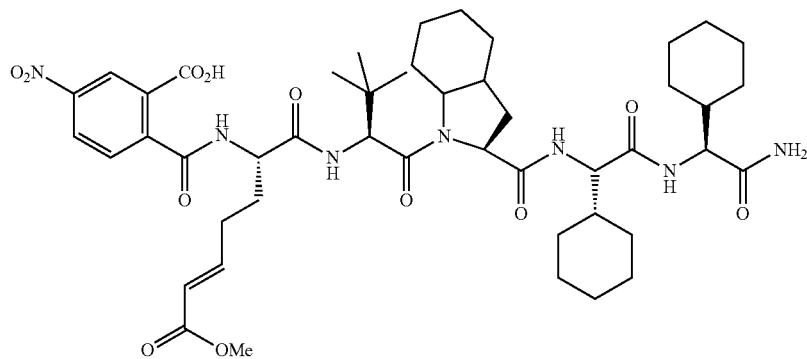
Compound 20a
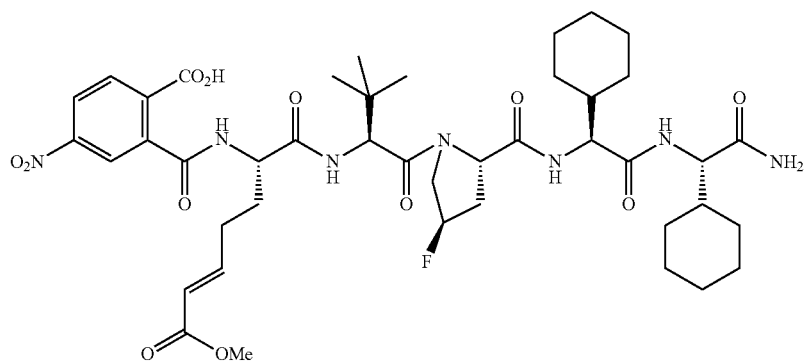
Compound 20b
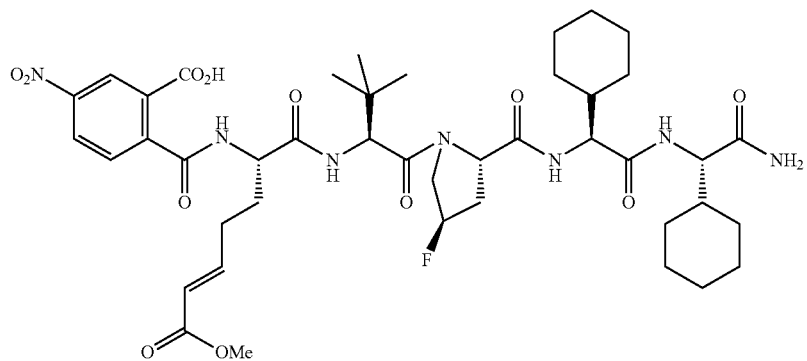
Compound 21a
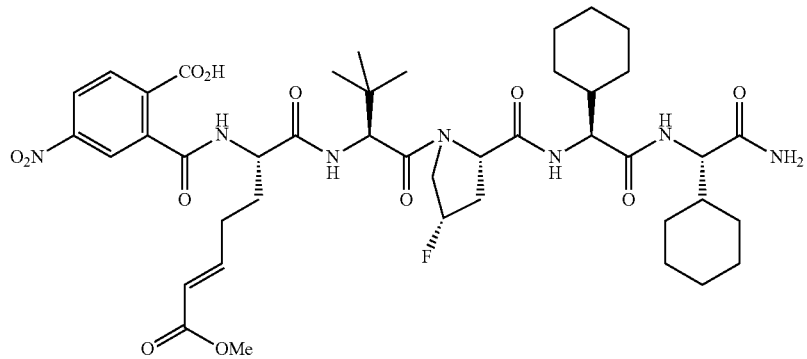

Compound 21b
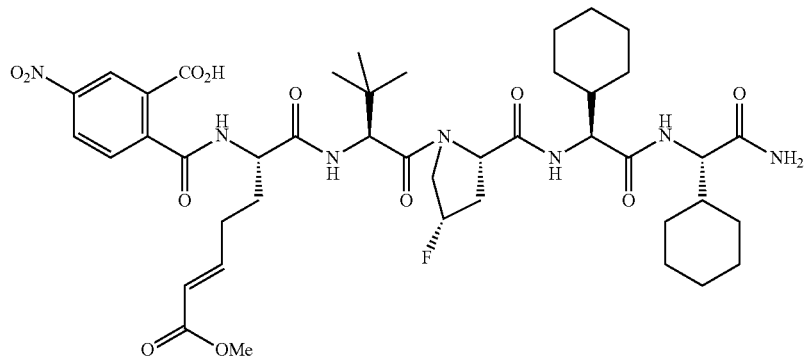
Compound 22a
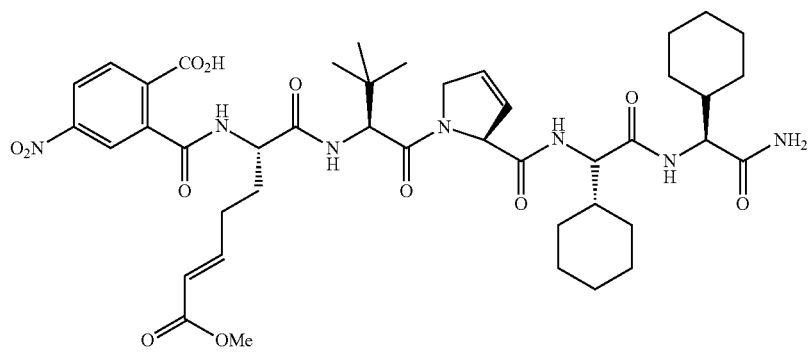
Compound 22b
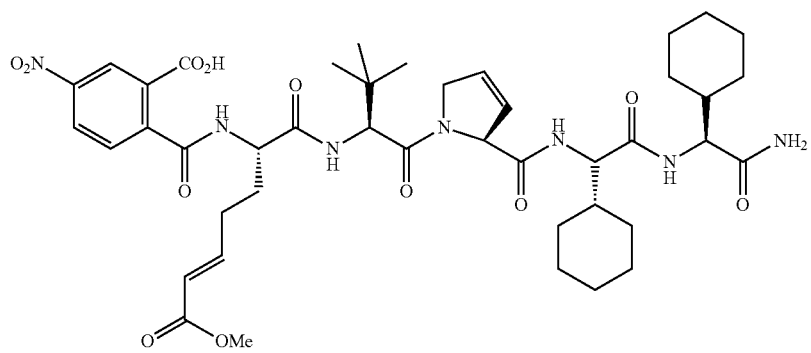
Compound 23a
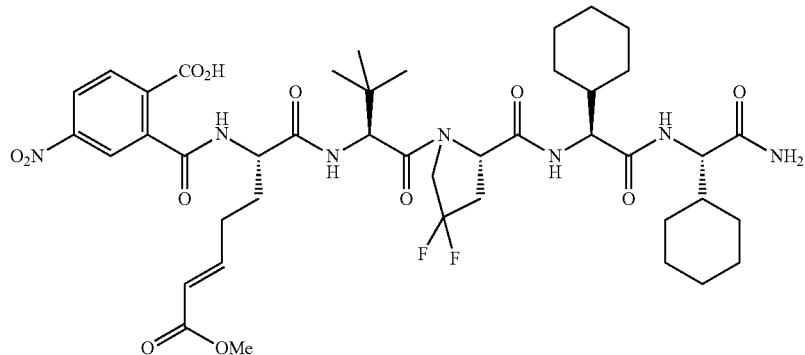

Compound 23b
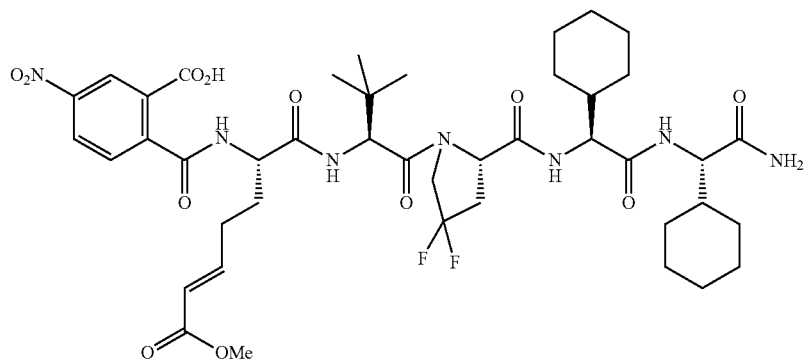
Compound 24a
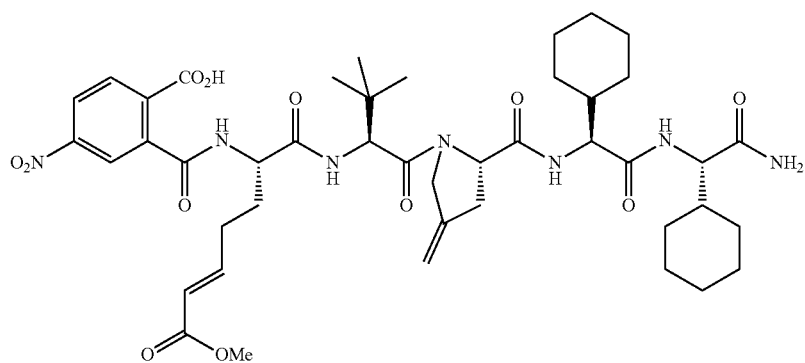
Compound 24b
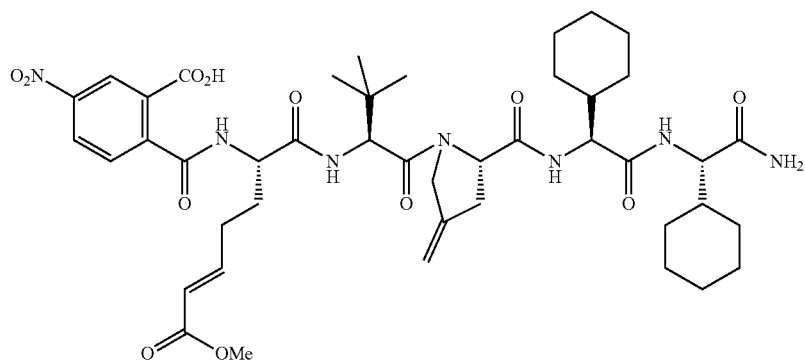
Compound 25a
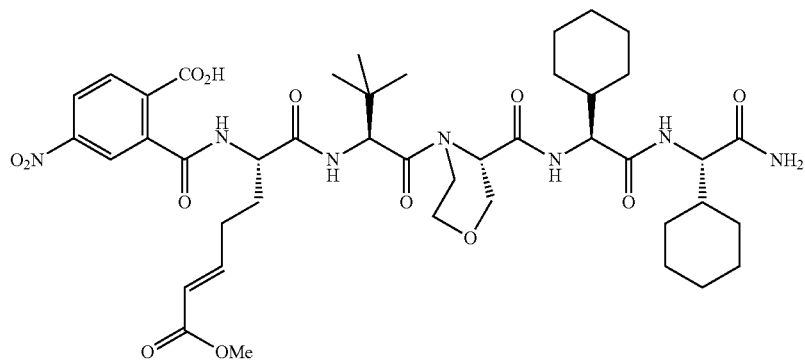

-continued
Compound 25b
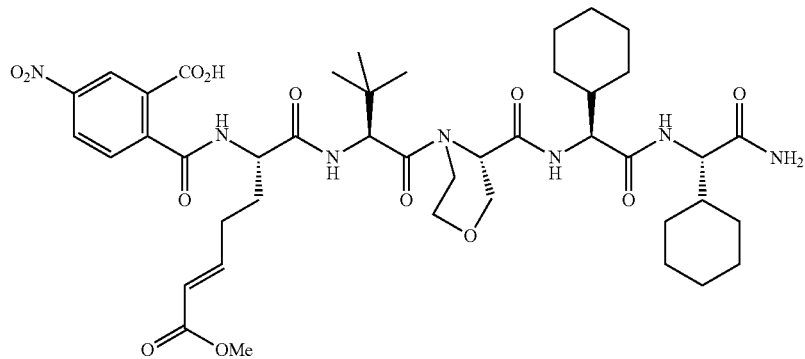
Compound 26a
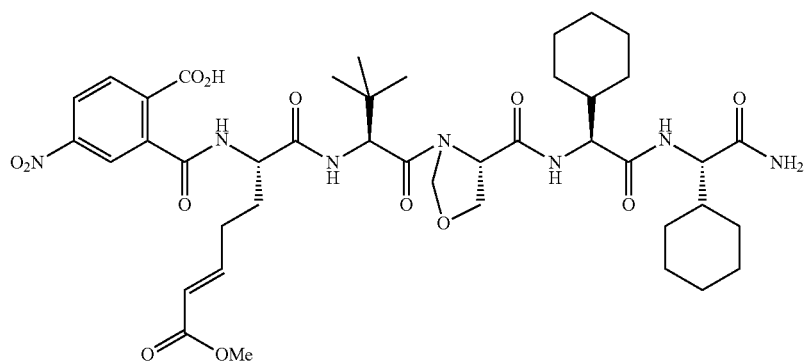
Compound 26b
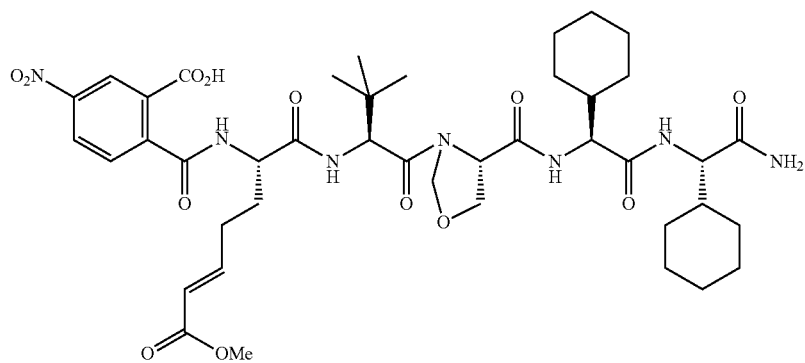
Compound 27
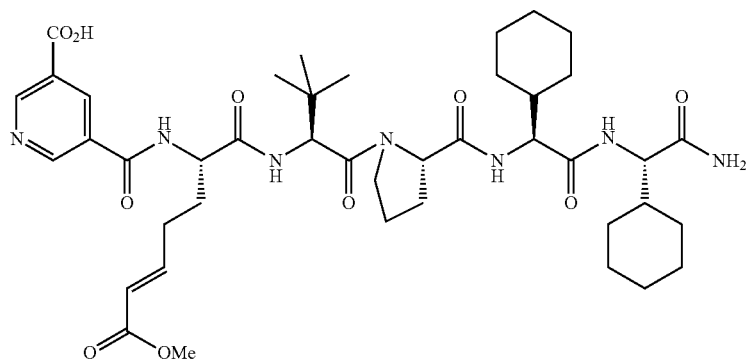

Compound 28
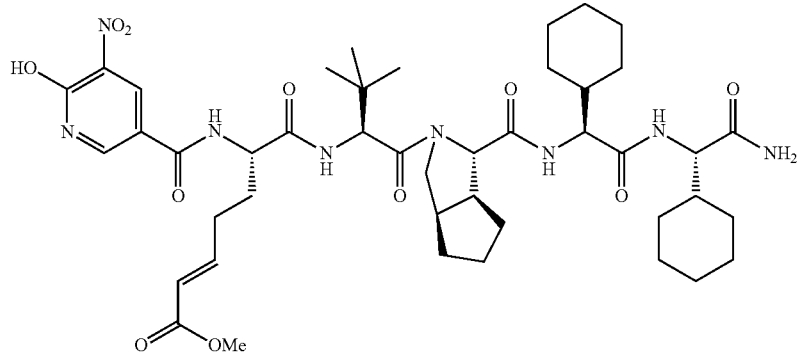
Compound 29
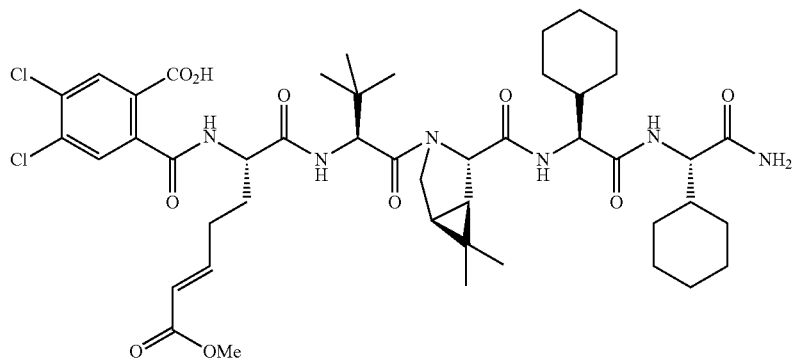
Compound 30
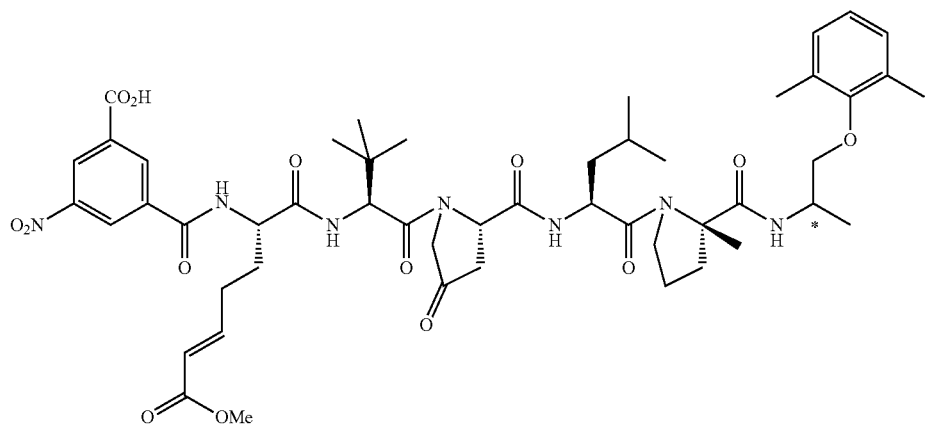
Compound 31a
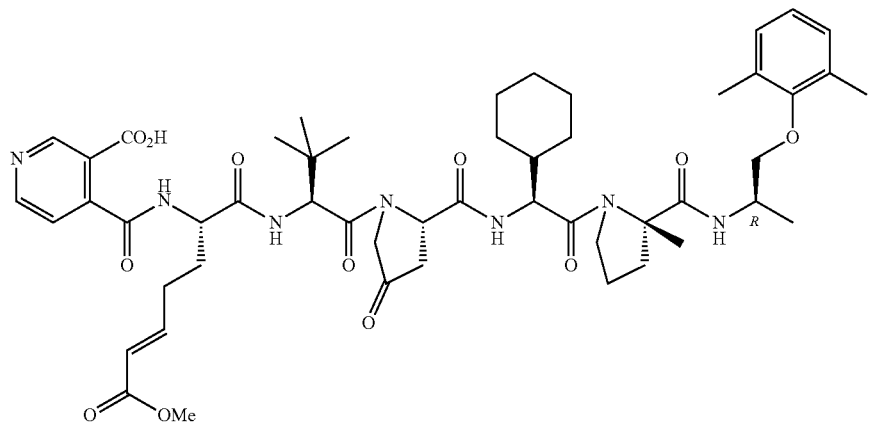

Compound 31b
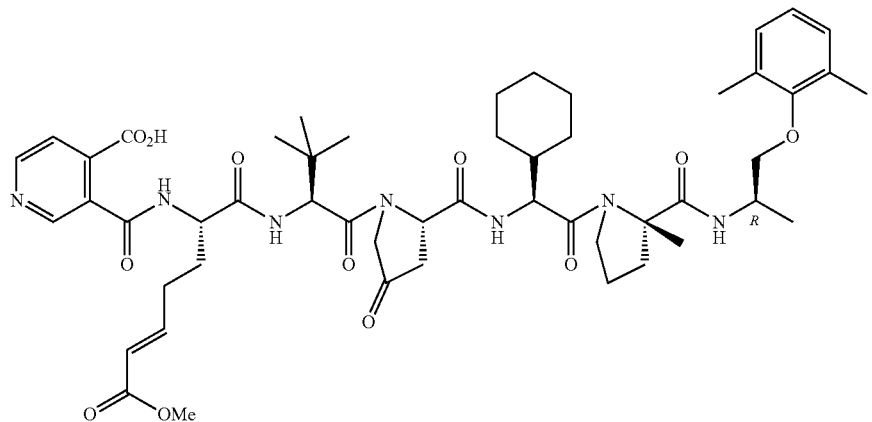
Compound 32a
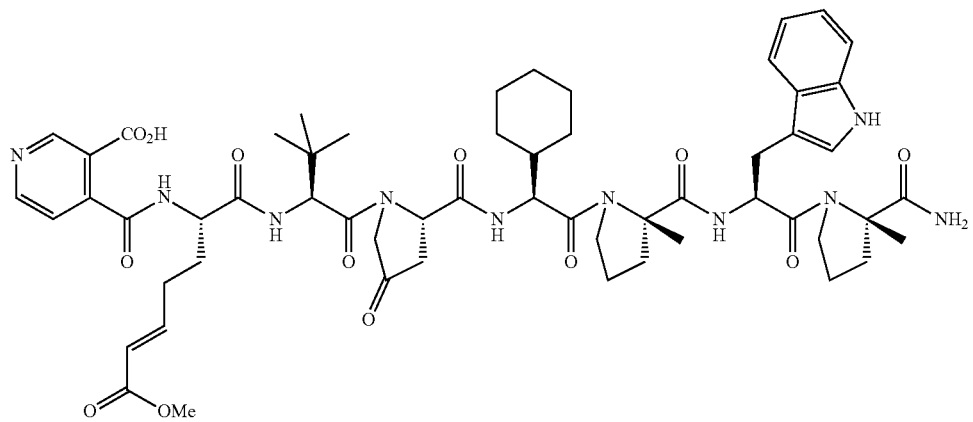
Compound 32b
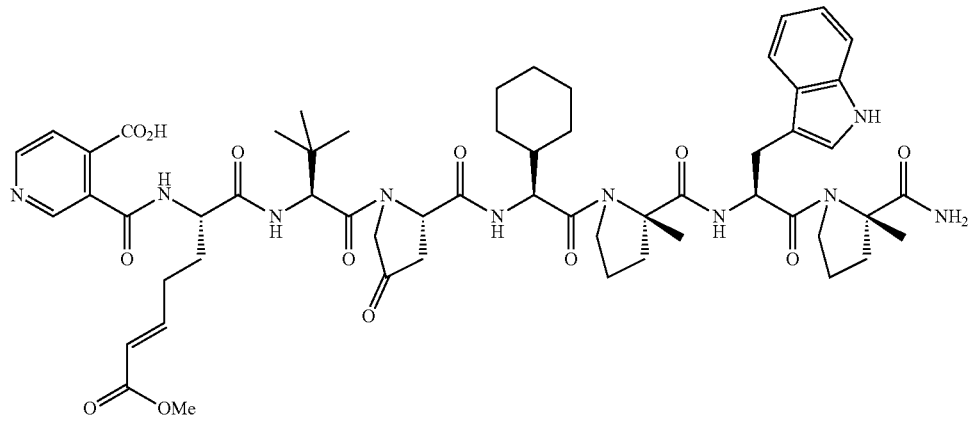

-continued
Compound 33a
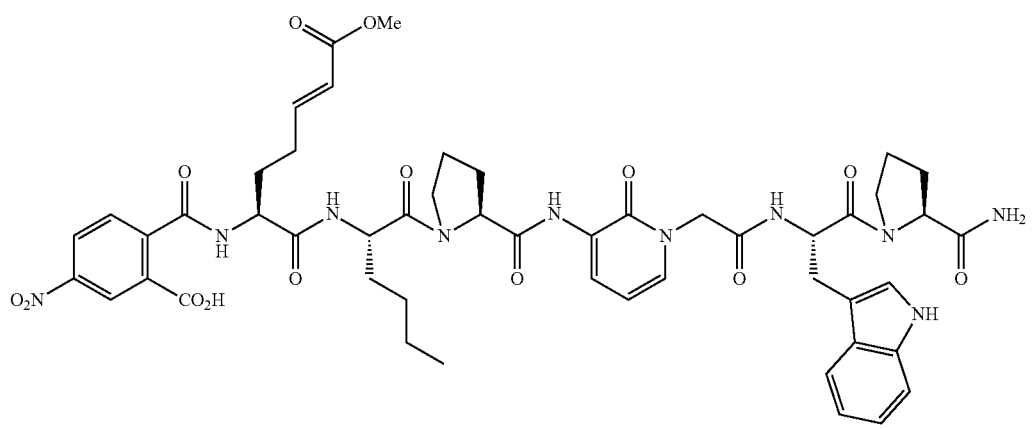
Compound 33b
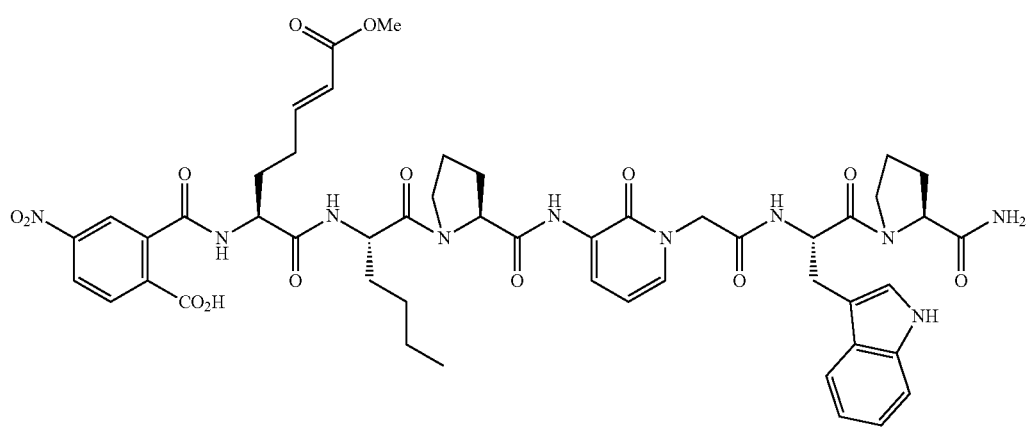
Compound 34a
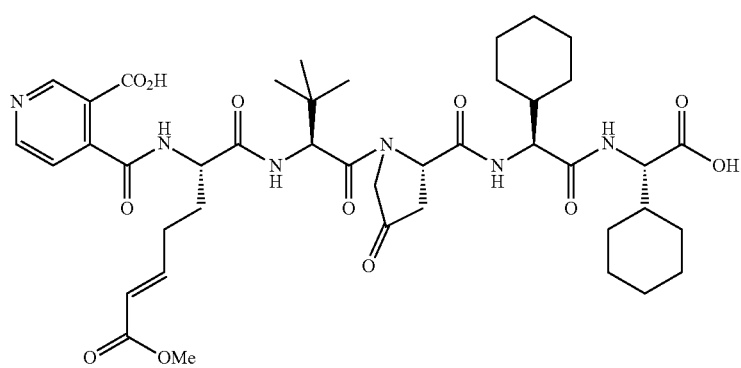
Compound 34b
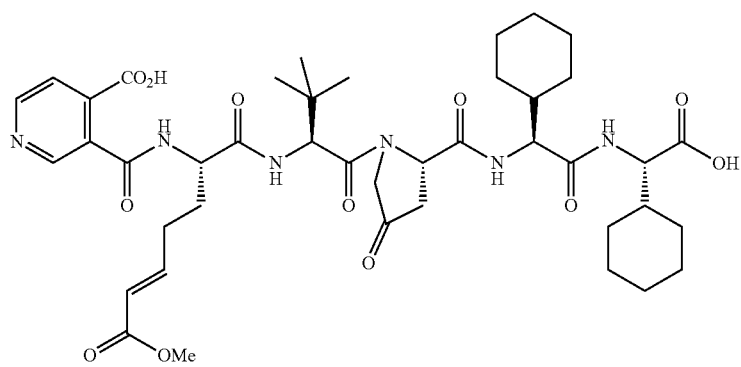

Compound 35a
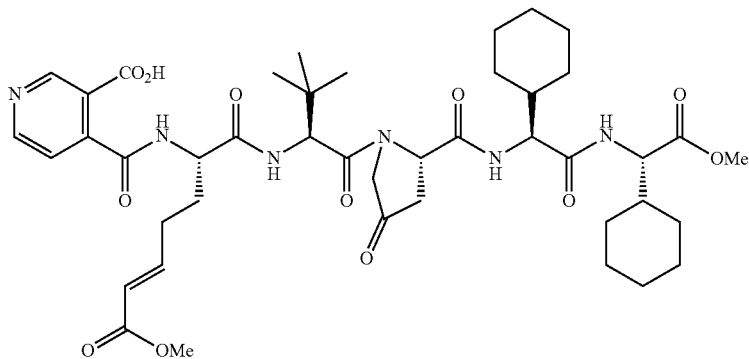
Compound 35b
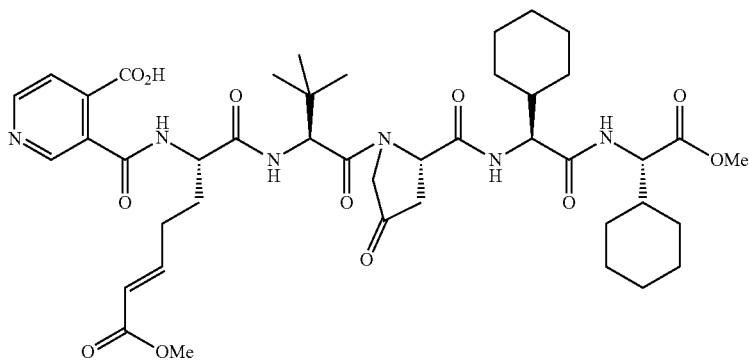
Compound 36a
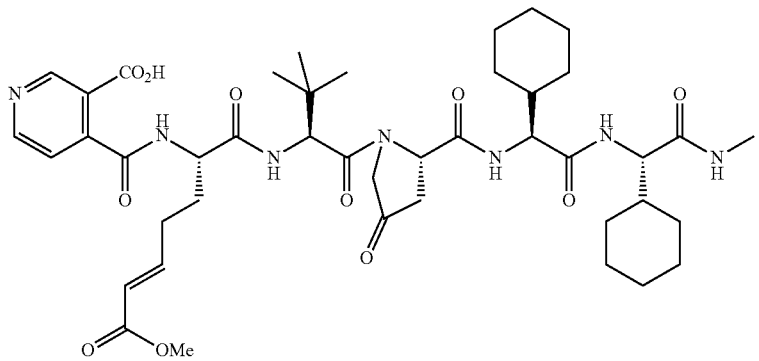
Compound 36b
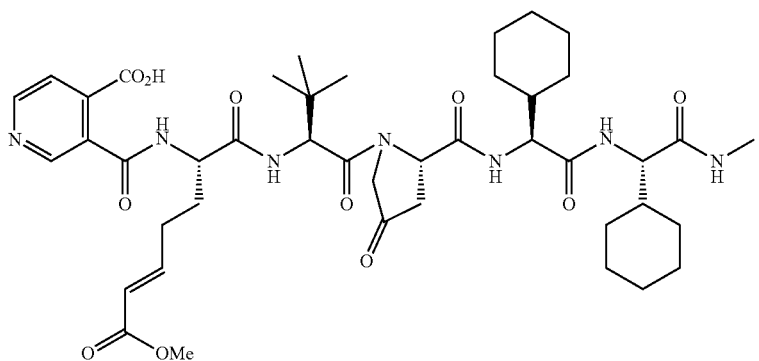

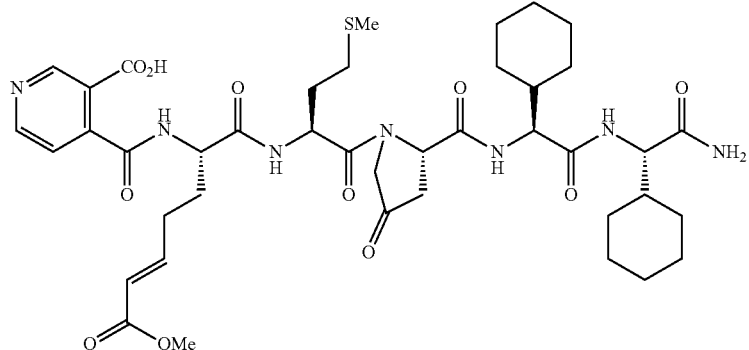
Compound 37a
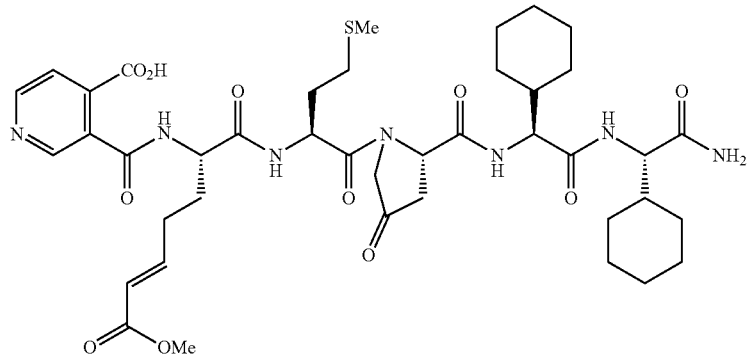
Compound 37b
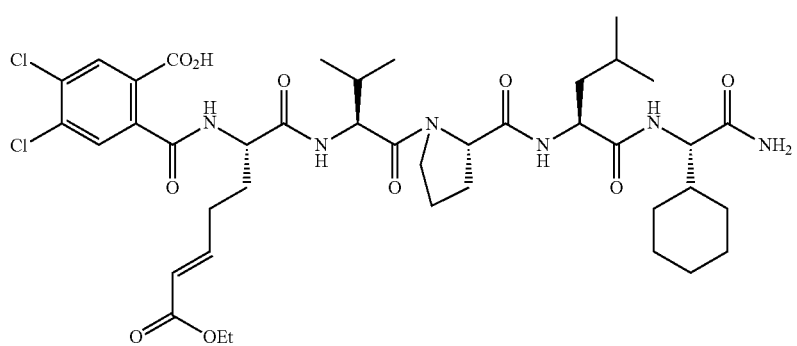
Compound 38
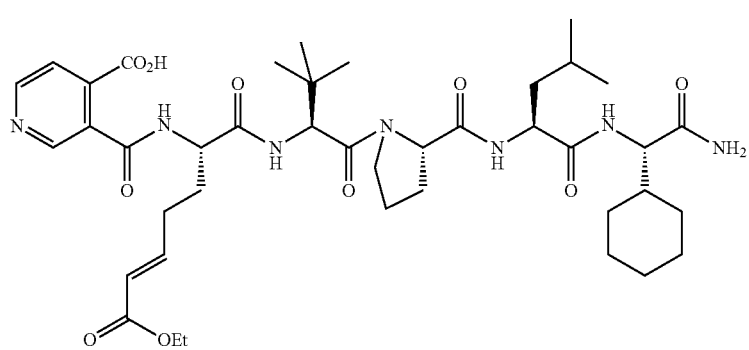
Compound 39a Compound 39b
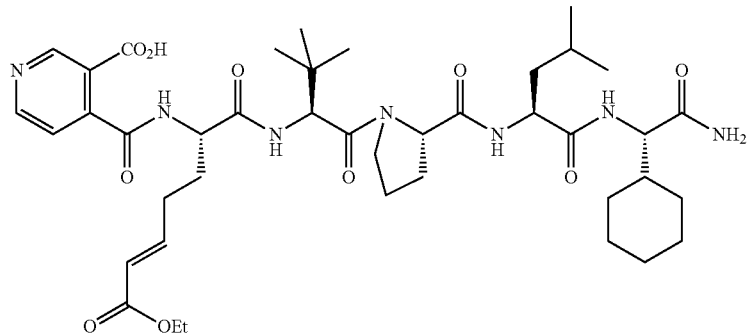
Compound 40
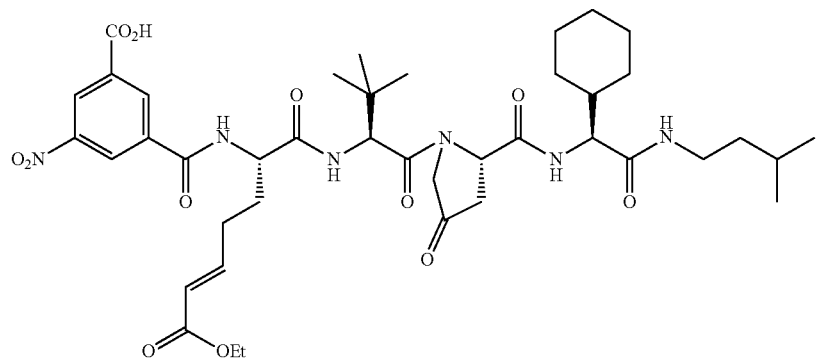
Compound 41
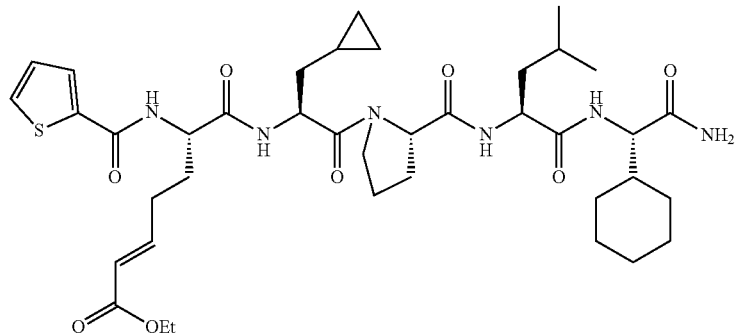
Compound 42a
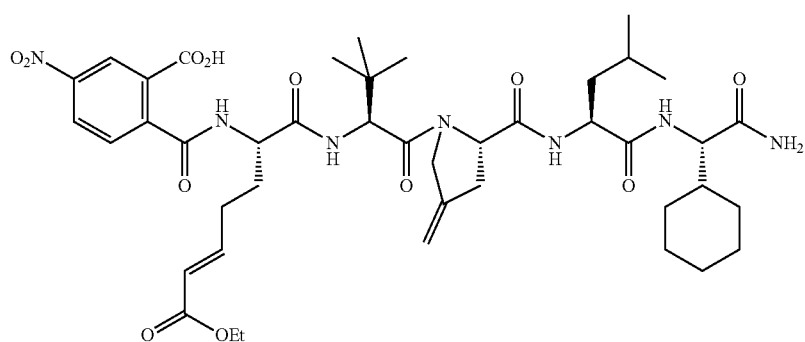

Compound 42b
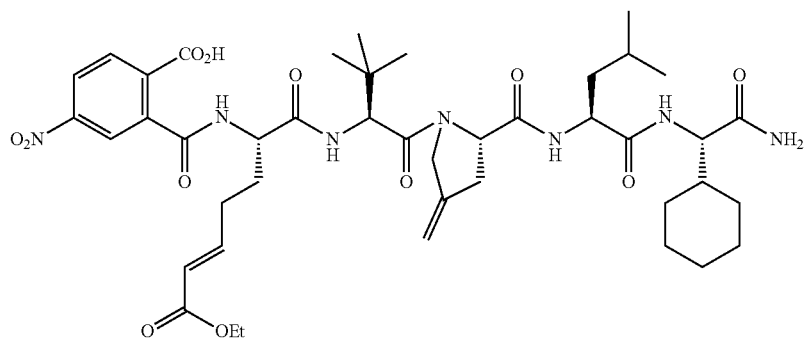
Compound 43
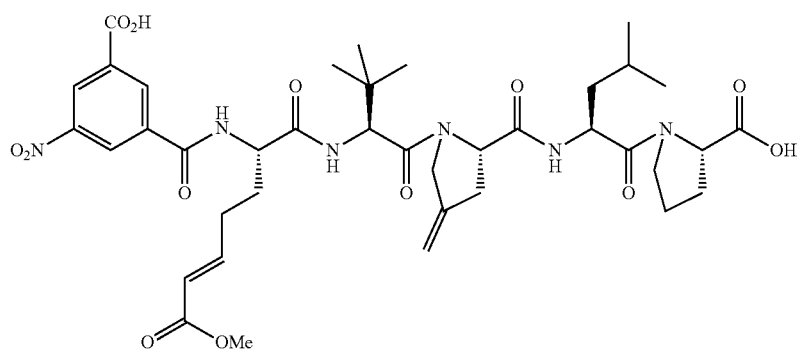
Compound 44
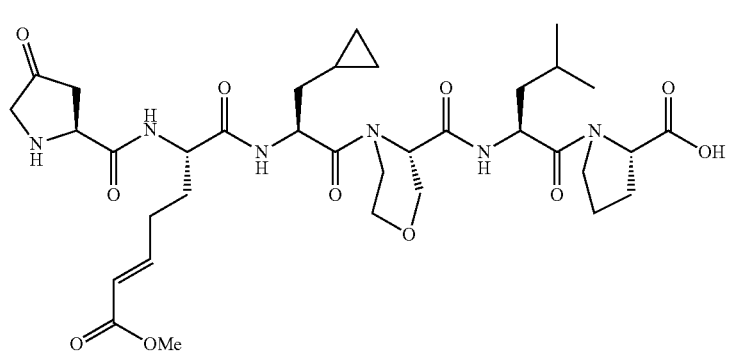
Compound 45a
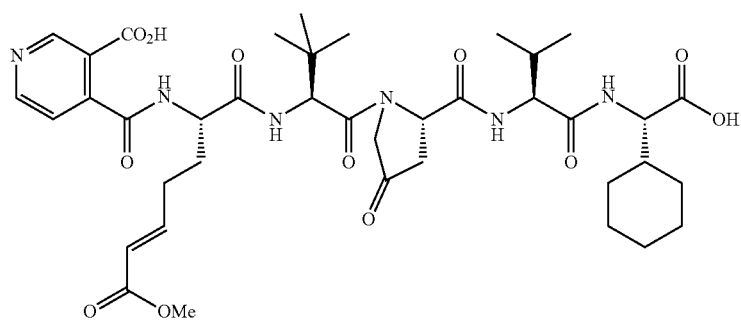

-continued

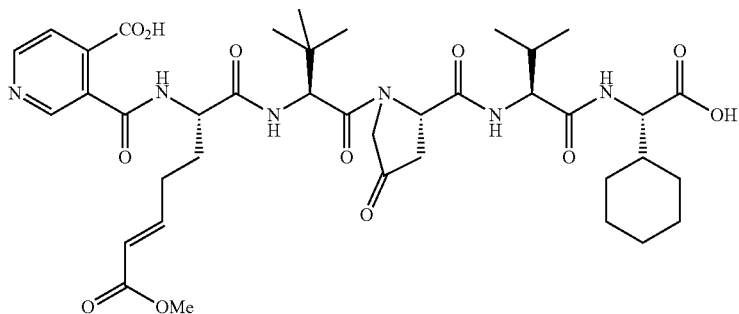

Compound 45b

A further aspect of the present invention relates to the production of compound of the formula (I). As shown in Scheme 1, a method for producing the compound of the present invention comprises:

Step (0): providing a protected amino acid Ia

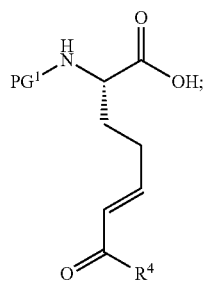

Ia

Step 1: (a) performing coupling reaction of the protected amino acid Ia with an amino acid building block IIa.

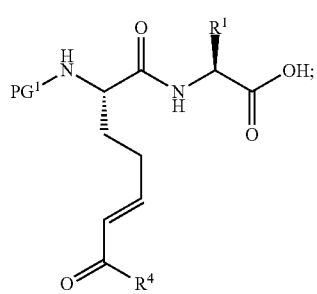

IIa (b) deprotecting an amino protecting group $PG^2$ of a resulting compound after Step (a); to obtain an intermediate compound 3a

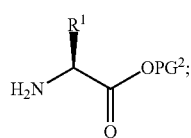

IIIa

Step 2: (a) performing coupling reaction of the intermediate compound IIIa of Step 1 with a corresponding C-terminal amino acid building block $H_2$-$A^i$-$OPG^3$;

(b) deprotecting the protecting group $PG^3$ of a resulting compound after Step (a);

(c) repeating the steps (a) and (b) i times, wherein i is 1-5, to obtain an intermediate compound IVa

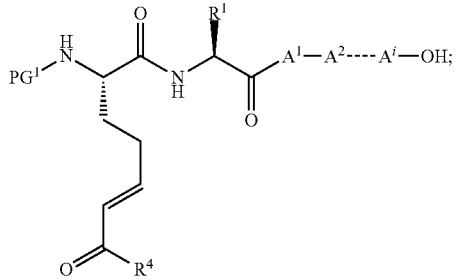

IVa

Step 3: performing coupling reaction of the intermediate compound IVa of Step 2 with a corresponding C-terminal building block H-E;

to obtain an intermediate compound Va

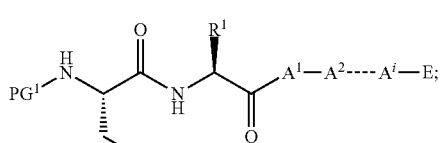

Va

Step 4: (a) deprotecting the protecting group $PG^1$ of the intermediate compound Va; (b) performing coupling reaction of a resulting compound after Step (a) with a N-terminal building block $R^3$—$CO_2H$ to produce the compound of the formula (I).

Scheme 1
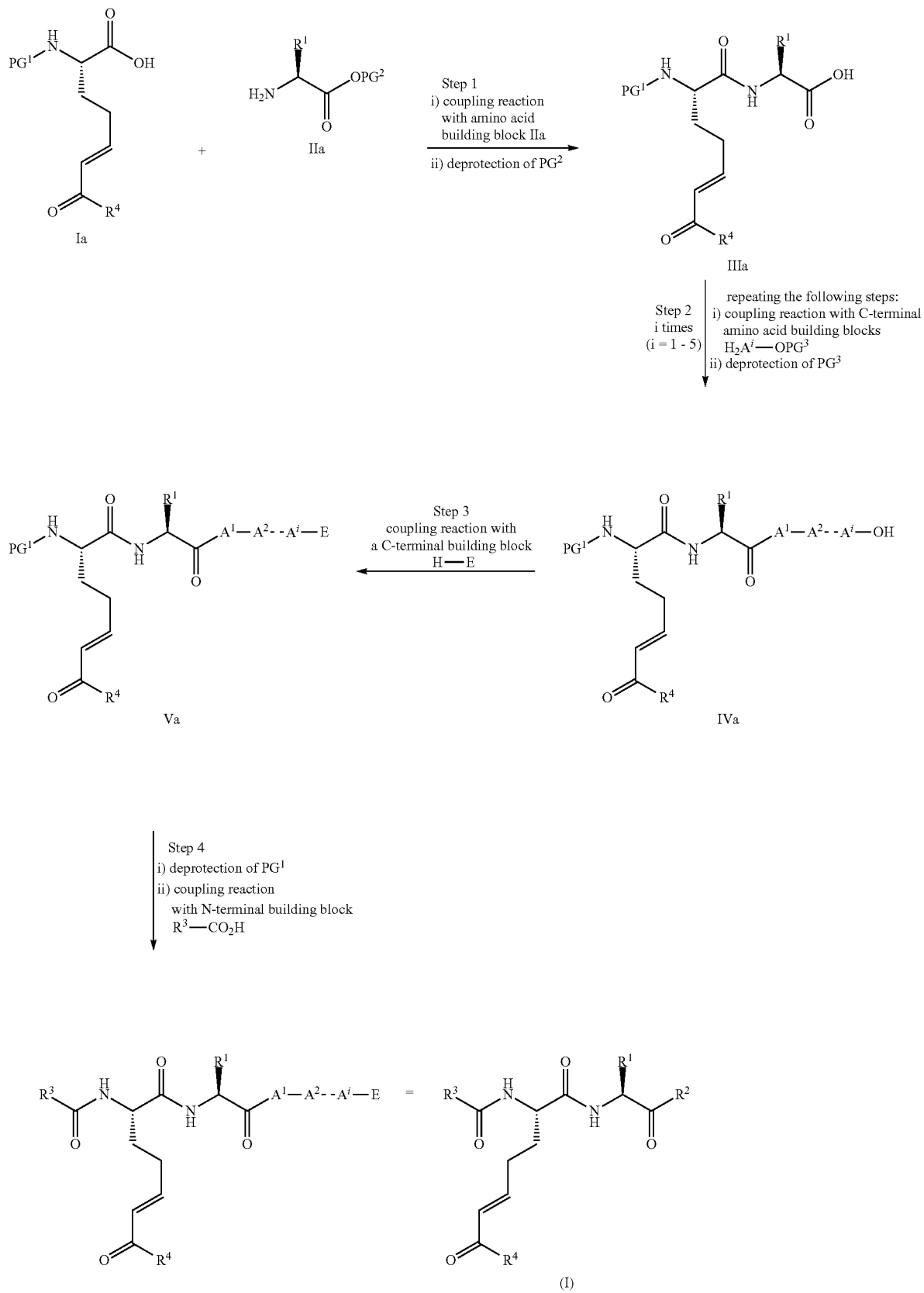

As shown in Scheme 2, an alternative method for producing the compound of the present invention comprises:
Step (0): providing a protected amino acid IIb

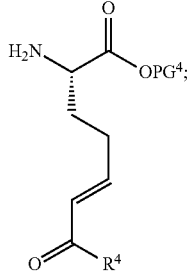

IIb

Step 1A: (a) performing coupling reaction of the protected amino acid IIb with a N-terminal building block $R^3$—$CO_2H$,
(b) deprotecting an amino protecting group $PG^4$ of a resulting compound after Step (a), to obtain an intermediate compound IIb

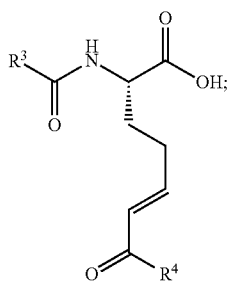

IIb

Step 2A: (a) performing coupling reaction of the intermediate compound IIb with an amino acid building block IIa

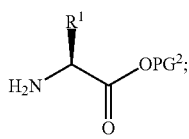

IIa (b) deprotecting an amino protecting group $PG^2$ of a resulting compound after Step (a); to obtain an intermediate compound IIIb.

IIIb

Step 3A: (a) performing coupling reaction of the intermediate compound IIIb with a corresponding C-terminal amino acid building block $H_2$-$A^i$-$OPG^3$;
(b) deprotecting the protecting group $PG^3$ of a resulting compound after Step (a);
(c) repeating the steps (a) and (b) i times, wherein i is 1-5, to obtain an intermediate compound IVb

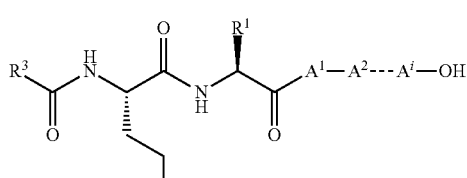

IVb

Step 4A: performing coupling reaction of the intermediate compound IVb with a corresponding C-terminal building block H-E to produce the compound of the formula (I).

Scheme 2

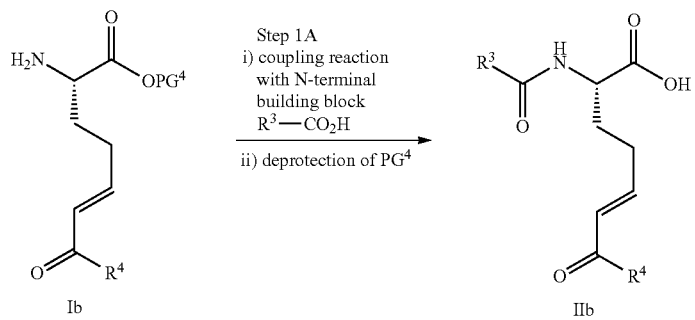

-continued

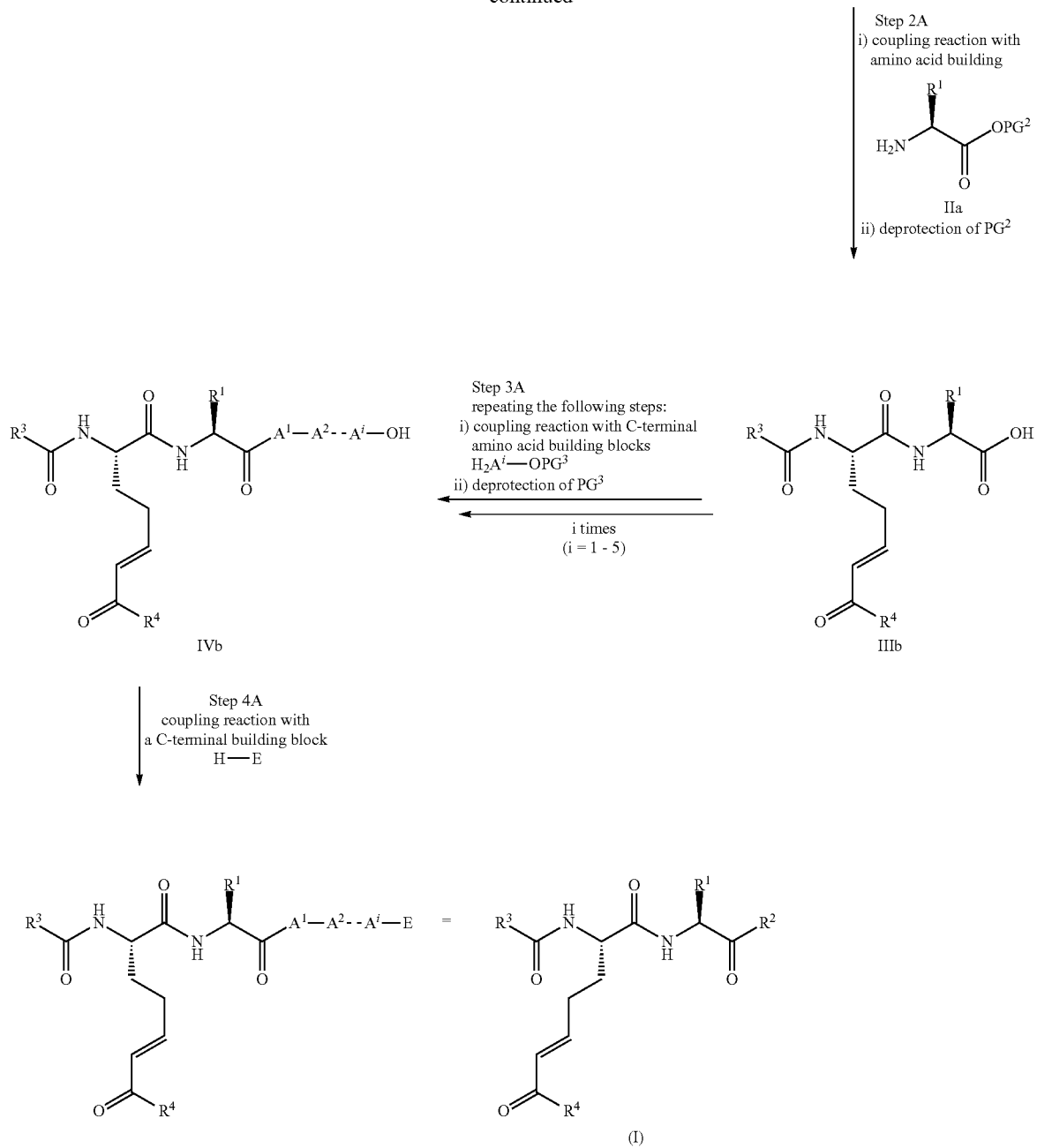

IVb

IIIb (I)

As shown in Scheme 3, an alternative method for producing the compound of the present invention comprises:

Step (0B): providing a resin, suitable for solid-phase peptide synthesis (SPPS).

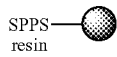

Step (1B) (a): performing coupling reaction of the corresponding C-terminal amino acid building block $PG^4NH-A^i$-OH.

(b) deprotecting the protecting group $PG^4$ of a resulting compound after Step (a);

(c) repeating the steps (a) and (b) i times, wherein i is 1-5, to obtain a resin bound intermediate compound (IIIc).

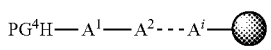

IIIc

Step (2B): cleavage from resin and deprotecting the protecting group $PG^4$ to obtain an intermediate compound (IIId).

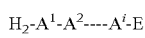

IIId-

Step (3B): performing coupling reaction of the intermediate compound IIId with an amino acid building block A0

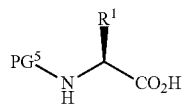

to obtain a compound IVc.

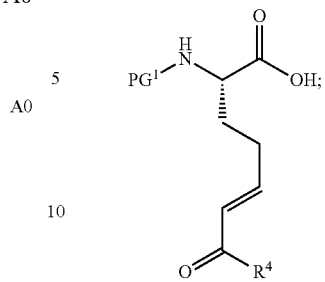

to obtain compound Vc

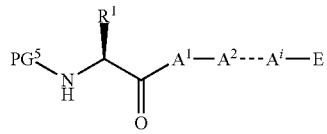

IVc

Step (4B): deprotecting the protecting group $PG^5$ and subsequent coupling reaction with protected amino acid Ia

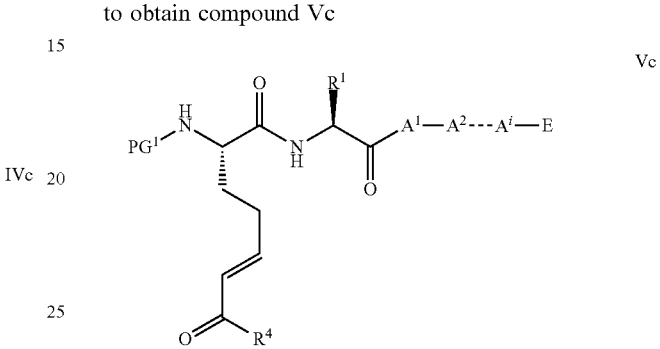

Step (5B): deprotecting the protecting group $PG^1$ and subsequent coupling reaction with a N-terminal building block $R^3$—$CO_2H$ to produce the compound of the formula (I).

Scheme 3

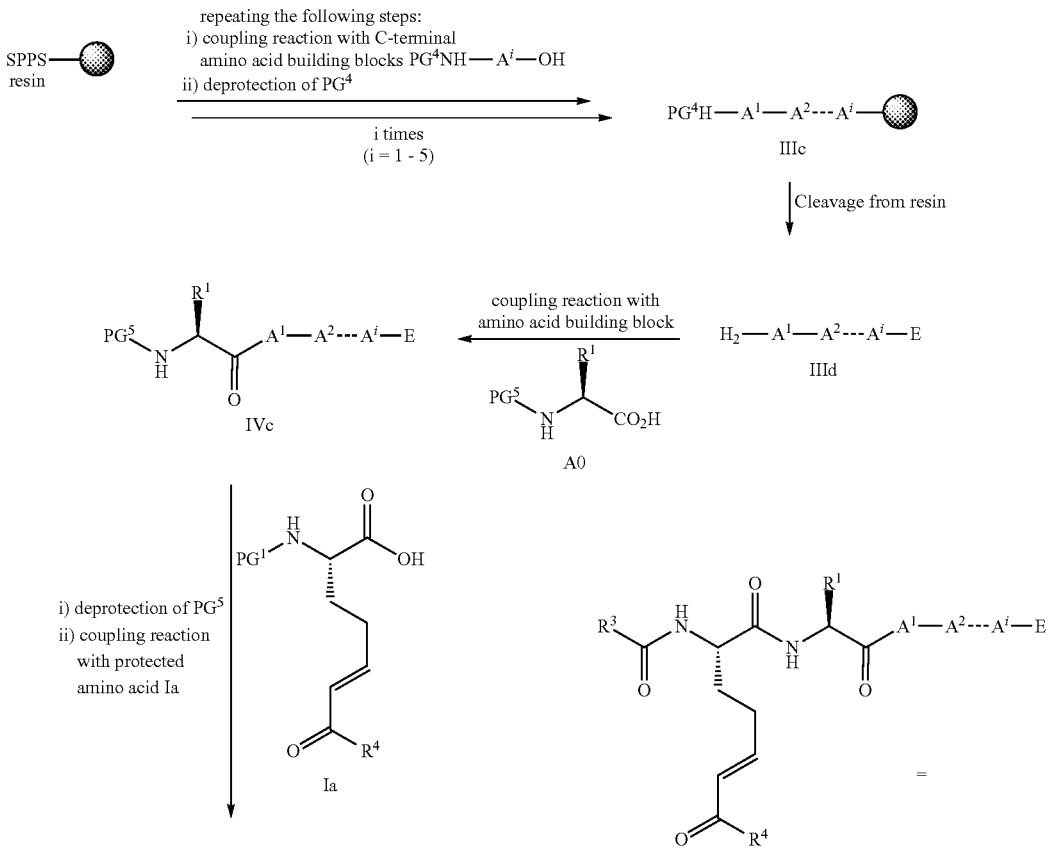

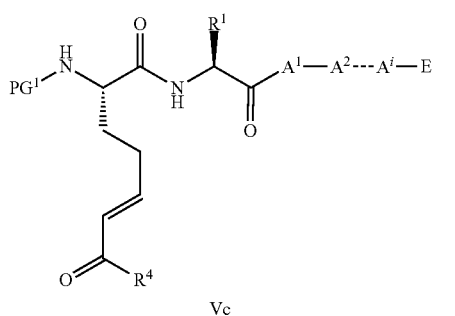

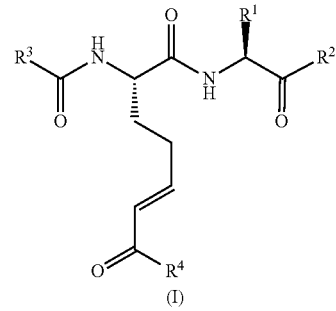

i) deprotection of PG¹ ii) coupling reaction with N-terminal building block R³—CO₂H

Vc (I)

As shown in Scheme 4, an alternative method for producing the compound of the present invention comprises:

Step (0C): providing a N-deprotected C-terminal building block H-E or H-A$^i$E.

Step (1C): (a) performing coupling reaction of the corresponding C-terminal amino acid building block PG⁴NH-A$^i$-OH or PG⁴NH-A$^{i-1}$-OH.

(b) deprotecting the protecting group PG⁴ of a resulting compound after Step (a);

(c) repeating the steps (a) and (b) i times, wherein i is 1-5 or 1-4, to obtain intermediate compound (IIId).

H₂-A¹-A²----A$^i$-E       (IIId)

Step (3B): performing coupling reaction of the intermediate compound IIId with an amino acid building block A0

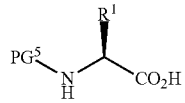

A0 to obtain a compound IVc.

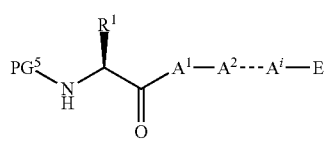

IVc

Step (4B): deprotecting the protecting group PG⁵ and subsequent coupling reaction with protected amino acid Ia

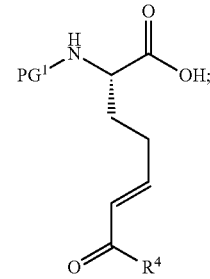

to obtain compound Vc

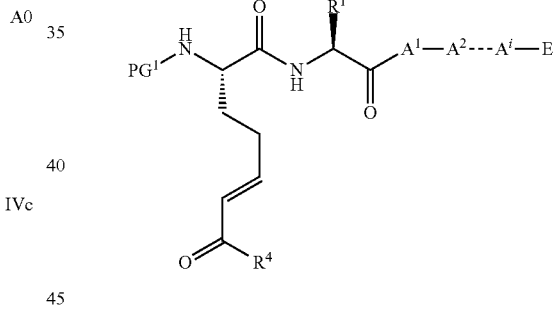

Vc

Step (5B): deprotecting the protecting group PG¹ and subsequent coupling reaction with a N-terminal building block R³—CO₂H to produce the compound of the formula (I).

Scheme 4

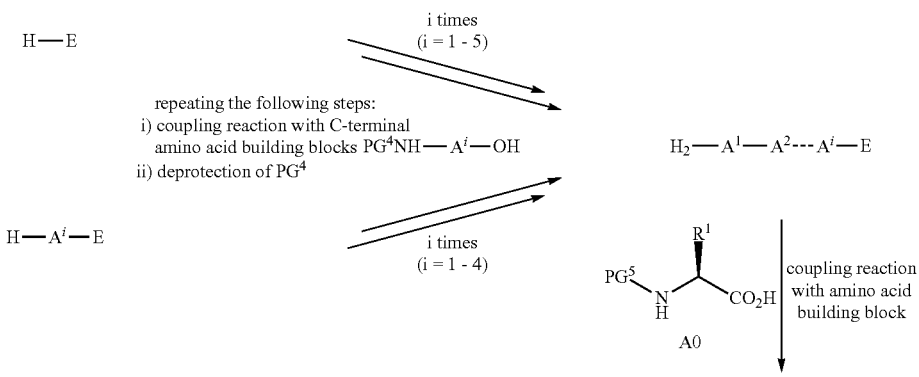

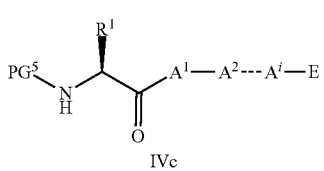
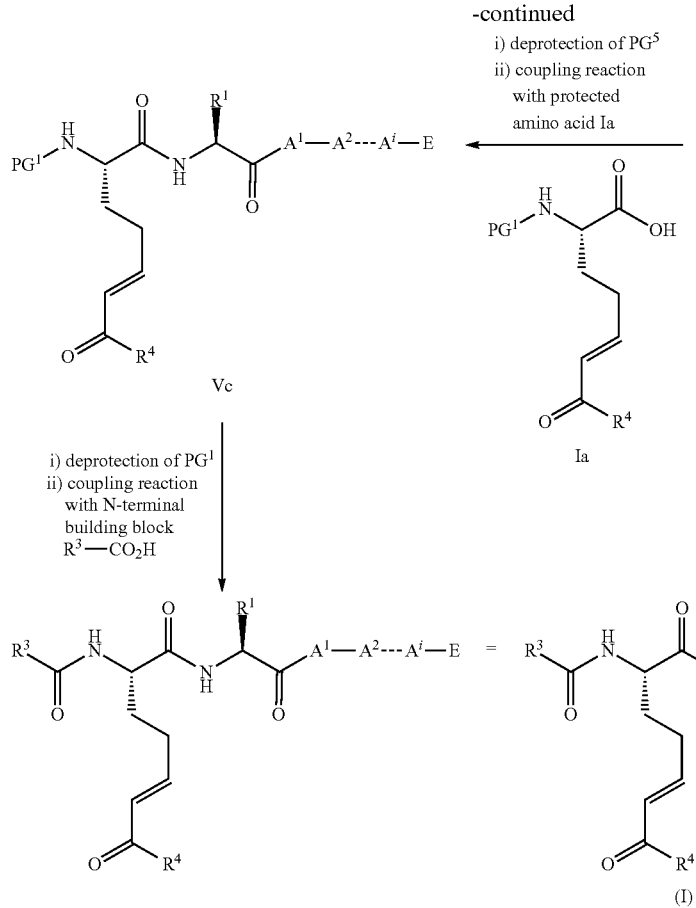

The above-described methods in schemes 3 and 4 may be also combined as follows:

A method for producing the compound of the present invention comprises:

Step (0B): providing a resin, suitable for solid-phase peptide synthesis (SPPS).

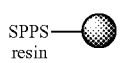

Step (1B) (a): performing coupling reaction of the corresponding C-terminal amino acid building block $PG^4NH$-$A^i$-OH.
(b) deprotecting the protecting group $PG^4$ of a resulting compound after Step (a);
(c) repeating the steps (a) and (b) i times, wherein i is 1-5, to obtain a resin bound intermediate compound (IIIc).

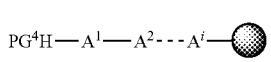

Step (2B): cleavage from resin and deprotecting the protecting group $PG^4$ to obtain an intermediate compound (IIId).

Step (3B): performing coupling reaction of the intermediate compound IIId with an amino acid building block A0

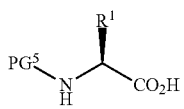

to obtain a compound IVc.

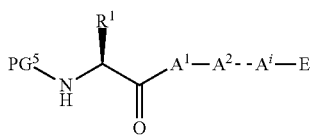

Step (4B): deprotecting the protecting group $PG^5$ and subsequent coupling reaction with protected amino acid Ia

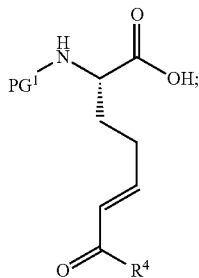

to obtain compound Vc

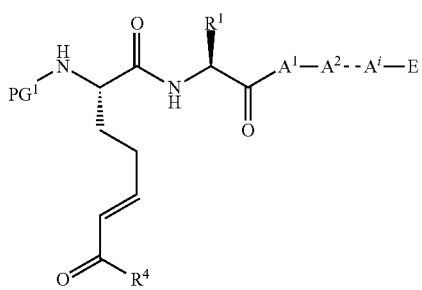

Step (5B): deprotecting the protecting group PG$^1$ and subsequent coupling reaction with a N-terminal building block R$^3$—CO$_2$H to produce the compound of the formula (I);

or

Step (0C): providing a N-deprotected C-terminal building block H-E or H-A$^i$-E.

Step (1C): (a) performing coupling reaction of the corresponding C-terminal amino acid building block PG$^4$NH-A$^i$-OH or PG$^4$NH-A$^{i-1}$-OH.

(b) deprotecting the protecting group PG$^4$ of a resulting compound after Step (a);

(c) repeating the steps (a) and (b) i times, wherein i is 1-5 or 1-4, to obtain intermediate compound (IIId).

Step (3B): performing coupling reaction of the intermediate compound IIId with an amino acid building block A0

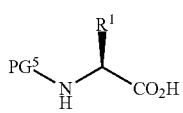

to obtain a compound IVc.

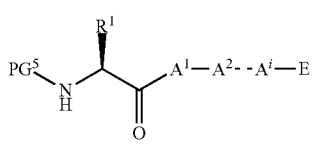

Step (4B): deprotecting the protecting group PG$^5$ and subsequent coupling reaction with protected amino acid Ia

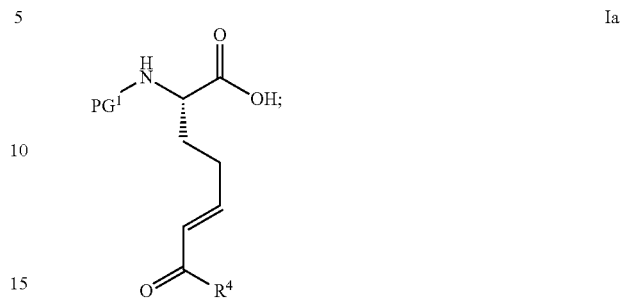

to obtain compound Vc

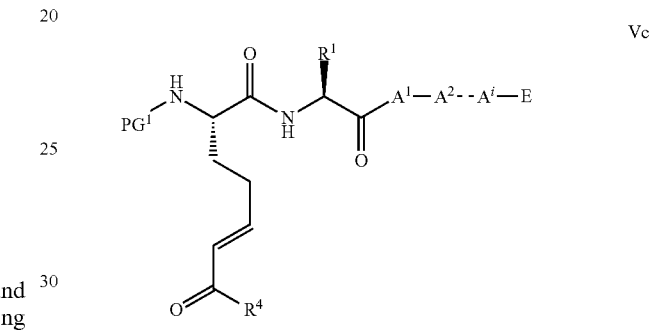

Step (5B): deprotecting the protecting group PG$^1$ and subsequent coupling reaction with a N-terminal building block R$^3$—CO$_2$H to produce the compound of the formula (I).

Herein, A$^i$ represents one of A$^1$, A$^2$, A$^3$, A$^4$, and A$^5$. H$_2$-A$^i$-OPG$^3$ means amino acid having A$^i$ (one of A$^1$-A$^5$) backbone and unprotected free amino (H$_2$N—) group and carboxyl moiety protected by PG$^3$ group.

The term "protecting groups" as used herein refers to commonly used protection groups in organic synthesis, preferably for amino and carboxyl groups. PG$^1$ and PG$^5$ are suitable protecting group for amino group. PG$^2$, PG$^3$ and PG$^4$ are suitable protecting groups for carboxyl groups. Preferably, PG$^1$ may be selected from the group consisting of or comprising: acetyl, benzoyl, benzyloxycarbonyl (Cbz), tert-butylcarbonyl, tert-butyloxycarbonyl (Boc), and fluorenylmethylenoxy group (Fmoc). PG$^2$, PG$^3$ and PG$^4$ may be selected from the group consisting of or comprising: methoxy, ethoxy, isobutoxy, tert-butoxy, benzyloxy; preferably, tert-butoxy group.

For the coupling reaction performed in Steps 1-4, 1A-4A, 1B, 1C, 3B-5B, the coupling reaction as used herein refers to commonly used in peptide synthesis. For preforming the coupling reaction, firstly carboxylic acid group is activated by introducing an activating group and promote the coupling reaction with amino group of amino acid building block. The activating group of carboxylic acid may be introduced by a separate reaction or in situ reaction. Preferably, the activating group may be selected from the group consisting of or comprising: halides such as —F, —Br, —Cl, —I, anhydride group such as —OCOCH$_3$, N-oxy-benzotriazol group and N-oxy-succinimide. Preferably, the activating group is introduced in situ and it is well-known in peptide chemistry. Any of the following coupling reagent can be used to introduce activating group: BOP, PyBOP, AOP, PyAOP, TBTU, EEDQ, Polyphosphoric Acid (PPA), DPPA, HATU, HOBt, HOAt, DCC, EDCl, BOP-Cl, TFFH, Brop, PyBrop, and CIP.

The warhear was synthesized following the route shown in Scheme 5.

medicament as well as use thereof in medicine. Especially preferred is the use in anticoagulation and as an inhibitor of transglutaminases, in particular factor XIII.

The compounds according to general formula (I) described herein are especially suitable for the treatment and

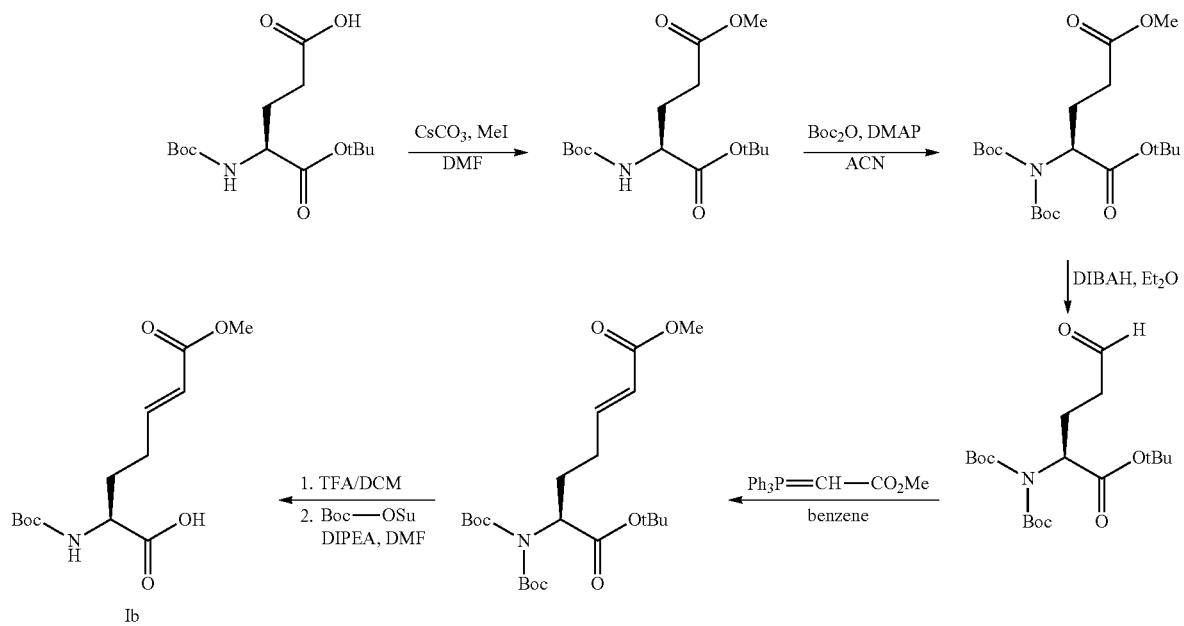

Scheme 5: Synthesis of Michael acceptor warhead Ib

The pharmaceutically acceptable salts of the compound of the present invention may be formed with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyttartaric acid, tartronic acid, (o, m, p)-toluic acid, naphthylamine sulfonic acid, trifluoroacetic acid, and other mineral or carboxylic acids well known to those skilled in the art. The salts are prepared by contacting the free base form with a sufficient amount of the desired acid to produce a salt in the conventional manner.

In the case the inventive compounds bear acidic groups, salts could also be formed with inorganic or organic bases. Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Therefore another aspect of the present invention relates to compound according to the general formula (I) for use as prophylaxis of diseases associated with and/or caused by transglutaminases, in particular factor XIII.

Therefore, another aspect of the present invention is the use of the inventive compounds of the general formula (I) for the treatment or prophylaxis of cardiovascular diseases, atherosclerosis, thrombosis, autoimmune diseases, neurodegenerative diseases, fibrotic disorders, dermatological diseases, wound healing and inflammatory diseases.

In particular, the compound of any one of the formulae (I), (II-1)-(II-3), (III), (III-2), (IV-1)-(IV-5), (V-1)-(V-2) and (VI) is useful for the treatment or prophylaxis of coeliac disease, Duhring-Brocq-disease, gluten ataxia, tissue fibrosis, cystic fibrosis, kidney fibrosis and diabetic nephropathy, liver fibrosis, cataract, ichthyosis, acne, psoriasis, skin aging, candidosis, neurodegenerative disorders including Huntington's disease, Parkinson's disease and Alzheimer's disease as well as atherosclerosis, thrombosis, thrombocytopenia and thrombopreventive indications and for use as anticoagulant in the treatment of sepsis, stroke, recurrent occlusion and acute care setting including acute kidney injury, acute lung injury and acute coronary syndrome.

Preferred potential indications for the compounds of the present invention mainly include thrombopreventive indications in groups of risk patients showing permanent plasmatic clotting activation. These groups include patients suffering from tumour diseases and, first and foremost, patients who need to undergo regular haemodialysis therapy. Preferred is anticoagulation using FXIII-inhibitors in patients with a high risk for bleeding and/or side-effects like heparin induced thrombocytopenia.

Further indications include older, multimorbid patients suffering from cardiac arrest and/or dysrhythmia, which are frequently associated with discrete vascular clotting diseases as well as progressive chronic renal diseases. Due to the unique mode-of-action, the compounds are preferred anticoagulants in the acute care setting like acute kidney injury, acute lung injury and acute coronary syndrome. Further indications include sepsis, stroke, and recurrent occlusion also in combination with plasminogen activators (e.g. tPA and uPA). However the most important indications are the prevention and treatment of atherosclerosis and thrombosis.

Due to the possible inactivation of other transglutaminase isoenzymes at least of some compounds also treatment or prophylaxis of, coeliac disease, Duhring-Brocq-disease, gluten ataxia, tissue fibrosis, cystic fibrosis, kidney fibrosis and diabetic nephropathy, liver fibrosis, cataract, ichthyosis, acne, psoriasis, skin aging and candidosis is claimed. Further blood brain barrier permeable compounds may be used for the treatment of neurodegenerative disorders including Huntington's disease, Parkinson's disease and Alzheimer's disease.

The term "transglutaminase dependent diseases" comprises all diseases, dysfunctions or other impairments of the health, which are caused by or in connection with a dysfunction, perturbance or hyperactivity of transglutaminases in the body. Alternatively, it might be of benefit for certain at risk patients to prophylactically block a transglutaminase like FXIII e.g. in thrombophilic patients.

The particular suitability of the inventive compounds of the general formula (I) is connected to the sterical and electronical properties which result from the molecule structure. The electrophilic warhead group appears to be an essential unit of the irreversible transglutaminase inhibitors, and especially in combination with the certain peptidomimetic backbone with certain kinds of amino acids at defined positions (like the position of the conformationally constrained proline or the unnatural proline-based amino acids called herein proline derivatives or proline analogues) results in potent transglutaminase inhibitors, especially blood coagulation factor XIII and transglutaminase 2. Selectivity is obtained by implementing said components at selected positions within the backbone.

The pharmaceutical compositions according to the present invention comprise at least one compound according to the present invention. Preferably, the pharmaceutical compositions according to the present invention comprise at least one compound according to the present invention as an active ingredient together with at least one pharmaceutically acceptable (i.e. non-toxic) carrier, excipient and/or diluent.

The Pharmaceutical composition according to the present invention is useful for the treatment or prophylaxis of coeliac disease, Duhring-Brocq-disease, gluten ataxia, tissue fibrosis, cystic fibrosis, kidney fibrosis and diabetic nephropathy, liver fibrosis, cataract, ichthyosis, acne, psoriasis, skin aging, candidosis, neurodegenerative disorders including Huntington's disease, Parkinson's disease and Alzheimer's disease as well as atherosclerosis, thrombosis, thrombocytopenia and thrombopreventive indications and for use as anticoagulant in the treatment of sepsis, stroke, recurrent occlusion and acute care setting including acute kidney injury, acute lung injury and acute coronary syndrome.

The present invention also includes pharmaceutical preparations for parenteral application, including dermal, intradermal, intragastral, intracutaneous, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen.

The following abbreviations are used for the common and modified amino acids referred to herein.

| Abbreviation | Amino acid |
| --- | --- |
| Ala | Alanine |
| Arg | Arginine |
| Asn | Asparagine |
| Asp | Aspartic acid (Aspartate) |
| Chg | Cyclohexylglycin |
| Cys | Cysteine |
| Gln | Glutamine |
| Glu | Glutamic acid (Glutamate) |
| Gly | Glycine |
| His | Histidine |
| Ile | Isoleucine |
| Leu | Leucine |
| Lys | Lysine |
| Met | Methionine |
| Nle | Norleucine |
| Phe | Phenylalanine |
| Pro | Proline |
| Ser | Serine |
| Sec | Selenocysteine |
| Thr | Threonine |
| Trp | Tryptophan |
| Tyr | Tyrosine |
| Val | Valine |

A: Gel permeation chromatography of hydrolyzed fibrinclots. Inhibition of cFXIII by compound 5 (dashed line) during fibrin clotting resulted in a shift of the main peak towards lower molecular weight products compared to control without inhibitor (solid line). Void volume ($V_0$) and total volume ($V_t$) of the GPC column as well as the apparent molecular mass of the (x)FDPs are indicated.

B: SDS-PAGE and Western blot analysis of human fibrinogen (FGN) and the main peak fractions (xFDPs/FDPs) of the gel permeation chromatography. Samples were analyzed under non-reducing conditions. SDS-PAGE revealed either the most characteristic "D-dimer" band or the "D-domain" degradation products (Fragments D). The monoclonal antibody against the fibrin γ-chain showed a pattern similar to the Coomassie staining while the novel "DD-XLink-mab" (Zedira, A076) specifically recognized the isopeptide bond in the D-dimer product.

Figure 2:
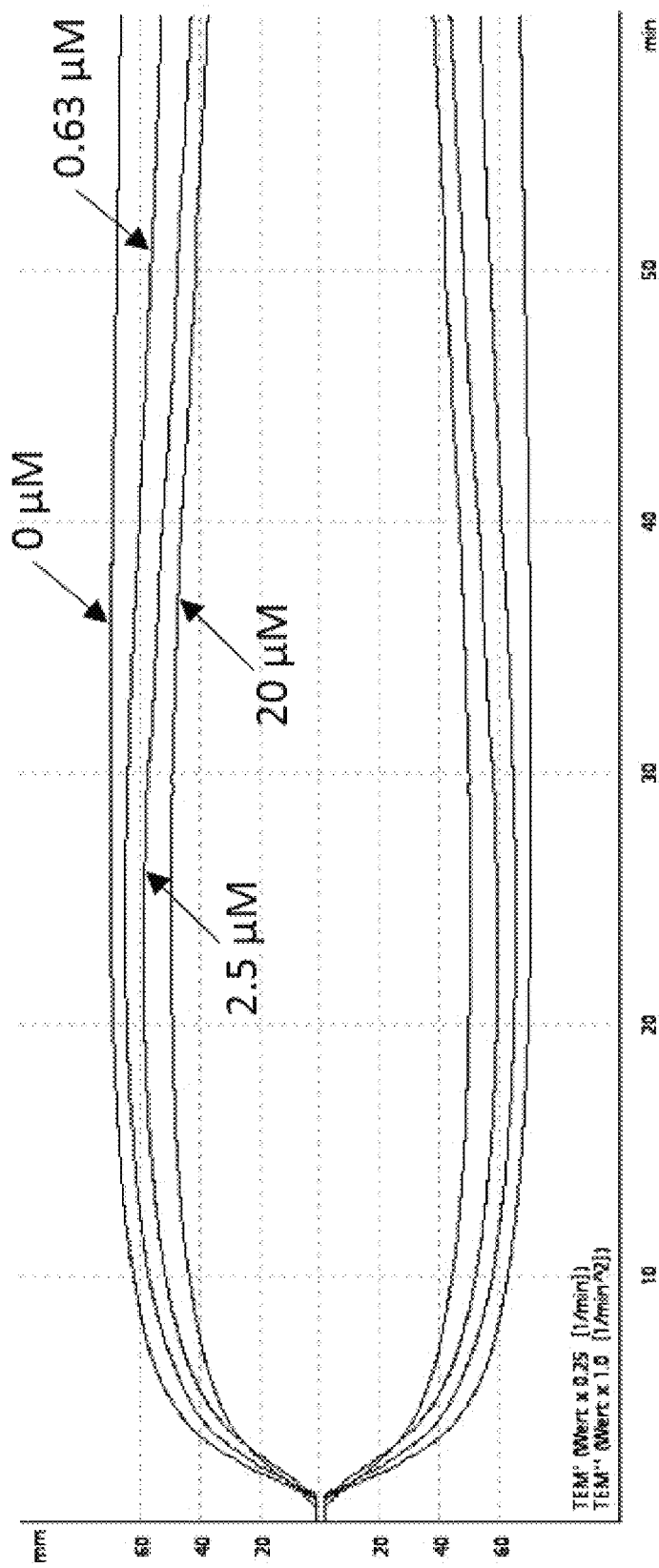

FIG. 2 shows the thromboelastogram of whole human blood spiked with compound 5. Graphs represent concentrations [µM] of 0, 0.63, 2.5, 20 µM from high MCF [mm] to low.

Figure 3:
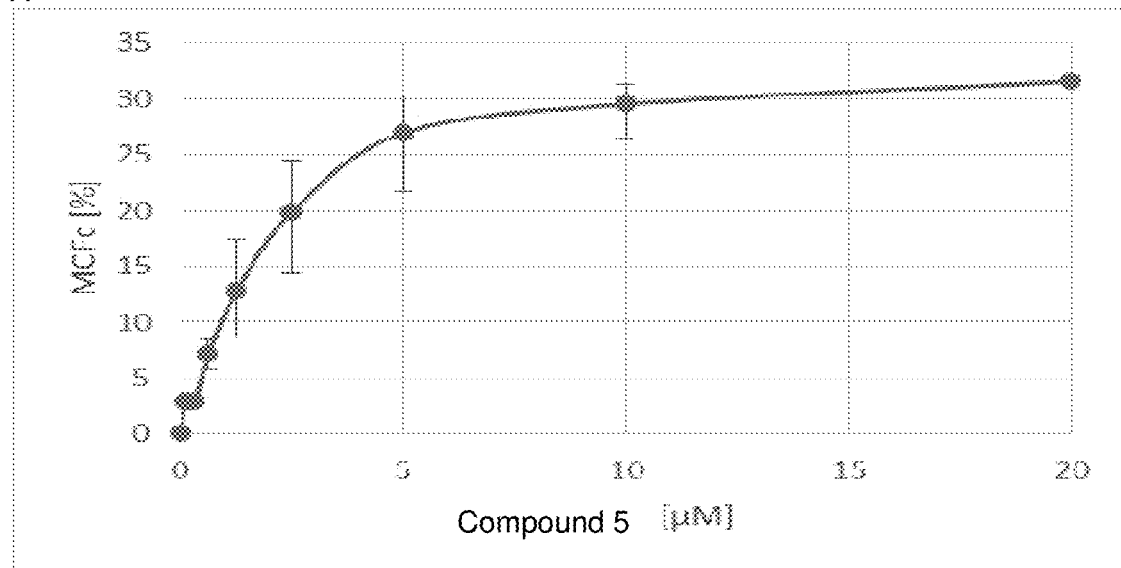
Figure 3:
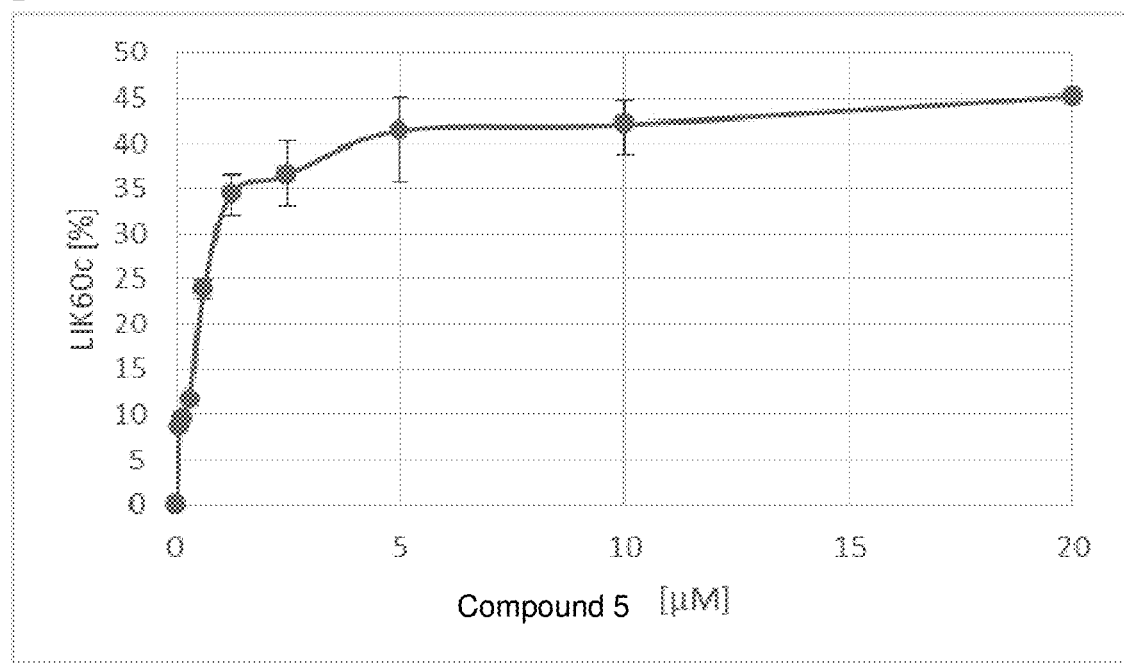

FIG. 3: two graphs (A) and (B) show the reduction of maximum clot firmness compared to inhibitor-free control (MCFc) and the increase in clot lysis at 60 minutes compared to control (Ll60c).

FIG. 4:

A: Experimental schedule of the rabbit model of venous stasis and reperfusion. B.S.: Blood sample; BL: Baseline; TEG: Thromboelastography.

B: The in vivo experiment proofs significantly higher flow rates after compound 5 infusion compared to PBS control animals. Data is depicted as mean±S.E.M. (n=6-7)

C: The area under the curve of flow rate is in accordance to the vein flow rate. In the compound 5 group the mean areas under the curve (AUC) of the jugular flow rate normalized to baseline between time points 35 and 135 minutes are significantly higher. Data is depicted as mean±S.E.M. (n=6-7).

D: The Thrombus wet weight is significantly reduced in the compound 5 group. Thrombus wet weight was determined after 135 min of infusion. Data is depicted as dot plot with mean±S.E.M. (n=6-7, p=0.0265).

E: Most importantly the template skin bleeding time is not influenced. Template skin bleeding time was determined after 60 min of infusion. No difference between PBS and compound 5 was observed. Maximal observation time was pre-defined at 300 seconds. Data is depicted as dot plot with mean±S.E.M. (n=7-8).

EXAMPLES

Following abbreviations used in the examples have the following meaning.

DMAP: 4-(Dimethylamino)-pyridine
TEA: Triethylamine
DMF: Dimethylformamide
DIPEA: N-Ethyldiisopropylamine
TFA: Trifluoroacetic acid
EtOAc Ethyl acetate
HATU 1-[Bis(dimethylamino)methylene]-1H-1,2,3-triazolo[4,5-b]pyridinium 3-oxid hexafluorophosphate
PyAOP (7-Azabenzotriazol-1-yloxy)tripyrrolidinophosphonium hexafluorophosphate

CHEMICAL EXAMPLES

The following examples are intended to illustrate the invention with selected compounds without limiting the protecting scope of the present intellectual property right on these concrete examples. It is clear for a person skilled in the art that analogous compounds and compounds produced according to analogous synthetic ways fall under the protecting scope of the present intellectual property right.

Preparation of Compound ZED788

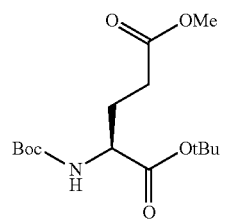

(S)-1-tert-butyl 5-methyl 2-(tert-butoxycarbonylamino)pentanedioate
Chemical Formula: $C_{15}H_{27}NO_6$
Exact Mass: 317.18
Molecular Weight: 317.38

12.0 g of Boc-L-Glu-OtBu (39.6 mmol) and 7.09 g of cesium carbonate (21.8 mmol, 0.55 eq) were suspended in 100 ml of DMF and stirred for 1 h at room temperature. 2.47 ml iodomethane (39.6 mmol) we added and the mixture was stirred at room temperature over night. The solvent was evaporated and the residue was dissolved in ethyl acetate and washed with twice with each citric acid solution (10%), $NaHCO_3$ solution (10%) and brine. The organic phase was dried over $Na_2SO_4$, filtered and the solvent was evaporated. The raw product was used without further purification.

Yield: 13.4 g, >100%; ESI-MS: 318.3 [M+H]$^+$

Preparation of Compound ZED720

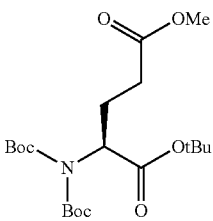

(S)-1-tert-butyl 5-methyl 2-(bis(tert-butoxycarbonyl)amino)pentanedioate
Chemical Formula: $C_{20}H_{35}NO_8$
Exact Mass: 417.24
Molecular Weight: 417.49

13.4 g of ZED788 (~39.6 mmol) and 986 mg of N,N-dimethyl-4-aminopyridine (DMAP) were dissolved in 30 ml of acetonitrile. 17.6 g of di-tert-butyl bicarbonate (77.1 mmol) in 100 ml of acetonitrile was added and the solution was stirred at room temperature over night. The solvent was evaporated and the residue was dissolved in ethyl acetate and washed with twice with each citric acid solution (10%), $NaHCO_3$ solution (10%) and brine. The organic phase was dried over $Na_2SO_4$, filtered and the solvent was evaporated. The raw product was used without further purification.

Yield: 13.7 g, 83%
ESI-MS: 418.3 [M+H]$^+$

Preparation of Compound ZED721

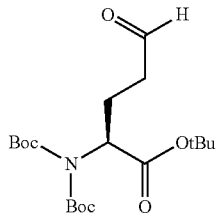

(S)-tert-butyl 2-(bis(tert-butoxycarbonyl)amino)-5-oxopentanoate
Chemical Formula: $C_{19}H_{33}NO_7$
Exact Mass: 387.23
Molecular Weight: 387.47

13.7 g of ZED720 (32.8 mmol) were dissolved in 200 ml of dry diethyl ether and cooled to −78° C. under argon atmosphere. 36.1 ml of diisobutylaluminum hydride (1M in hexane) were added dropwise and the solution was stirred for 30 min at −78° C. before being quenched with potassium sodium tartrate (Rochelle salt) solution. The organic layer was separated, dried over Na$_2$SO$_4$, filtered and concentrated to dryness. The raw product was used without further purification.

Yield: 13.3 g, >100%
ESI-MS: 388.3 [M+H]$^+$

Preparation of Compound ZED755

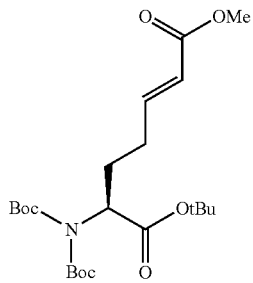

(S,E)-7-tert-butyl 1-methyl 6-(bis(tert-butoxycarbonyl)amino)hept-2-enedioate
Chemical Formula: C$_{22}$H$_{37}$NO$_8$
Exact Mass: 443.25
Molecular Weight: 443.53

13.3 g of ZED721 (~32.8 mmol) were dissolved in 60 ml of benzene and 11.2 g of (carbmethoxymethylene)-triphenylphosphorane (1 eq) was added portionwise. After stirring overnight, the solvent was evaporated. The residue was purified by flash chromatography.

Yield: 12.0 g, 83%
ESI-MS: 444.3 [M+H]$^+$

Preparation of compound Ib

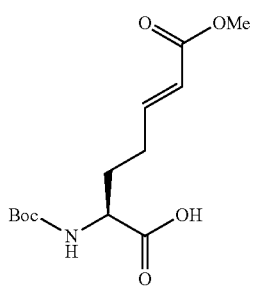

(S,E)-2-(tert-butoxycarbonylamino)-7-methoxy-7-oxohept-5-enoic acid
Chemical Formula: C$_{13}$H$_{21}$NO$_6$
Exact Mass: 287.14
Molecular Weight: 287.31

12.0 g of ZED755 (27.1 mmol) are dissolved in 100 ml DCM/TFA (1:1) and stirred at room temperature for 1 h. The solvent was evaporated and the residue was dissolved in 100 ml DMF and 9.23 ml DIPEA (2 eq). 7.15 g of N-(tert-Butoxycarbonyloxy)succinimide were added and the reaction was stirred at room temperature overnight. The solvent was evaporated and the residue was dissolved in ethyl acetate and washed with twice with each citric acid solution (10%) and brine. The organic phase was dried over Na$_2$SO$_4$, filtered and the solvent was evaporated. The residue was purified by flash chromatography.

Yield: 5.89 g, 76%
ESI-MS: 288.3 [M+H]$^+$

Preparation of Compound Ic

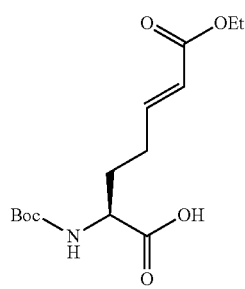

(S,E)-2-(tert-butoxycarbonylamino)-7-ethoxy-7-oxohept-5-enoic acid
Chemical Formula: C$_{14}$H$_{23}$NO$_6$
Exact Mass: 301.15
Molecular Weight: 301.34

The synthesis of Ic was performed according to Ib, using (carbethoxymethylene)-triphenylphosphorane in step 4.

Yield: 3.27 g, 59% (last step)
ESI-MS: 302.3 [M+H]$^+$

Preparation of Compound Id

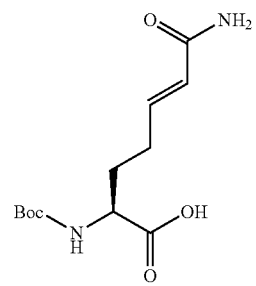

(S,E)-7-amino-2-(tert-butoxycarbonylamino)-7-oxohept-5-enoic acid
Chemical Formula: C$_{12}$H$_{20}$NO$_5$
Exact Mass: 272.14
Molecular Weight: 272.30

The synthesis of Id was performed according to Ib, using triphenylphosphonium carbamoylmethylide in step 4.

Yield: 623 mg, 36% (last step)
ESI-MS: 273.3 [M+H]$^+$

Preparation of Compound Ie

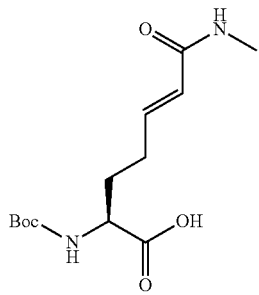

(S,E)-2-(tert-butoxycarbonylamino)-7-
(methylamino)-7-oxohept-5-enoic acid
Chemical Formula: $C_{13}H_{22}N_2O_5$
Exact Mass: 286.15
Molecular Weight: 286.32

The synthesis of Ie was performed according to Ib, using N-methyl-triphenylphosphonium carbamoylmethylide in step 4.

Yield: 241 mg, 32% (last step)

ESI-MS: 287.3 $[M+H]^+$

Preparation of Compound ZED3478

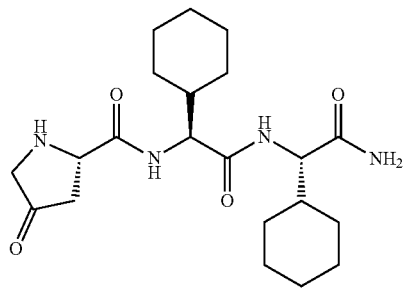

(S)-N-((S)-2-((S)-2-amino-1-cyclohexyl-2-oxoethylamino)-
1-cyclohexyl-2-oxoethyl)-4-oxopyrrolidine-2-carboxamide
Chemical Formula: $C_{21}H_{34}N_4O_4$
Exact Mass: 406,26
Molecular Weight: 406,52

ZED3478 was synthesized by standard Fmoc solid-phase peptide chemistry (reactions in DMF, coupling with TBTU/HOBt/DIPEA, deprotection with piperidine) using 0.41 g (0.28 mmol) Rink Amide MBHA resin as starting material. Coupling of N-alpha-(9-Fluorenylmethyloxycarbonyl)-L-cyclohexylglycine (twice), followed by (S)—N-Boc-4-oxopyrrolidine-2-carboxylic acid led to Boc-protected resin bound "Boc-ZED3478-resin". Subsequently, ZED3478 was cleaved from the resin (using 95% TFA/2.5% water/2.5% triisopropylsilane). The solution was reduced and the raw product (TFA salt) was precipitated from diethyl ether.

Yield: 124 mg, 85%; ESI-MS: 407.3 $[M+H]^+$

Preparation of Compound ZED3480

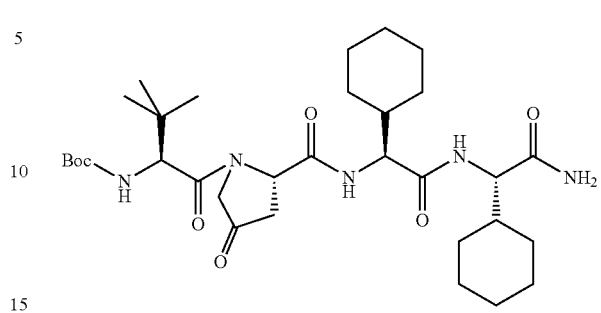

tert-butyl (S)-1-((S)-2-((S)-2-((S)-2-amino-1-cyclohexyl-2-
oxoethylamino)-1-cyclohexyl-2-oxoethylcarbamoyl)-4-
oxopyrrolidin-1-yl)-3,3-dimethyl-1-oxobutan-2-ylcarbamate
Chemical Formula: $C_{32}H_{53}N_5O_7$
Exact Mass: 619,39
Molecular Weight: 619,79

124 mg (0.24 mmol) of ZED3478 were dissolved in 5 ml DMF. 55.5 mg (1 eq) Boc-L-tert-leucine, 91.3 mg (1 eq) HATU and 81.6 µl (2 eq) DIPEA were added and the reaction was stirred at room temperature overnight. The solvent was evaporated and the residue was dissolved in ethyl acetate and washed with twice with each citric acid solution (10%), NaHCO$_3$ solution (10%) and brine. The organic phase was dried over Na$_2$SO$_4$, filtered and the solvent was evaporated. The raw product was used without further purification.

Yield: 119 mg, 80%; ESI-MS: 620.5 $[M+H]^+$

Preparation of Compound ZED3481

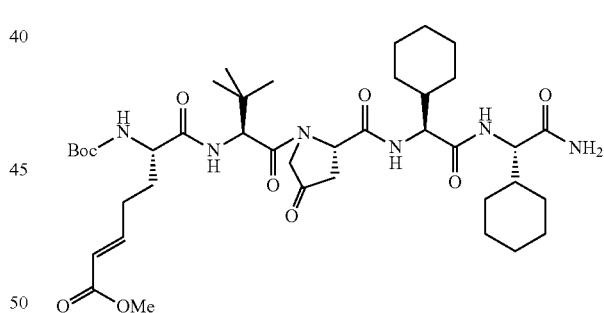

(S,E)-methyl 7-((S)-1-((S)-2-((S)-2-((S)-2-amino-1-cyclohexyl-2-
oxoethylamino)-1-cyclohexyl-2-oxoethylcarbamoyl)-4-oxopyrrolidin-1-
yl)-3,3-dimethyl-1-oxobutan-2-ylamino)-6-(tert-butoxycarbonylamino)-
7-oxohept-2-enoate
Chemical Formula: $C_{40}H_{64}N_6O_{10}$
Exact Mass: 788,47
Molecular Weight: 788,97

119 mg (0.19 mmol) of ZED3480 were dissolved in 6 ml DCM/TFA (1:1) and stirred at room temperature for 1 h. The solvent was evaporated and the residue was dissolved in 5 ml DMF. 54.6 mg (1 eq) Ib, 72.2 mg (1 eq) HATU and 64.6 µl (2 eq) DIPEA were added and the reaction was stirred at room temperature overnight. The solvent was evaporated and the residue was dissolved in ethyl acetate and washed with twice with each citric acid solution (10%), NaHCO$_3$ solution (10%) and brine. The organic phase was dried over $Na_2SO_4$, filtered and the solvent was evaporated. The raw product was used without further purification.

Yield: 86 mg, 57%; ESI-MS: 789.6 $[M+H]^+$

Example 1-1. Preparation of Compounds 1a/b

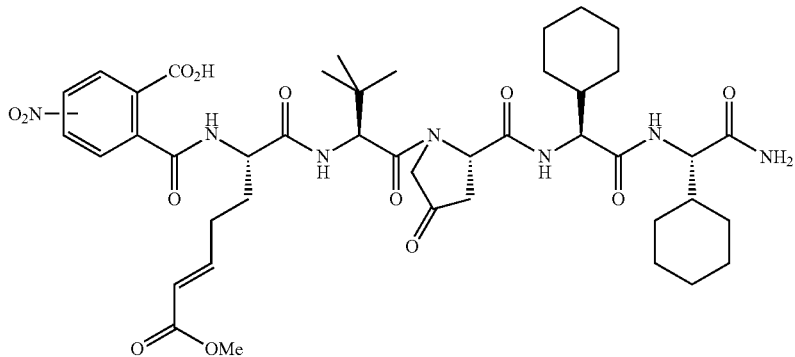

2-((S,E)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-7-methoxy-1,7-dioxohept-5-en-2-ylcarbamoyl)-4/5-nitrobenzoic acid Chemical Formula: $C_{43}H_{59}N_7O_{13}$ Exact Mass: 881,42

Molecular Weight: 881,97

86 mg (0.11 mmol) of ZED3481 were dissolved in 5 ml DCM/TFA (1:1) and stirred at room temperature for 1 h. The solvent was evaporated and the residue was dissolved in 3 ml DMF. 19.6 mg (1 eq) 4-nitrophthalic anhydride and 37 µl (2 eq) DIPEA were added and the reaction was stirred at room temperature overnight. The solvent was evaporated and the residue was purified by HPLC.

Yield: 26 mg, 27%, ratio of regioisomers: approximately 1:1

ESI-MS: 882.5 $[M+H]^+$

Example 1-2. Preparation of Compounds 2a/b

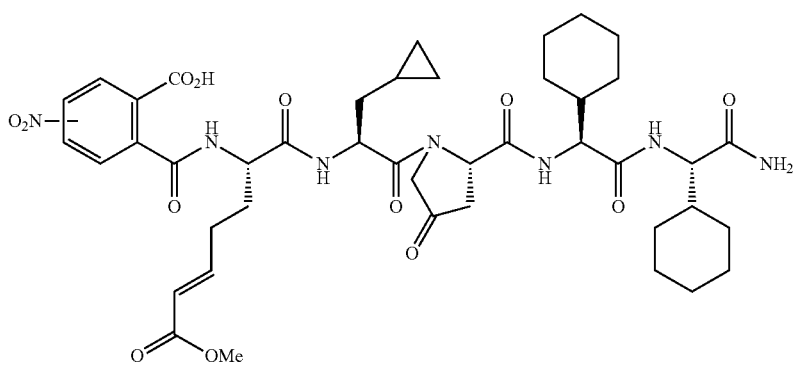

2-((S,E)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3-cyclopropyl-1-oxopropan-2-ylamino)-7-methoxy-1,7-dioxohept-5-en-2-ylcarbamoyl)-4/5-nitrobenzoic acid Chemical Formula: $C_{43}H_{52}N_7O_{13}$ Exact Mass: 879,40

Molecular Weight: 879,95

The synthesis of example 1-2 was performed according to example 1-1, using the corresponding amino acids.
Yield: 21 mg, 36%, ratio of regioisomers: approximately 1:1
ESI-MS: 880.5 [M+H]⁺

Example 1-3. Preparation of Compound 3

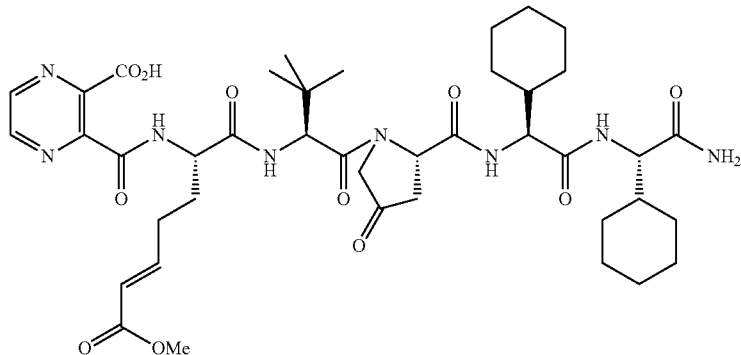

3-((S,E)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-7-methoxy-1,7-dioxohept-5-en-2-ylcarbamoyl)pyrazine-2-carboxylic acid
Chemical Formula: $C_{41}H_{58}N_8O_{11}$
Exact Mass: 838,42
Molecular Weight: 838,95

The synthesis of example 1-3 was performed according to example 1-1, using the corresponding anhydride.
Yield: 39 mg, 49%
ESI-MS: 839.5 [M+H]⁺

Example 1-4. Preparation of Compound 4

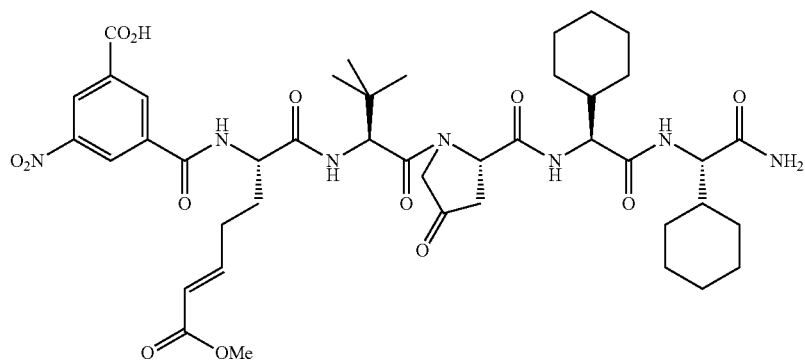

3-((S,E)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-7-methoxy-1,7-dioxohept-5-en-2-ylcarbamoyl)-5-nitrobenzoic acid
Chemical Formula: $C_{43}H_{59}N_7O_{13}$
Exact Mass: 881,42
Molecular Weight: 881,97

The synthesis of example 1-4 was performed according to example 1-1, using the corresponding carboxylic acid.
Yield: 18 mg, 26%
ESI-MS: 882.5 [M+H]⁺

Example 1-5. Preparation of Compounds 5a/b

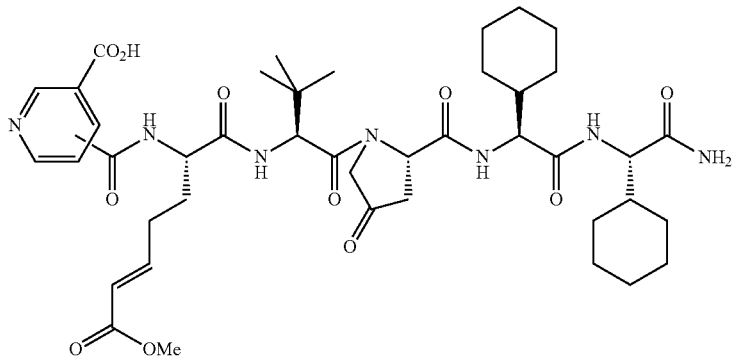

3/4-((S,E)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-7-methoxy-1,7-dioxohept-5-en-2-ylcarbamoyl)iso/nicotinic acid
Chemical Formula: $C_{42}H_{59}N_7O_{11}$
Exact Mass: 837,43
Molecular Weight: 837,96

The synthesis of example 1-5 was performed according to example 1-1, using the corresponding anhydride.
Yield: 1.03 g, 48%, ratio of regioisomers: approximately 1:1
ESI-MS: 838.6 [M+H]$^+$ Example 1-6. Preparation of Compound 6

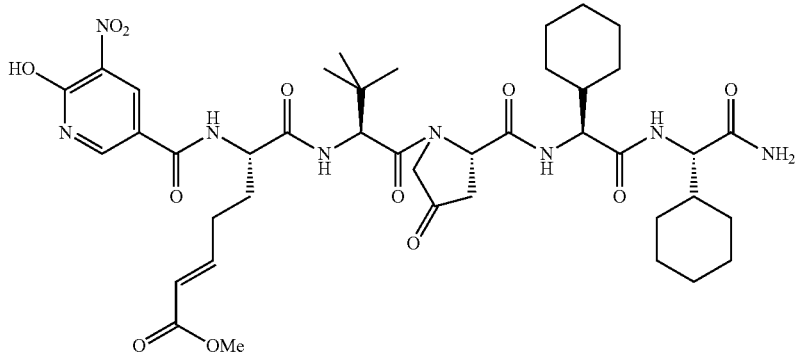

((S,E)-methyl 7-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(6-hydroxy-5-nitronicotinamido)-7-oxohept-2-enoate
Chemical Formula: $C_{41}H_{58}N_8O_{12}$
Exact Mass: 854,42
Molecular Weight: 854,95

The synthesis of example 1-6 was performed according to example 1-1, using the corresponding carboxylic acid.
Yield: 12 mg, 18%
ESI-MS: 855.5 [M+H]$^+$ Example 1-7. Preparation of Compounds 7a/b

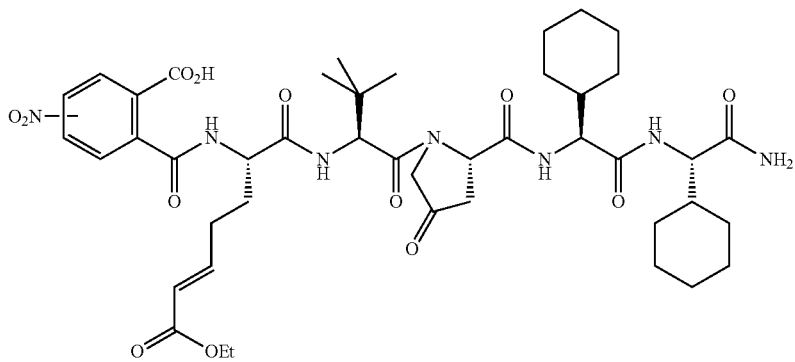

2-((S,E)-1-((S)-1-((S)-2-((S)-2-((S)-2-amino-1-cyclohexyl-2-oxoethylamino)-1-
cyclohexyl-2-oxoethylcarbamoyl)-4-oxopyrrolidin-1-yl)-3,3-dimethyl-1-oxobutan-2-
ylamino)-7-ethoxy-1,7-dioxohept-5-en-2-ylcarbamoyl)-4/5-nitrobenzoic acid
Chemical Formula: $C_{44}H_{61}N_7O_{13}$
Exact Mass: 895,43
Molecular Weight: 895,99

The synthesis of example 1-7 was performed according to example 1-1, using the corresponding building block Ic.
Yield: 63 mg, 52%, ratio of regioisomers: approximately 1:1
ESI-MS: 896.6 [M+H]$^+$ Example 1-8. Preparation of Compounds 8a/b

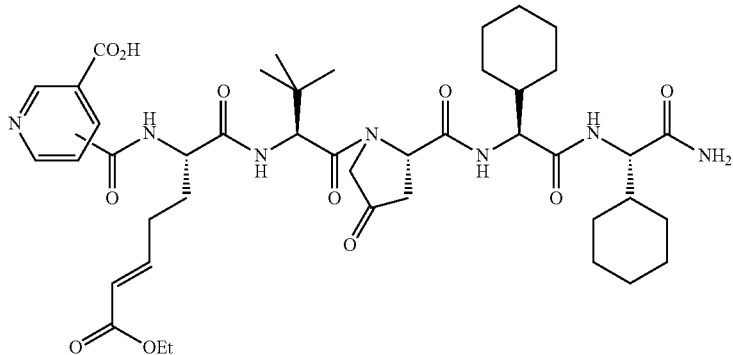

3/4-((S,E)-1-((S)-1-((S)-2-((S)-2-((S)-2-amino-1-cyclohexyl-2-oxoethylamino)-1-
cyclohexyl-2-oxoethylcarbamoyl)-4-oxopyrrolidin-1-yl)-3,3-dimethyl-1-oxobutan-2-
ylamino)-7-ethoxy-1,7-dioxohept-5-en-2-ylcarbamoyl)iso/nicotinic acid
Chemical Formula: $C_{43}H_{61}N_7O_{11}$
Exact Mass: 851,44
Molecular Weight: 851,98

The synthesis of example 1-8 was performed according to example 1-1, using the corresponding anhydride and building block Ic.
Yield: 46 mg, 49%, ratio of regioisomers: approximately 1:1
ESI-MS: 852.6 [M+H]$^+$ Example 1-9. Preparation of Compounds 9a/b

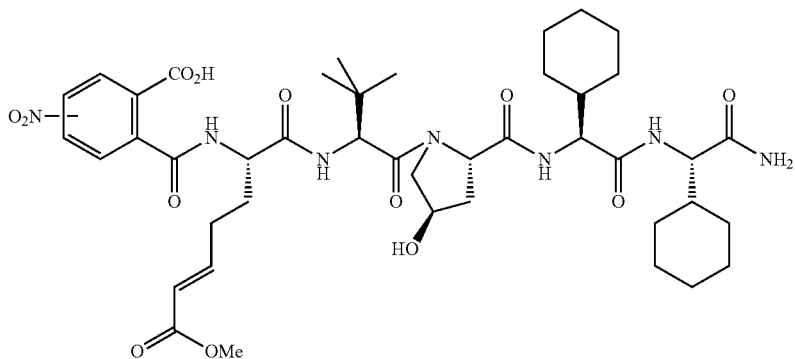

2-((S,E)-1-(((S)-1-(((2S,4R)-2-((S)-2-((S)-2-amino-1-cyclohexyl-2-oxoethylamino)-1-
cyclohexyl-2-oxoethylcarbamoyl)-4-hydroxypyrrolidin-1-yl)-3,3-dimethyl-1-oxobutan-2-
ylamino)-7-methoxy-1,7-dioxohept-5-en-2-ylcarbamoyl)-4/5-nitrobenzoic acid
Chemical Formula: $C_{43}H_{61}N_7O_{13}$
Exact Mass: 883,43
Molecular Weight: 883,98

The synthesis of example 1-9 was performed according to example 1-1, using the corresponding amino acids.
Yield: 79 mg, 56%, ratio of regioisomers: approximately 1:1
ESI-MS: 884.6 [M+H]$^+$ Example 1-10. Preparation of Compounds 10a/b

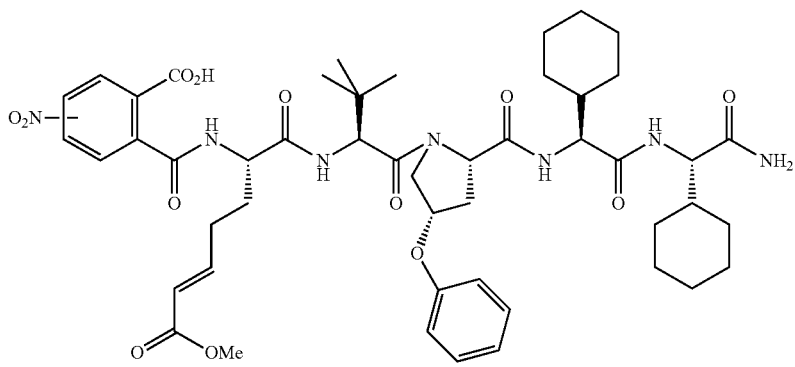

2-((S,E)-1-(((S)-1-(((2S,4R)-2-((S)-2-((S)-2-amino-1-cyclohexyl-2-oxoethylamino)-1-
cyclohexyl-2-oxoethylcarbamoyl)-4-phenoxypyrrolidin-1-yl)-3,3-dimethyl-1-oxobutan-2-
ylamino)-7-methoxy-1,7-dioxohept-5-en-2-ylcarbamoyl)-4/5-nitrobenzoic acid
Chemical Formula: $C_{49}H_{65}N_7O_{13}$
Exact Mass: 959,46
Molecular Weight: 960,08

The synthesis of example 1-10 was performed according to example 1-1, using the corresponding amino acids.
Yield: 21 mg, 32%, ratio of regioisomers: approximately 1:1
ESI-MS: 960.6 [M+H]$^+$ Example 1-11. Preparation of Compounds 11a/b

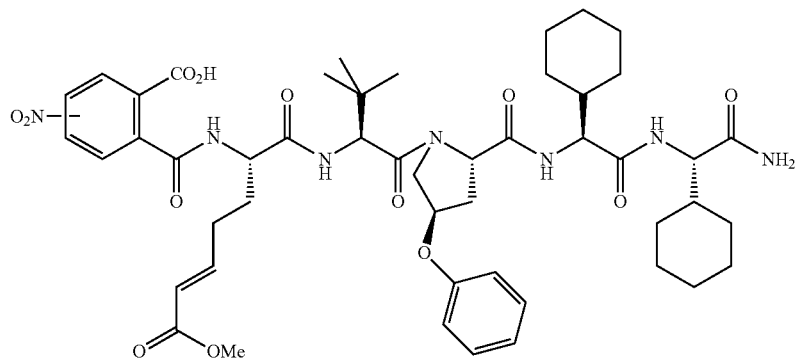

2-((S,E)-1-((S)-1-((2S,4R)-2-((S)-2-((S)-2-amino-1-cyclohexyl-2-oxoethylamino)-1-
cyclohexyl-2-oxoethylcarbamoyl)-4-phenoxypyrrolidin-1-yl)-3,3-dimethyl-1-oxobutan-2-
ylamino)-7-methoxy-1,7-dioxohept-5-en-2-ylcarbamoyl)-4/5-nitrobenzoic acid
Chemical Formula: $C_{49}H_{65}N_7O_{13}$
Exact Mass: 959,46
Molecular Weight: 960,08

The synthesis of example 1-11 was performed according to example 1-1, using the corresponding amino acids.
Yield: 36 mg, 43%, ratio of regioisomers: approximately 1:1
ESI-MS: 960.6 [M+H]$^+$ Example 1-12. Preparation of Compounds 12a/b

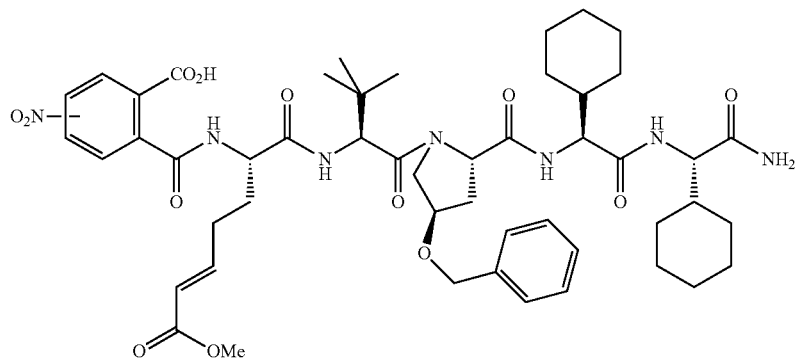

2-((S,E)-1-((S)-1-((2S,4R)-2-((S)-2-((S)-2-amino-1-cyclohexyl-2-oxoethylamino)-1-
cyclohexyl-2-oxoethylcarbamoyl)-4-(benzyloxy)pyrrolidin-1-yl)-3,3-dimethyl-1-oxobutan-2-
ylamino)-7-methoxy-1,7-dioxohept-5-en-2-ylcarbamoyl)-4/5-nitrobenzoic acid
Chemical Formula: $C_{50}H_{67}N_7O_{13}$
Exact Mass: 973,48
Molecular Weight: 974,11

The synthesis of example 1-12 was performed according to example 1-1, using the corresponding amino acids.
Yield: 13 mg, 23%, ratio of regioisomers: approximately 1:1
ESI-MS: 974.6 [M+H]$^+$ Example 1-13. Preparation of Compounds 13a/b

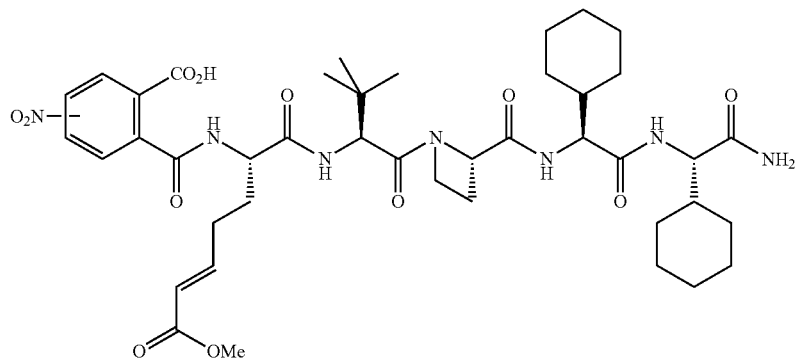

2-((S,E)-1-((S)-1-((S)-2-((S)-2-((S)-2-amino-1-cyclohexyl-2-oxoethylamino)-1-cyclohexyl-
2-oxoethylcarbamoyl)azetidin-1-yl)-3,3-dimethyl-1-oxobutan-2-ylamino)-7-methoxy-1,7-
dioxohept-5-en-2-ylcarbamoyl)-4/5-nitrobenzoic acid
Chemical Formula: $C_{42}H_{59}N_7O_{12}$
Exact Mass: 853.42
Molecular Weight: 853.96

The synthesis of example 1-13 was performed according to example 1-1, using the corresponding amino acids.
Yield: 36 mg, 56%, ratio of regioisomers: approximately 1:1
ESI-MS: 854.5 $[M+H]^+$ Example 1-14. Preparation of Compounds 14a/b

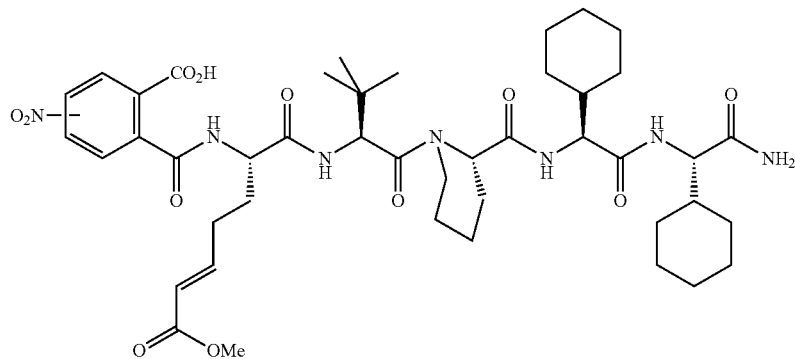

2-((S,E)-1-((S)-1-((R)-2-((S)-2-((S)-2-amino-1-cyclohexyl-2-oxoethylamino)-1-cyclohexyl-
2-oxoethylcarbamoyl)piperidin-1-yl)-3,3-dimethyl-1-oxobutan-2-ylamino)-7-methoxy-1,7-
dioxohept-5-en-2-ylcarbamoyl)-4/5-nitrobenzoic acid
Chemical Formula: $C_{44}H_{63}N_7O_{12}$
Exact Mass: 881.45
Molecular Weight: 882.01

The synthesis of example 1-14 was performed according to example 1-1, using the corresponding amino acids.
Yield: 26 mg, 41%, ratio of regioisomers: approximately 1:1
ESI-MS: 882.5 $[M+H]^+$

Example 1-15. Preparation of Compounds 15a/b

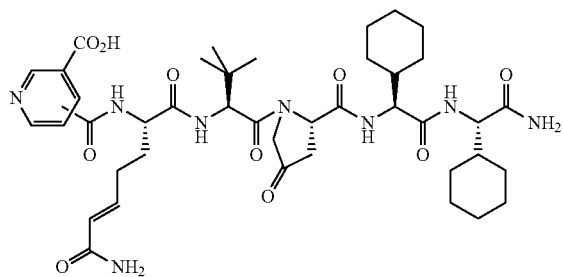

3/4-((S,E)-7-amino-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-1,7-dioxohept-5-en-2-ylcarbamoyl)iso/nicotinic acid
Chemical Formula: $C_{41}H_{58}N_8O_{10}$
Exact Mass: 822,43
Molecular Weight: 822,95

The synthesis of example 1-15 was performed according to example 1-1, using the corresponding anhydride and building block Id.
Yield: 18 mg, 26%, ratio of regioisomers: approximately 1:1
ESI-MS: 823.6 [M+H]$^+$

Example 1-16. Preparation of Compounds 16a/b

The synthesis of example 1-16 was performed according to example 1-1, using the corresponding amino acids.
Yield: 39 mg, 56%, ratio of regioisomers: approximately 1:1
ESI-MS: 882.6 [M+H]$^+$

Example 1-17. Preparation of Compounds 17a/b

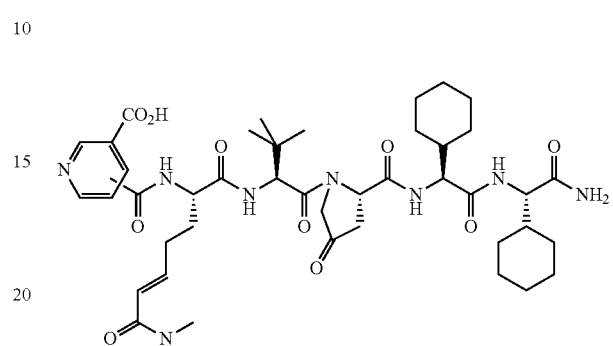

3/4-((S,E)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-7-(methylamino)-1,7-dioxohept-5-en-2-ylcarbamoyl)iso/nicotinic acid
Chemical Formula: $C_{42}H_{60}N_8O_{10}$
Exact Mass: 836,44
Molecular Weight: 836,97

The synthesis of example 1-17 was performed according to example 1-1, using the corresponding anhydride and building block Ie.
Yield: 9 mg, 23%, ratio of regioisomers: approximately 1:1
ESI-MS: 837.6 [M+H]$^+$

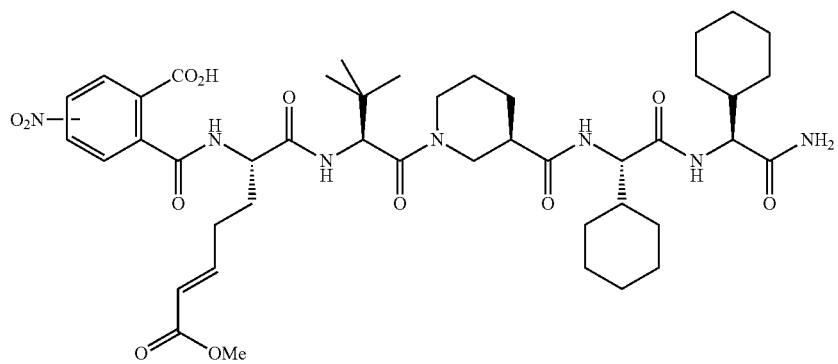

2-((S,E)-1-((S)-1-((R)-3-((S)-2-((S)-2-amino-1-cyclohexyl-2-oxoethylamino)-1-cyclohexyl-2-oxoethylcarbamoyl)piperidin-1-yl)-3,3-dimethyl-1-oxobutan-2-ylamino)-7-methoxy-1,7-dioxohept-5-en-2-ylcarbamoyl)-4/5-nitrobenzoic acid
Chemical Formula: $C_{44}H_{63}N_7O_{12}$
Exact Mass: 881,45
Molecular Weight: 882,01

Example 1-18. Preparation of Compounds 18a/b

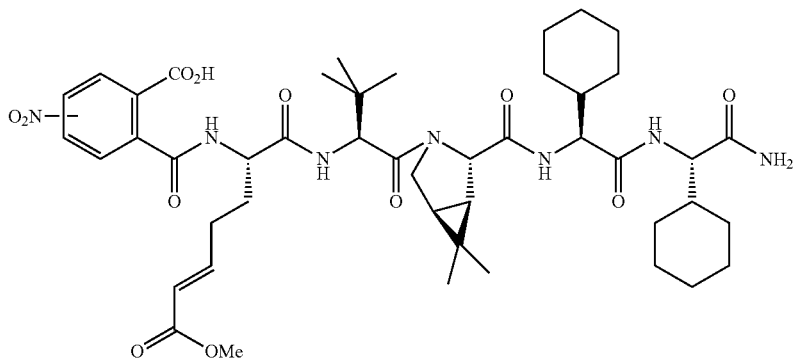

2-((S,E)-1-((S)-1-((1R,2S,5S)-2-((S)-2-((S)-2-amino-1-cyclohexyl-2-oxoethylamino)-1-cyclohexyl-
2-oxoethylcarbamoyl)-6,6-dimethyl-3-azabicyclo[3.1.0]hexan-3-yl)-3,3-dimethyl-1-oxobutan-2-
ylamino)-7-methoxy-1,7-dioxohept-5-en-2-ylcarbamoyl)-4/5-nitrobenzoic acid
Chemical Formula: $C_{46}H_{65}N_7O_{12}$
Exact Mass: 907,47
Molecular Weight: 908,05

The synthesis of example 1-18 was performed according to example 1-1, using the corresponding amino acids.
Yield: 17 mg, 31%, ratio of regioisomers: approximately 1:1
ESI-MS: 908.6 [M+H]$^+$ Example 1-19. Preparation of Compounds 19a/b

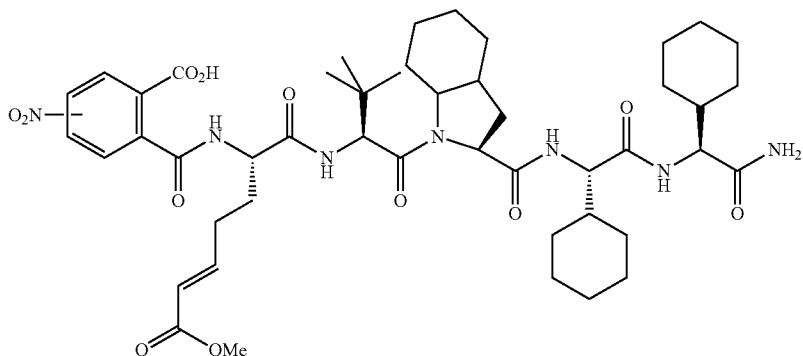

2-((2S,E)-1-((2S)-1-((2S)-2-((R)-2-((S)-2-amino-1-cyclohexyl-2-oxoethylamino)-1-cyclohexyl-
2-oxoethylcarbamoyl)octahydro-1H-indol-1-yl)-3,3-dimethyl-1-oxobutan-2-ylamino)-7-methoxy-1,7-
dioxohept-5-en-2-ylcarbamoyl)-4/5-nitrobenzoic acid
Chemical Formula: $C_{47}H_{67}N_7O_{12}$
Exact Mass: 921,48
Molecular Weight: 922,07

The synthesis of example 1-19 was performed according to example 1-1, using the corresponding amino acids.
Yield: 25 mg, 36%, ratio of regioisomers: approximately 1:1
ESI-MS: 922.7 [M+H]$^+$ Example 1-20. Preparation of Compounds 20a/b

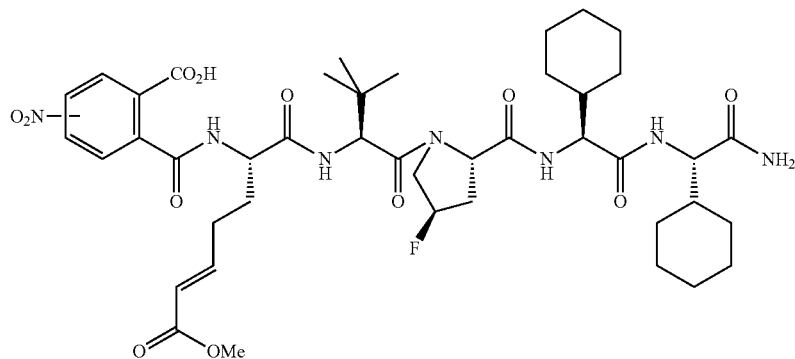

2-((S,E)-1-((S)-1-((2S,4R)-2-((S)-2-((S)-2-amino-1-cyclohexyl-2-oxoethylamino)-1-
cyclohexyl-2-oxoethylcarbamoyl)-4-fluoropyrrolidin-1-yl)-3,3-dimethyl-1-oxobutan-2-
ylamino)-7-methoxy-1,7-dioxohept-5-en-2-ylcarbamoyl)-4/5-nitrobenzoic acid
Chemical Formula: $C_{43}H_{60}FN_7O_{12}$
Exact Mass: 885,43
Molecular Weight: 885,97

The synthesis of example 1-20 was performed according to example 1-1, using the corresponding amino acids.
Yield: 12 mg, 29%, ratio of regioisomers: approximately 1:1
ESI-MS: 886.6 [M+H]$^+$ Example 1-21. Preparation of Compounds 21a/b

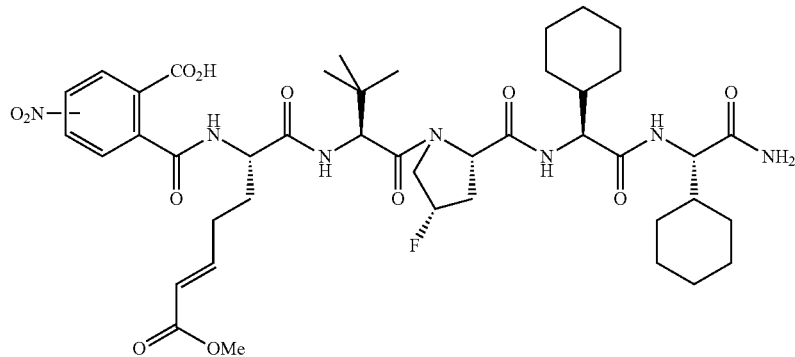

2-((S,E)-1-((S)-1-((2S,4R)-2-((S)-2-((S)-2-amino-1-cyclohexyl-2-oxoethylamino)-1-
cyclohexyl-2-oxoethylcarbamoyl)-4-fluoropyrrolidin-1-yl)-3,3-dimethyl-1-oxobutan-2-
ylamino)-7-methoxy-1,7-dioxohept-5-en-2-ylcarbamoyl)-4/5-nitrobenzoic acid
Chemical Formula: $C_{43}H_{60}FN_7O_{12}$
Exact Mass: 885,43
Molecular Weight: 885,97

The synthesis of example 1-21 was performed according to example 1-1, using the corresponding amino acids.
Yield: 19 mg, 36%, ratio of regioisomers: approximately 1:1
ESI-MS: 886.6 [M+H]$^+$ Example 1-22. Preparation of Compounds 22a/b

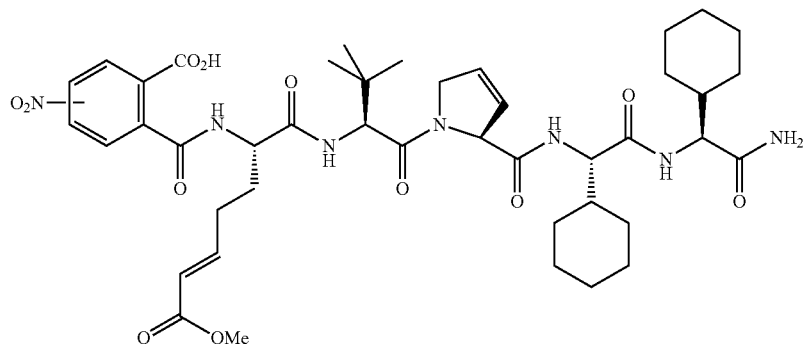

2-((2S,E)-1-((S)-1-((S)-2-((R)-2-((S)-2-amino-1-cyclohexyl-2-oxoethylamino)-1-cyclohexyl-
2-oxoethylcarbamoyl)-2,5-dihydro-1H-pyrrol-1-yl)-3,3-dimethyl-1-oxobutan-2-ylamino)-7-
methoxy-1,7-dioxohept-5-en-2-ylcarbamoyl)-4/5-nitrobenzoic acid
Chemical Formula: $C_{43}H_{59}N_7O_{12}$
Exact Mass: 865,42
Molecular Weight: 865,97

The synthesis of example 1-22 was performed according to example 1-1, using the corresponding amino acids.
Yield: 36 mg, 53%, ratio of regioisomers: approximately 1:1
ESI-MS: 866.6 $[M+H]^+$ Example 1-23. Preparation of Compounds 23a/b

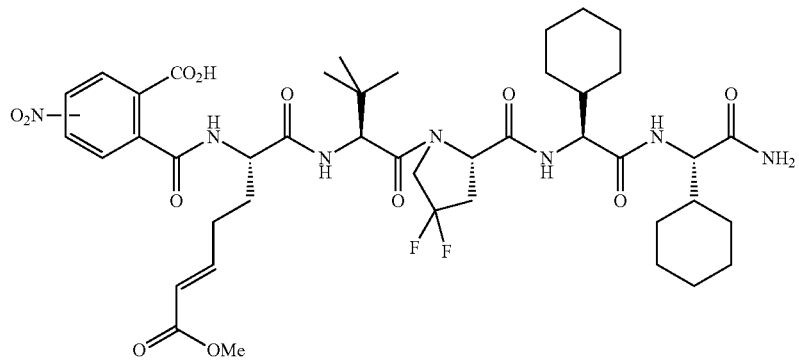

2-((S,E)-1-((S)-1-((S)-2-((S)-2-((S)-2-amino-1-cyclohexyl-2-oxoethylamino)-1-cyclohexyl-
2-oxoethylcarbamoyl)-4,4-difluoropyrrolidin-1-yl)-3,3-dimethyl-1-oxobutan-2-ylamino)-
7-methoxy-1,7-dioxohept-5-en-2-ylcarbamoyl)-4/5-nitrobenzoic acid
Chemical Formula: $C_{43}H_{59}F_2N_7O_{12}$
Exact Mass: 903,42
Molecular Weight: 903,97

The synthesis of example 1-23 was performed according to example 1-1, using the corresponding amino acids.
Yield: 14 mg, 26%, ratio of regioisomers: approximately 1:1
ESI-MS: 904.5 $[M+H]^+$ Example 1-24. Preparation of Compounds 24a/b

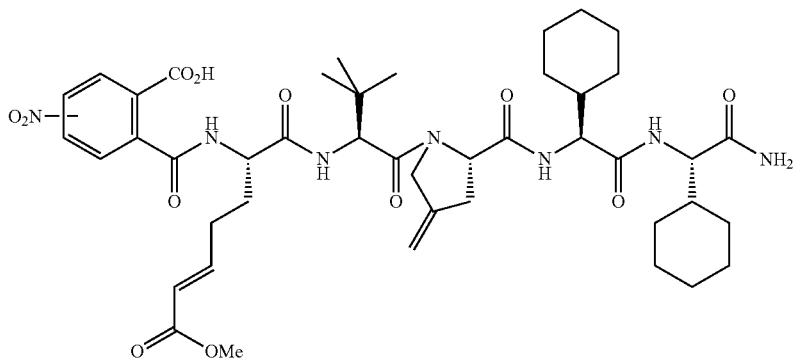

2-((S,E)-1-((S)-1-((S)-2-((S)-2-((S)-2-amino-1-cyclohexyl-2-oxoethylamino)-1-cyclohexyl-
2-oxoethylcarbamoyl)-4-methylenepyrrolidin-1-yl)-3,3-dimethyl-1-oxobutan-2-ylamino)-
7-methoxy-1,7-dioxohept-5-en-2-ylcarbamoyl)-4/5-nitrobenzoic acid
Chemical Formula: $C_{44}H_{61}N_7O_{12}$
Exact Mass: 879,44
Molecular Weight: 879,99

The synthesis of example 1-24 was performed according to example 1-1, using the corresponding amino acids.
Yield: 23 mg, 32%, ratio of regioisomers: approximately 1:1
ESI-MS: 880.6 [M+H]$^+$ Example 1-25. Preparation of Compounds 25a/b

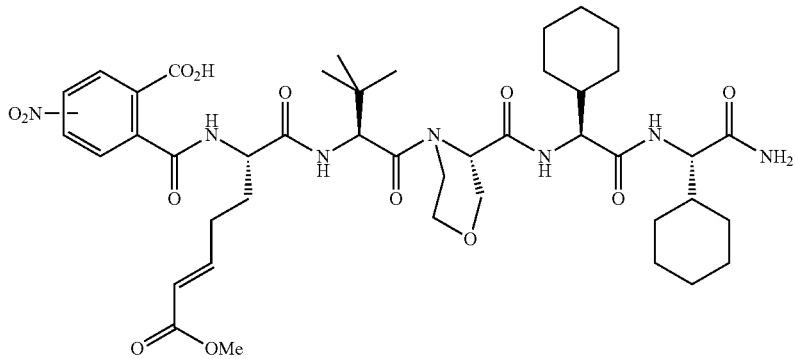

2-((S,E)-1-((S)-1-((R)-3-((S)-2-((S)-2-amino-1-cyclohexyl-2-oxoethylamino)-1-cyclohexyl-
2-oxoethylcarbamoyl)morpholino)-3,3-dimethyl-1-oxobutan-2-ylamino)-7-methoxy-1,7-
dioxohept-5-en-2-ylcarbamoyl)-4/5-nitrobenzoic acid
Chemical Formula: $C_{43}H_{61}N_7O_{12}$
Exact Mass: 883,43
Molecular Weight: 883,98

The synthesis of example 1-25 was performed according to example 1-1, using the corresponding amino acids.
Yield: 39 mg, 53%, ratio of regioisomers: approximately 1:1
ESI-MS: 884.6 [M+H]$^+$ Example 1-26. Preparation of Compounds 26a/b

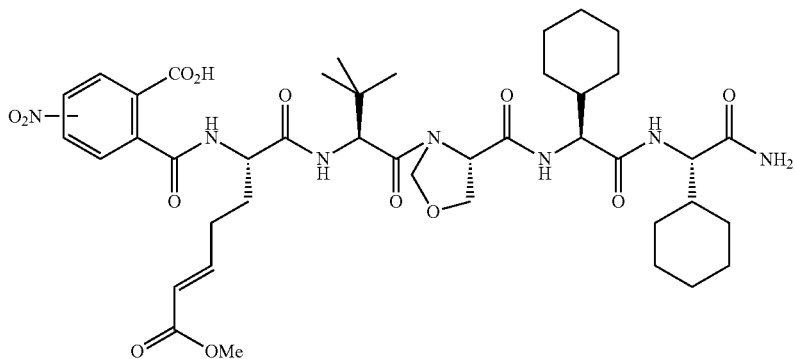

2-((S,E)-1-((S)-1-((S)-4-((S)-2-((S)-2-amino-1-cyclohexyl-2-oxoethylamino)-1-cyclohexyl-
2-oxoethylcarbamoyl)oxazoidin-3-yl)-3,3-dimethyl-1-oxobutan-2-ylamino)-
7-methoxy-1,7-dioxohept-5-en-2-ylcarbamoyl)-4/5-nitrobenzoic acid
Chemical Formula: $C_{42}H_{59}N_7O_{13}$
Exact Mass: 869,42
Molecular Weight: 869,96

25

The synthesis of example 1-26 was performed according to example 1-1, using the corresponding amino acids.
Yield: 56 mg, 59%, ratio of regioisomers: approximately 1:1
ESI-MS: 870.5 $[M+H]^+$ Example 1-27. Preparation of Compound 27

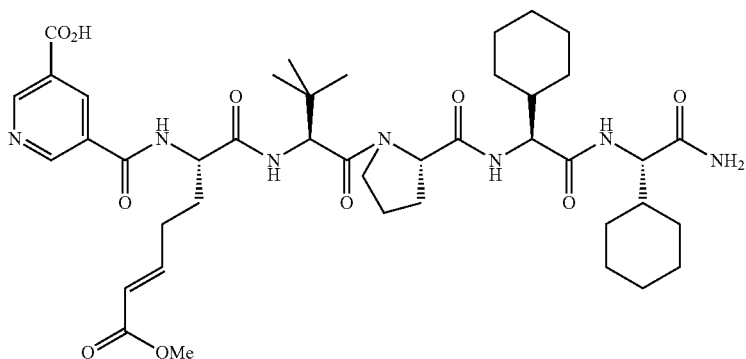

5-((S,E)-1-((S)-1-((S)-2-((S)-2-((S)-2-amino-1-cyclohexyl-2-oxoethylamino)-1-
cyclohexyl-2-oxoethylcarbamoyl)pyrrolidin-1-yl)-3,3-dimethyl-1-oxobutan-2-
ylamino)-7-methoxy-1,7-dioxohept-5-en-2-ylcarbamoyl)nicotinic acid
Chemical Formula: $C_{42}H_{61}N_7O_{10}$
Exact Mass: 823,45
Molecular Weight: 823,97

The synthesis of example 1-27 was performed according to example 1-1, using the corresponding carboxylic acid and amino acids.
Yield: 79 mg, 52%
ESI-MS: 824.6 $[M+H]^+$ Example 1-28. Preparation of Compound 28

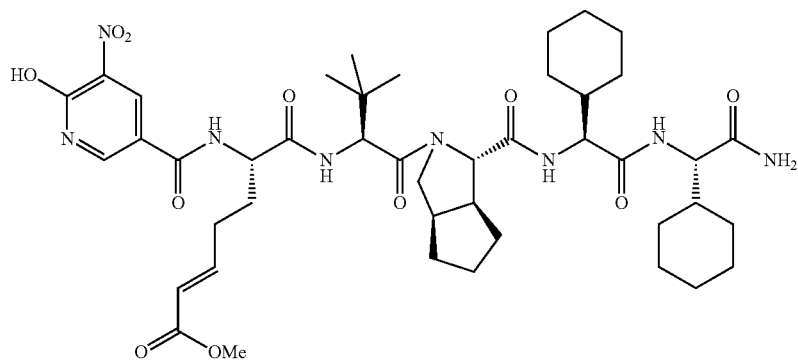

(S,E)-methyl 7-((S)-1-((1S,3aR,6aS)-1-((S)-2-((S)-2-amino-1-cyclohexyl-2-oxoethylamino)-
1-cyclohexyl-2-oxoethylcarbamoyl)hexahydrocyclopenta[c]pyrrol-2(1H)-yl)-3,3-dimethyl-1-
oxobutan-2-ylamino)-6-(6-hydroxy-5-nitronicotinamido)-7-oxohept-2-enoate
Chemical Formula: $C_{44}H_{64}N_8O_{11}$
Exact Mass: 880,47
Molecular Weight: 881, 03

The synthesis of example 1-28 was performed according to example 1-1, using the corresponding carboxylic acid and amino acids.
Yield: 26 mg, 32%
ESI-MS: 881.6 [M+H]$^+$ Example 1-29. Preparation of Compound 29

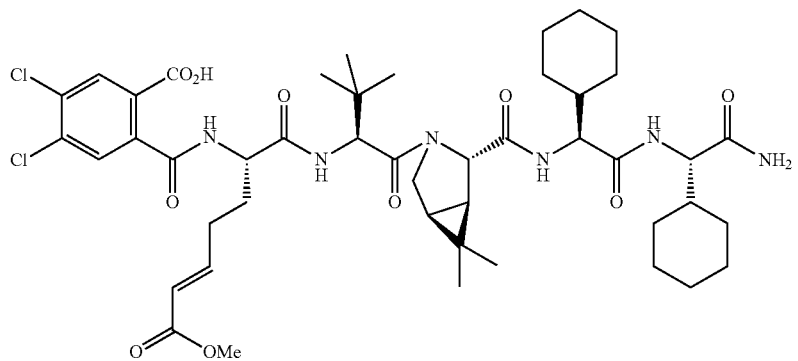

2-((S,E)-1-((S)-1-((1R,2S,5S)-2-((S)-2-((S)-2-amino-1-cyclohexyl-2-oxoethylamino)-1-
cyclohexyl-2-oxoethylcarbamoyl)-6,6-dimethyl-3-azabicyclo[3.1.0]hexan-3-yl)-3,3-dimethyl-1-
oxobutan-2-ylamino)-7-methoxy-1,7-dioxohept-5-en-2-ylcarbamoyl)-4,5-dichlorobenzoic acid
Chemical Formula: $C_{46}H_{64}Cl_2N_6O_{10}$
Exact Mass: 930,41
Molecular Weight: 931,94

The synthesis of example 1-29 was performed according to example 1-1, using the corresponding anhydride and amino acids.
Yield: 15 mg, 27%
ESI-MS: 931.6 [M+H]$^+$ Example 1-30. Preparation of Compound 30

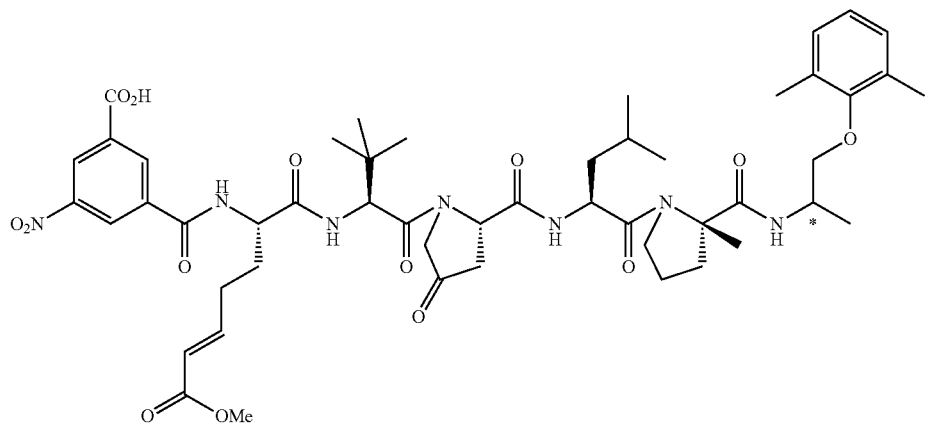

3-((2S,E)-1-((2S)-1-((2S)-2-((2S)-1-((2S)-2-(1-(2,6-dimethylphenoxy)propan-2-ylcarbamoyl)-2-methylpyrrolidin-1-yl)-4-methyl-1-oxopentan-2-ylcarbamoyl)-4-oxopyrrolidin-1-yl)-3,3-dimethyl-1-oxobutan-2-ylamino)-7-methoxy-1,7-dioxohept-5-en-2-ylcarbamoyl)-5-nitrobenzoic acid
Chemical Formula: $C_{50}H_{67}N_7O_{14}$
Exact Mass: 989,47
Molecular Weight: 990,11

The synthesis of example 1-30 was performed according to scheme 4, using the corresponding carboxylic acid, amine 30 (H-E) and amino acids.
Yield: 36 mg, 52%
ESI-MS: 990.7 $[M+H]^+$ Example 1-31. Preparation of Compounds 31a/b

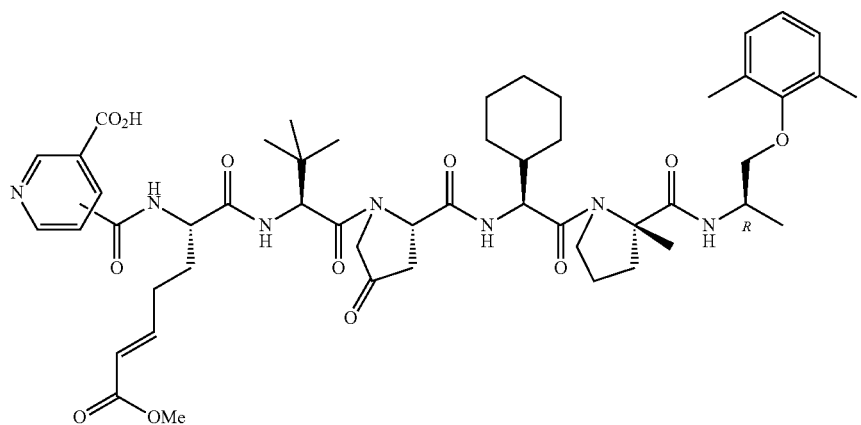

3/4-((S,E)-1-((S)-1-((S)-2-((S)-1-cyclohexyl-2-((S)-2-((R)-1-(2,6-dimethylphenoxy)propan-2-ylcarbamoyl)-2-methylpyrrolidin-1-yl)-2-oxoethylcarbamoyl)-4-oxopyrrolidin-1-yl)-3,3-dimethyl-1-oxobutan-2-ylamino)-7-methoxy-1,7-dioxohept-5-en-2-ylcarbamoyl)iso/nicotinic acid
Chemical Formula: $C_{51}H_{69}N_7O_{12}$
Exact Mass: 971,50
Molecular Weight: 972,13

The synthesis of example 1-31 was performed according to scheme 4, using the corresponding anhydride, amine (H-E) and amino acids.
Yield: 26 mg, 48%, ratio of regioisomers: approximately 1:1
ESI-MS: 972.7 $[M+H]^+$ Example 1-32. Preparation of Compounds 32a/b

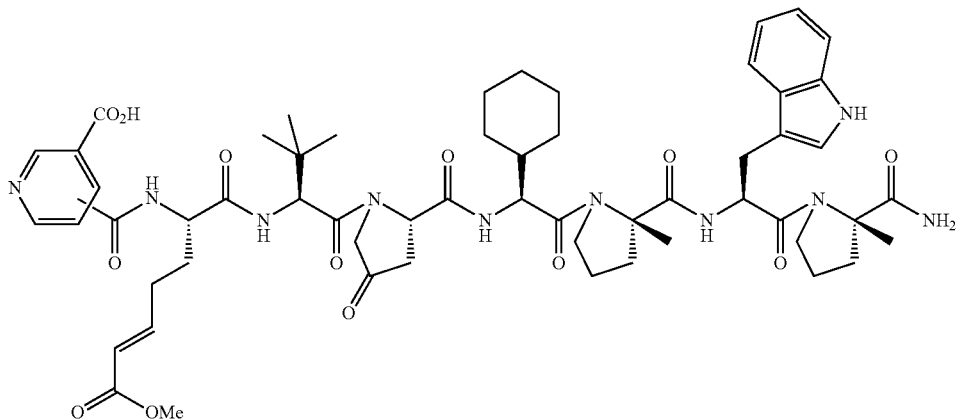

3/4-((S,E)-1-((S)-1-((S)-2-((S)-2-((S)-2-((S)-1-((S)-2-carbamoyl-2-methylpyrrolidin-1-yl)-3-(1H-indol-3-yl)-1-
oxopropan-2-ylcarbamoyl)-2-methylpyrrolidin-1-yl)-1-cyclohexyl-2-oxoethylcarbamoyl)-4-oxopyrrolidin-1-yl)-
3,3-dimethyl-1-oxobutan-2-ylamino)-7-methoxy-1,7-dioxohept-5-en-2-ylcarbamoyl)iso/nicotinic acid
Chemical Formula: $C_{57}H_{74}N_{10}O_{13}$
Exact Mass: 1106,54
Molecular Weight: 1107,26

The synthesis of example 1-32 was performed according to example 1-1, using the corresponding anhydride and amino acids.

Yield: 56 mg, 53%, ratio of regioisomers: approximately 1:1

ESI-MS: 1107.8 $[M+H]^+$

Example 1-33. Preparation of Compounds 33a/b

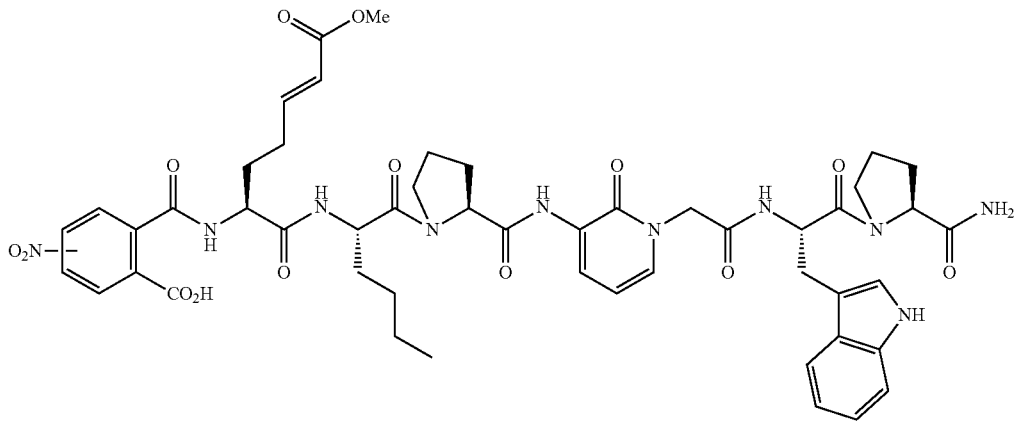

2-((S,E)-1-((S)-1-((S)-2-(1-(2-((S)-1-((S)-2-carbamoylpyrrolidin-1-yl)-3-(1H-indol-3-yl)-1-oxopropan-
2-ylamino)-2-oxoethyl)-2-oxo-1,2-dihydropyridin-3-ylcarbamoyl)pyrrolidin-1-yl)-1-oxohexan-2-
ylamino)-7-methoxy-1,7-dioxohept-5-en-2-ylcarbamoyl)-4/5-nitrobenzoic acid
Chemical Formula: $C_{50}H_{58}N_{10}O_{14}$
Exact Mass: 1022,41
Molecular Weight: 1023,05

The synthesis of example 1-33 was performed according to example 1-1, using the corresponding anhydride and amino acids.

Yield: 32 mg, 65%, ratio of regioisomers: approximately 1:1

ESI-MS: 1145.5 $[M+Na]^+$

Example 1-34. Preparation of Compounds 34a/b

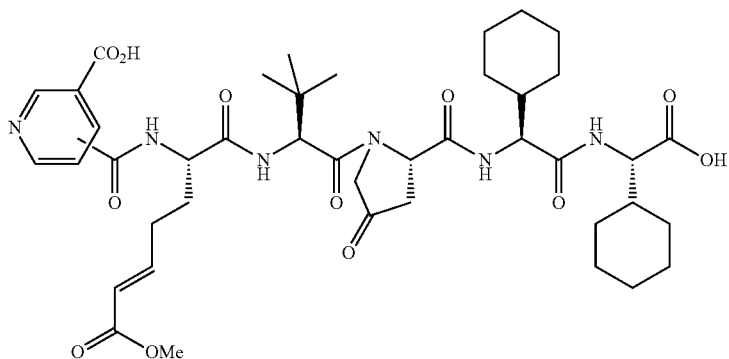

3/4-((S,E)-1-((S)-1-((S)-2-((S)-2-((S)-carboxy(cyclohexyl)methylamino)-1-cyclohexyl-
2-oxoethylcarbamoyl)-4-oxopyrrolidin-1-yl)-3,3-dimethyl-1-oxobutan-2-ylamino)-7-
methoxy-1,7-dioxohept-5-en-2-ylcarbamoyl)iso/nicotinic acid
Chemical Formula: $C_{42}H_{58}N_6O_{12}$
Exact Mass: 838,41
Molecular Weight: 838,94

The synthesis of example 1-34 was performed according to example 1-1, using the corresponding anhydride, amino acids and Wang resin.

Yield: 15 mg, 24%, ratio of regioisomers: approximately 1:1

ESI-MS: 839.4 $[M+H]^+$

Example 1-35. Preparation of Compounds 35a/b

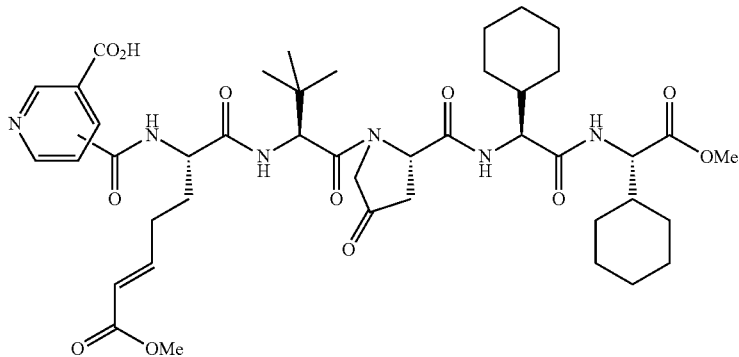

3/4-((S,E)-1-((S)-1-((S)-2-((S)-1-cyclohexyl-2-((S)-1-cyclohexyl-2-methoxy-2-oxoethylamino)-
2-oxoethylcarbamoyl)-4-oxopyrrolidin-1-yl)-3,3-dimethyl-1-oxobutan-2-ylamino)-7-methoxy-
1,7-dioxohept-5-en-2-ylcarbamoyl)iso/nicotinic acid
Chemical Formula: $C_{43}H_{60}N_6O_{12}$
Exact Mass: 852,43
Molecular Weight: 852,97

The synthesis of example 1-35 was performed according to scheme 4, using the corresponding anhydride and amino acids.

Yield: 24 mg, 41%, ratio of regioisomers: approximately 1:1

ESI-MS: 853.6 $[M+H]^+$

Example 1-36. Preparation of Compounds 36a/b

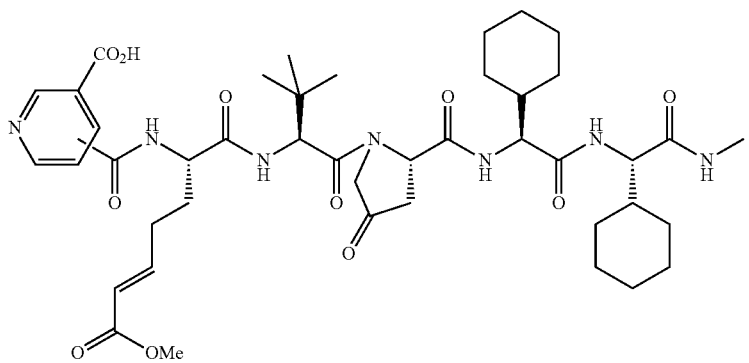

3/4-((S,E)-1-((S)-1-((S)-2-((S)-1-cyclohexyl-2-((S)-1-cyclohexyl-2-(methylamino)-2-
oxoethylamino)-2-oxoethylcarbamoyl)-4-oxopyrrolidin-1-yl)-3,3-dimethyl-1-oxobutan-
2-ylamino)-7-methoxy-1,7-dioxohept-5-en-2-ylcarbamoyl)iso/nicotinic acid
Chemical Formula: $C_{43}H_{61}N_7O_{11}$
Exact Mass: 851,44
Molecular Weight: 851,98

The synthesis of example 1-36 was performed according to example 1-1, using the corresponding anhydride, amino acids and Methyl Indole AM resin.

Yield: 36 mg, 32%, ratio of regioisomers: approximately 1:1

ESI-MS: 852.6 [M+H]$^+$

Example 1-37. Preparation of Compounds 37a/b

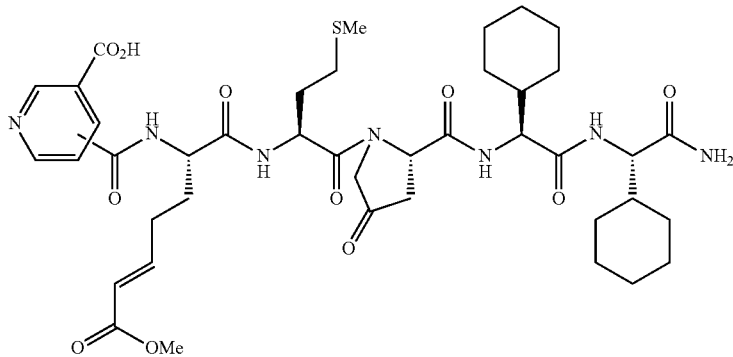

4-((S,E)-1-((S)-1-((S)-2-((S)-2-amino-1-cyclohexyl-2-oxoethylamino)-1-cyclohexyl-2-
oxoethylcarbamoyl)-4-oxopyrrolidin-1-yl)-4-(methylthio)-1-oxobutan-2-ylamino)-7-methoxy-
1,7-dioxohept-5-en-2-ylcarbamoyl)nicotinic acid
Chemical Formula: $C_{41}H_{57}N_7O_{11}S$
Exact Mass: 855,38
Molecular Weight: 856,00

The synthesis of example 1-37 was performed according to example 1-1, using the corresponding anhydride and amino acids.

Yield: 31 mg, 42%, ratio of regioisomers: approximately 1:1

ESI-MS: 856.5 [M+H]$^+$

Example 1-38

1.1 Preparation of Compound Ref. 08

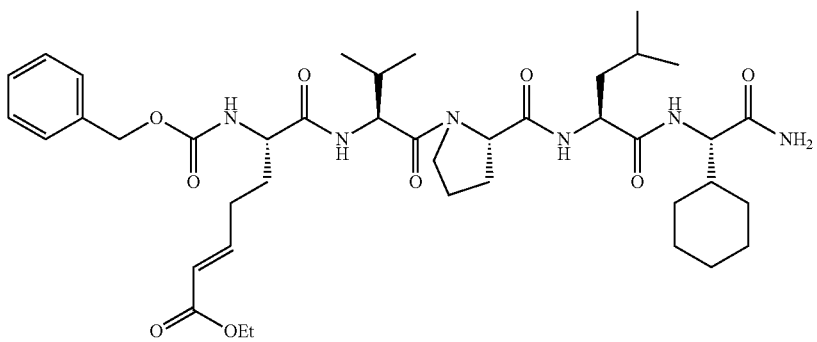

(S,E)-ethyl 7-((S)-1-((S)-2-((S)-1-((S)-2-amino-1-cyclohexyl-2-oxoethylamino)-4-methyl-1-oxopentan-2-ylcarbamoyl)pyrrolidin-1-yl)-3-methyl-1-oxobutan-2-ylamino)-6-(benzyloxycarbonylamino)-7-oxohept-2-enoate Chemical Formula: $C_{41}H_{62}N_6O_9$
Exact Mass: 782,46
Molecular Weight: 782,97

The backbone tetrapeptide H-Val-Pro-Leu-Chg-Nhfe was built by standard Fmoc solid-phase peptide chemistry according to compound ZED3478, using the corresponding amino acids. The Michael acceptor (ethyl acrylate) was directly coupled according to compound ZED3481, using compound Ic. Finally, compound Ref. 08 was synthesized according to Example 1-1, using Cbz-Cl.

Yield: 86 mg, 61%
ESI-MS: 783.6 [M+H]$^+$

1.2 Preparation of Compound 38

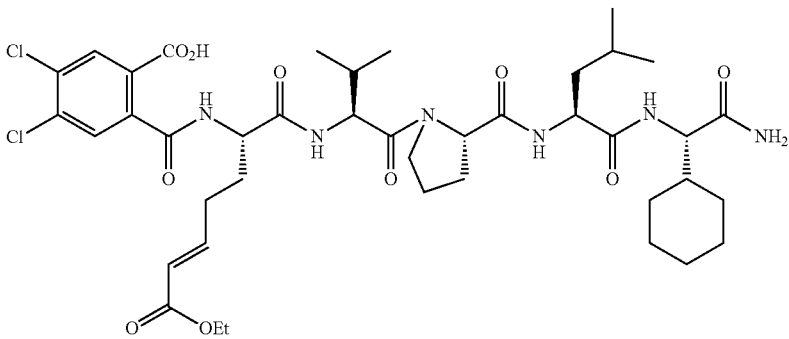

2-((S,E)-1-((S)-1-((S)-2-((S)-1-((S)-2-amino-1-cyclohexyl-2-oxoethylamino)-4-methyl-1-oxopentan-2-ylcarbamoyl)pyrrolidin-1-yl)-3-methyl-1-oxobutan-2-ylamino)-7-ethoxy-1,7-dioxohept-5-en-2-ylcarbamoyl)-4,5-dichlorobenzoic acid Chemical Formula: $C_{41}H_{58}Cl_2N_6O_{10}$
Exact Mass: 864,36
Molecular Weight: 865,84

The synthesis of compound 38 was performed according to compound Ref. 06, using 4,5-dichlorophthalic anhydride instead of Cbz-Cl in the final step.

Yield: 36 mg, 51%
ESI-MS: 865.5 [M+H]$^+$

Example 1-39

1. Preparation of Compound Ref. 09

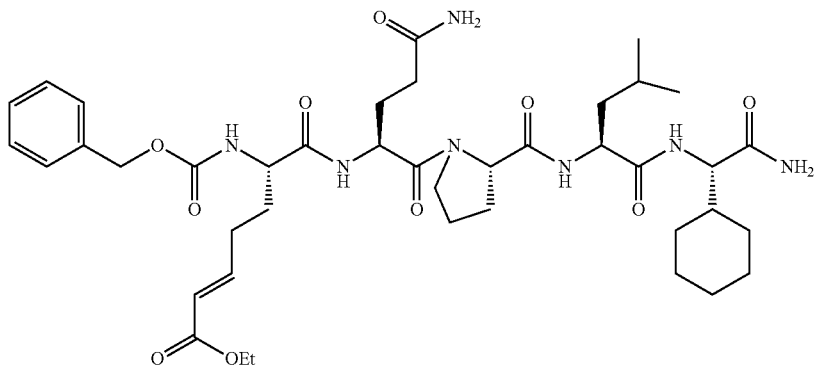

(S,E)-ethyl 7-((S)-5-amino-1-((S)-2-((S)-1-((S)-2-amino-1-cyclohexyl-2-oxoethylamino)-4-methyl-1-oxopentan-2-ylcarbamoyl)pyrrolidin-1-yl)-1,5-dioxopentan-2-ylamino)-6-(benzyloxycarbonylamino)-7-oxohept-2-enoate Chemical Formula: $C_{41}H_{61}N_7O_{10}$
Exact Mass: 811,45
Molecular Weight: 811,96

The synthesis of compound Ref. 09 was performed according to compound Ref. 08, using the corresponding amino acids for the synthesis of the backbone tetrapeptide by standard Fmoc solid-phase peptide chemistry.

Yield: 93 mg, 57%
ESI-MS: 812.6 [M+H]$^+$

2. Preparation of Compound 39a/39b (Regioisomers)

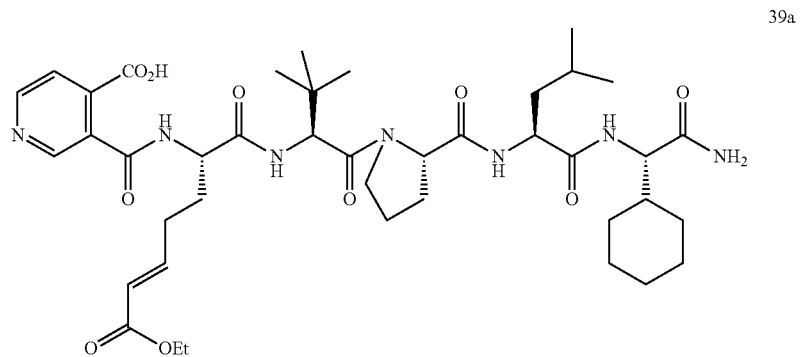

39a

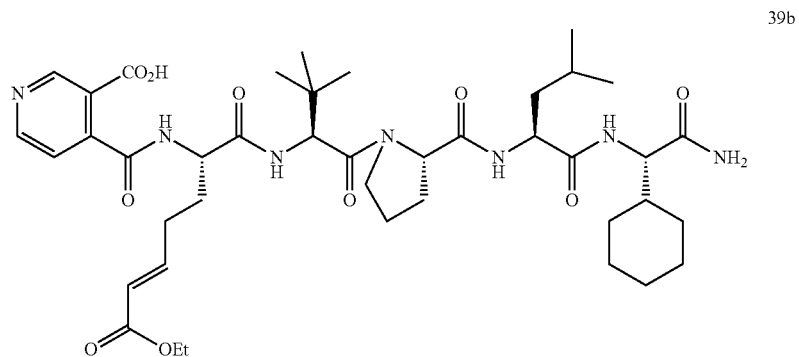

39b

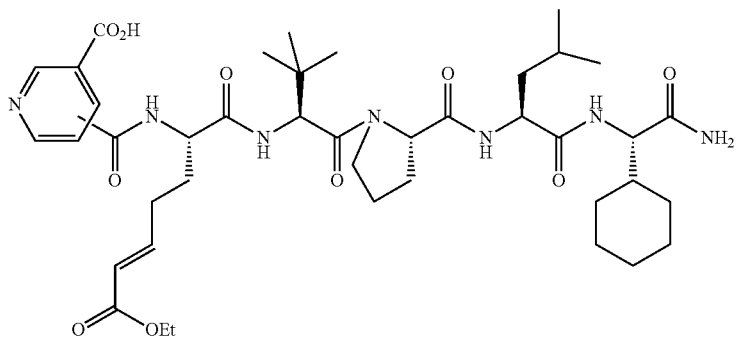

3/4-((S,E)-1-((S)-1-((S)-2-((S)-1-((S)-2-amino-1-cyclohexyl-2-oxoethylamino)-4-methyl-
1-oxopentan-2-ylcarbamoyl)pyrrolidin-1-yl)-3,3-dimethyl-1-oxobutan-2-ylamino)-7-
ethoxy-1,7-dioxohept-5-en-2-ylcarbamoyl)nicotinic acid
Chemical Formula: $C_{41}H_{61}N_7O_{10}$
Exact Mass: 811,45
Molecular Weight: 811,96

The synthesis of compound 39 (39a/39b) was performed according to compound Ref. 09, using the corresponding amino acids for the buildup of the backbone tetrapeptide and 3,4-pyridinedicarboxylic anhydride instead of Cbz-Cl in the final step.

Yield: 41 mg, 36%, ratio of regioisomers: approximately 1:1

ESI-MS: 812.6 $[M+H]^+$

Example 1-40

1. Preparation of Compound Ref. 10

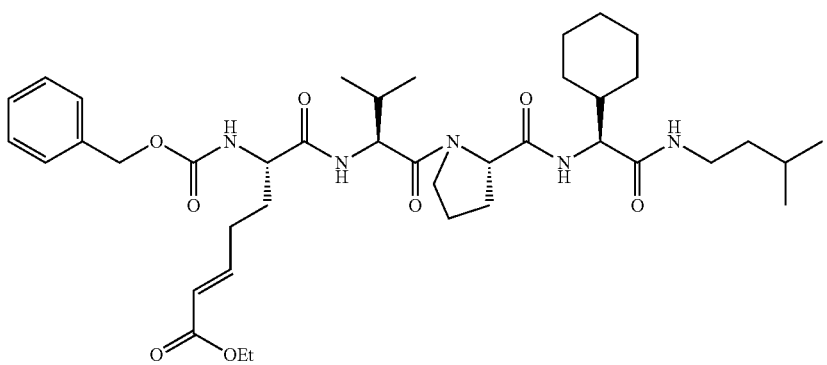

(S,E)-ethyl 6-(benzyloxycarbonylamino)-7-((S)-1-((S)-2-((S)-1-cyclohexyl-2-(isopentylamino)-2-
oxoethylcarbamoyl)pyrrolidin-1-yl)-3-methyl-1-oxobutan-2-ylamino)-7-oxohept-2-enoate
Chemical Formula: $C_{40}H_{61}N_5O_8$
Exact Mass: 739,45
Molecular Weight: 739,94

The backbone tripeptide Fmoc-Val-Pro-Chg-OH was built by standard Fmoc solid-phase peptide chemistry according to compound ZED3478, using 2-chlorotrityl resin and the corresponding amino acids. After cleavage from the resin (using 95% TFA/2.5% water/2.5% triisopropylsilane), C-terminal coupling of isopentylamine was performed according to compound ZED3480 with HATU/DIPEA. Subsequently the Fmoc protecting group was removed with piperidine in DMF and the Michael acceptor (ethyl acrylate) was coupled according to compound ZED3481, using compound Ic. Finally, compound Ref. 10 was synthesized according to Example 1-1, using Cbz-Cl.

Yield: 72 mg, 45%

ESI-MS: 740.6 $[M+H]^+$

2. Preparation of Compound 40

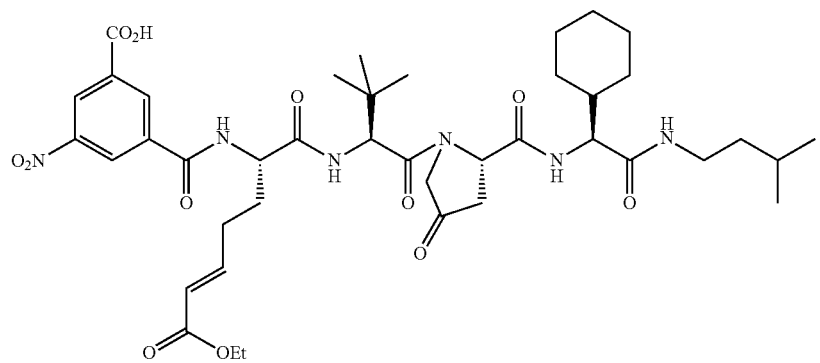

3-((S,E)-1-((S)-1-((S)-2-((S)-1-cyclohexyl-2-(isopentylamino)-2-oxoethylcarbamoyl)-4-oxopyrrolidin-1-yl)-3,3-dimethyl-1-oxobutan-2-ylamino)-7-ethoxy-1,7-dioxohept-5-en-2-ylcarbamoyl)-5-nitrobenzoic acid Chemical Formula: $C_{41}H_{58}N_6O_{12}$
Exact Mass: 826,41
Molecular Weight: 826,93

The synthesis of compound 40 was performed according to compound Ref. 10, using the corresponding amino acids for the buildup of the backbone tripeptide but 5-nitroisophthalic acid (coupling according to compound ZED3480 with HATU/DIPEA) instead of Cbz-Cl in the final step.

Yield: 56 mg, 62%
ESI-MS: 827.7 [M+H]$^+$

Example 1-41

1. Preparation of Compound Ref. 11

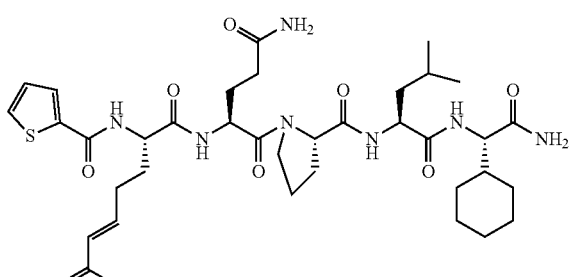

(S,E)-ethyl 7-((S)-5-amino-1-((S)-2-((S)-1-((S)-2-amino-1-cyclohexyl-2-oxoethylamino)-4-methyl-1-oxopentan-2-ylcarbamoyl)pyrrolidin-1-yl)-1,5-dioxopentan-2-ylamino)-7-oxo-6-(thiophene-2-carboxamido)hept-2-enoate Chemical Formula: $C_{38}H_{57}N_7O_9S$
Exact Mass: 787.39
Molecular Weight: 787.97

The synthesis of compound Ref. 11 was performed according to compound Ref. 08, using the corresponding amino acids for the synthesis of the backbone tetrapeptide and 2-Thiophenecarboxylic acid (coupling according to compound ZED3480 with HATU/DIPEA) instead of Cbz-Cl in the final step.

Yield: 69 mg, 56%
ESI-MS: 788.5 [M+H]$^+$

2. Preparation of Compound 41

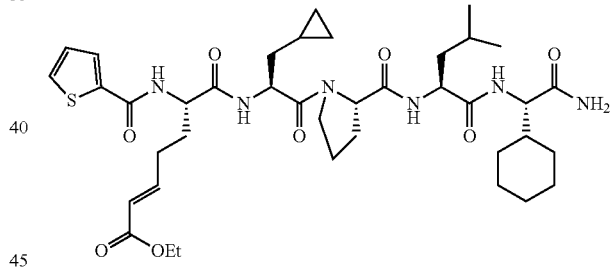

(S,E)-ethyl 7-((S)-1-((S)-2-((S)-1-((S)-2-amino-1-cylcohexyl-2-oxoethylamino)-4-methyl-1-oxopentan-2-ylcarbamoyl)pyrrolidin-1-yl)-3-cyclopropyl-1-oxopropan-2-ylamino)-7-oxo-6-(thiophene-2-carboxamido)hept-2-enoate Chemical Formula: $C_{39}H_{58}N_6O_8S$
Exact Mass: 770.40
Molecular Weight: 770.98

The synthesis of compound 41 was performed according to compound Ref. 11, using the corresponding amino acids for the buildup of the backbone tetrapeptide.

Yield: 45 mg, 61%
ESI-MS: 771.7 [M+H]$^+$

Example 1-42

1. Preparation of Compound Ref. 12

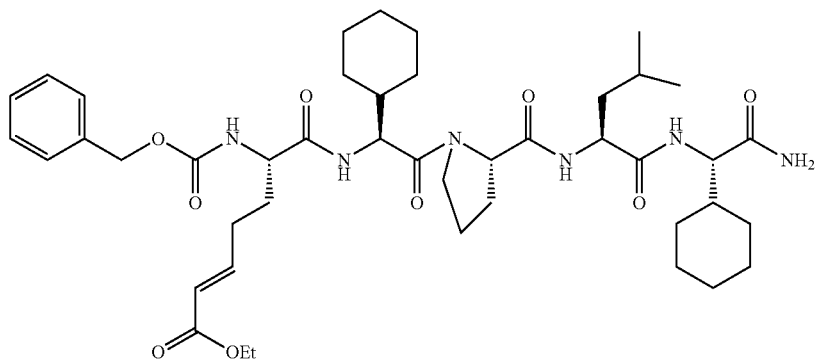

(S,E)-ethyl 7-((S)-2-((S)-2-((S)-1-((S)-2-amino-1-cyclohexyl-2-oxoethylamino)-4-methyl-1-oxopentan-2-ylcarbamoyl)pyrrolidin-1-yl)-1-cyclohexyl-2-oxoethylamino)-6-(benzyloxycarbonylamino)-7-oxohept-2-enoate
Chemical Formula: $C_{44}H_{66}N_6O_9$
Exact Mass: 822.49
Molecular Weight: 823.03

The synthesis of compound Ref. 12 was performed according to compound Ref. 08, using the corresponding amino acids for the solid phase chemistry yielding the backbone tetrapeptide.
Yield: 78 mg, 52%
ESI-MS: 823.8 $[M+H]^+$ 2. Preparation of Compound 42a/42b
(Regioisomers)

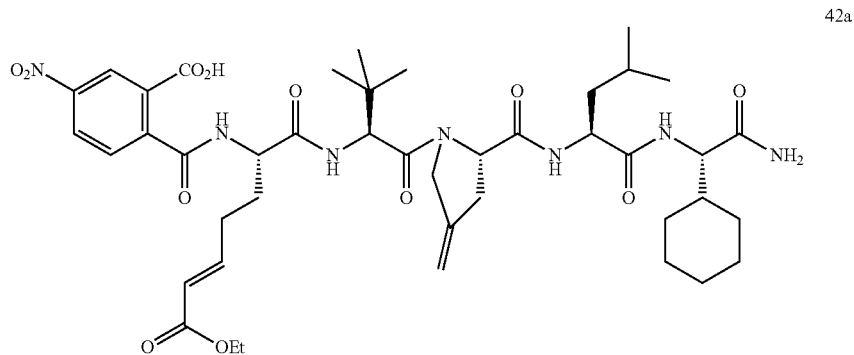

42a

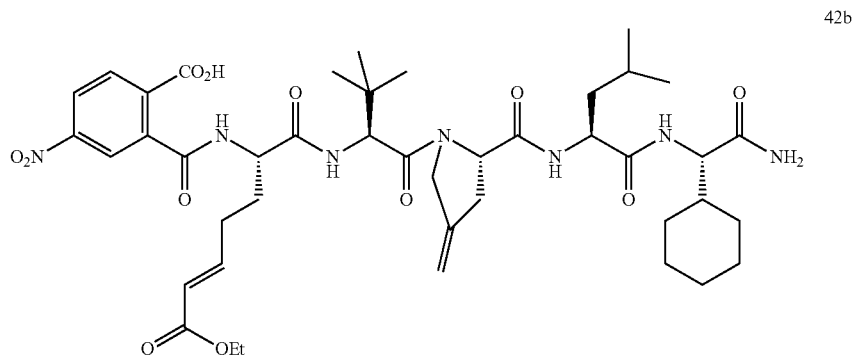

42b

-continued

42

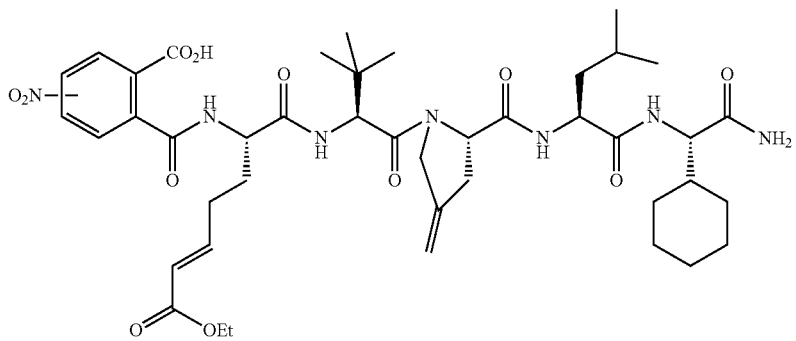

2-((S,E)-1-((S)-1-((S)-2-((S)-1-((S)-2-amino-1-cyclohexyl-2-oxoethylamino)-4-methyl-
1-oxopentan-2-ylcarbamoyl-4-methylenepyrrolidin-1-yl)-3,3-dimethyl-1-oxobutan-2-
ylamino)-7-ethoxy-1,7-dioxohept-5-en-2-ylcarbamoyl)-4/5-nitrobenzoic acid
Chemical Formula: $C_{43}H_{61}N_7O_{12}$
Exact Mass: 867.44
Molecular Weight: 867.98

The synthesis of compound 42a/42b was performed according to compound Ref. 12, using the corresponding amino acids for the buildup of the backbone tetrapeptide and 4-nitrophthalic anhydride instead of Cbz-Cl in the final step.

Yield: 32 mg, 37%, ratio of regioisomers: approximately 1:1

ESI-MS: 868.7 [M+H]$^+$

Example 1-43

1. Preparation of Compound Ref. 13

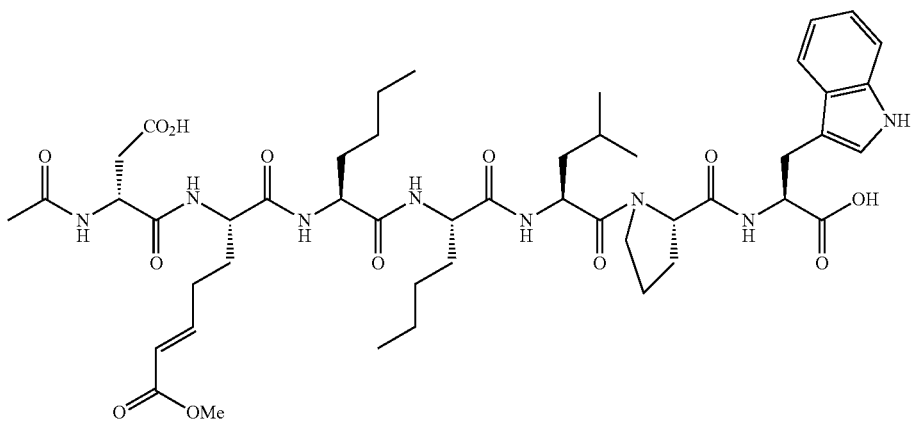

(S)-2-((S)-1-((4R,7S,10S,13S,16S)-4-(carboxymethyl)-10,13-dibutyl-7-((E)-
5-methoxy-5-oxopent-3-enyl)-18-methyl-2,5,8,11,14-pentaoxo-3,6,9,12,15-
pentaazanonadecanecarbonyl)pyrrolidine-2-carboxamido)-3-(1H-indol-3-
yl)propanoic acid
Chemical Formula: $C_{48}H_{70}N_8O_{13}$
Exact Mass: 966.51
Molecular Weight: 967.12

The backbone pentapeptide H-Nle-Nle-Leu-Pro-Trp-OH was built by standard Fmoc solid-phase peptide chemistry according to compound ZED3478, using 2-chlorotrityl resin and the corresponding amino acids. The Michael acceptor (methyl acrylate) was directly coupled according to compound ZED3481, using compound Ib. Finally, compound Ref. 13 was synthesized according to compound ZED3480 by coupling Ac-(D)-Asp(OtBu)-OH with HATU/DIPEA followed by cleavage of the tort-butyl ester with TFA in DCM.

Yield: 142 mg, 65%

ESI-MS: 967.8 [M+H]$^+$

2. Preparation of Compound Ref. 14

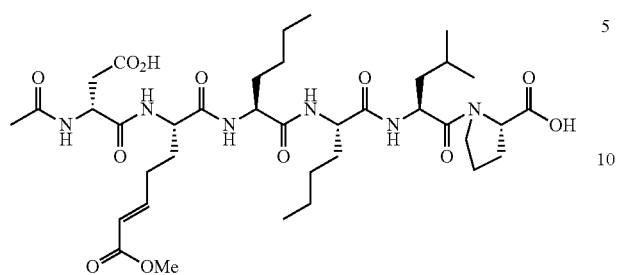

(S)-1-((4R, 7S, 10S, 13S, 16S)-10, 13-dibutyl-4-(carboxymethyl)-7-
((E)-5-methoxy-5-oxopent-3-enyl)-18-methyl-2, 5, 8, 11, 14-pentaoxo-
3, 6, 9, 12, 15-pentaazanonadecanecarbonyl)pyrrolidine-2-carboxylic-
acid Chemical Formula: $C_{37}H_{60}N_6O_{12}$ Exact Mass: 780,43
Molecular Weight: 780,91

The synthesis of compound Ref. 14 was performed according to Ref. 13, using the corresponding amino acids for the buildup of the backbone tetrapeptide.
Yield: 107 mg, 59%
ESI-MS: 781.7 [M+H]$^+$ 3. Preparation of Compound 43

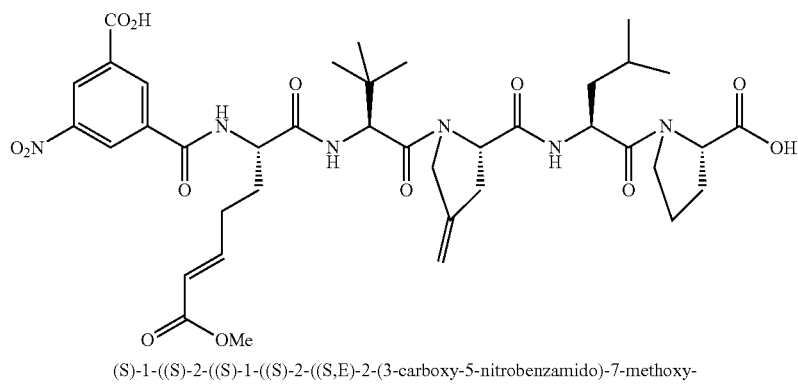

(S)-1-((S)-2-((S)-1-((S)-2-((S,E)-2-(3-carboxy-5-nitrobenzamido)-7-methoxy-
7-oxohept-5-enamido)-3,3-dimethylbutanoyl)-4-methylenepyrrolidine-2-
carboxamido)-4-methylpentanoyl)pyrrolidine-2-carboxylic acid
Chemical Formula: $C_{39}H_{52}N_6O_{13}$
Exact Mass: 812.36
Molecular Weight: 812.86

The synthesis of compound 43 was performed according to Ref. 14 using the corresponding amino acids for the synthesis of the backbone tetrapeptide. N-terminal capping was obtained by 5-nitroisophthalic acid (coupling according to compound ZED3480 with HATU/DIPEA) instead of Ac-D-Asp(OtBu)-OH in the final step.
Yield: 65 mg, 57%
ESI-MS: 813.6 [M+H]$^+$ Example 1-44

1. Preparation of Compound Ref. 15

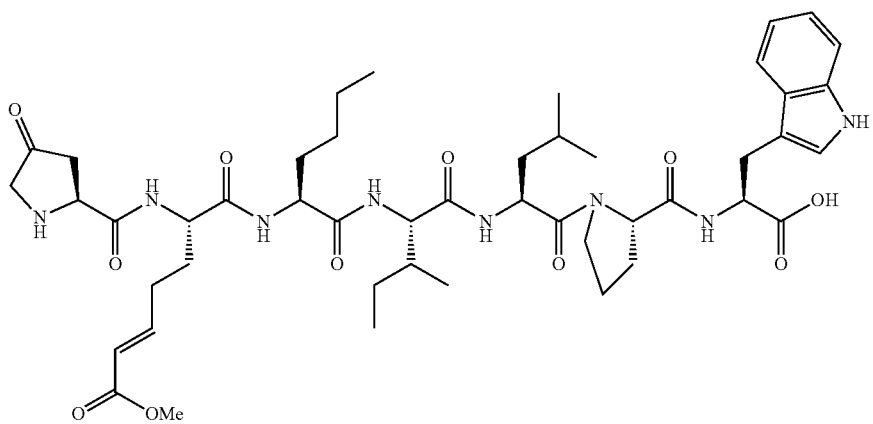

(S)-2-((S)-1-((8S,11S,14S,17S,E)-14-sec-butyl-11-butyl-17-isobutyl-3,9,12,15-
tetraoxo-8-((S)-4-oxopyrrolidine-2-carboxamido)-2-oxa-10,13,16-triazaoctadec-
4-ene)pyrrolidine-2-carboxamido-3-(1H-indol-3-yl)propanoic acid
Chemical Formula: $C_{47}H_{68}N_8O_{11}$
Exact Mass: 920.50
Molecular Weight: 921.09

The synthesis of compound Ref. 15 was performed according to Ref. 13, using the corresponding amino acids for the buildup of the backbone pentapeptide and (S)—N-Boc-4-oxopyrrolidine-2-carboxylic acid (coupling according to compound ZED3480 with HATU/DIPEA) instead of Ac-D-Asp(OtBu)-OH in the final step. The Boc protecting group is cleaved with TFA in DCM accordingly.

Yield: 127 mg, 57%
ESI-MS: 921.8 [M+H]+

2. Preparation of Compound Ref. 16

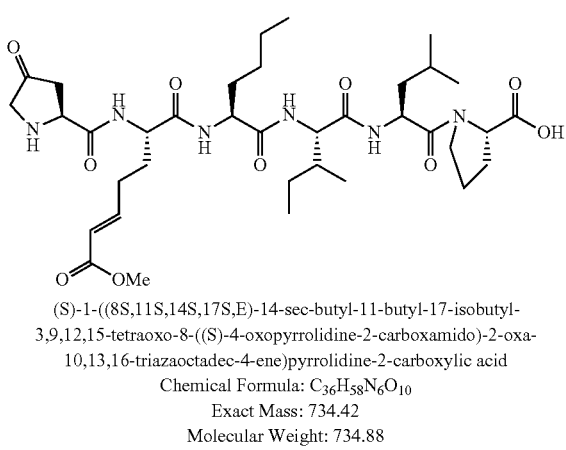 [SMILES: CCCC[C@H](NC(=O)[C@H](CC/C=C/C(=O)OC)NC(=O)[C@@H]1CC(=O)CN1)C(=O)N[C@H](C(=O)N[C@@H](CC(C)C)C(=O)N1CCC[C@H]1C(=O)O)C(C)CC]

(S)-1-((8S,11S,14S,17S,E)-14-sec-butyl-11-butyl-17-isobutyl-
3,9,12,15-tetraoxo-8-((S)-4-oxopyrrolidine-2-carboxamido)-2-oxa-
10,13,16-triazaoctadec-4-ene)pyrrolidine-2-carboxylic acid
Chemical Formula: $C_{36}H_{58}N_6O_{10}$
Exact Mass: 734.42
Molecular Weight: 734.88

The synthesis of compound Ref. 16 was performed according to Ref. 15, using the corresponding amino acids for the buildup of the backbone tetrapeptide.

Yield: 93 mg, 47%
ESI-MS: 735.6 [M+H]+

3. Preparation of Compound 44

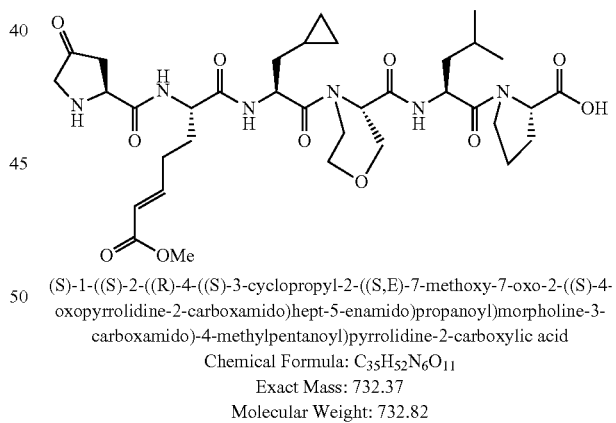

(S)-1-((S)-2-((R)-4-((S)-3-cyclopropyl-2-((S,E)-7-methoxy-7-oxo-2-((S)-4-
oxopyrrolidine-2-carboxamido)hept-5-enamido)propanoyl)morpholine-3-
carboxamido)-4-methylpentanoyl)pyrrolidine-2-carboxylic acid
Chemical Formula: $C_{35}H_{52}N_6O_{11}$
Exact Mass: 732.37
Molecular Weight: 732.82

The synthesis of compound 44 was performed according to Ref. 14 using the corresponding amino acids for the buildup of the backbone tetrapeptide.

Yield: 78 mg, 59%
ESI-MS: 733.6 [M+H]+

Example 1-45

1. Preparation of Compound Ref. 17 (ZED1265)

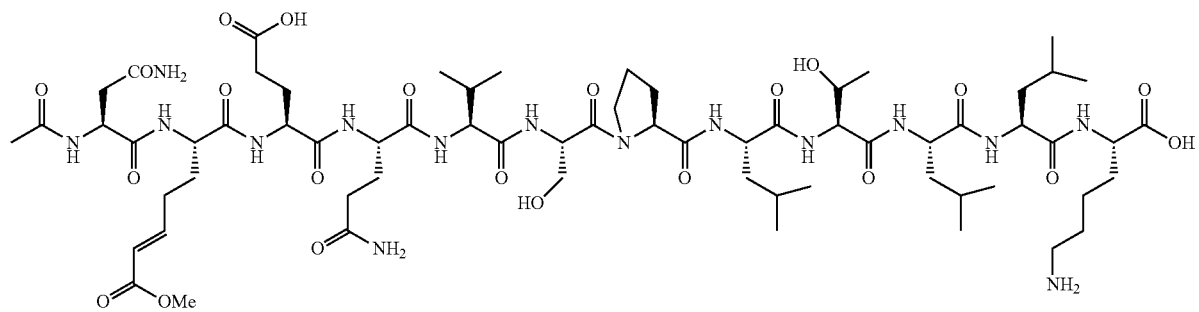

(3S,6S,9S,12S,15S)-1-((S)-1-((2S,5S,8S,11S,14S,17S)-17-(2-amino-2-oxoethyl)-8-(3-amino-3-oxopropyl)-
11-(2-carboxyethyl)-2-(hydroxymethyl)-5-isopropyl-14-((E)-5-methoxy-5-oxopent-3-enyl)-4,7,10,13,16,19-
hexaoxo-3,6,9,12,15,18-hexaazaicosane)pyrrolidin-2-yl)-15-(4-aminobutyl)-6-((R)-1-hydroxyethyl)-3,9,12-
triisobutyl-1,4,7,10,13-pentaoxo-2,5,8,11,14-pentaazahexadecan-16-oic acid Chemical Formula: $C_{65}H_{109}N_{15}O_{22}$
Exact Mass: 1451.79
Molecular Weight: 1452.65

The backbone decapeptide H-Glu-Gln-Val-Ser-Pro-Leu-Thr-Leu-Lys(Alloc)-OH was built by standard Fmoc solid-phase peptide chemistry according to compound ZED3478, using 2-chlorotrityl resin and the corresponding (side chain protected) amino acids. The Michael acceptor (methyl acrylate) was directly coupled according to compound ZED3481, using compound Ib. Finally, compound ZED1265 was synthesized according to compound ZED3480 by coupling Ac-Asn-OH with HATU/DIPEA followed by cleavage of the alloc protecting group with Tetrakis(triphenylphosphine)palladium(0) in DCM.

Yield: 177 mg, 36%
ESI-MS: 1453.2 [M+H]$^+$

2. Preparation of Compound Ref. 18 (ZED1246)

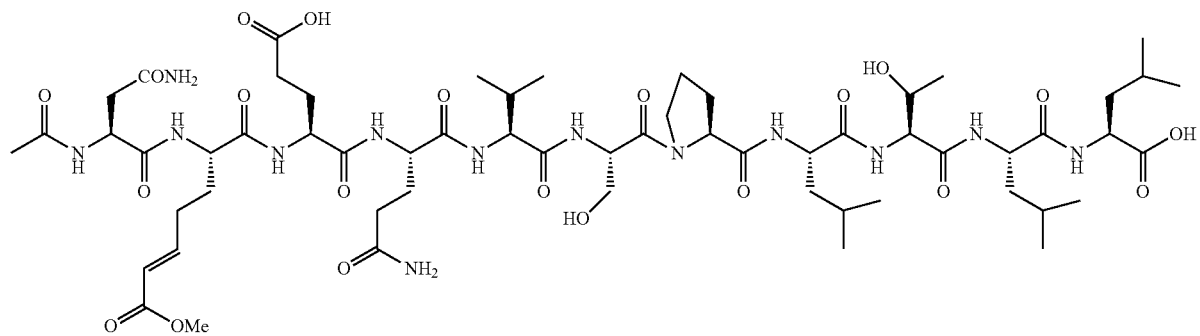

(3S,6S,9S,12S)-1-((S)-1-((2S,5S,8S,11S,14S,17S)-17-(2-amino-2-oxoethyl)-8-(3-amino-3-
oxopropyl)-11-(2-carboxyethyl)-2-(hydroxymethyl)-5-isopropyl-14-((E)-5-methoxy-5-oxopent-
3-enyl)-4,7,10,13,16,19-hexaoxo-3,6,9,12,15,18-hexaazaicosane)pyrrolidin-2-yl)-6-((R)-1-
hydroxyethyl)-3,9,12-triisobutyl-1,4,7,10-tetraoxo-2,5,8,11-tetraazatridecan-13-oic acid Chemical Formula: $C_{59}H_{97}N_{13}O_{21}$
Exact Mass: 1323.69
Molecular Weight: 1324.48

The synthesis of compound ZED1246 was performed according to ZED1265, using the corresponding amino acids for the buildup of the backbone nonapeptide.

Yield: 158 mg, 39%
ESI-MS: 1325.1 [M+H]$^+$

3. Preparation of Compound Ref. 19 (ZED1274)

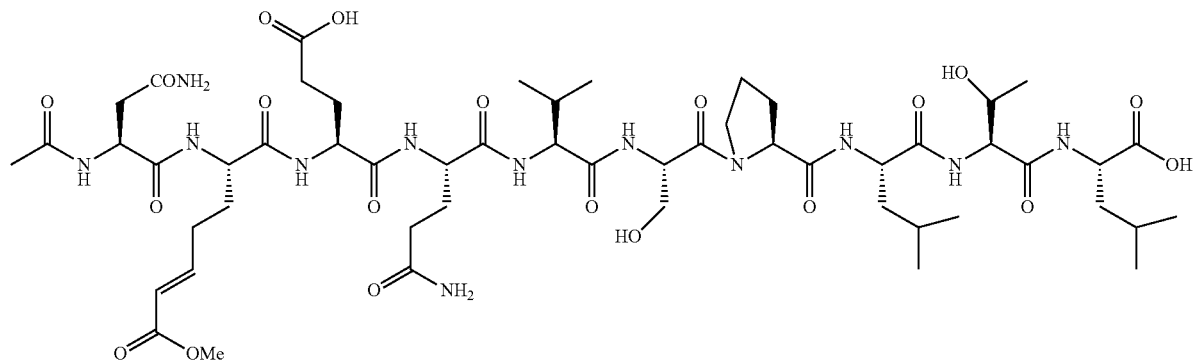

(S)-4-((S,E)-2-((S)-2-acetamido-4-amino-4-oxobutanamido)-7-methoxy-7-oxohept-5-enamido)-5-
((S)-5-amino-1-((S)-1-((S)-1-((S)-2-((S)-1-((2S,3R)-1-((S)-1-carboxy-3-methylbutylamino)-3-hydroxy-
1-oxobutan-2-ylamino)-4-methyl-1-oxopentan-2-ylcarbamoyl)pyrrolidin-1-yl)-3-hydroxy-1-oxopropan-
2-ylamino)-3-methyl-1-oxobutan-2-ylamino)-1,5-dioxopentan-2-ylamino)-5-oxopentanoic acid
Chemical Formula: $C_{53}H_{86}N_{12}O_{20}$
Exact Mass: 1210.61
Molecular Weight: 1211.32

The synthesis of compound ZED1274 was performed according to ZED1265, using the corresponding amino acids for the buildup of the backbone octapeptide.
Yield: 132 mg, 45%
ESI-MS: 1212.0 [M+H]$^+$ 4. Preparation of Compound Ref. 20 (ZED1282)

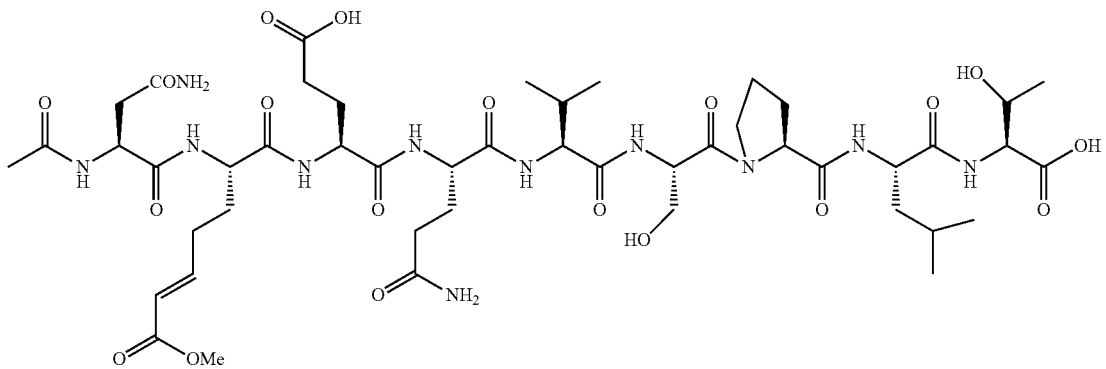

(S)-4-((S,E)-2-((S)-2-acetamido-4-amino-4-oxobutanamido)-7-methoxy-7-oxohept-5-enamido)-
5-((S)-5-amino-1-((S)-1-((S)-1-((S)-2-((S)-1-((1S,2R)-1-carboxy-2-hydroxypropylamino)-4-
methyl-1-oxopentan-2-ylcarbamoyl)pyrrolidin-1-yl)-3-hydroxy-1-oxopropan-2-ylamino)-3-
methyl-1-oxobutan-2-ylamino)-1,5-dioxopentan-2-ylamino)-5-oxopentanoic acid
Chemical Formula: $C_{47}H_{75}N_{11}O_{19}$
Exact Mass: 1097.52
Molecular Weight: 1098.16

The synthesis of compound ZED1282 was performed according to ZED1265, using the corresponding amino acids for the buildup of the backbone heptapeptide.
Yield: 165 mg, 61% ESI-MS: 1098.8 [M+H]$^+$ 5. Preparation of Compound Ref. 21 (ZED1283)

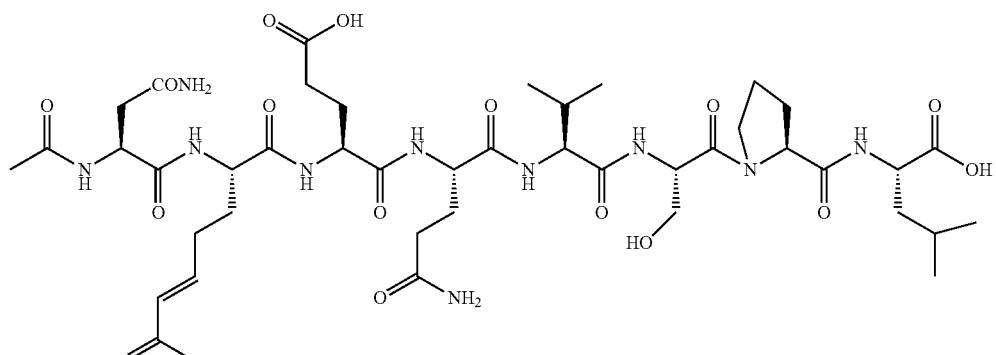

(S)-4-((S,E)-2-((S)-2-acetamido-4-amino-4-oxobutanamido)-7-methoxy-7-oxohept-5-enamido)-5-((S)-5-amino-1-((S)-1-((S)-1-((S)-2-((S)-1-carboxy-3-methylbutylcarbamoyl)pyrrolidin-1-yl)-3-hydroxy-1-oxopropan-2-ylamino)-3-methyl-1-oxobutan-2-ylamino)-1,5-dioxopentan-2-ylamino)-5-oxopentanoic acid
Chemical Formula: C$_{43}$H$_{68}$N$_{10}$O$_{17}$
Exact Mass: 996.48
Molecular Weight: 997.06

The synthesis of compound ZED1283 was performed according to ZED1265, using the corresponding amino acids for the buildup of the backbone hexapeptide.

Yield: 127 mg, 47%

ESI-MS: 997.8 [M+H]$^+$

Example 1-46: Preparation of Compound 45a/45b (Regioisomers)

45a

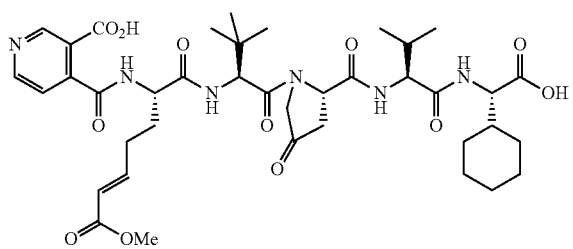

45b

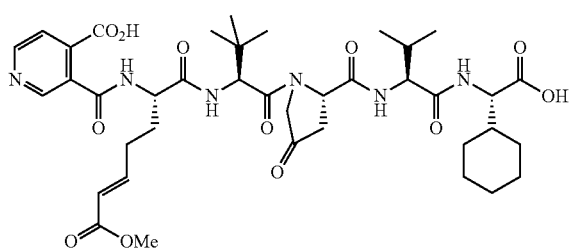

-continued

45

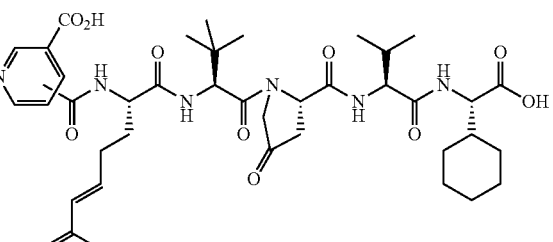

3/4-((S,E)-1-((S)-1-((S)-2-((S)-1-((S)-carboxyl(cyclohexyl)methylamino)-3-methyl-1-oxobutan-2-ylcarbamoyl)-4-oxopyrrolidin-1-yl)-3,3-dimethyl-1-oxobutan-2-ylamino)-7-methoxy-1,7-dioxohept-5-en-2-ylcarbamoyl)isonicotinic acid
Chemical Formula: C$_{39}$H$_{54}$N$_6$O$_{12}$
Exact Mass: 798.38
Molecular Weight: 798.88

The synthesis of compound 45a/45b was performed according to Ref. 11 using the corresponding amino acids for the buildup of the backbone tetrapeptide and capping by 3,4-pyridinedicarboxylic anhydride instead of Ac-(D)-Asp(OtBu)-OH in the final step.

Yield: 77 mg, 32%, ratio of regioisomers: approximately 1:1

ESI-MS: 799.6 [M+H]$^+$

Example 1-47

Reference Example 1 (Ref. 1)

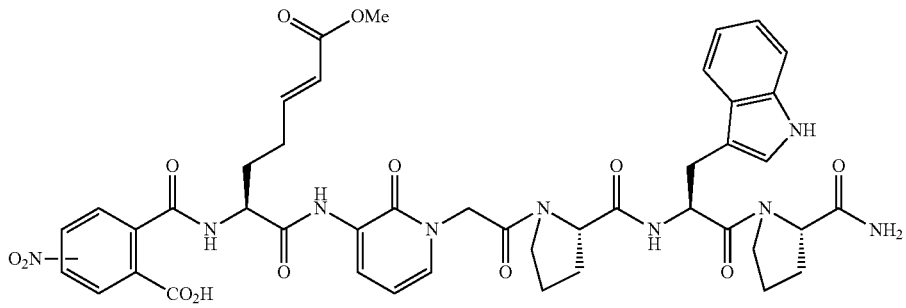

2-((S,E)-1-(1-(2-((S)-2-((S)-1-((S)-2-carbamoylpyrrolidin-1-yl)-3-(1H-indol-3-yl)-1-oxopropan-2-ylcarbamoyl)pyrrolidin-1-yl)-2-oxoethyl)-2-oxo-1,2-dihydropyridin-3-ylamino)-7-methoxy-1,7-dioxohept-5-en-2-ylcarbamoyl)-4/5-nitrobenzoic acid
Chemical Formula: $C_{44}H_{47}N_9O_{13}$
Exact Mass: 909,33
Molecular Weight: 909,90

The synthesis of Ref. 1 was performed according to example 1-1, using the corresponding anhydride and amino acids.

Yield: 12 mg, 26%, ratio of regioisomers: approximately 1:1

ESI-MS: 910.5 $[M+H]^+$

Reference Example 2 (Ref. 2)

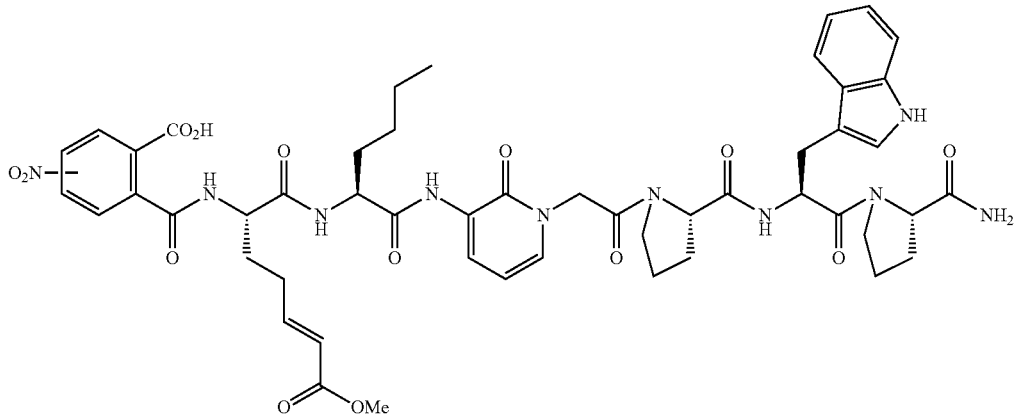

2-((S,E)-1-((S)-1-(1-(2-((S)-2-((S)-1-((S)-2-carbamoylpyrrolidin-1-yl)-3-(1H-indol-3-yl)-1-oxopropan-2-ylcarbamoyl)pyrrolidin-1-yl)-2-oxoethyl)-2-oxo-1,2-dihydropyridin-3-ylamino)-1-oxohexan-2-ylamino)-7-methoxy-1,7-dioxohept-5-en-2-ylcarbamoyl)-4/5-nitrobenzoic acid
Chemical Formula: $C_{50}H_{58}N_{10}O_{14}$
Exact Mass: 1022,41
Molecular Weight: 1023,05

The synthesis of Ref. 2 was performed according to example 1-1, using the corresponding anhydride and amino acids.

Yield: 16 mg, 23%, ratio of regioisomers: approximately 1:1

ESI-MS: 1023.5 $[M+H]^+$

Reference Example 3 (Ref. 3)

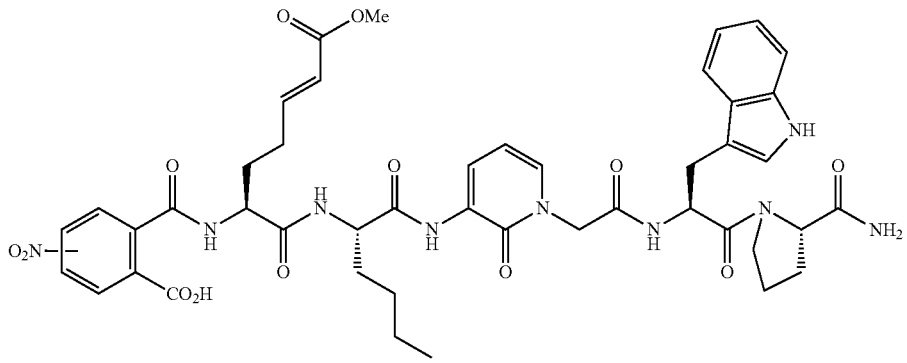

2-((S,E)-1-((S)-1-(1-(2-((S)-1-((S)-2-carbamoylpyrrolidin-1-yl)-3-(1H-indol-3-yl)-1-oxopropan-2-ylamino)-2-oxoethyl)-2-oxo-1,2-dihydropyridin-3-ylamino)-1-oxohexan-2-ylamino)-7-methoxy-1,7-dioxohept-5-en-2-ylcarbamoyl)-4/5-nitrobenzoic acid Chemical Formula: $C_{45}H_{51}N_9O_{13}$
Exact Mass: 925,36
Molecular Weight: 925,94

The synthesis of Ref. 3 was performed according to example 1-1, using the corresponding anhydride and amino acids.

Yield: 11 mg, 19%, ratio of regioisomers: approximately 1:1

ESI-MS: 926.5 [M+H]$^+$

Reference Example 4 (Ref. 4)

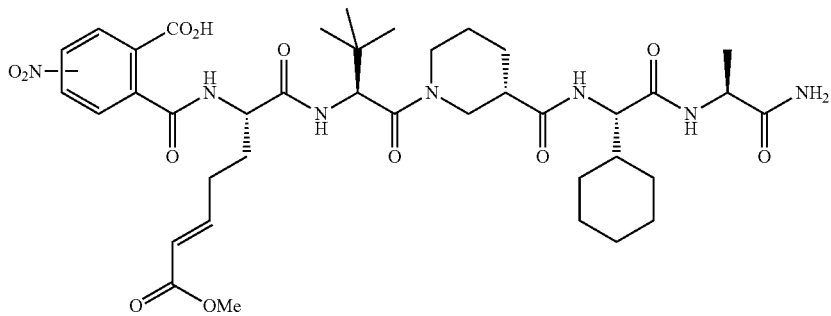

2-((S,E)-1-((S)-1-((S)-3-((S)-2-((S)-2-amino-1-cyclohexyl-2-oxoethylamino)-1-cyclohexyl-2-oxoethylcarbamoyl)piperidin-1-yl)-3,3-dimethyl-1-oxobutan-2-ylamino)-7-methoxy-1,7-dioxohept-5-en-2-ylcarbamoyl)-4/5-nitrobenzoic acid Chemical Formula: $C_{44}H_{63}N_7O_{12}$
Exact Mass: 881,45
Molecular Weight: 882,01

The synthesis of Ref. 4 was performed according to example 1-1, using the corresponding anhydride and amino acids.

Yield: 79 mg, 58%, ratio of regioisomers: approximately 1:1

ESI-MS: 882.6 [M+H]$^+$

Reference Example 5 (Ref. 5)

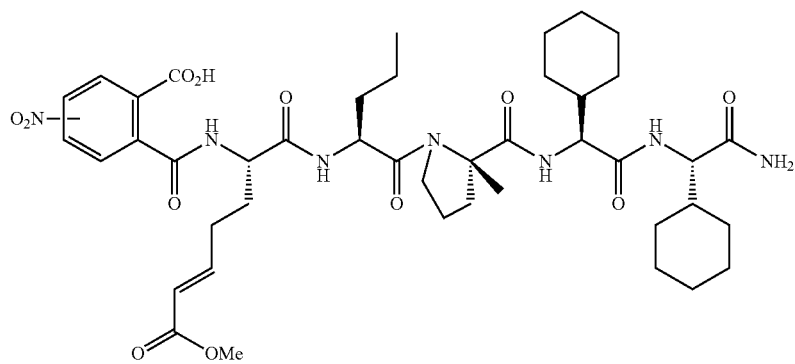

2-((S,E)-1-((S)-1-((S)-2-((S)-2-((S)-2-amino-1-cyclohexyl-2-oxoethylamino)-1-cyclohexyl-2-oxoethylcarbamoyl)-2-methylpyrrolidin-1-yl)-1-oxobutan-2-ylamino)-7-methoxy-1,7-dioxohept-5-en-2-ylcarbamoyl)-4/5-nitrobenzoic acid
Chemical Formula: $C_{43}H_{61}N_7O_{12}$
Exact Mass: 867,44
Molecular Weight: 867,98

The synthesis of Ref. 5 was performed according to example 1-1, using the corresponding anhydride and amino acids.
Yield: 41 mg, 56%, ratio of regioisomers: approximately 1:1
ESI-MS: 868.6 $[M+H]^+$ Reference Compound 6 (Ref. 6) Disclosed in WO 2008055488 A1 as Compound 38

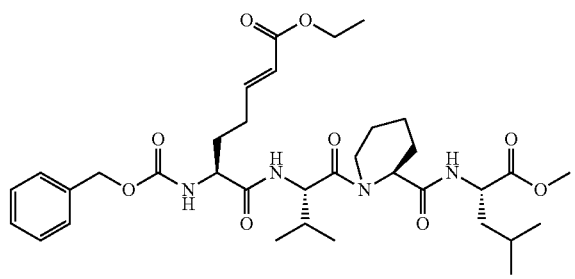 [SMILES: CCOC(=O)/C=C/CC[C@H](NC(=O)OCc1ccccc1)C(=O)N[C@H](C(=O)N1CCCC[C@H]1C(=O)N[C@@H](CC(C)C)C(=O)OC)C(C)C]

Reference Compound 7 (Ref. 7) Disclosed in WO 2008055488 A1 as Compound 4.1

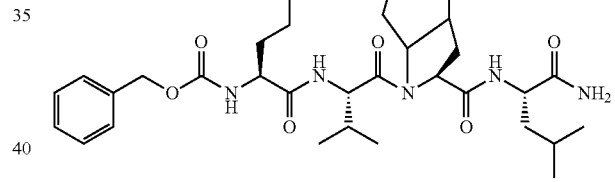

Reference Compound 22 (Ref. 22-ZED1301): Compound 4 of WO2014/090835

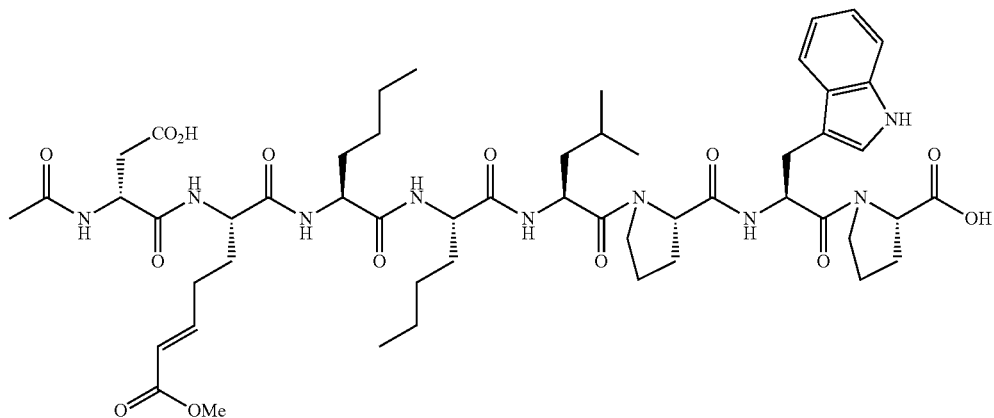 [SMILES: CCCC[C@H](NC(=O)[C@H](CC/C=C/C(=O)OC)NC(=O)[C@@H](CC(=O)O)NC(C)=O)C(=O)N[C@@H](CCCC)C(=O)N[C@@H](CC(C)C)C(=O)N1CCC[C@H]1C(=O)N[C@@H](Cc1c[nH]c2ccccc12)C(=O)N1CCC[C@H]1C(=O)O]

Reference Compound 23 (Ref. 23-ZED1390):
Compound 7 of WO2014/090835

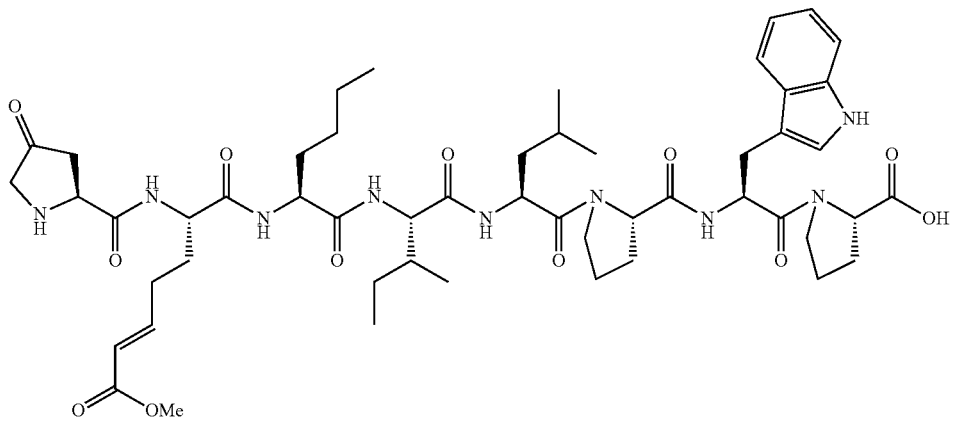 [SMILES: CCCC[C@H](NC(=O)[C@H](CC/C=C/C(=O)OC)NC(=O)[C@@H]1CC(=O)CN1)C(=O)N[C@H](C(=O)N[C@@H](CC(C)C)C(=O)N1CCC[C@H]1C(=O)N[C@@H](Cc1c[nH]c2ccccc12)C(=O)N1CCC[C@H]1C(=O)O)C(C)CC]

Reference Compound 24 (Ref. 24-ZED1251)
Disclosed in *Thrombosis Research*, 2013, 131, 0214-6222

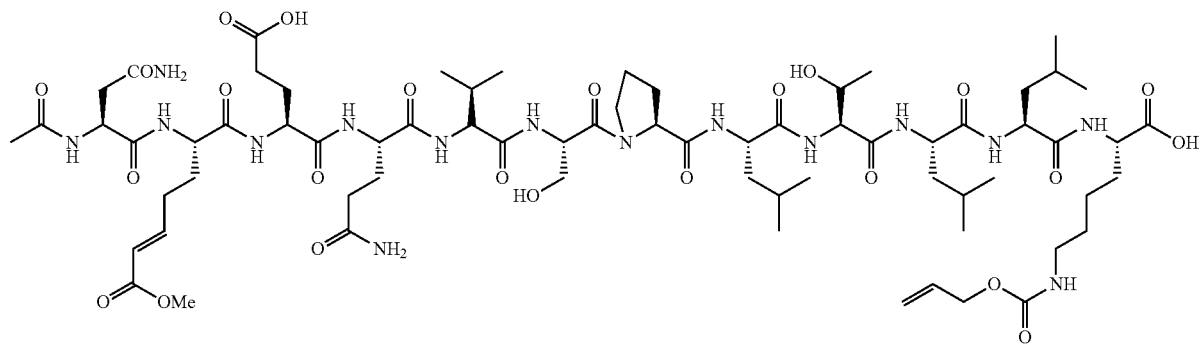

Reference compound 25 (Ref. 25-ZED1227)
disclosed in Amino Adds, 2017, 49, 585-595

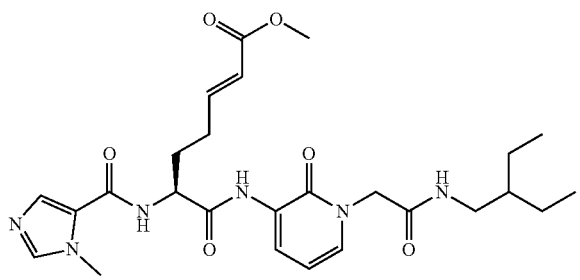 [SMILES: CCC(CC)CNC(=O)Cn1cccc(NC(=O)[C@H](CC/C=C/C(=O)OC)NC(=O)c2cncn2C)c1=O]

lyzes by its isopeptidase activity the release of dark quencher dinitrophenyl at the original substrate glutamine position resulting in fluorescence increase (based on the N-terminal 2-aminobenzoyl fluorescent dye) (Oertel K, HunfekJ A, Specker E, Reiff C, Seitz R, Pasternack R, Dodt J. A highly sensitive fluorometric assay for determination of human coagulation factor XIII in plasma. *Anal Biochem* 2007; 367:152-8.)

Briefly, 12 µL recombinant cFXIII-A2 (T027, Zedira GmbH, Darmstadt, Germany) or FXIII-$A_2B_2$ derived from human plasma (T007) (25 µg/mL) and 3 µL human α-thrombin (0.5 U/mL, T056, Zedira) were mixed with 270 µL assay buffer (50 mM Tris-HCl, 10 mM $CaCl_2$), 150 mM NaCl, 5.56 mM glycine methyl ester, 5 mM DTT, pH 7.5) containing 55 µM A101 substrate. The mixture was incubated for 20 min at room temperature to activate FXIII. 15 µL of inhibitor solution (serial dilution from 1.25 µM to 1.25 nM) dissolved in DMSO/assay buffer were added, mixed and the kinetic measurement started after 3 min. Fluorescence emission was monitored at 418 nm ($\lambda_{ex}$=313 nm) and 37° C. for 30 min using a CLARIOstar fluorescence micro plate reader (BMG Labtech, Ortenberg, Germany). For measurements without inhibitor, 15 µL of assay buffer/2% (v/v) DMSO were added. All measurements were performed in triplicate. The respective $IC_{50}$ values were calculated by non-linear regression using the MARS software package (BMG Labtech).

BIOLOGICAL EXAMPLES

Example 2-1: FXIII Activity Assays

A: Isopeptidase Assay for Estimating Inhibitor Potency

FXIIIa activity has been determined using substrate A101 (Zedira GmbH, Darmstadt, Germany), which is based on the N-terminal dodecapeptide of $\alpha_2$-antipiasmin. FXIIIa cata- The inhibition of FXIIIa from animal species was performed accordingly using 36 µg/mL mouse FXIII-$A_2$ (T061, Zedira), 27 µg/mL rat FXIII-$A_2$ (T065), 11 µg/mL pig FXIII-$A_2$ (T066), 32 µg/mL dog FXIII-$A_2$ (T062), and 22 µg/mL cynomolgus CFXIII-$A_2$ (T161), all produced recombinantly.

B: Transamidation Assay for Determining Inhibitor Selectivity

The most relevant off-targets are the transglutaminase isoenzymes especially tissue transglutaminase (TG2) because the enzyme is ubiquitously expressed throughout the human body. To determine selectivity, the fluorescence increase upon transglutaminase-catalyzed incorporation of dansylcadaverine into the universal transglutaminase substrate N,N-dimethylcasein was used (Lorand L, Lockridge O M, Campbell L K, Myhrman R, Bruner-Lorand J. Transamidating enzymes. *Anal Biochem* 1971; 44: 221-31.).

Briefly, 15 µL of recombinant transglutaminase enzyme [5] [15 µg/mL hTG1 (T035, Zedira), 69 µg/mL hTG2 (T022), 29 µg/mL hTG6 (T021), 18 µg/mL hTG7 (T011)] were mixed with 270 µL assay buffer containing dansylcadaverine and N,N-dimethyl casein. In the case of FXIII, 12 µL cFXIII (25 µg/mL) and 3 µL human α-thrombin (0.5 U/mL, T056, Zedira) were mixed with 270 µL assay buffer. The mixture was incubated for 20 min at room temperature to activate FXIII. In the case of TG3 78 µg hTG3 (T024) were activated using 14 µg dispase II (Roche, Mannheim, Germany) in the presence of 1.4 mM $CaCl_2$) and incubated for 30 min at 25° C. The activated hTG3 was subsequently assayed as described above. 15 µL of inhibitor solution dissolved in DMSO/assay buffer were added, mixed and the kinetic measurement started after 3 min. Fluorescence emission was continuously monitored for 30 min at 500 nm ($\lambda_{ex}$=330 nm) and 37° C. using the CLARIOstar fluorescence plate reader. All measurements were performed in triplicate. The respective $IC_{50}$ values were calculated by non-linear regression using the MARS software package (BMG Labtech, Ortenberg, Germany).

The following tables summarize the inhibition data of compound 5 (=5a/b) against human plasma derived FXIII-$A_2B_2$ and the recombinant cellular form (FXIII-$A_2$). In addition, the inhibition of cFXIII from mouse, rat, rabbit, dog, pig and cynomolgus is shown using different assays.

TABLE 1

| Transglutaminase | Species | Isopeptidase Assay $IC_{50}$ [nM] | Transamidation Assay $IC_{50}$ [nM] |
|---|---|---|---|
| pFXIII | human | 10 ± 0.1 | 4 ± 0.4 |
| cFXIII | human | 16 ± 0.6 | 24 ± 1.5 |
| cFXIII | mouse | 19 ± 0.6 | 15 ± 1.2 |
| cFXIII | rat | 8 ± 0.1 | 17 ± 0.6 |
| cFXIII | rabbit | 20 ± 1.0 | 7 ± 1.7 |
| cFXIII | dog | 28 ± 0.6 | 24 ± 0.6 |
| cFXIII | pig | 365 ± 8.0 | 16 ± 1.5 |
| cFXIII | cynomolgus | 15 ± 0.1 | 19 ± 0.6 |

TABLE 2

The selectivity against human transglutaminases iso-enzymes.

| Transglutaminase | Transamidation Assay $IC_{50}$ [nM] | Selectivity |
|---|---|---|
| cFXIII | 24 ± 1.5 | 1 |
| TG1 | 11035 ± 1003 | 463 |
| TG2 | 445 ± 20 | 19 |
| TG3 | 66511 ± 4544 | 2791 |
| TG6 | 17 ± 0.6 | 0.7 |
| TG7 | 1330 ± 102 | 56 |

TABLE 3 inhibitory activity of the inventive compounds against FXIII and TG2 selectivity for selected compounds (isopeptidase assay)

| Compound | $IC_{50}$ [nM] FXIII | $IC_{50}$ [nM] TG2 | selectivity |
|---|---|---|---|
| 1a/b | 11 | 75 | 6.8 |
| 2a/b | 16 | 69 | 4.3 |
| 3 | 20 | 16 | 0.8 |
| 4 | 13 | 14 | 1.1 |
| 5a/b | 16 | 67 | 4.2 |
| 6 | 17 | 12 | 0.7 |
| 7a/b | 21 | 610 | 29.0 |
| 8a/b | 21 | 417 | 19.9 |
| 9a/b | 139 | 501 | 3.6 |
| 10a/b | 42 | 38 | 0.9 |
| 11a/b | 70 | 178 | 2.5 |
| 12a/b | 51 | 257 | 5.0 |
| 13a/b | 96 | 221 | 2.3 |
| 14a/b | 26 | 59 | 2.3 |
| 15a/b | 69 | 483 | 7.0 |
| 16a/b | 106 | 204 | 1.9 |
| 17a/b | 41 | 295 | 7.2 |
| 18a/b | 510 | 239 | 0.5 |
| 19a/b | 141 | 298 | 2.1 |
| 20a/b | 156 | 218 | 1.4 |
| 21a/b | 59 | 100 | 1.7 |
| 22a/b | 42 | 56 | 1.3 |
| 23a/b | 91 | 160 | 1.8 |
| 24a/b | 18 | 63 | 3.5 |
| 25a/b | 20 | 35 | 1.8 |
| 26a/b | 43 | 98 | 2.3 |
| 27 | 27 | 64 | 2.4 |
| 28 | 36 | 41 | 1.1 |
| 29 | 24 | 32 | 1.3 |
| 30 | 15 | 16 | 1.1 |
| 31a/b | 10 | 27 | 2.7 |
| 32a/b | 12 | 72 | 6.0 |
| 33a/b | 2138 | 7980 | 3.7 |
| 34a/b | 123 | 356 | 2.7 |
| 35a/b | 86 | 198 | 2.3 |
| 36a/b | 41 | 168 | 4.1 |
| 37a/b | 69 | 324 | 4.7 |
| Ref. 1 | >10000 | 7040 | — |
| Ref. 2 | >10000 | >10000 | — |
| Ref. 3 | >10000 | >10000 | — |
| Ref. 4 | >10000 | 7039 | — |
| Ref. 5 | 9762 | 3462 | 0.4 |
| Ref. 6 | >10000 | 48 | — |
| Ref. 7 | >10000 | 32 | — |

*Compounds a/b means 1 to 1 mixuter of two regiomers

TABLE 4 inhibitory activity of the inventive compounds against FXIII and TG2 selectivity of prior art compounds

| Compound | FXIII $IC_{50}$ [nM] | TG2 $IC_{50}$ [nM] | Selectivity |
|---|---|---|---|
| Ref. 08 | 3648 | 36 | 0.01 |
| 38 | 47 | 760 | 16.17 |
| Ref. 09 | 5690 | 26 | 0.00 |
| 39a/b | 39 | 698 | 17.90 |
| Ref. 10 | 8183 | 176 | 0.02 |
| 40 | 81 | 848 | 10.47 |
| Ref. 11 | 5361 | 253 | 0.05 |

TABLE 4-continued inhibitory activity of the inventive compounds against
FXIII and TG2 selectivity of prior art compounds

| Compound | FXIII IC$_{50}$ [nM] | TG2 IC$_{50}$ [nM] | Selectivity |
|---|---|---|---|
| 42a/b | 127 | 1207 | 9.50 |
| Ref. 12 | 6771 | 345 | 0.05 |
| 42a/b | 56 | 679 | 12.13 |
| Ref. 13 | 465 | 2800 | 6.02 |
| Ref. 14 | >10.000 | 2150 | — |
| 43 | 158 | 856 | 5.42 |
| Ref. 15 | 226 | 117 | 0.52 |
| Ref. 16 | >10.000 | 196 | — |
| 44 | 141 | 798 | 5.66 |
| Ref. 17 | 420 | 227 | 0.54 |
| Ref. 18 | 995 | 341 | 0.34 |
| Ref. 19 | 4975 | 370 | 0.07 |
| Ref. 20 | 8475 | 381 | 0.04 |
| Ref. 21 | >10.000 | 421 | — |
| 45a/b | 35 | 705 | 20.14 |
| Ref. 22 | 110 | 2919 | 26.54 |
| Ref. 23 | 56 | 102 | 1.82 |
| Ref. 24 | 306 | 169 | 0.55 |
| Ref. 25 | >10.000 | 45 | — |

Example 2-2: Inhibition of Fibrin Cross-Linking and Size Exclusion Chromatography of Fibrin Degradation Products For the in vitro preparation of fibrin clots, HSA-free human fibrinogen (2.5 mg/mL, FIB3, Enzyme Research Laboratories, South Bend, Ind., USA), diluted in 20 mM Tris-HCl, 300 mM NaCl, pH 7.4, was mixed with cFXIII (10 µg/mL, T027, Zedira), and 5 mM CaCl$_2$). Prior to the addition of 50 U human thrombin (T053, Zedira), either DMSO (2.4% v/v) or the inventive compound as inhibitor (10 µM final concentration dissolved in DMSO) were added to the mixture. To allow completion of fibrin cross-linking, incubation was performed at 37° C. for 16 h. Subsequently, recombinant human plasmin (0.2 mg/mL, P012, Zedira) was added to the mixture and incubated at 37° C. for 1 h to solubilize the fibrin clots. Separation of cross-linked and non-cross-linked fibrin degradation products (xFDPs/FDPs, respectively) was performed using a Sephacryl S-200 column (CV-120 mL, GE Healthcare, Uppsala, Sweden) equilibrated in 20 mM Tris-HCl, 500 mM NaCl, pH 7.4.

Figure 1:
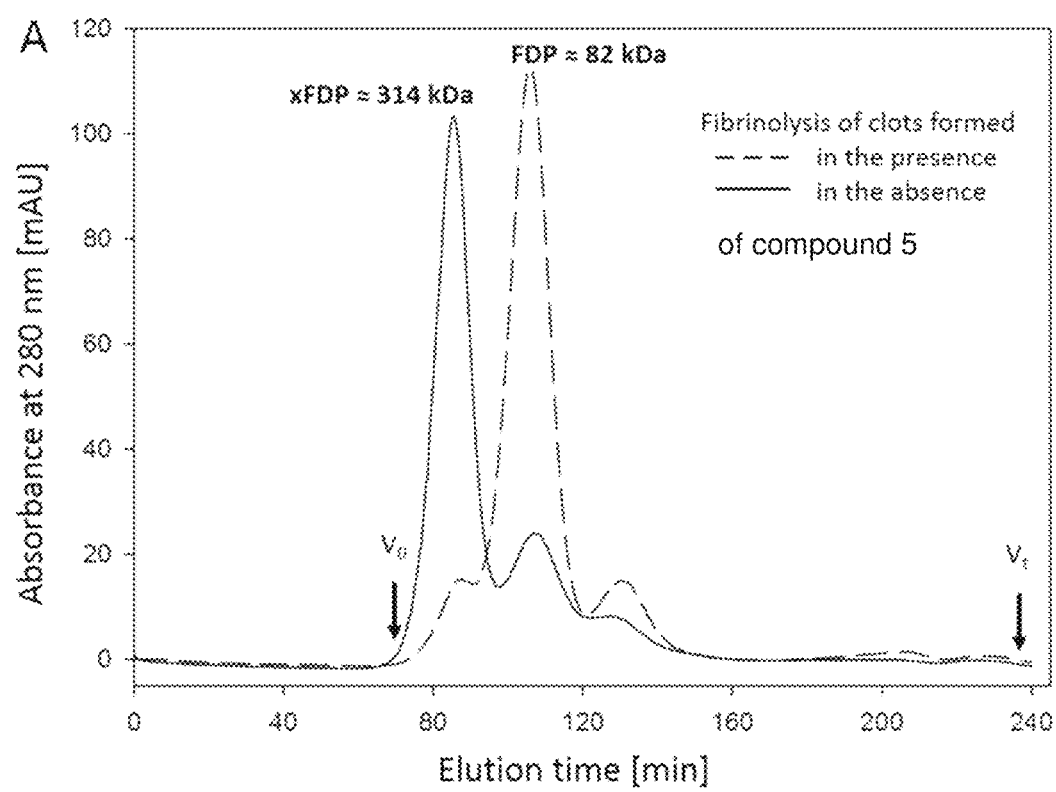
FIG. 1.
Figure 1:
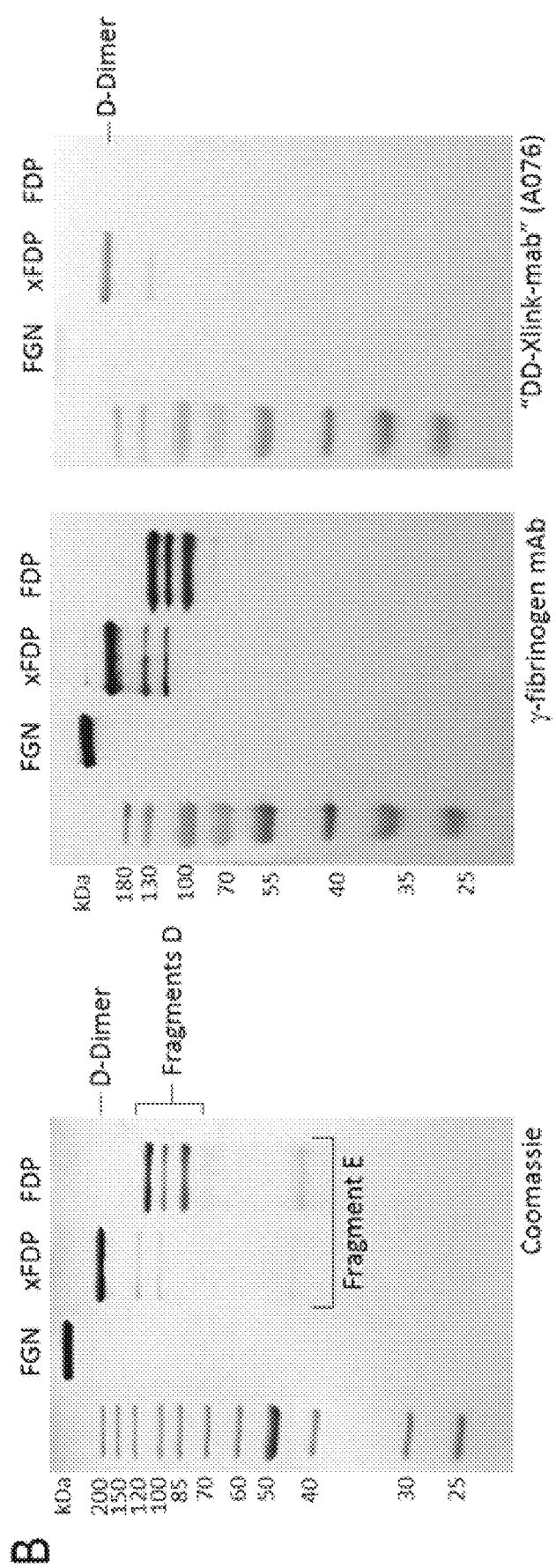

Sodium dodecyl sulfate polyacrylamide gel electrophoresis (SDS-PAGE) was performed according to Laemmli (Laemmli U K. Cleavage of structural proteins during the assembly of the head of bacteriophage T4. *Nature* 1970; 227: 680-5.). Briefly, samples were mixed with non-reducing 5×SDS-PAGE loading buffer (128 mM Tris-HCl at pH 6.8, 30% glycerol, 10% SDS, and 0.05% bromophenol blue), and loaded on a 10% polyacrylamide gel. Separation was performed at 200 V for 40 min. Gels were stained with Coomassie Brilliant Blue R-250. Electro-blotting was performed in a Trans-Blot SD semi-dry transfer cell (Bio-Rad, Hercules, Calif., U.S.A.) at 20 V for 80 min. After blotting, the nitrocellulose membranes were pre-soaked in 48 mM Tris, 39 mM glycine, 1.3 mM SDS, and 20% (v/v) methanol. Residual binding sites were blocked in 5% skimmed milk powder in TBS-T [10 mM Tris, 150 mM NaCl, and 0.05% (v/v) Tween 20 at pH 8.0] for 60 min. The membrane was washed in TBS-T wash buffer and incubated for 1 h. with primary antibody (diluted 10,000-fold in TBS-T). After washing for 3×5 min in TBS-T, anti-mouse IgG (Sigma-Aldrich, Schnelldorf, Germany) conjugated to alkaline phosphatase and diluted 10,000-fold in TBS-T buffer was added to the membranes followed by 1 h incubation. The membranes were placed in detection reagent (100-fold dilution of AP color reagent in color development buffer, Bio-Rad, Hercules, Calif., U.S.A.). Excess detection reagent was drained off, and the staining reaction was stopped with 20 mM Tris-HCl and 5 mM EDTA at pH 8.0. All steps were performed at room temperature on a shaker (FIG. 1).

Example 2-3: Thromboelastometry (TEM)

Thromboelastometry is a visco-elastic method for the assessment of blood coagulation (Lang T, von Depka M. Possibilities and limitations of thrombelastometry/-graphy. *Hamostaseologie* 2006; 26: S20-9.). Clotting time (CT), clot formation time (CFT), maximum clot firmness (MCF) and lysis index at 60 min (LI60) were obtained using fresh whole blood in the ROTEM® delta device according to the manufacturer's instructions.

The potency of the inventive compounds as inhibitors (serial dilution covering 20.0 µM to 0.08 µM final concentration) in the presence of 0.02 µg/mL tissue plasminogen activator (t-PA; P016, Zedira) was investigated. Briefly, 20 µL star-TEM® (0.2 mol/L CaCl$_2$)), 20 µL r ex-TEM® (recombinant tissue factor, phospholipids, heparin inhibitor), 10 µL inhibitor stock solution (720 µM-2.88 µM), combined with 10 µL t-PA stock solution (0.72 µg/mL) to yield concentrations of 360 µM-1.44 µM in 7.2% DMSO/PBS with 0.36 µg/mL t-PA and 300 µL fresh citrated whole blood (from healthy consenting donors) were mixed in a disposable cuvette. As a control the inhibitor stock solution was replaced by 3.6% DMSO/0.36 µg/mL t-PA in PBS.

The FIG. 2 shows the thromboelastogram of whole human blood spiked with compound 5 at serial dilution 20 µM-0.63 µM compared to control in the presence of 0.02% t-PA In FIG. 3, two graphs (A) and (B) show the reduction of maximum clot firmness compared to inhibitor-free control (MCFc) and the increase in clot lysis at 60 minutes compared to control (LI60c).

The inhibitor has no influence on the clotting time (CT) indicating that the compound does not interfere with other coagulation factors leaving the coagulation cascade, the fibrin formation, and the platelet activation untapped.

The potency of several published FXIII inhibitors (e.g. Ref. 22, Ref. 23, Ref. 24 as well as reference molecules Ref. 13, Ref. 14, Ref. 15, and Ref. 16) was evaluated using thromboelastometry. The detailed dose-dependent influence on key coagulation parameters of compound 5, as novel preferred compound, is shown in FIGS. 2, 3A and 3B. Compound 5 reduced the maximum clot firmness (MCFc, FIG. 3A) and increased the clot lysis at 60 minutes (LI60c, FIG. 3B) compared to control lacking the FXIII inhibitor. As detailed in the graphs 3A/3B, at a concentration of 2.5 µM, compound 5 lowers the clot firmness (MCFc) by 20% while increasing the lysis by 35% compared to control.

The potency of Ref. 22, Ref. 23, Ref. 24 as well as reference molecules Ref. 13, Ref. 14, Ref. 15, and Ref. 16 were determined at fixed concentration of 2.5 µM in the same experimental setting. Spiked into whole human blood the compounds did not influence the clot parameters MCFc and LI60c. Therefore, the molecules were considered being not preferred, while missing the novel structural features claimed herein. In contrast, novel compounds 43, 44, and 45a/b (also spiked at 2.5 µM) showed efficacy in reducing clot firmness MCFc by 8%, 7%, and 17% (compare to FIG. 3A) while facilitating clot lysis to 14%, 11%, and 27% (LI60c, compare to FIG. 3B). Compounds 43, 44, and 45a/b are novel displaying the structural features claimed herein to design potent drug-like FXIII inhibitors.

Further, the stability of compounds in plasma was determined as prerequisite for drug-likeness. Briefly, after spiking the chemical entities, the plasma was incubated at 37° C. At certain time points (e.g. at 15 and 120 minutes), 3 vol. cold MeOH were added to extract the compounds. After centrifugation, the supernatant was analyzed by HPLC. The half life was calculated based on the respective calibration curve. Compounds Ref. 22, Ref. 23, Ref. 24 as well as reference molecules Ref. 13, Ref. 14, Ref. 15, Ref. 16, Ref. 17, and Ref. 18 were unstable in plasma as indicated by plasma half life below 15 minutes. Therefore, they were considered being not suitable FXIII inhibitors due to the short half life in blood. These compounds are missing the novel structural features disclosed herein. In contrast, compounds 1a/b, 2a/b, 3, 4, 5a/b, 6, 7a/b, 8a/b, 9a/b, 10a/b, 11a/b, 12a/b, 13a/b, 14a/b, 15a/b, 16a/b, 17a/b, 18a/b, 19a/b, 20a/b, 21a/b, 22a/b, 23a/b, 24a/b, 25a/b, 26a/b, 27, 28, 29, 30, 31a/b, 32a/b, 33a/b, 34a/b, 35a/b, 36a/b, 37a/b, 38, 39a/b, 40, 41, 42a, 42b, 43, 44, and 45a/b were found to be stable in plasma over a period of 2 hours (>75% recovery each determined by HPLC).

In contrast to the reference compounds exceeding a length of 7 amino acids, each inventive compound showed a plasma half-life exceeding 2 h so that the FXIII inhibitors discloses herein are sufficiently drug-like in contrast to the reference compounds having a half-life in blood of less than 15 minutes.

Example 2-4: Anti-Coagulation in a Rabbit Model of Venous Stasis and Reperfusion Purpose bred animals were identified upon arrival in the test facility according to the respective guidelines. Male New Zealand White rabbits (2-3 kg) were anesthetized for the duration of the procedure. The rabbit's right jugular vein was exposed and any collateral veins to the venous stasis segment were ligated. In order to prevent embolization, approximately 4 cm of a 10 cm long polyester suture thread was inserted from upstream into the lumen of the designated stasis segment prior to the ligations to allow thrombus formation around the thread. An ultrasound probe was placed perivascularly on the right jugular vein downstream to the venous stasis segment, and blood flow was recorded continuously (3 mm probe, Transonic Systems Inc, Ithaca, USA). Blood samples were taken from the right femoral artery (1 mL in 150 mM sodium citrate) as shown below. Test compound 5 (n=7) or negative control (n=6) were administered at the selected concentration and flow rate through an i.v. bolus or infusion via the right femoral vein as visualized below. The negative control animals received 2×PBS/5% glucose containing in mM: NaCl 273.8, $NaH_2PO_4 \times 2$ $H_2O$ 14.2, KCl 5.4 and $KH_2PO_4$ 2.9, pH 7.4±0.05/5% (w/v) glucose. This solution was administered at the same volume, via the same route and at the same flow rate as the test compound 5 (identical formulation). Fifteen min (counting from the end of the injection) after the slow bolus injection (approx. 60 s injection time) of test article or vehicle, the right jugular vein was clamped, starting with the downstream clamp, followed 10 s later by the upstream one. 150 μL of blood were collected from the femoral artery and supplemented with 45 μL of 0.25 M calcium chloride. Next, 25 μL of human α-thrombin (2.5 U/mL, Sigma-AkJrich) was added to the blood mixture to induce coagulation. Immediately after mixing the blood, the clotting blood was administered in the isolated part of the right jugular vein. After a venous stasis period of 15 min, the vessel clamps were removed to restore blood flow from the jugular vein. The test article was infused during this venous stasis period. Blood flow was recorded with the transonic flow probe for a period of two h while the test article was infused at the selected concentration (see Table 4). 2 h after reperfusion, the venous stasis segment was removed, opened longitudinally and emptied into a petri dish containing 5% sodium citrate solution. Any existing thrombi were removed and blotted on a filter paper. The thrombi were measured, weighed and the appearance was judged.

A bleeding time was performed 30 min after beginning of reperfusion using an ITC Surgicutt™ Bleeding Time Device (International Technidyne SU50I via Fisher Scientific, Ottawa, Canada). Bleeding time was assessed with a filter paper by carefully collecting blood from the wound rim until no red staining of the filter paper could be observed. For each measure, a different non-stained part of the filter paper was used. The maximum bleeding time was defined as 300 s.

For each blood sample time point, plasma samples were generated using 150 mM sodium citrate as anticoagulant. Samples were stored at −20° C. until further analysis: determination of compound 5 concentration by HPLC and determination of residual FXIII activity after thrombin activation using the isopeptidase assay described above. In addition, one blood sample was taken at 60 min after the test article administration for thromboelastography (TEG). The TEG 5000 traces were recorded on the fresh whole blood sample for a period of 60 min according to the manufacturer. The read-outs are similar to the thromboelastometry and key parameters were combined to give the coagulation index (CI). Subsequent to the observation period of about 150 min after reperfusion, the animals were euthanized following an intracardiac blood draw by administering an overdose of pentobarbital.

Statistical Analysis

Unpaired Student's t-tests were performed on all experimental conditions, comparing the values obtained from rabbits injected with the test article to the values obtained from the negative control rabbits. Statistical significance is indicated if p≤0.05 compared to negative control animals. For each group, data is expressed as the mean±S.E.M.

Figure 4:
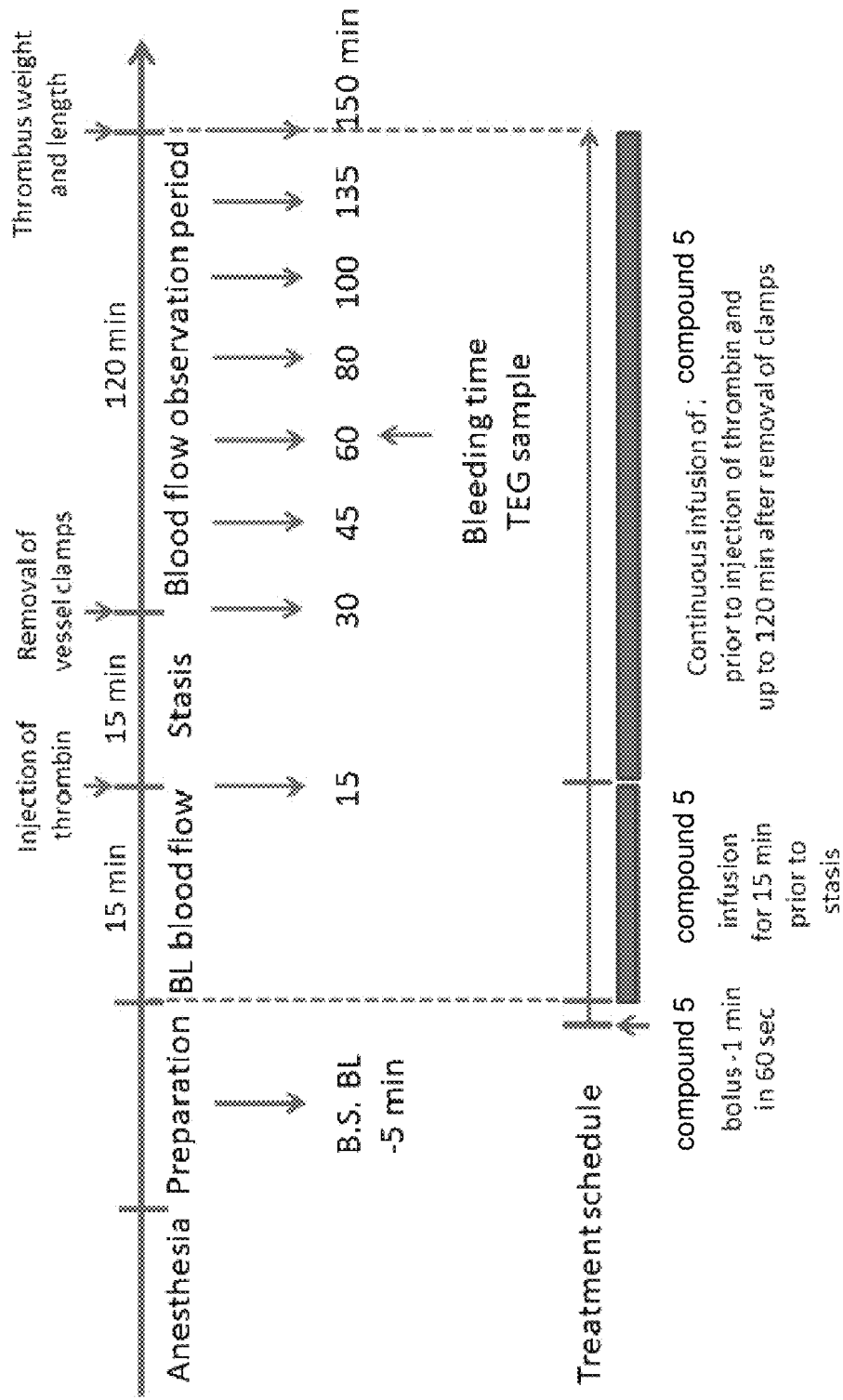
Figure 4:
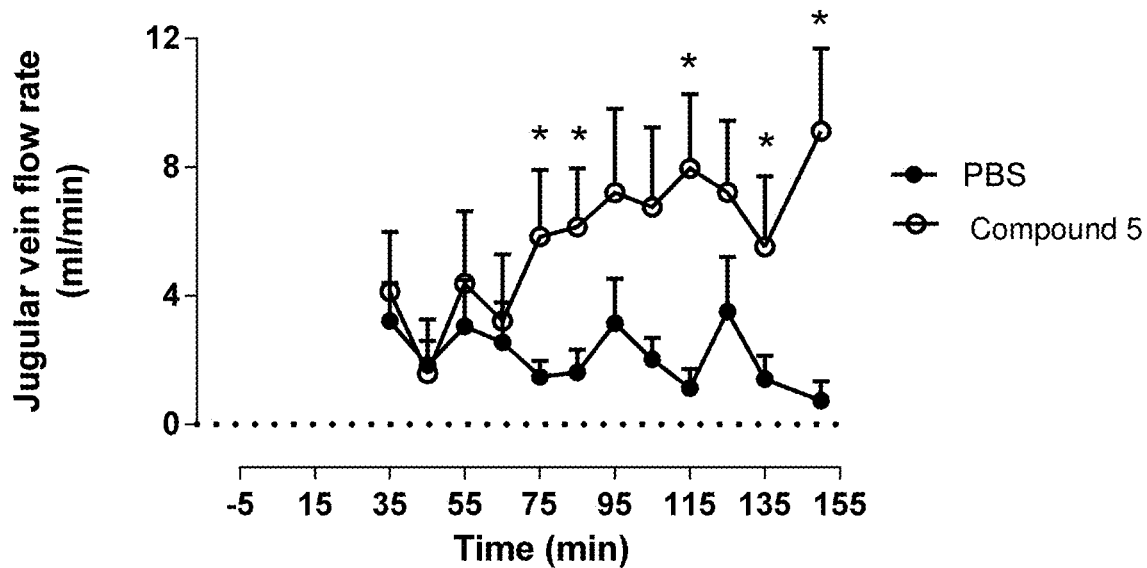
Figure 4:
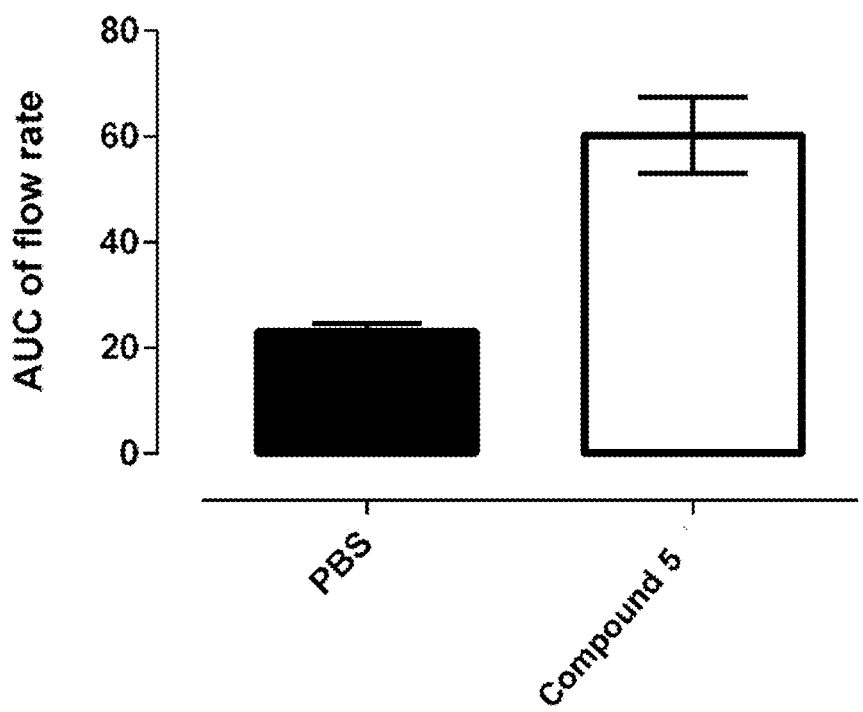
Figure 4:
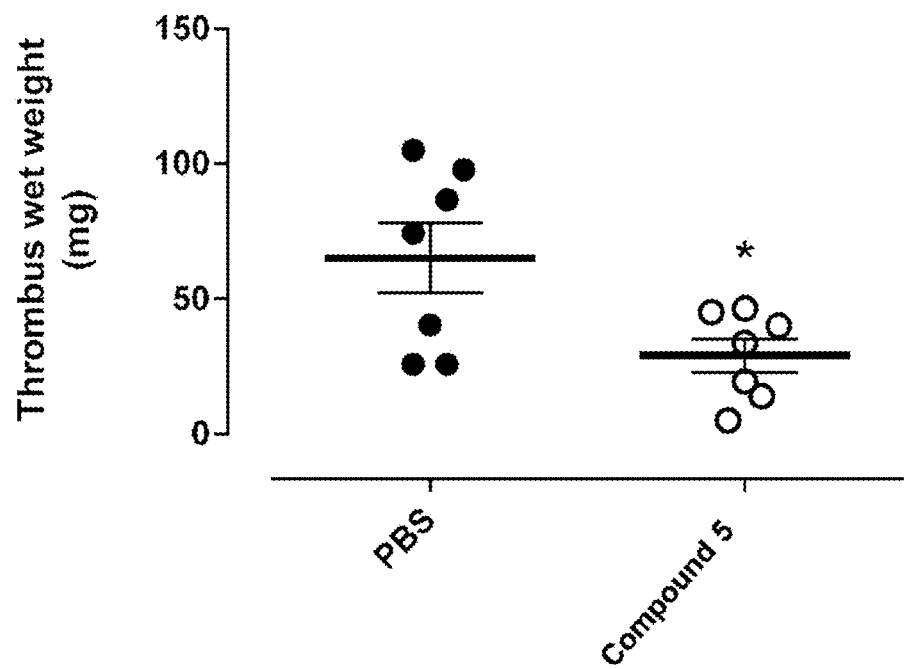
Figure 4:
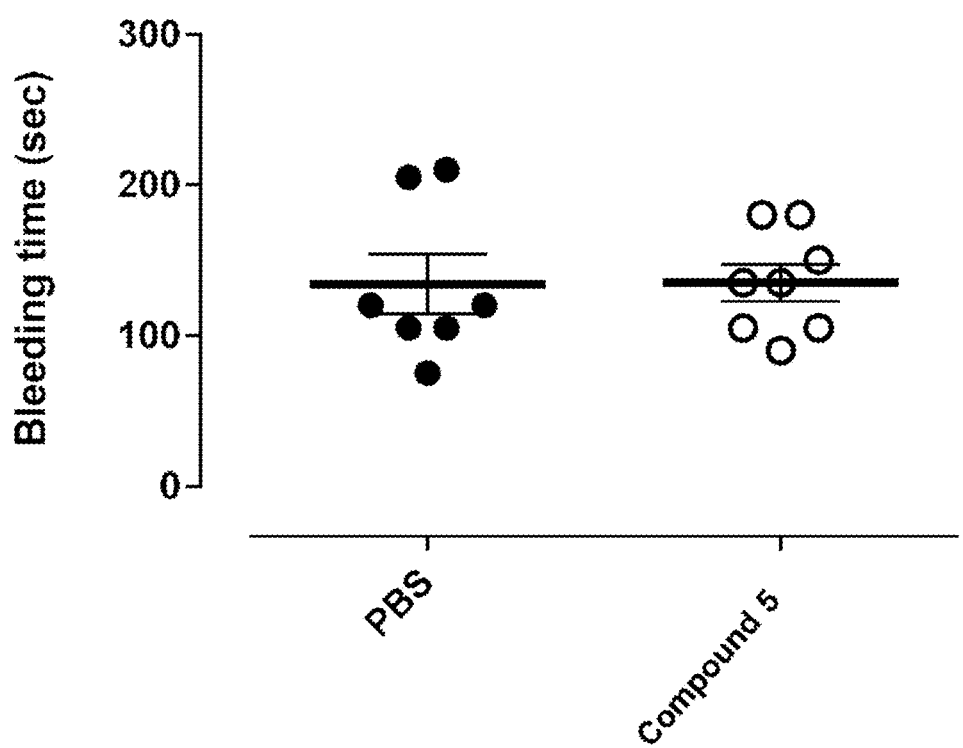

Experimental schedule of the rabbit model of venous stasis and reperfusion is briefly presented in FIG. 4A.

TABLE 4

Intravenous Injection Parameters

| Injection | Injection Time (min) | Compound 5 (=5a/b) Concentration (mg/mL) | Volume (mL) | Flow Rate (mL/min) | Total Dose (mg) |
|---|---|---|---|---|---|
| Bolus | 1 | 4 | 8 | 8 | 32 |
| Infusion | 15 | 4 | 2 | 0.13 | 8 |
| Infusion | 135 (15 stasis + 120 post stasis) | 4 | 18 | 0.13 | 72 |

The in vivo experiment proofs significantly higher flow rates after compound 5 infusion compared to PBS control animals (FIG. 4B). The area under the curve of flow rate is in accordance to the vein flow rate. In the compound 5 group the mean areas under the curve (AUC) of the jugular flow rate normalized to baseline between time points 35 and 135 minutes are significantly higher (FIG. 4C). The Thrombus wet weight is significantly reduced in the compound 5 group. Thrombus wet weight was determined after 135 min of infusion (FIG. 4D). Most importantly the template skin bleeding time is not influenced. Template skin bleeding time was determined after 60 min of infusion. No difference between PBS and compound 5 was observed. Maximal observation time was pre-defined at 300 seconds (FIG. 4E).

What is claimed is:

1. A compound of the general formula (I):

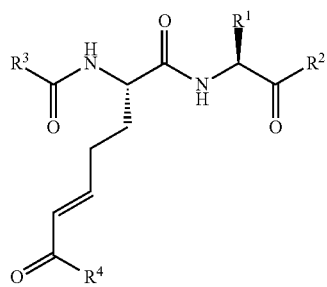

wherein
$R^1$ represents —H, —CH$_3$, —C(CH$_3$)$_3$, -cyclo-C$_3$H$_5$, -cyclo-C$_4$H$_7$, -cyclo-C$_5$H$_9$, -cyclo-C$_6$H$_{11}$, —CH$_2$—CH(CH$_3$)$_2$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_3$, —CH(CH$_3$)$_2$, —CH$_2$—C(CH$_3$)$_3$, —CH$_2$CH$_2$SCH$_3$, —CH$_2$-cyclo-C$_3$H$_5$, —CH$_2$-cyclo-C$_4$H$_7$, —CH$_2$-cyclo-C$_5$H$_9$ or —CH$_2$-cyclo-C$_6$H$_{11}$;
$R^2$ represents -A$^1$-A$^2$-A$^3$-E, -A$^1$-A$^2$-A$^3$-A$^4$-E or -A$^1$-A$^2$-A$^3$-A$^4$-A$^5$-E;
$R^3$ represents

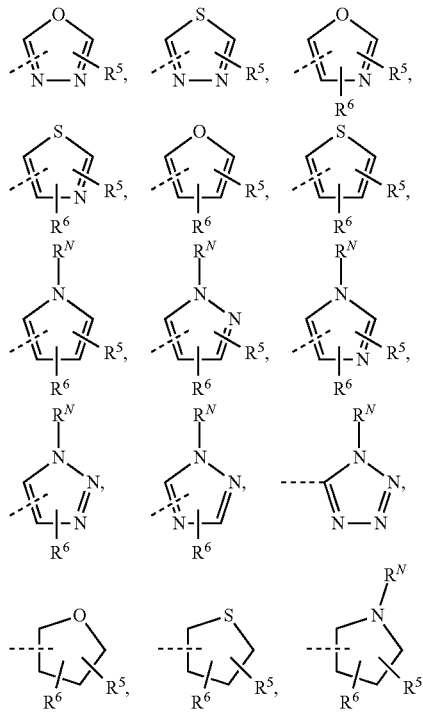

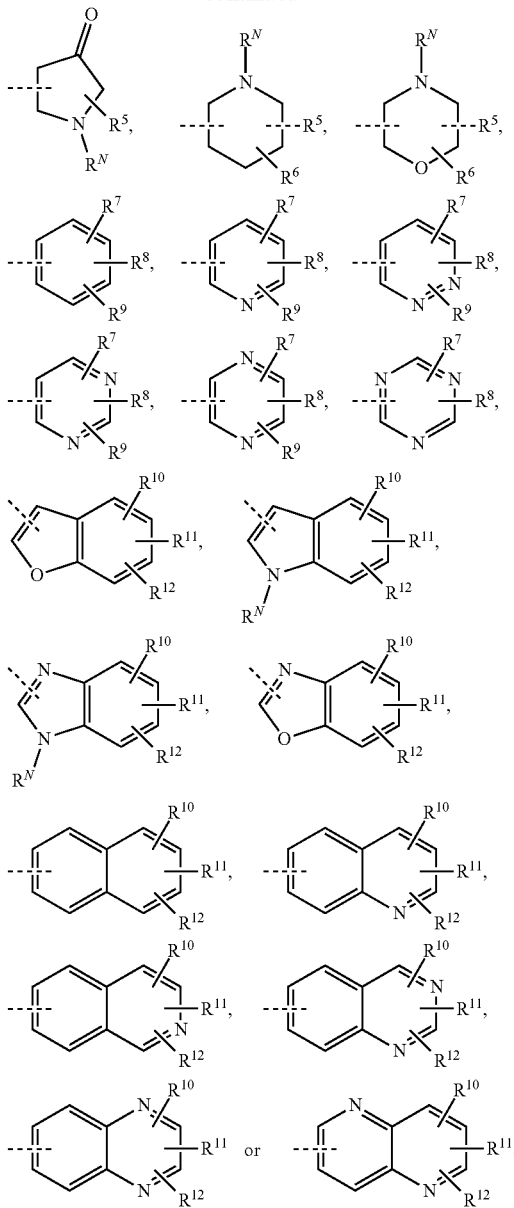

$R^4$ represents —OR*, —NH$_2$, —NHR$^\#$ or —NR*R$^\#$;
R* and R$^\#$ represent independently of each other —CH$_3$, —CH$_2$CH$_3$, —CH(CH$_3$)$_2$, —CH$_2$CH$_2$CH$_3$, —CH$_2$CH(CH$_3$)$_2$, —C(CH$_3$)$_3$, -cyclo-C$_3$H$_5$, -cyclo-C$_4$H$_7$, -cyclo-C$_5$H$_9$, -cyclo-C$_6$H$_{11}$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, —CH$_2$-Ph, —CH$_2$OCH$_3$, —CH$_2$OCH$_2$CH$_3$, —CH$_2$CH$_2$OCH$_3$, or —CH$_2$CH$_2$SCH$_3$;
$A^1$ represents

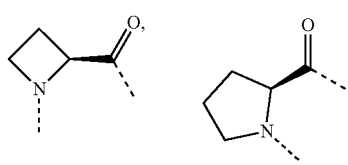

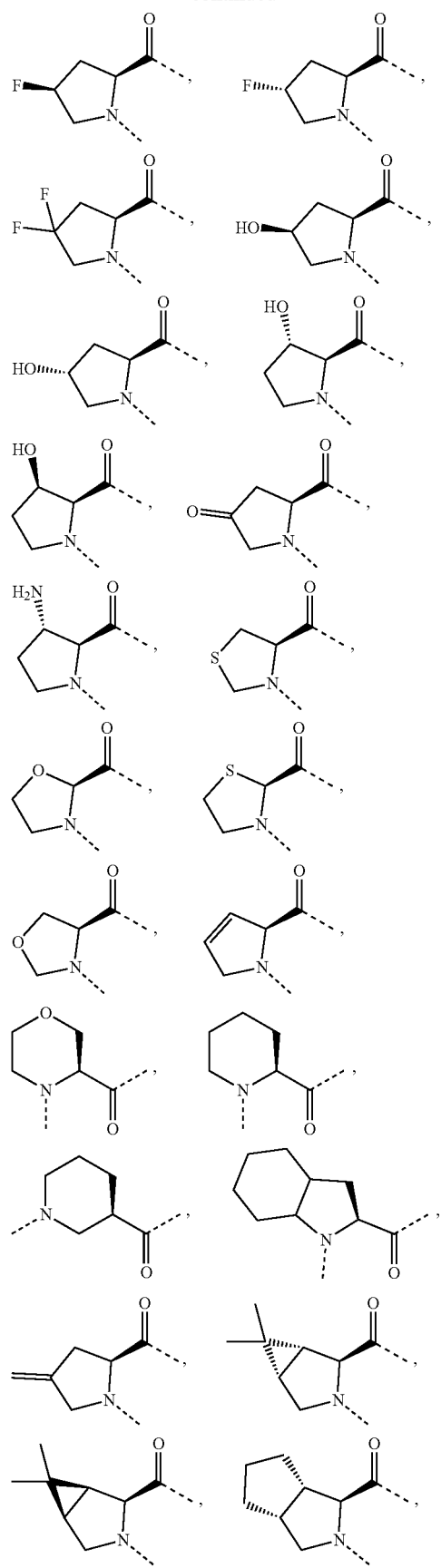
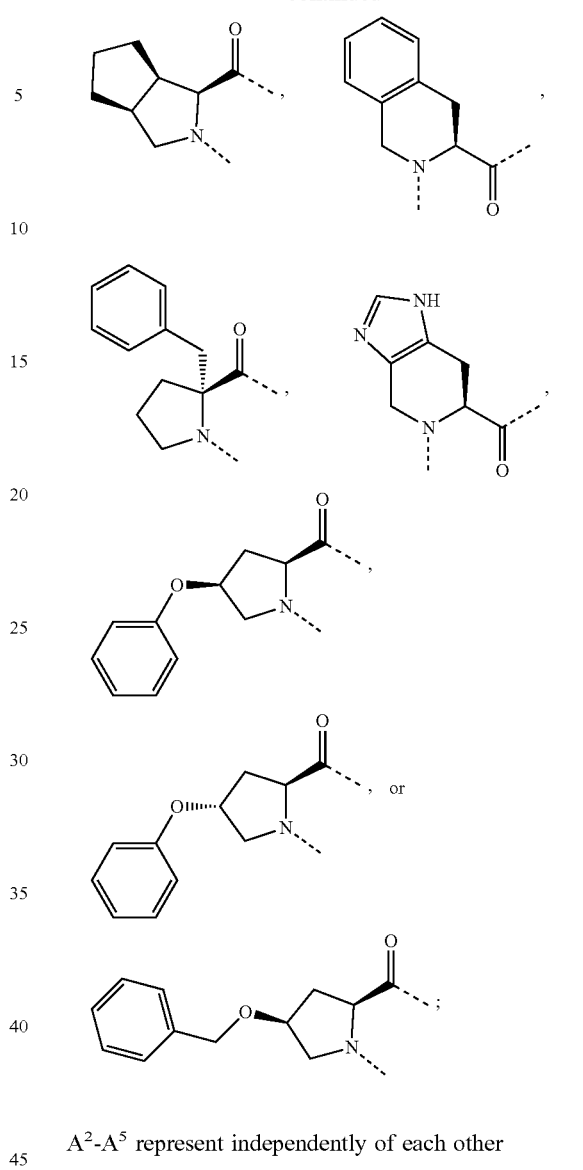
$A^2$-$A^5$ represent independently of each other
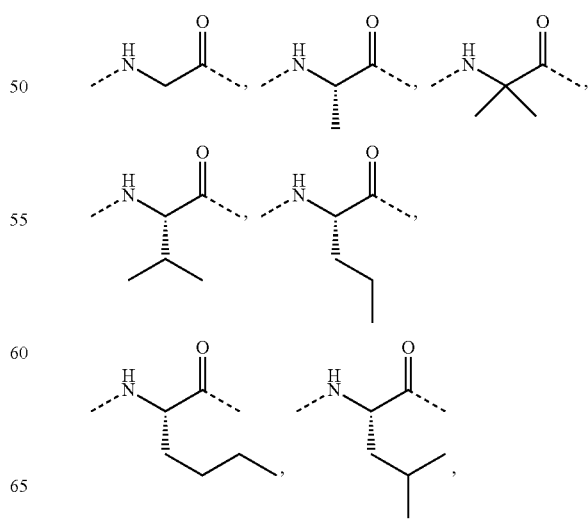

199
-continued
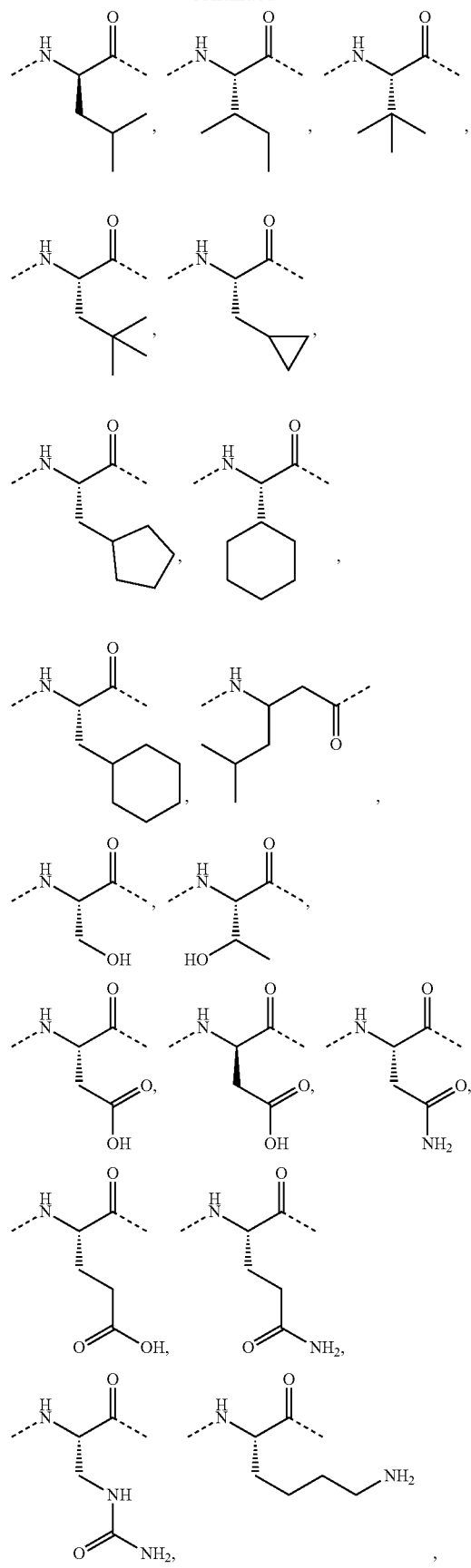
200
-continued
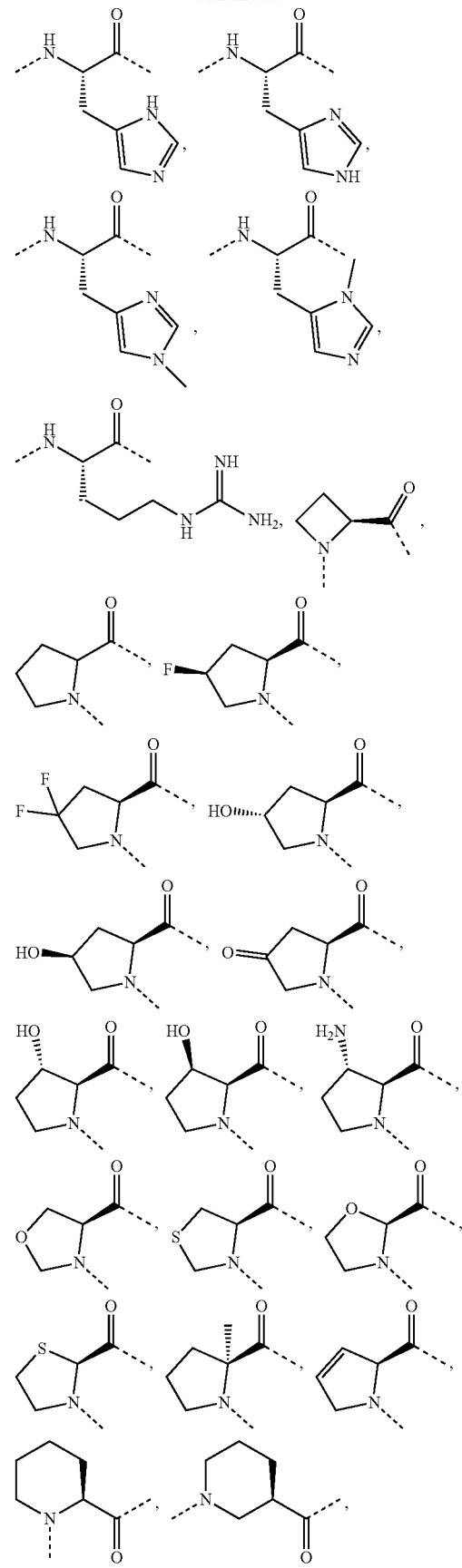

201
-continued
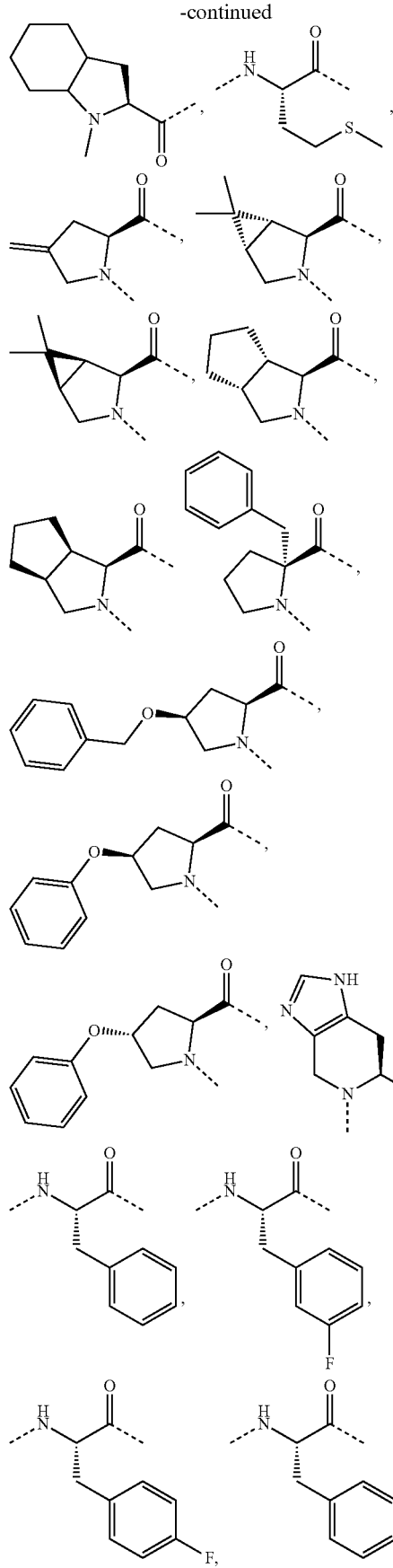
202
-continued
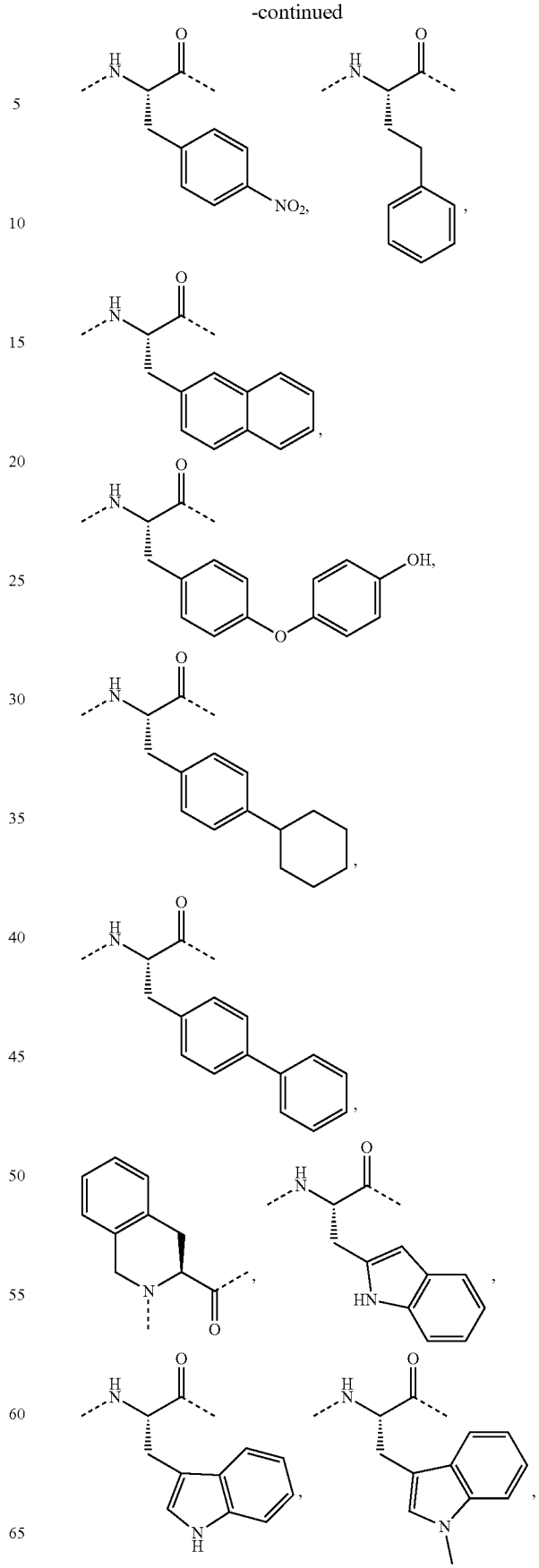

-continued
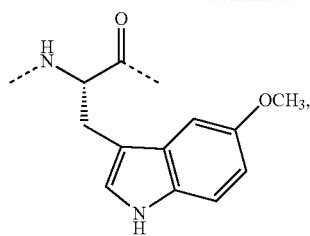
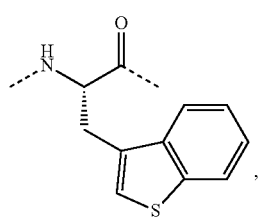
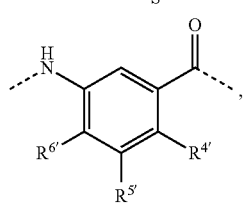
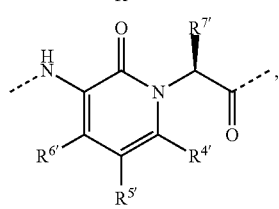
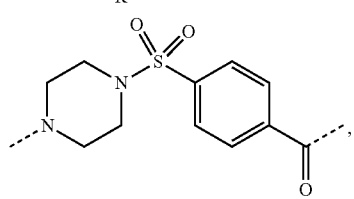
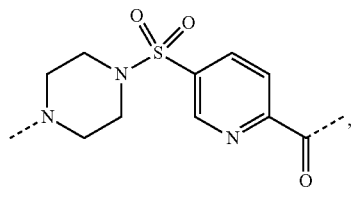
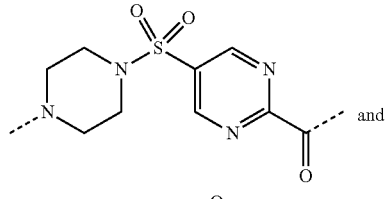
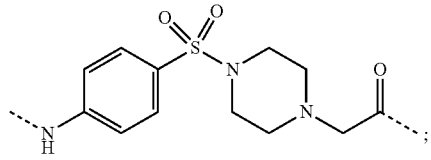
E represents: —$OR^{13}$, —$NR^{13}R^{14}$, —$NHSO_2R^{13}$, —O—$L_1$-$R^{13}$, —O—$L_1$-O—$R^{13}$, —NH—$L_1$-O—$R^{13}$, —NH—$L_1$-$NR^{13}R^{14}$, —$NHSO_2$—$L_1$-$R^{13}$,
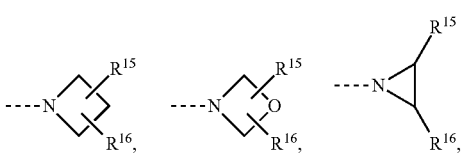
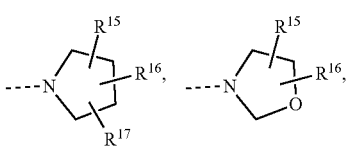
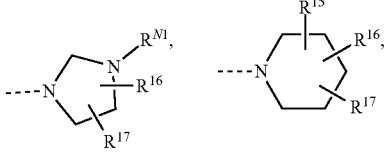
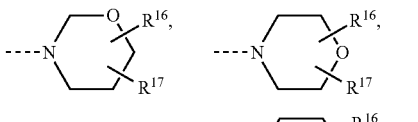
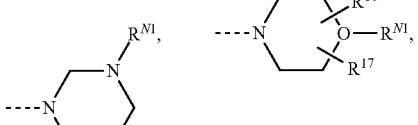
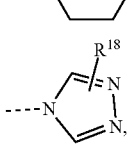
$R^{13}$ and $R^{14}$ represent independently of each other: —H, —$CH_3$, —$CH_2CH_3$, —$C(CH_3)_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$,
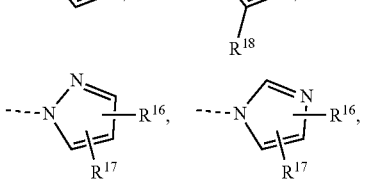
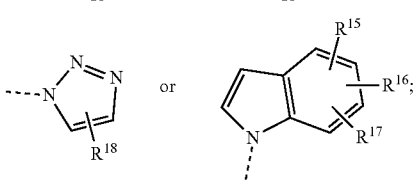
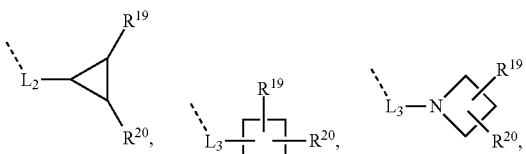
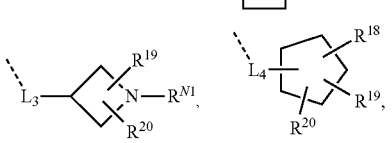

-continued

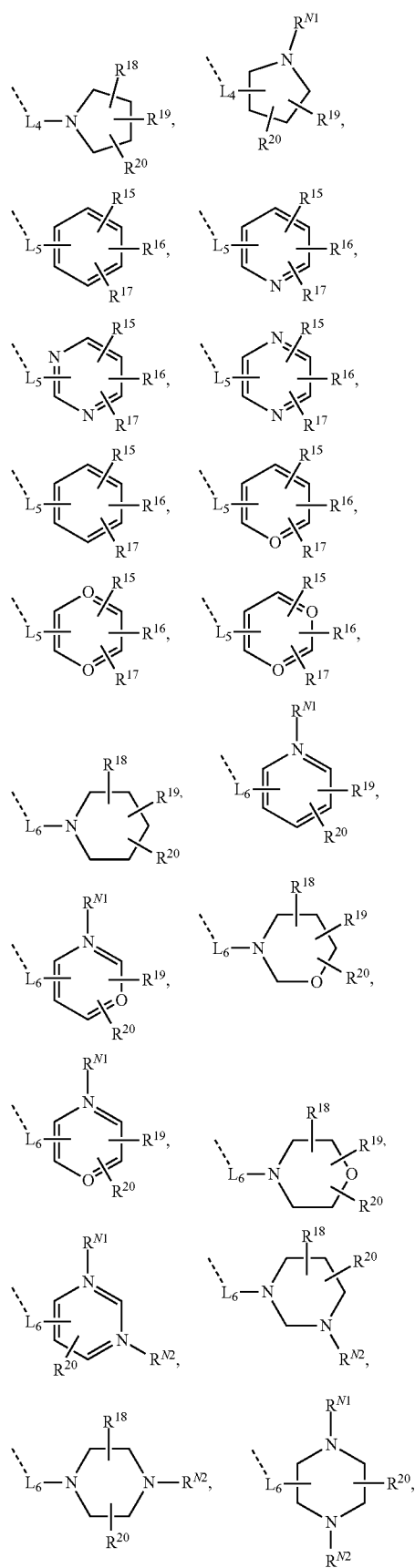

-continued

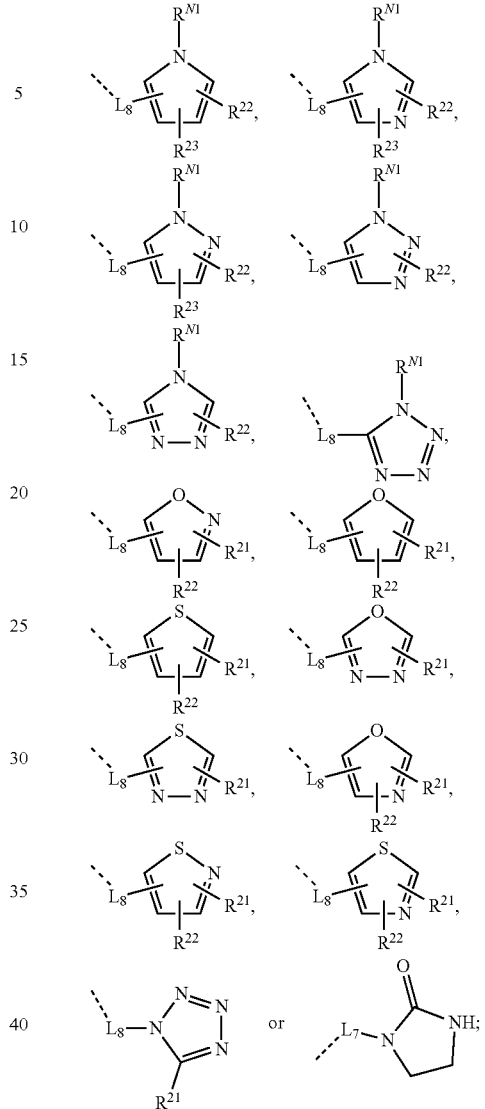

$R^N$, $R^{N1}$ and $R^{N2}$ represents independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, or —COOC(CH$_3$)$_3$;

$L^1$-$L^8$ represents independently of each other a covalent bond, —CH$_2$—, —CH(CH$_3$)—, —CH(CH$_3$)$_2$—, —CO—, —SO—, —SO$_2$—,

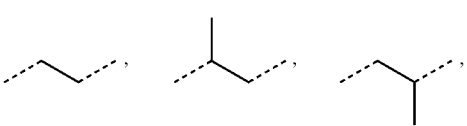

207
-continued

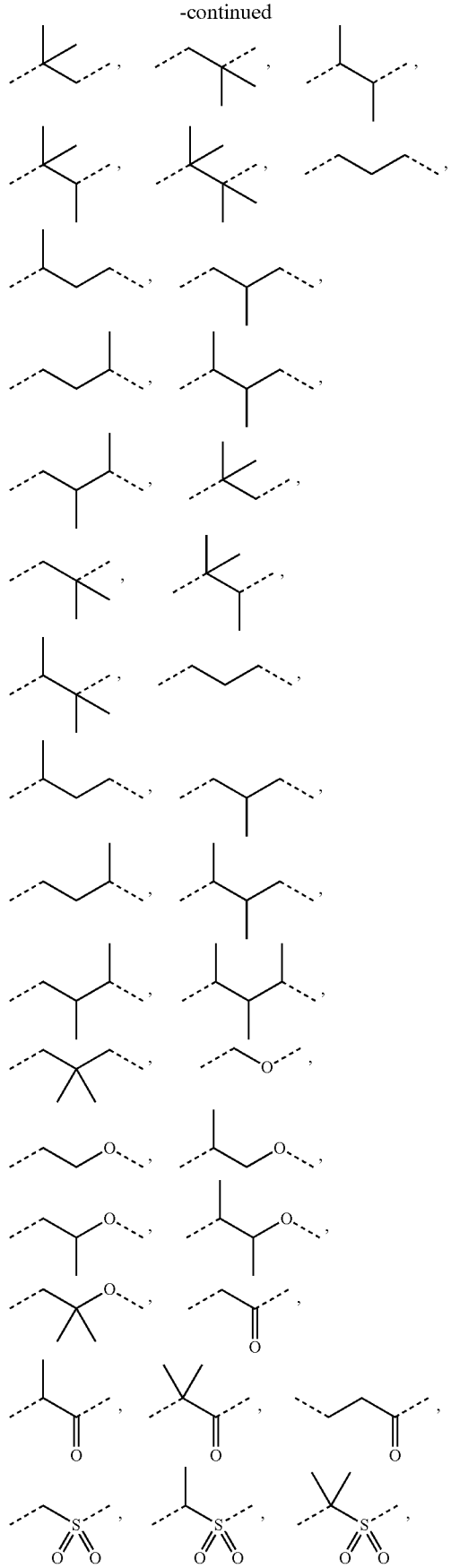

208
-continued

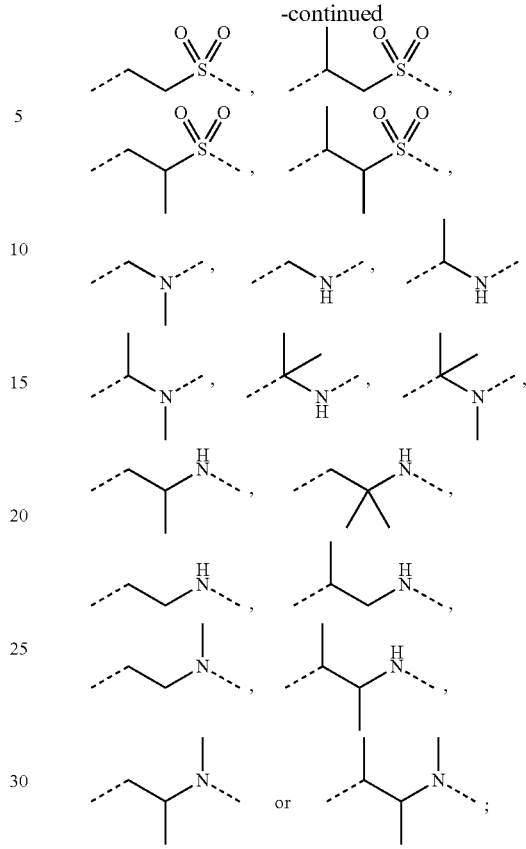

$R^5-R^{12}$, $R^{4'}-R^{7'}$, and $R^{15}-R^{23}$ represents independently of each other —H, —F, —Cl, —Br, —I, —OH, —CN, —NO₂, —CH₃, —C₂H₅, —C₃H₇, —CH(CH₃)₂, —C₄H₉, —CH₂—CH(CH₃)₂, —CH(CH₃)—C₂H₅, —C(CH₃)₃, -cyclo-C₃H₅, —CH₂-cyclo-C₃H₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —OCH₃, —OC₂H₅, —OC₃H₇, —OCH(CH₃)₂, —OC(CH₃)₃, —OC₄H₉, —OCHF₂, —OCF₃, —OCH₂CF₃, —OC₂F₅, —OCH₂OCH₃, —O-cyclo-C₃H₅, —OCH₂-cyclo-C₃H₅, —O—C₂H₄-cyclo-C₃H₅, —CHO, —COCH₃, —COCF₃, —COC₂H₅, —COC₃H₇, —COCH(CH₃)₂, —COC(CH₃)₃, —COOH, —COOCH₃, —COOC₂H₅, —COOC₃H₇, —COOCH(CH₃)₂, —COOC(CH₃)₃, —OOC—CH₃, —OOC—CF₃, —OOC—C₂H₅, —OOC—C₃H₇, —OOC—CH(CH₃)₂, —OOC—C(CH₃)₃, —NH₂, —NHCH₃, —NHC₂H₅, —NHC₃H₇, —NHCH(CH₃)₂, —NHC(CH₃)₃, —N(CH₃)₂, —N(C₂H₅)₂, —N(C₃H₇)₂, —N[CH(CH₃)₂]₂, —N[C(CH₃)₃]₂, —NHCOCH₃, —NHCOCF₃, —NHCOC₂H₅, —NHCOC₃H₇, —NHCOCH(CH₃)₂, —NHCOC(CH₃)₃, —CONH₂, —CONHCH₃, —CONHC₂H₅, —CONHC₃H₇, —CONHCH(CH₃)₂, —CONH-cyclo-C₃H₅, —CONHC(CH₃)₃, —CON(CH₃)₂, —CON(C₂H₅)₂, —CON(C₃H₇)₂, —CON[CH(CH₃)₂]₂, —CON[C(CH₃)₃]₂, —SO₂NH₂, —SO₂NHCH₃, —SO₂NHC₂H₅, —SO₂NHC₃H₇, —SO₂NHCH(CH₃)₂, —SO₂NH-cyclo-C₃H₅, —SO₂NHC(CH₃)₃, —SO₂N(CH₃)₂, —SO₂N(C₂H₅)₂, —SO₂N(C₃H₇)₂, —SO₂N[CH(CH₃)₂]₂, —SO₂N[C(CH₃)₃]₂, —NHSO₂CH₃, —NHSO₂CF₃, —NHSO₂C₂H₅, —NHSO₂C₃H₇, —NHSO₂CH(CH₃)₂,    —NHSO₂C(CH₃)₃,
—CH=CH₂, —CH₂—CH=CH₂, —C(CH₃)=CH₂,
—CH=CH—CH₃, —C≡CH, —C≡C—CH₃, —CH₂—
C≡CH, -Ph, —O-Ph, or —O—CH₂-Ph,

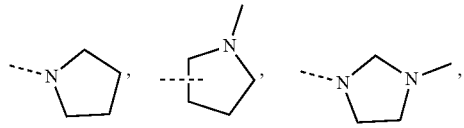

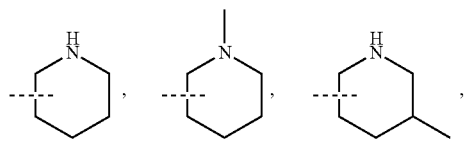

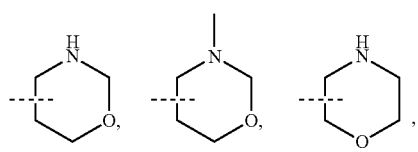

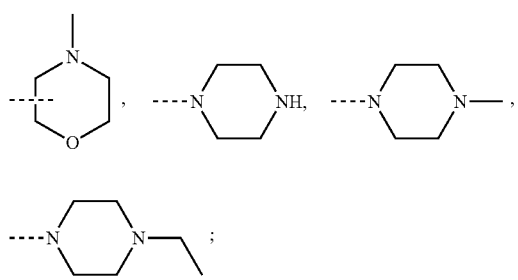

or R⁷ and R⁸ or R⁸ and R⁹ form together one of the following ring moieties;

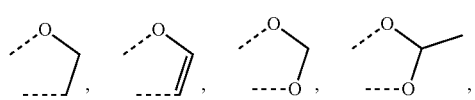

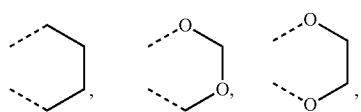

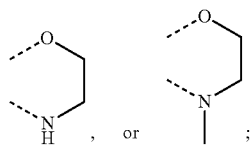

or E/Z-isomer, regiomer, diastereomer, enantiomer, a mixture of E/Z-isomers, a mixture of regiomers, a mixture of diastereomers, a mixture of enantiomers, prodrug, solvate, hydrate, or pharmaceutically acceptable salts thereof.

2. The compound according to claim 1, wherein the compound has any one of the formulae (II-1) to (II-3):

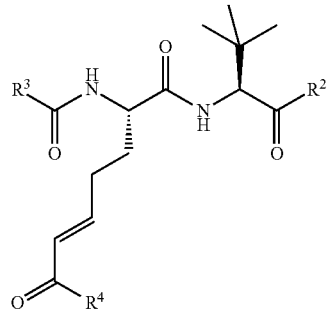

(II-1)

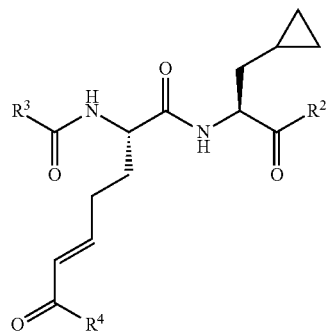

(II-2)

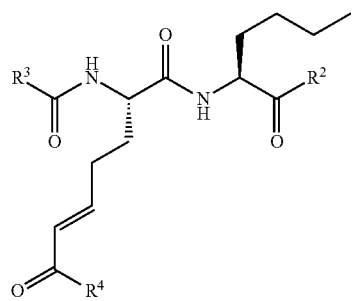

(II-3)

wherein R², R³ and R⁴ have the meanings as defined in claim 1.

3. The compound according to claim 1, wherein A² is selected from:

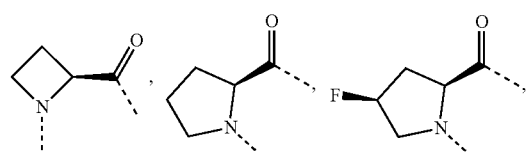

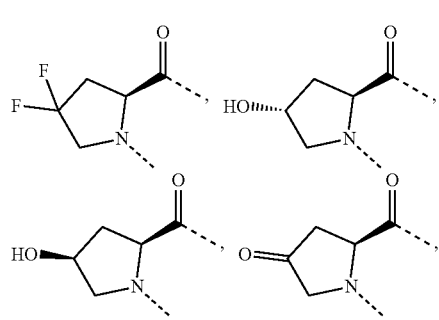

-continued and/or A² is selected from:

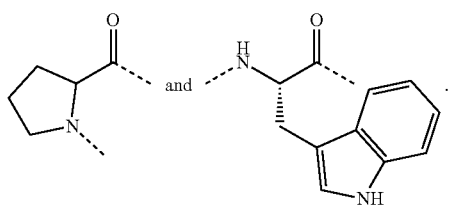 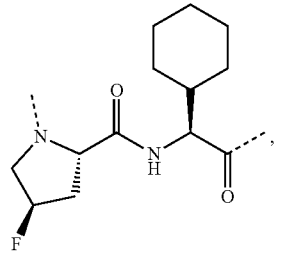
4. The compound according to claim 1, wherein -A$^1$-A$^2$- represents
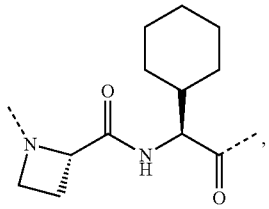 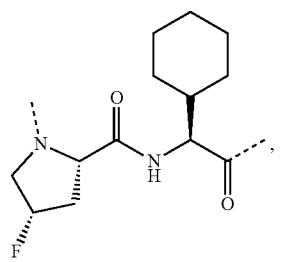
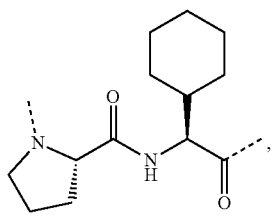 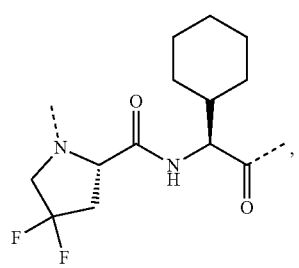
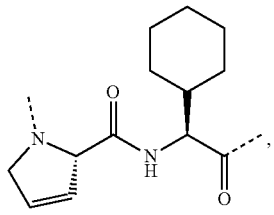 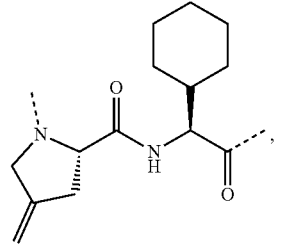
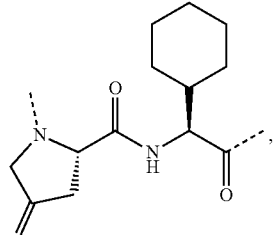 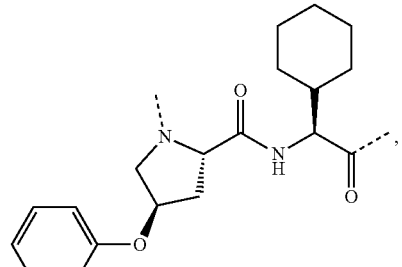
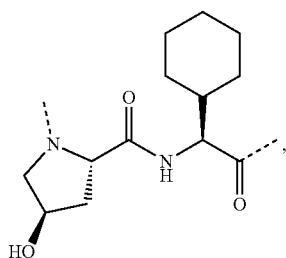 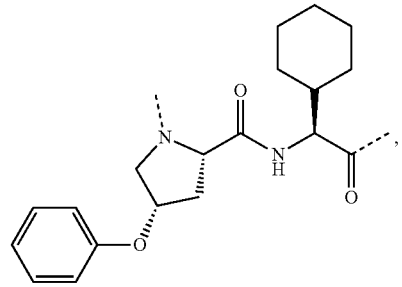

215
-continued
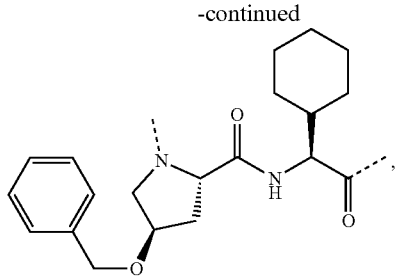
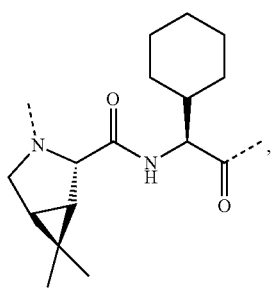
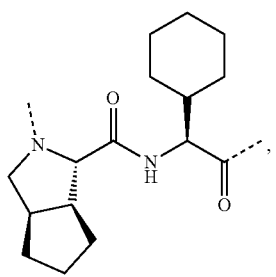
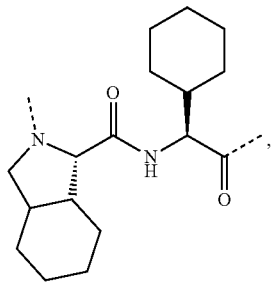
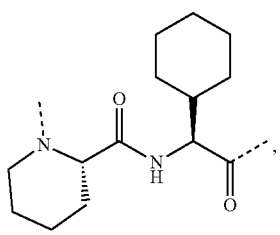
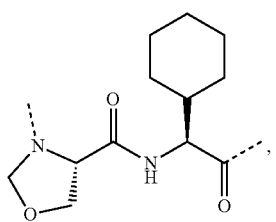
216
-continued
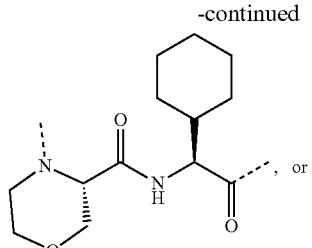, or
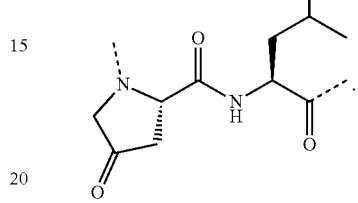
5. The compound according to claim 1, wherein -A²-A³- represents
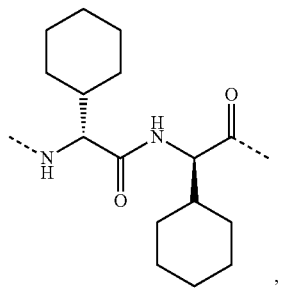

-continued

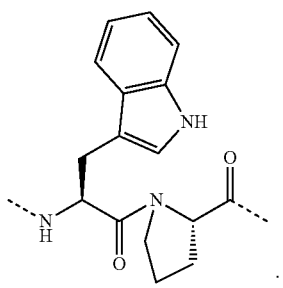

6. The compound according to claim 1, wherein $R^3$ represents

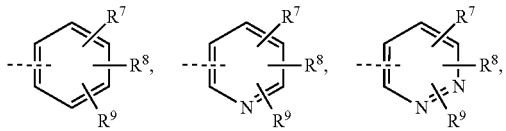

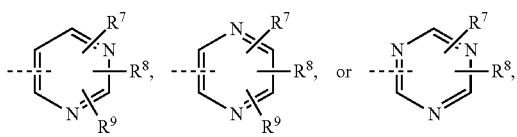

and $R^7$, $R^8$ and $R^9$ have the meanings as defined in claim 1.

7. The compound according to claim 1 of the general formula (III):

(III)

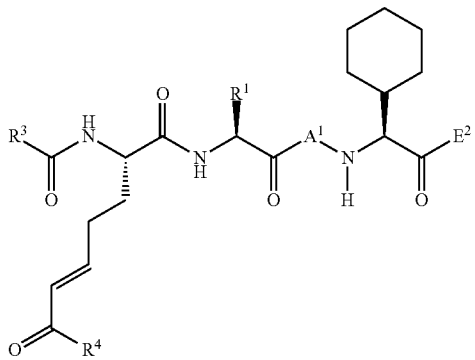

wherein $E^2$ represents -E, -$A^3$-E, -$A^3$-$A^4$-E, or -$A^3$-$A^4$-$A^5$-E; and $A^1$, $A^3$, $A^4$, $A^5$, $R^1$, $R^3$, $R^4$, and E have the meanings as defined in claim 1.

8. The compound according to claim 1 or 7 having any one of the formulae (IV-1) to (IV-4):

(IV-1)

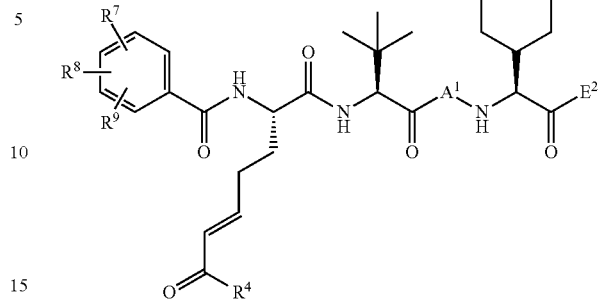

(IV-2)

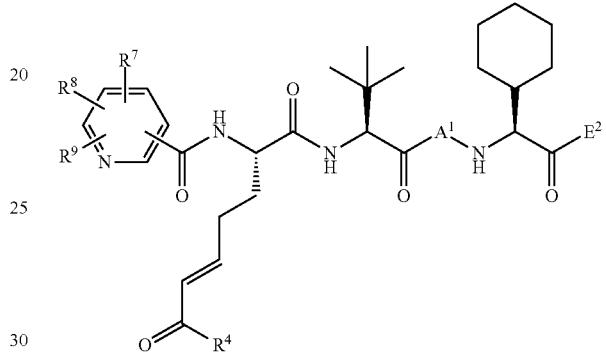

(IV-3)

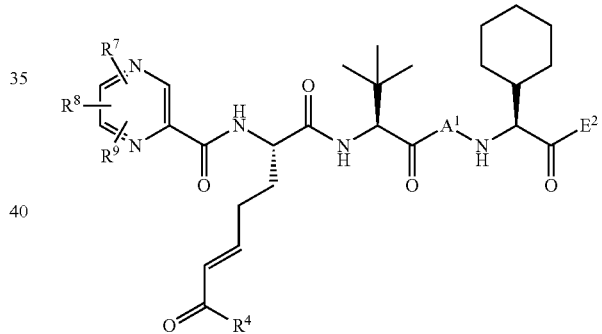

(IV-4)

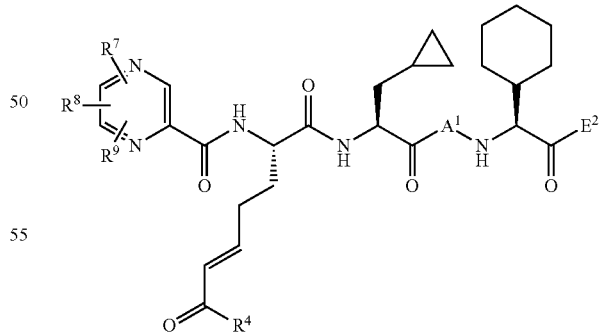

wherein $E^2$ represents -E, -$A^3$-E, -$A^3$-$A^4$-E or -$A^3$-$A^4$-$A^5$-E;

$R^4$ represents —OCH$_3$ or —OCH$_2$CH$_3$;

$R^7$, $R^8$ and $R^9$ are independently of each other selected from —H, —Cl, —OH, —NO$_2$ or —COOH; and $A^1$, $A^3$, $A^4$, $A^5$ and E have the meanings as defined in claim 1.

9. The compound according to claim 1, wherein the compound has any one of the formulae (V-1) and (V-2):
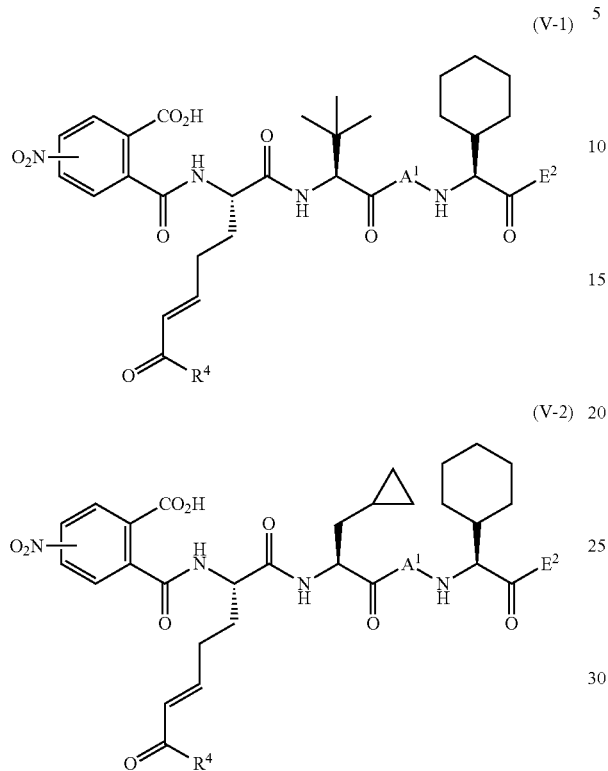
(V-1)
(V-2)
wherein
$E^2$ represents -E, -$A^3$-E, -$A^3$-$A^4$-E or -$A^3$-$A^4$-$A^5$-E;
$R^4$ represents —$OCH_3$ or —$OCH_2CH_3$;
$A^1$ represents
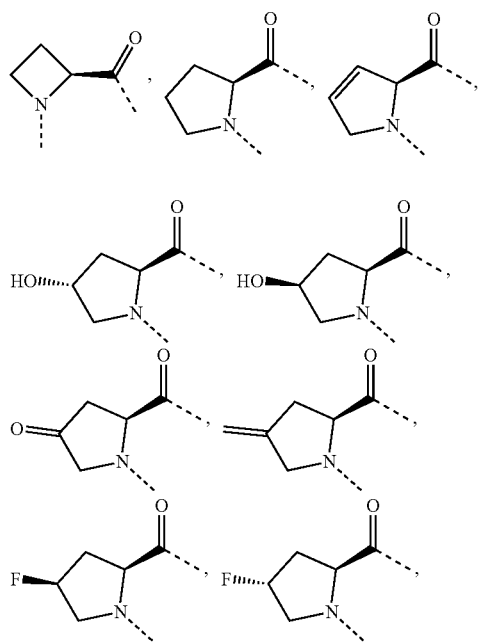
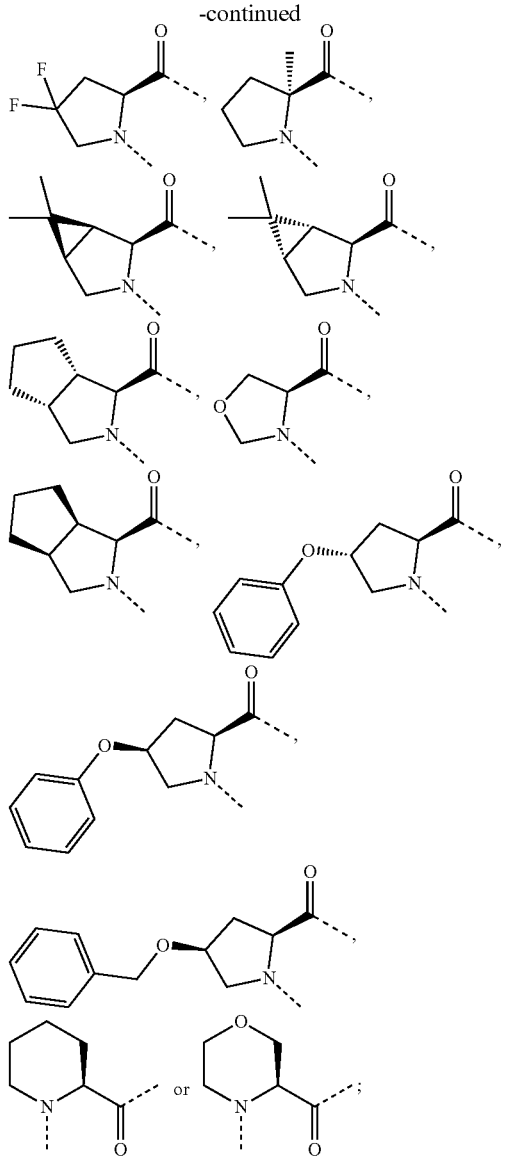
and $A^3$, $A^4$, $A^5$ and E have the meanings as defined in claim 1.
10. The compound according to claim 7 having the formula (VI):
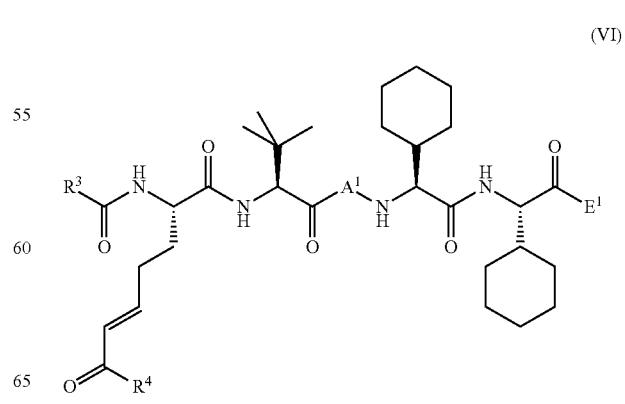
(VI)

wherein $E^1$ represents -E, -$A^4$-E or -$A^4$-$A^5$-E;

$R^3$ represents

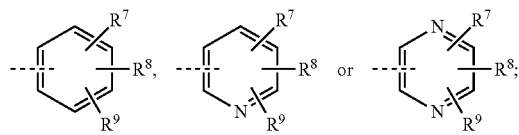

and $A^1$, $A^4$, $A^5$, $R^4$, $R^7$, $R^8$, $R^9$ and E have the meanings as defined in claim 7.

11. The compound according to claim 1 selected from a group consisting of: compounds 1a, 1b, 2a, 2b, 3, 4, 5a, 5b, 6, 7a, 7b, 8a, 8b, 9a, 9b, 10a, 10b, 11a, 11b, 12a, 12b, 13a, 13b, 14a, 14b, 15a, 15b, 16a, 16b, 17a, 17b, 18a, 18b, 19a, 19b, 20a, 20b, 21a, 21b, 22a, 22b, 23a, 23b, 24a, 24b, 25a, 25b, 26a, 26b, 27, 28, 29, 30, 31a, 31b, 32a, 32b, 33a, 33b, 34a, 34b, 35a, 35b, 36a, 36b, 37a, 37b, 38, 39a, 39b, 40, 41, 42a, 42b, 43, 44, 45a, and 45b.

12. A pharmaceutical composition comprising at least one compound according to claim 1 as an active ingredient together with at least one pharmaceutically acceptable carrier, excipient and/or diluent.

13. A Method for producing compound according to claim 1 comprising:

Step (0B): providing a resin, suitable for solid-phase peptide synthesis (SPPS);

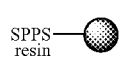

Step (1B) (a): performing coupling reaction of the corresponding C-terminal amino acid building block $PG^4NH$-$A^i$-OH;

(b) deprotecting the protecting group $PG^4$ of a resulting compound after Step (a);

(c) repeating the steps (a) and (b)/times, wherein i is 1-5, to obtain a resin bound intermediate compound (IIIc);

                                   IIIc

Step (2B): cleavage from resin and deprotecting the protecting group $PG^4$ to obtain an intermediate compound (IIId);

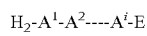   IIId

Step (3B): performing coupling reaction of the intermediate compound IIId with an amino acid building block A0

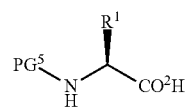

to obtain a compound IVc;

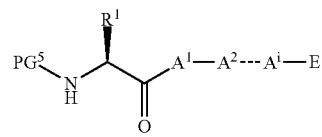

Step (4B): deprotecting the protecting group $PG^5$ and subsequent coupling reaction with protected amino acid Ia

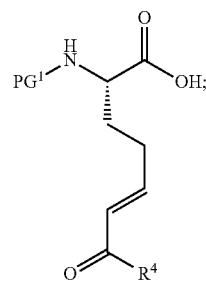

to obtain compound Vc

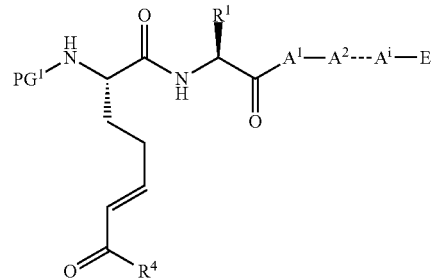

Step (5B): deprotecting the protecting group $PG^1$ and subsequent coupling reaction with a N-terminal building block $R^3$—$CO_2H$ to produce the compound of the formula (I);

or

Step (0C): providing a N-deprotected C-terminal building block H-E or H-$A^i$-E;

Step (1C): (a) performing coupling reaction of the corresponding C-terminal amino acid building block $PG^4NH$-$A^i$-OH or $PG^4NH$-$A^{i-1}$-OH;

(b) deprotecting the protecting group PG⁴ of a resulting compound after Step (a);
(c) repeating the steps (a) and (b) i times, wherein i is 1-5 or 1-4, to obtain intermediate compound (IIId);

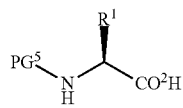     (IIId)

Step (3B): performing coupling reaction of the intermediate compound IIId with an amino acid building block A0

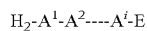     A0 to obtain a compound IVc;

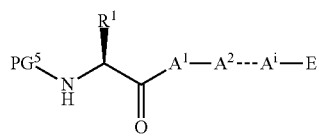     IVc

Step (4B): deprotecting the protecting group PG⁵ and subsequent coupling reaction with protected amino acid 1a

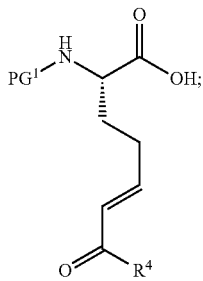     Ia to obtain compound Vc

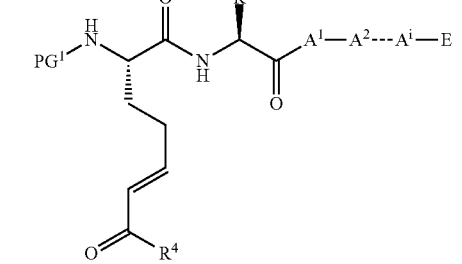     Vc

Step (5B): deprotecting the protecting group PG¹ and subsequent coupling reaction with a N-terminal building block R³—CO₂H to produce the compound of the formula (I).

* * * * *